(12) United States Patent
Gavai et al.

(10) Patent No.: US 9,242,941 B2
(45) Date of Patent: Jan. 26, 2016

(54) ALKYL, FLUOROALKYL-1,4-BENZODIAZEPINONE COMPOUNDS

(71) Applicant: BRISTOL-MYERS SQUIBB COMPANY, Princeton, NJ (US)

(72) Inventors: Ashvinikumar V. Gavai, Princeton Junction, NJ (US); Yufen Zhao, Pennington, NJ (US); Daniel O'Malley, New Hope, PA (US); Claude A. Quesnelle, Skillman, NJ (US); Brian E. Fink, Yardley, PA (US); Derek J. Norris, Hopewell, NJ (US); Wen-Ching Han, Newtown, PA (US); George V. DeLucca, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/429,935

(22) PCT Filed: Sep. 20, 2013

(86) PCT No.: PCT/US2013/060799
§ 371 (c)(1),
(2) Date: Mar. 20, 2015

(87) PCT Pub. No.: WO2014/047374
PCT Pub. Date: Mar. 27, 2014

(65) Prior Publication Data
US 2015/0239851 A1    Aug. 27, 2015

Related U.S. Application Data

(60) Provisional application No. 61/772,583, filed on Mar. 5, 2013, provisional application No. 61/703,917, filed on Sep. 21, 2012.

(51) Int. Cl.
| | |
|---|---|
| C07D 401/04 | (2006.01) |
| C07D 243/24 | (2006.01) |
| C07F 9/12 | (2006.01) |
| C07F 9/645 | (2006.01) |
| A61K 31/5513 | (2006.01) |
| A61K 31/675 | (2006.01) |

(Continued)

(52) U.S. Cl.
CPC .......... *C07D 243/24* (2013.01); *A61K 31/5513* (2013.01); *A61K 31/675* (2013.01); *A61K 45/06* (2013.01); *C07D 401/04* (2013.01); *C07D 403/12* (2013.01); *C07F 9/12* (2013.01); *C07F 9/645* (2013.01)

(58) Field of Classification Search
CPC ........................... C07D 401/04; C07D 243/24
See application file for complete search history.

(56) References Cited

U.S. PATENT DOCUMENTS

| 4,981,847 A | 1/1991 | Sato et al. |
| 5,322,842 A | 6/1994 | Sato et al. |

(Continued)

FOREIGN PATENT DOCUMENTS

| EP | 0669334 | 8/1995 |
| WO | WO 97/36879 | 10/1997 |

(Continued)

OTHER PUBLICATIONS

U.S. Appl. No. 14/627,573, filed Feb. 20, 2015, Gavai et al.
Groth, C., et al., "Therapeutic approaches to modulating Notch signaling: Current challenges and future prospects," Seminars in Cell & Developmental Biology, (2012), doi:10.1016/j.semcdb2012.01.016; available online Mar. 7, 2012.
Seiffert, D., et al., "Presenilin-1 and -2 Are Molecular Targets for gamma-Secretase Inhibitors," The Journal of Biological Chemistry, vol. 275, No. 44, pp. 34086-34091 (2000).
Beher, D., et al., "Pharmacological Knock-down of the Presenilin 1 Heterodimer by a Novel gamma-Secretase Inhibitor," The Journal of Biological Chemistry, vol. 276, No. 48, pp. 45394-45402 (2001).
Iben, L.G., et al., "Signal Peptide Peptidase and gamma-Secretase Share Equivalent Inhibitor Binding Pharmacology," The Journal of Biological Chemistry, vol. 282, No. 51, pp. 36829-36836 (2007).
Meredith, Jere, "Characterization of APP Activity and Notch Toxicity with gamma-Secretase Inhibitors," 8th International AD/PD Meeting, Salzberg, Austria, Mar. 17, 2007.

(Continued)

*Primary Examiner* — Bruck Kifle
(74) *Attorney, Agent, or Firm* — Gary D. Greenblatt

(57) ABSTRACT

Disclosed are compounds of Formula (I) and/or salts thereof: (I) wherein: $R_1$ is $CH_2CH_2CF_3$; $R_2$ is $CH_2$(cyclopropyl), $CH(CH_3)$(cyclopropyl), or $CH_2CH_2CH_3$; $R_3$ is H, $CH_3$, or $R_x$; $R_4$ is H or $R_y$; and $R_x$, $R_y$, $R_a$, $R_b$, $R_c$, y, and z are defined herein. Also disclosed are methods of using such compounds to inhibit the Notch receptor, and pharmaceutical compositions comprising such compounds. These compounds are useful in treating, preventing, or slowing the progression of diseases or disorders in a variety of therapeutic areas, such as cancer. The compounds of Formula (I) also include prodrugs of the Notch inhibitor compounds.

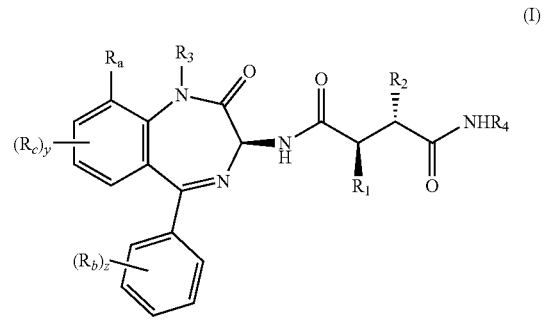

(I)

8 Claims, 11 Drawing Sheets

(51) Int. Cl.
*A61K 45/06* (2006.01)
*C07D 403/12* (2006.01)

(56) References Cited

U.S. PATENT DOCUMENTS

| | | | |
|---|---|---|---|
| 5,324,726 | A | 6/1994 | Bock et al. |
| 5,852,010 | A | 12/1998 | Graham et al. |
| 5,998,407 | A | 12/1999 | Graham et al. |
| 6,331,408 | B1 | 12/2001 | Zaczek et al. |
| 6,495,540 | B2 | 12/2002 | Thompson |
| 6,503,901 | B1 | 1/2003 | Thompson et al. |
| 6,503,902 | B2 | 1/2003 | Olson et al. |
| 6,509,333 | B2 | 1/2003 | Olson |
| 6,525,044 | B2 | 2/2003 | Olson et al. |
| 6,544,978 | B2 | 4/2003 | Wu et al. |
| 6,632,812 | B2 | 10/2003 | Han et al. |
| 6,653,303 | B1 | 11/2003 | Wu et al. |
| 6,713,476 | B2 | 3/2004 | Yang et al. |
| 6,737,038 | B1 | 5/2004 | Zaczek et al. |
| 6,756,511 | B2 | 6/2004 | Castro Pineiro et al. |
| 6,759,404 | B2 | 7/2004 | Yang et al. |
| 6,794,381 | B1 | 9/2004 | Olson et al. |
| 6,878,363 | B2 | 4/2005 | Zaczek et al. |
| 6,900,199 | B2 | 5/2005 | Han et al. |
| 6,958,329 | B2 | 10/2005 | Olson |
| 6,960,576 | B2 | 11/2005 | Olson et al. |
| 6,962,913 | B2 | 11/2005 | Olson et al. |
| 6,984,626 | B2 | 1/2006 | Nadin et al. |
| 7,001,901 | B2 | 2/2006 | Yang |
| 7,053,081 | B2 | 5/2006 | Olson et al. |
| 7,053,084 | B1 | 5/2006 | Olson |
| 7,101,870 | B2 | 9/2006 | Olson et al. |
| 7,105,509 | B2 | 9/2006 | Castro Pineiro et al. |
| 7,112,583 | B2 | 9/2006 | Olson et al. |
| 7,125,866 | B1 | 10/2006 | Glick et al. |
| 7,153,491 | B2 | 12/2006 | Zaczek et al. |
| 7,160,875 | B2 | 1/2007 | Flohr et al. |
| 7,276,495 | B2 | 10/2007 | Han et al. |
| 7,276,496 | B2 | 10/2007 | Olson et al. |
| 7,304,049 | B2 | 12/2007 | Olson |
| 7,304,055 | B2 | 12/2007 | Olson et al. |
| 7,304,056 | B2 | 12/2007 | Olson et al. |
| 7,342,008 | B2 | 3/2008 | Olson et al. |
| 7,354,914 | B2 | 4/2008 | Olson |
| 7,375,099 | B2 | 5/2008 | Galley et al. |
| 7,390,802 | B2 | 6/2008 | Han et al. |
| 7,390,896 | B2 | 6/2008 | Olson et al. |
| 7,423,033 | B2 | 9/2008 | Olson et al. |
| 7,456,172 | B2 | 11/2008 | Olson |
| 7,456,278 | B2 | 11/2008 | Olson |
| 7,498,324 | B2 | 3/2009 | Han et al. |
| 7,528,249 | B2 | 5/2009 | Olson et al. |
| 7,544,679 | B2 | 6/2009 | Flohr et al. |
| 7,582,624 | B2 | 9/2009 | Carter et al. |
| 7,655,647 | B2 | 2/2010 | Han et al. |
| 7,718,795 | B2 | 5/2010 | Olson |
| 8,629,136 | B2 | 1/2014 | Gavai et al. |
| 8,822,454 | B2 | 9/2014 | Gavai et al. |
| 8,999,918 | B2 | 4/2015 | Gavai et al. |
| 2007/0185094 | A1 | 8/2007 | Lattmann et al. |
| 2009/0181944 | A1 | 7/2009 | Boylan et al. |
| 2014/0357805 | A1 | 12/2014 | Gavai et al. |

FOREIGN PATENT DOCUMENTS

| | | |
|---|---|---|
| WO | WO 01/74796 | 10/2001 |
| WO | WO 01/90084 | 11/2001 |
| WO | WO 2007/067048 | 6/2007 |
| WO | WO 2009/023453 | 2/2009 |
| WO | WO 2014/047369 | 3/2014 |
| WO | WO 2014/047370 | 3/2014 |
| WO | WO 2014/047390 | 3/2014 |
| WO | WO 2014/047391 | 3/2014 |
| WO | WO 2014/047392 | 3/2014 |
| WO | WO 2014/047393 | 3/2014 |
| WO | WO 2014/047397 | 3/2014 |

OTHER PUBLICATIONS

Prasad, C.V.C., et al., "Discovery of (S)-2-((S)-2(3,5-difluorophenyl)-2-hydroxyacetamido)-*N*-((S,Z)-3-methyl-4-oxo-4,5-dihydro-*3H*-benzo[*d*][1,2]diazepin-5-yl)propanamide (BMS-433796): A gamma-secretase inhibitor with with A beta lowering activity in a transgenic mouse model of Alzheimer's disease," Bioorganic & Medicinal Chemistry Letters 17 pp. 4006-4011 (2007).

Jun, H.T., et al., "Top NOTCH Targets: Notch Signaling in Cancer," Drug Development Research, 69, pp. 319-328 (2008).

Meredith, J.E., et al., gamma-Secretase activity is not involved in presenilin-mediated regulation of beta-catenin, Biochemical and Biophysical Research Communications 299 pp. 744-750 (2002).

Shih, L., et al., Notch Signaling, gamma-Secretase Inhibitors, and Cancer Therapy, Cancer Res. 67, pp. 1879-1882 (2007).

Olson, Richard, "Optimizing gamma-secretase Inhibitors for safety and efficacy," 8th International AD/PD Meeting, Mar. 14-18th, 2007, Salzberg, Austria.

PCT/US2013/060799 International Search Report mailed Jan. 29, 2014.

PCT/US2013/060799 Preliminary Report on Patentability issued Mar. 24, 2015.

ALKYL, FLUOROALKYL-1,4-BENZODIAZEPINONE COMPOUNDS

CROSS REFERENCE TO RELATED APPLICATIONS

This application is a national phase application under 35 U.S.C. §371 of International Patent Application No. PCT/US2013/060,799, filed Sep. 20, 2013, which claims priority to U.S. Provisional Application 61/772,583, filed Mar. 5, 2013 and U.S. Provisional Application 61/703,917, filed Sep. 21, 2012, which are expressly incorporated fully herein by reference.

The present invention generally relates to benzodiazepinone compounds useful as Notch inhibitors. The invention further pertains to pharmaceutical compositions comprising at least one compound according to the invention that is useful for the treatment of conditions related to the Notch pathway, such as cancer and other proliferative diseases.

Notch signaling has been implicated in a variety of cellular processes, such as cell fate specification, differentiation, proliferation, apoptosis, and angiogenesis. (Bray, *Nature Reviews Molecular Cell Biology,* 7:678-689 (2006); Fortini, *Developmental Cell* 16:633-647 (2009)). The Notch proteins are single-pass heterodimeric transmembrane molecules. The Notch family includes 4 receptors, NOTCH 1-4, which become activated upon binding to ligands from the DSL family (Delta-like 1, 3, 4 and Jagged 1 and 2).

The activation and maturation of NOTCH requires a series of processing steps, including a proteolytic cleavage step mediated by gamma secretase, a multiprotein complex containing Presenilin 1 or Presenilin 2, nicastrin, APH1, and PEN2. Once NOTCH is cleaved, NOTCH intracellular domain (NICD) is released from the membrane. The released NICD translocates to the nucleus, where it functions as a transcriptional activator in concert with CSL family members (RBPSUH, "suppressor of hairless", and LAG1). NOTCH target genes include HES family members, such as HES-1. HES-1 functions as transcriptional repressors of genes such as HERP1 (also known as HEY2), HERP2 (also known as HEY1), and HATH1 (also known as ATOH1).

The aberrant activation of the Notch pathway contributes to tumorigenesis. Activation of Notch signaling has been implicated in the pathogenesis of various solid tumors including ovarian, pancreatic, as well as breast cancer and hematologic tumors such as leukemias, lymphomas, and multiple myeloma. The role of Notch inhibition and its utility in the treatment of various solid and hematological tumors are described in Miele, L. et al., *Current Cancer Drug Targets,* 6:313-323 (2006); Bolos, V. et al., *Endocrine Reviews,* 28:339-363 (2007); Shih, I-M. et al., *Cancer Research,* 67:1879-1882 (2007); Yamaguchi, N. et al., *Cancer Research,* 68:1881-1888 (2008); Miele, L., *Expert Review Anticancer Therapy,* 8:1197-1201 (2008); Purow, B., *Current Pharmaceutical Biotechnology,* 10:154-160 (2009); Nefedova, Y. et al., *Drug Resistance Updates,* 11:210-218 (2008); Dufraine, J. et al., *Oncogene,* 27:5132-5137 (2008); and Jun, H. T. et al., *Drug Development Research,* 69:319-328 (2008).

There remains a need for compounds that are useful as Notch inhibitors and that have sufficient metabolic stability to provide efficacious levels of drug exposure. Further, there remains a need for compounds useful as Notch inhibitors that can be orally or intravenously administered to a patient.

U.S. Pat. No. 7,053,084 B1 discloses succinoylamino benzodiazepine compounds useful for treating neurological disorders such as Alzheimer's Disease. The reference discloses that these succinoylamino benzodiazepine compounds inhibit gamma secretase activity and the processing of amyloid precursor protein linked to the formation of neurological deposits of amyloid protein.

Applicants have found potent compounds that have activity as Notch inhibitors and have sufficient metabolic stability to provide efficacious levels of drug exposure upon intravenous or oral administration. These compounds are provided to be useful as pharmaceuticals with desirable stability, bioavailability, therapeutic index, and toxicity values that are important to their drugability.

SUMMARY OF THE INVENTION

The present invention fills the foregoing need by providing 1,4-benzodiazepinone compounds that are useful as selective inhibitors of Notch signaling pathway, including prodrugs thereof.

The present invention also provides pharmaceutical compositions comprising a pharmaceutically acceptable carrier; and at least one compound of Formula (I).

The present invention also provides a method of treating a disease or disorder associated with the activity of the Notch receptor, the method comprising administering to a mammalian patient at least one compound of Formula (I).

The present invention also provides processes and intermediates for making the compounds of Formula (I).

The present invention also provides the compounds of Formula (I) for use in therapy.

The present invention also provides the use of the compounds of Formula (I) for the manufacture of a medicament for the treatment of cancer.

The compounds of Formula (I) and compositions comprising the compounds may be used in treating, preventing or curing various Notch receptor-related conditions. Pharmaceutical compositions comprising these compounds are useful in treating, preventing, or slowing the progression of diseases or disorders in a variety of therapeutic areas, such as cancer.

These and other features of the invention will be set forth in expanded form as the disclosure continues.

BRIEF DESCRIPTION OF THE DRAWINGS

The invention is illustrated by reference to the accompanying drawings described below.

DETAILED DESCRIPTION

Figure 1:
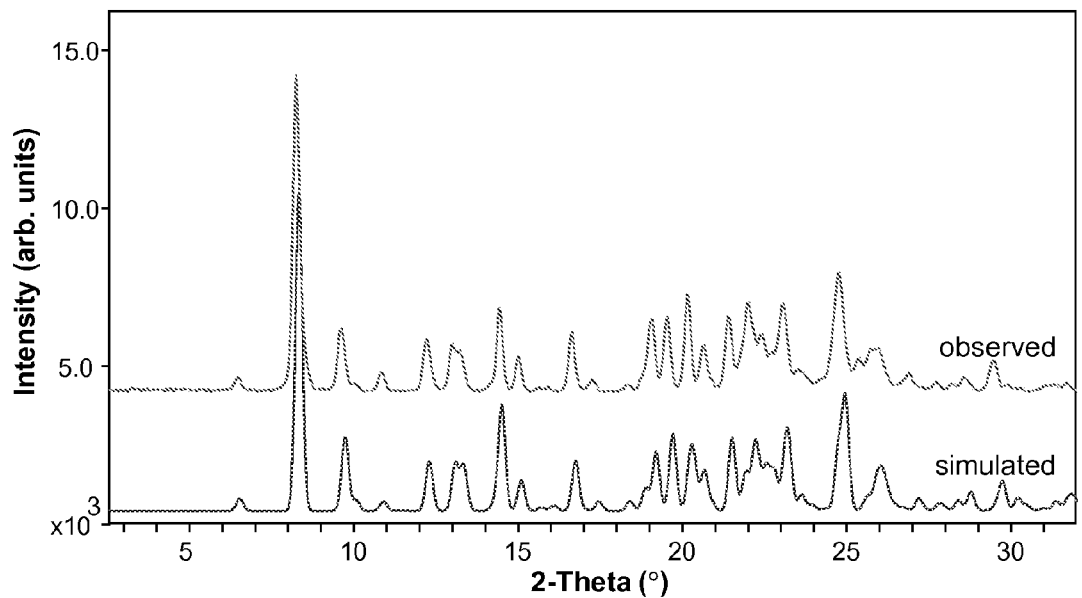
FIG. 1 shows the experimental (at approximately 25° C.) and the simulated (at approximately 25° C.) PXRD patterns (CuKα λ=1.5418 Å) of the M3-1 Form of the compound of Example 1.
Figure 2:
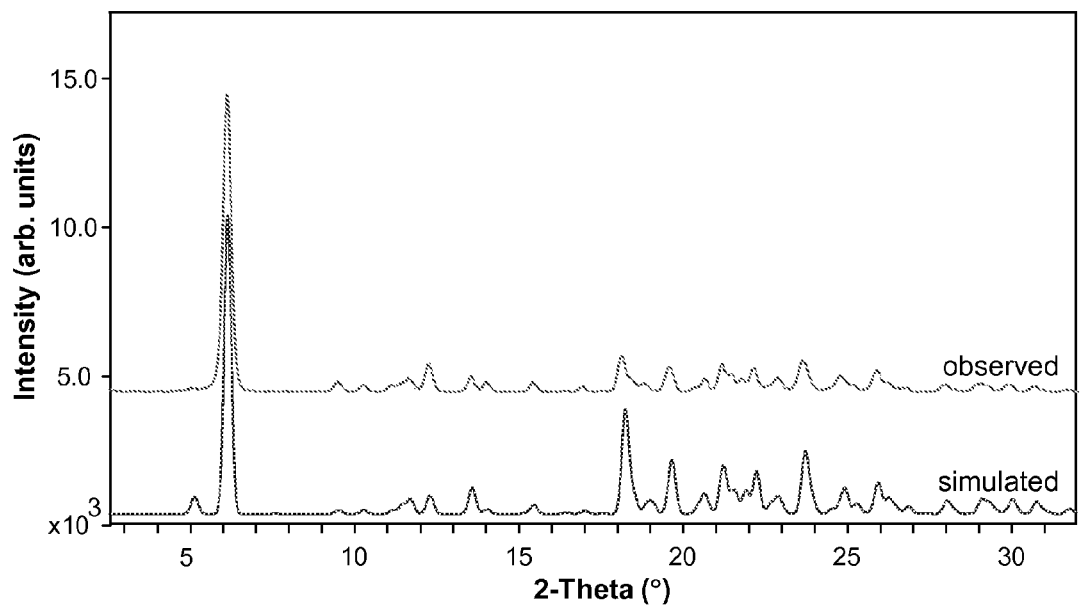
FIG. 2 shows the experimental (at approximately 25° C.) and the simulated (at approximately 25° C.) PXRD patterns (CuKα λ=1.5418 Å) of the CA-2 Form of the compound of Example 1.
Figure 3:
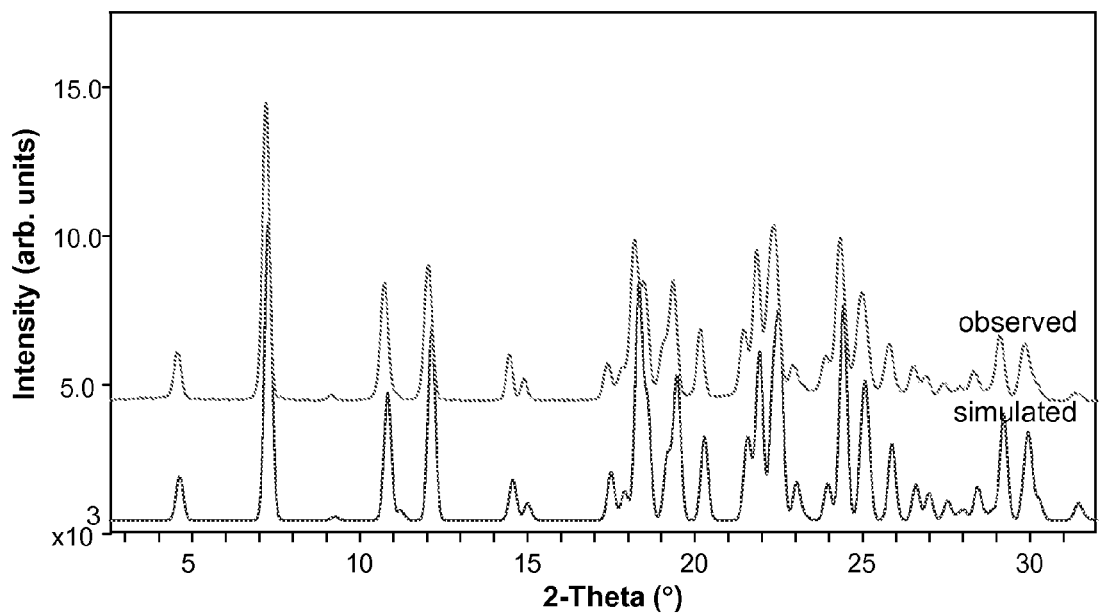
FIG. 3 shows the experimental (at approximately 25° C.) and the simulated (at approximately 25° C.) PXRD patterns (CuKα λ=1.5418 Å) of the SA-3 Form of the compound of Example 1.
Figure 4:
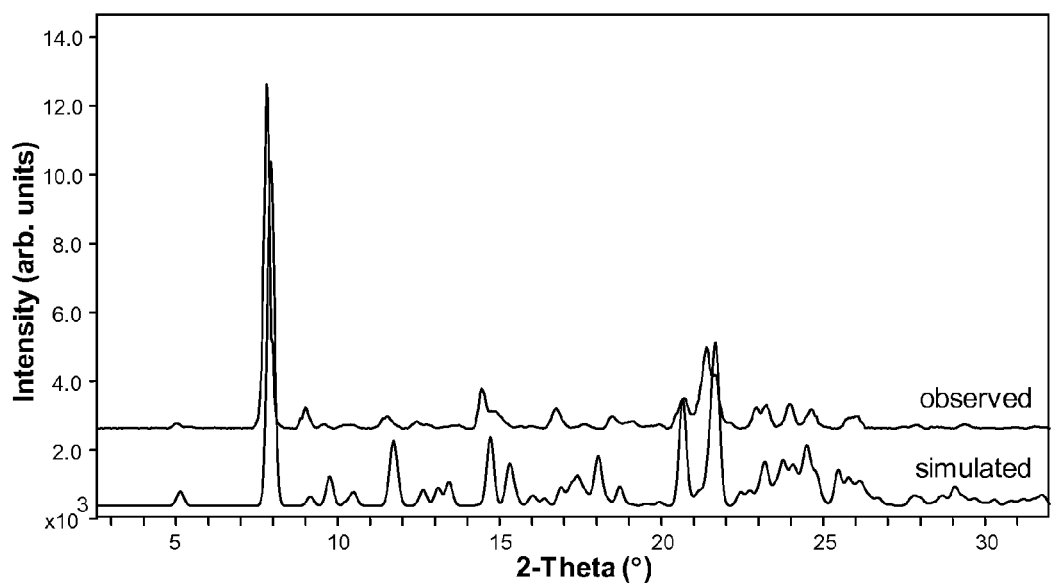
FIG. 4 shows the experimental (at approximately 25° C.) and the simulated (at approximately 25° C.) PXRD patterns (CuKα λ=1.5418 Å) of the E2.5-4 Form of the compound of Example 1.
Figure 5:
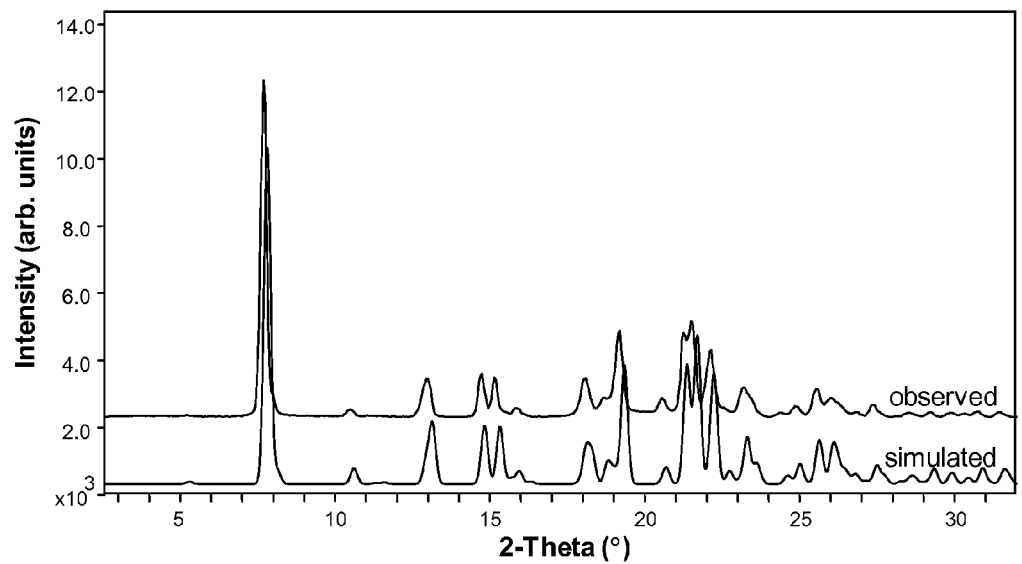
FIG. 5 shows the experimental (at approximately 25° C.) and the simulated (at approximately 25° C.) PXRD patterns (CuKα λ=1.5418 Å) of the IPA2-5 Form of the compound of Example 1.

The first aspect of the present invention provides at least one compound of Formula (I):

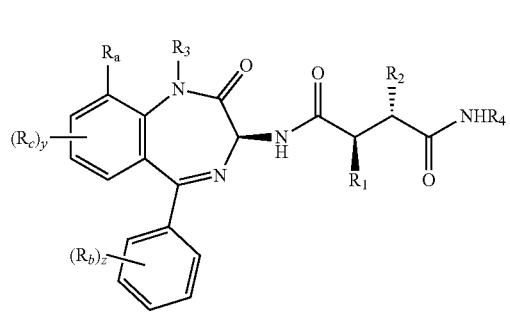

and/or at least one salt thereof, wherein:

$R_1$ is —$CH_2CH_2CF_3$;

$R_2$ is —$CH_2$(cyclopropyl), —$CH(CH_3)$(cyclopropyl), or —$CH_2CH_2CH_3$;

$R_3$ is H, —$CH_3$, or $R_x$;

$R_4$ is H or $R_y$;

$R_x$ is: —$CH_2OP(O)(OH)_2$, —$CH_2OC(O)CH(CH(CH_3)_2)NH_2$,

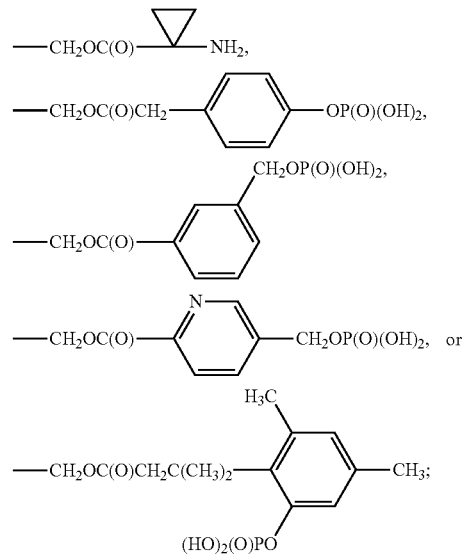

$R_y$ is —$SCH_2CH_2NH_2$, —$SCH_2CH(NH_2)C(O)OH$, —$SCH_2CH(NH_2)C(O)OCH_3$, or

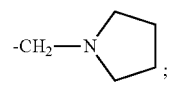

$R_a$ is F, Cl, Br, —CN, —OH, —$CH_3$, —$CH_2OH$, cyclopropyl, —$CF_3$, —$OCH_3$, or —O(cyclopropyl);

each $R_b$ is independently F, Cl, —$CH_3$, —$OCH_3$, and/or —$CF_3$;

$R_c$ is Cl, Br, —$CH_3$, —$OCH_3$, or —O(cyclopropyl);

y is zero or 1; and z is zero, 1, or 2;

provided that if $R_3$ is $R_x$, then $R_4$ is H; and if $R_4$ is $R_y$, then $R_3$ is H or —$CH_3$.

One embodiment provides at least one compound of Formula (I) or at least one salt thereof, wherein $R_3$ is H or —$CH_3$; and $R_1$, $R_2$, $R_4$, $R_a$, $R_b$, $R_c$, y, and z are defined in the first aspect. Included in this embodiment are compounds in which $R_4$ is H.

One embodiment provides at least one compound of Formula (I) wherein $R_3$ is H or —$CH_3$; $R_4$ is H; and $R_1$, $R_2$, $R_a$, $R_b$, $R_c$, y, and z are defined in the first aspect. This embodiment includes the compounds of Formula (II) in which $R_3$ is H and $R_4$ is H:

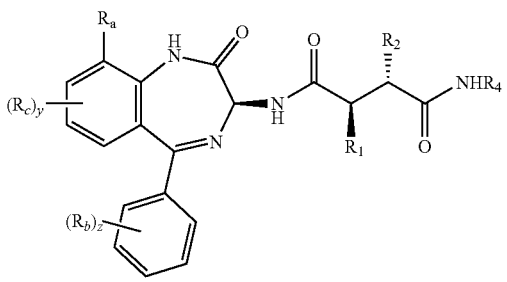

and the compounds of Formula (III) in which R$_3$ is —CH$_3$ and R$_4$ is H:

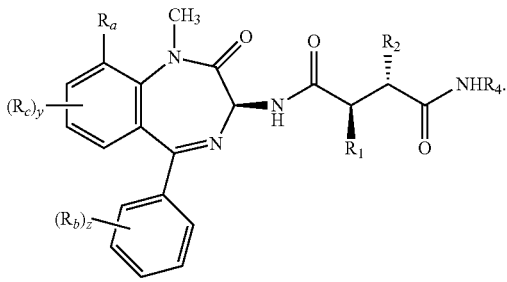

The compounds of Formula (II) and Formula (III) are useful as selective inhibitors of the Notch signaling pathway.

One embodiment provides at least one compound of Formula (I) and/or at least one salt thereof, wherein either (i) R$_3$ is R$_x$ and R$_4$ is H; or (ii) R$_4$ is R$_y$ and R$_3$ is H or —CH$_3$; and R$_1$, R$_2$, R$_a$, R$_b$, R$_c$, R$_x$, R$_y$, y, and z are defined in the first aspect. This embodiment includes the compounds of Formula (IV) in which R$_3$ is R$_x$ and R$_4$ is H:

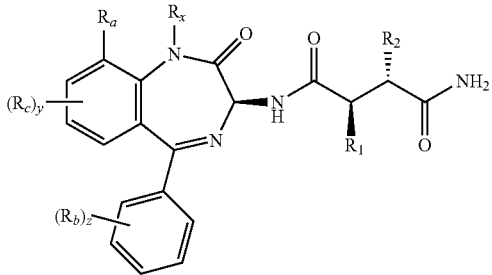

and the compounds of Formula (V) in which R$_4$ is R$_y$ and R$_3$ is H or —CH$_3$:

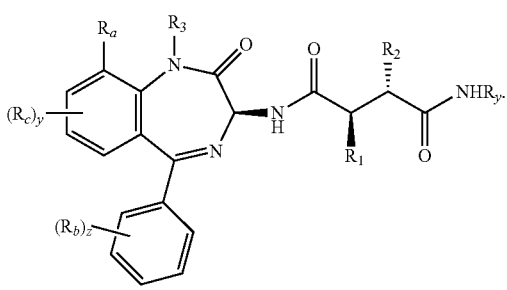

The compounds of this embodiment are useful as prodrugs of the compounds of Formula (II) and Formula (III).

One embodiment provides at least one compound of Formula (IV) and/or at least one salt thereof, wherein R$_3$ is R$_x$ and R$_4$ is H; and R$_1$, R$_2$, R$_x$, R$_a$, R$_b$, R$_c$, y, and z are defined in the first aspect. Included in this embodiment are compounds in which y is zero. The compounds of this embodiment are useful as prodrugs of the compounds of Formula (II) and Formula (III).

One embodiment provides at least one compound of Formula (V) and/or at least one salt thereof, wherein R$_4$ is R$_y$ and R$_3$ is H or —CH$_3$; and R$_1$, R$_2$, R$_y$, R$_a$, R$_b$, R$_c$, y, and z are defined in the first aspect. Included in this embodiment are compounds in which R$_3$ is H and y is zero. Also included in this embodiment are compounds in which R$_3$ is —CH$_3$ and y is zero. The compounds of this embodiment are useful as prodrugs of the compounds of Formula (II) and Formula (III).

One embodiment provides at least one compound of Formula (I) and/or at least one salt thereof, wherein z is zero or 1; and R$_1$, R$_2$, R$_3$, R$_4$, R$_x$, R$_y$, R$_a$, R$_b$, R$_c$, and y are defined in the first aspect. Included in this embodiment are compounds in which R$_3$ is H or —CH$_3$; and R$_4$ is H. Also included in this embodiment are compounds in which R$_3$ is H or —CH$_3$.

One embodiment provides at least one compound of Formula (I) and/or at least one salt thereof, wherein R$_1$ is —CH$_2$CH$_2$CF$_3$ and R$_1$, R$_3$, R$_4$, R$_x$, R$_y$, R$_a$, R$_b$, R$_c$, y, and z are defined in the first aspect. Included in this embodiment are compounds in which y is zero. Also included in this embodiment are compounds in which R$_3$ is H or —CH$_3$.

One embodiment provides at least one compound of Formula (I) and/or at least one salt thereof, wherein R$_1$ is —CH$_2$CH$_2$CF$_3$ and R$_2$ is —CH$_2$(cyclopropyl) or —CH(CH$_3$)(cyclopropyl); and R$_3$, R$_4$, A, R$_x$, R$_y$, R$_a$, R$_b$, R$_c$, y, and z are defined in the first aspect. Included in this embodiment are compounds in which y is zero. Also included in this embodiment are compounds in which R$_3$ is H or —CH$_3$.

One embodiment provides at least one compound of Formula (I) and/or at least one salt thereof, wherein R$_1$ is —CH$_2$CH$_2$CF$_3$ and R$_2$ is —CH$_2$(cyclopropyl); and R$_3$, R$_4$, R$_x$, R$_y$, R$_a$, R$_b$, R$_c$, y, and z are defined in the first aspect. Included in this embodiment are compounds in which y is zero. Also included in this embodiment are compounds in which R$_3$ is H or —CH$_3$.

One embodiment provides at least one compound of Formula (I) and/or at least one salt thereof, wherein R$_1$ is —CH$_2$CH$_2$CF$_3$ and R$_2$ is —CH(CH$_3$)(cyclopropyl); and R$_3$, R$_4$, R$_x$, R$_y$, R$_a$, R$_b$, R$_c$, y, and z are defined in the first aspect. Included in this embodiment are compounds in which y is zero. Also included in this embodiment are compounds in which R$_3$ is H or —CH$_3$.

One embodiment provides at least one compound of Formula (I) and/or at least one salt thereof, wherein R$_1$ is —CH$_2$CH$_2$CF$_3$ and R$_2$ is —CH$_2$CH$_2$CH$_3$; and R$_3$, R$_4$, R$_x$, R$_y$, R$_a$, R$_b$, R$_c$, y, and z are defined in the first aspect. Included in this embodiment are compounds in which y is zero. Also included in this embodiment are compounds in which R$_3$ is H or —CH$_3$.

One embodiment provides at least one compound of Formula (I) and/or at least one salt thereof, wherein y is 0, z is 0, and R$_1$, R$_2$, R$_3$, R$_4$, R$_x$, and R$_y$ are defined in the first aspect. Included in the embodiment are compounds in which R$_3$ is H or —CH$_3$.

One embodiment provides at least one compound of Formula (I) and/or at least one salt thereof, wherein y is 1, z is 1, and R$_1$, R$_2$, R$_3$, R$_4$, R$_x$, R$_y$ R$_a$, R$_b$, and R$_c$ are defined in the first aspect. Included in the embodiment are compounds in which R$_3$ is H or —CH$_3$.

One embodiment provides at least one compound of Formula (I) and/or at least salt thereof, having the structure:

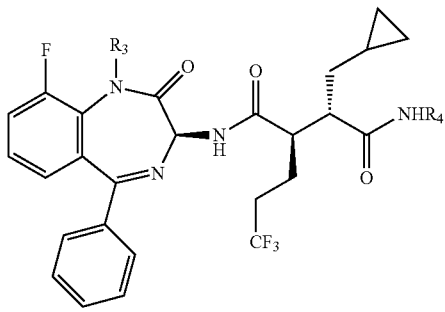

wherein $R_3$ and $R_4$ are defined in the first aspect. Included in this embodiment are compounds in which $R_4$ is H; $R_3$ is $R_x$; and $R_x$ is: —CH$_2$OP(O)(OH)$_2$, —CH$_2$OC(O)CH(CH(CH$_3$)$_2$)NH$_2$,

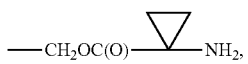

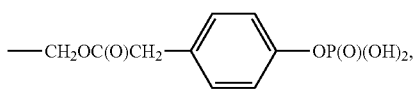

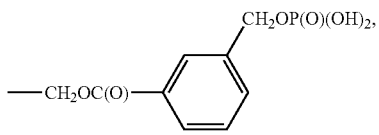

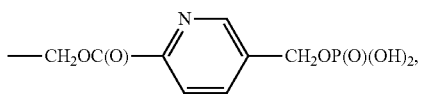 or

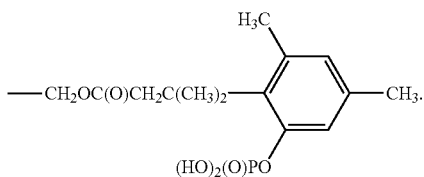

Also included in this embodiment are compounds in which $R_3$ is H; $R_4$ is $R_y$; and $R_y$ is —SCH$_2$CH$_2$NH$_2$, —SCH$_2$CH(NH$_2$)C(O)OH, —SCH$_2$CH(NH$_2$)C(O)OCH$_3$, or

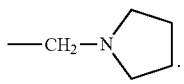.

One embodiment provides at least one compound of Formula (I) and/or at least salt thereof, having the structure:

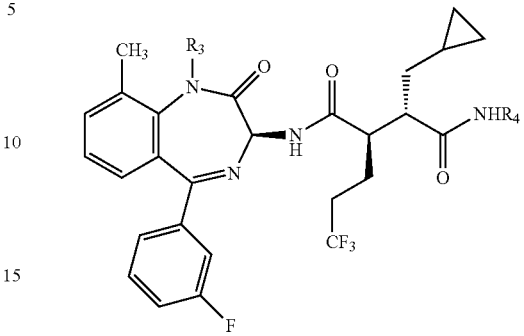

wherein $R_3$ is H or $R_x$; and $R_4$ is H or $R_y$; provided that if $R_3$ is $R_x$, then $R_4$ is H; and if $R_4$ is $R_y$, then $R_3$ is H. Included in this embodiment are compounds in which $R_4$ is H; $R_3$ is $R_x$; and $R_x$ is: —CH$_2$OP(O)(OH)$_2$, —CH$_2$OC(O)CH(CH(CH$_3$)$_2$)NH$_2$,

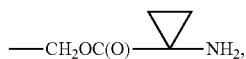

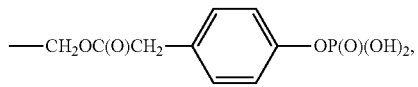

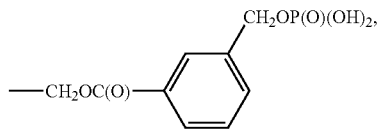

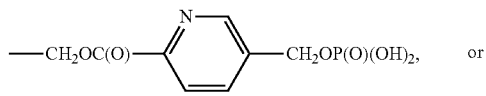

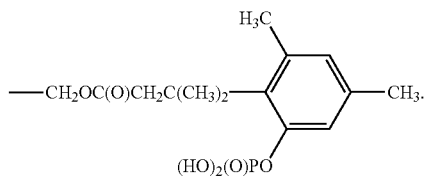

Also included in this embodiment are compounds in which $R_3$ is H; $R_4$ is $R_y$; and $R_y$ is —SCH$_2$CH$_2$NH$_2$, —SCH$_2$CH(NH$_2$)C(O)OH, —SCH$_2$CH(NH$_2$)C(O)OCH$_3$, or

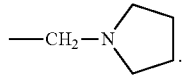.

One embodiment provides a composition comprising: (i) at least one compound of Formula (I) having the structure:

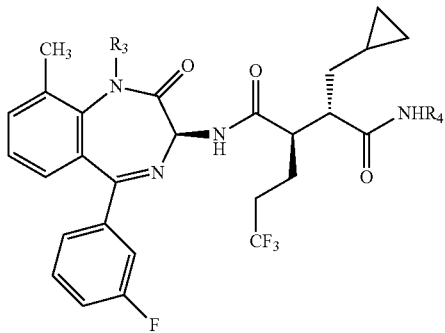

and/or salt thereof; (ii) a compound of Formula (I) having the structure:

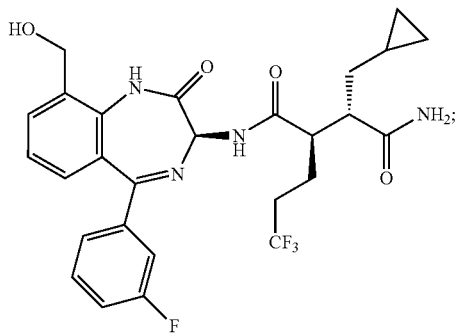 [SMILES: NC(=O)[C@@H](CC1CC1)[C@@H](CCC(F)(F)F)C(=O)N[C@H]1N=C(c2cccc(F)c2)c2cccc(CO)c2NC1=O]

or a mixture of (i) and (ii); wherein $R_3$ is H or $R_x$; $R_4$ is H or $R_y$; provided that if $R_3$ is $R_x$ then $R_4$ is H; and provided that if $R_4$ is $R_y$ then $R_3$ is H; and wherein $R_x$ and $R_y$ are defined in the first aspect.

One embodiment provides a compound of Formula (I) wherein $R_1$ is —$CH_2CH_2CF_3$; $R_2$ is —$CH_2$(cyclopropyl); $R_3$ is H or $R_x$; $R_4$ is H or $R_y$; $R_a$ is F, —$CH_3$, or —$CH_2OH$; $R_b$ is F; y is zero; and z is zero or 1; and $R_x$ and $R_y$ are defined in the first aspect. Included in embodiment are compounds in which $R_3$ is H and $R_4$ is H.

One embodiment provides a compound of Formula (I) wherein $R_3$ is H; and $R_1$, $R_2$, $R_4$, $R_a$, $R_b$, $R_c$, y, and z are defined in the first aspect. Included in this embodiment are compounds in which $R_3$ is deuterium (D) or tritium (T). Also included in this embodiment are compounds in which $R_2$ is —$CH_2CH_2CF_3$.

One embodiment provides a compound of Formula (I) wherein $R_3$ is —$CH_3$; and $R_1$, $R_2$, $R_4$, $R_a$, $R_b$, $R_c$, y, and z are defined in the first aspect. $R_3$ includes methyl groups in which one or more hydrogen atoms are isotopically substituted with deuterium (D) and/or tritium (T). In one example of this embodiment, $R_3$ is —$CD_3$. Also included in this embodiment are compounds in which $R_2$ is —$CH_2CH_2CF_3$.

One embodiment provides a compound of Formula (I) selected from: (2R,3S)-3-(Cyclopropylmethyl)-N-((3S)-9-fluoro-2-oxo-5-phenyl-2,3-dihydro-1H-1,4-benzodiazepin-3-yl)-2-(3,3,3-trifluoropropyl)succinamide (1); (2R,3S)-3-(cyclopropylmethyl)-N-((3S)-9-methoxy-2-oxo-5-(3-(trifluoromethyl)phenyl)-2,3-dihydro-1H-1,4-benzodiazepin-3-yl)-2-(3,3,3-trifluoropropyl)succinamide (2); (2R,3S)—N-((3S)-9-chloro-5-(3-fluoro-5-methylphenyl)-2-oxo-2,3-dihydro-1H-benzo[e][1,4]diazepin-3-yl)-3-(cyclopropylmethyl)-2-(3,3,3-trifluoropropyl)succinamide (3); (2R,3S)-3-(cyclopropylmethyl)-N-((3S)-5-(3-fluorophenyl)-9-methoxy-2-oxo-2,3-dihydro-1H-1,4-benzodiazepin-3-yl)-2-(3,3,3-trifluoropropyl)succinamide (4); (2R,3S)-3-(cyclopropylmethyl)-N-((3S)-9-(cyclopropyloxy)-5-(3-fluorophenyl)-2-oxo-2,3-dihydro-1H-1,4-benzodiazepin-3-yl)-2-(3,3,3-trifluoropropyl)succinamide (5); (2R,3S)-3-(cyclopropylmethyl)-N-((3S)-9-(cyclopyloxy)-2-oxo-5-phenyl-2,3-dihydro-1H-1,4-benzodiazepin-3-yl)-2-(3,3,3-trifluoropropyl)succinamide (6); (2R,3S)—N-((3S)-5-(4-chlorophenyl)-9-cyclopropyl-2-oxo-2,3-dihydro-1H-1,4-benzodiazepin-3-yl)-3-(cyclopropylmethyl)-2-(3,3,3-trifluoropropyl)succinamide (7); (2R,3S)-3-(cyclopropylmethyl)-N-((3S)-9-hydroxy-5-(3-methylphenyl)-2-oxo-2,3-dihydro-1H-1,4-benzodiazepin-3-yl)-2-(3,3,3-trifluoropropyl)succinamide (8); (2R,3S)-3-(cyclopropylmethyl)-N-((3S)-9-methyl-2-oxo-5-(3-(trifluoromethyl)phenyl)-2,3-dihydro-1H-1,4-benzodiazepin-3-yl)-2-(3,3,3-trifluoropropyl)succinamide (9); (2R,3S)-3-(cyclopropylmethyl)-N-((3S)-5-(3-fluorophenyl)-9-methyl-2-oxo-2,3-dihydro-1H-1,4-benzodiazepin-3-yl)-2-(3,3,3-trifluoropropyl)succinamide (10); (2R,3S)-3-(cyclopropylmethyl)-N-((3S)-9-methyl-2-oxo-5-phenyl-2,3-dihydro-1H-1,4-benzodiazepin-3-yl)-2-(3,3,3-trifluoropropyl)succinamide (11); (2R,3S)-3-(cyclopropylmethyl)-N-((3S)-5-(4-fluorophenyl)-9-methyl-2-oxo-2,3-dihydro-1H-1,4-benzodiazepin-3-yl)-2-(3,3,3-trifluoropropyl)succinamide (12); (2R,3S)—N-((3S)-9-chloro-5-(2-methylphenyl)-2-oxo-2,3-dihydro-1H-1,4-benzo diazepin-3-yl)-3-(cyclopropylmethyl)-2-(3,3,3-trifluoropropyl)succinamide (13); (2R,3S)-3-(cyclopropylmethyl)-N-(9-cyclopropyl-2-oxo-5-phenyl-2,3-dihydro-1H-1,4-benzodiazepin-3-yl)-2-(3,3,3-trifluoropropyl)succinamide (14); (2R,3S)—N-((3S)-9-methyl-2-oxo-5-phenyl-2,3-dihydro-1H-1,4-benzodiazepin-3-yl)-3-propyl-2-(3,3,3-trifluoropropyl)succinamide (15); (2R,3S)-3-(cyclopropylmethyl)-N-((3S)-9-fluoro-5-(4-methylphenyl)-2-oxo-2,3-dihydro-1H-1,4-benzodiazepin-3-yl)-2-(3,3,3-trifluoropropyl)succinamide (16); (2R,3S)-3-(cyclopropylmethyl)-N-((3S)-9-fluoro-7-methyl-2-oxo-5-phenyl-2,3-dihydro-1H-1,4-benzodiazepin-3-yl)-2-(3,3,3-trifluoropropyl)succinamide (17); (2R,3S)-3-(cyclopropylmethyl)-N-((3S)-9-fluoro-8-methyl-2-oxo-5-phenyl-2,3-dihydro-1H-1,4-benzodiazepin-3-yl)-2-(3,3,3-trifluoropropyl)succinamide (18); (2R,3S)-3-(cyclopropylmethyl)-N-((3S)-9-fluoro-5-(3-methylphenyl)-2-oxo-2,3-dihydro-1H-1,4-benzodiazepin-3-yl)-2-(3,3,3-trifluoropropyl)succinamide (19); (2R,3S)-3-(cyclopropylmethyl)-N-((3S)-9-fluoro-1-methyl-2-oxo-5-phenyl-2,3-dihydro-1H-1,4-benzodiazepin-3-yl)-2-(3,3,3-trifluoropropyl)succinamide (20); (2R,3S)—N-((3S)-5-(4-Chlorophenyl)-9-methoxy-2-oxo-2,3-dihydro-1H-1,4-benzodiazepin-3-yl)-3-(cyclopropylmethyl)-2-(3,3,3-trifluoropropyl)succinamide (21); (2R,3S)-3-(cyclopropylmethyl)-N-((3S)-9-fluoro-5-(3-methoxyphenyl)-2-oxo-2,3-dihydro-1H-1,4-benzodiazepin-3-yl)-2-(3,3,3-trifluoropropyl)succinamide (22); (2R,3S)-3-(cyclopropylmethyl)-N-((3S)-9-fluoro-5-(3-fluorophenyl)-2-oxo-2,3-dihydro-1H-1,4-benzodiazepin-3-yl)-2-(3,3,3-trifluoropropyl)succinamide (23); (2R,3S)—N-((3S)-5-(3-chlorophenyl)-9-fluoro-2-oxo-2,3-dihydro-1H-1,4-benzodiazepin-3-yl)-3-(cyclopropylmethyl)-2-(3,3,3-trifluoropropyl)succinamide (24); (2R,3S)—N-((3S)-5-(4-chlorophenyl)-9-methoxy-2-oxo-2,3-dihydro-1H-1,4-benzodiazepin-3-yl)-2-(3,3,3-trifluoropropyl)-3-propyl)succinamide (25); (2R,3S)—N-((3S)-9-chloro-5-(3- chlorophenyl)-2-oxo-2,3-dihydro-1H-benzo[e][1,4]diazepin-3-yl)-3-(cyclopropylmethyl)-2-(3,3,3-trifluoropropyl)succinamide (26); (2R,3S)—N-((3S)-9-chloro-5-(4-chlorophenyl)-2-oxo-2,3-dihydro-1H-1,4-benzodiazepin-3-yl)-3-(cyclopropylmethyl)-2-(3,3,3-trifluoropropyl)succinamide (27); (2R,3S)—N-((3S)-9-chloro-5-(4-chlorophenyl)-2-oxo-2,3-dihydro-1H-1,4-benzodiazepin-3-yl)-3-propyl-2-(3,3,3-trifluoropropyl)succinamide (28); (2R,3S)-3-(cyclopropylmethyl)-N-((3S)-9-fluoro-8-methoxy-2-oxo-5-phenyl-2,3-dihydro-1H-1,4-benzodiazepin-3-yl)-2-(3,3,3-trifluoropropyl)succinamide (29); (2R,3S)—N-((3S)-9-chloro-5-(3-methylphenyl)-2-oxo-2,3-dihydro-1H-1,4-benzodiazepin-3-yl)-3-(cyclopropylmethyl)-2-(3,3,3-trifluoropropyl)succinamide (30); (2R,3S)-3-(cyclopropylmethyl)-N-((3S)-9-methoxy-5-(3-methylphenyl)-2-oxo-2,3-dihydro-1H-1,4-benzodiazepin-3-yl)-2-(3,3,3-trifluoropropyl)succinamide (31); (2R,3S)—N-((3S)-9-cyano-2-oxo-5-phenyl-2,3-dihydro-1H-1,4-benzodiazepin-3-yl)-3-propyl-2-(3,3,3-trifluoropropyl)succinamide (32); (2R,3S)—N-((3S)-9-methoxy-2-oxo-5-phenyl-2,3-dihydro-1H-1,4-benzodiazepin-3-yl)-3-((1-methylcyclopropyl)methyl)-2-(3,3,3-trifluoropropyl)succinamide (33); (2R,3S)-3-(cyclopropylmethyl)-N-((3S)-8,9-dichloro-2-oxo-5-phenyl-2,3-dihydro-1H-1,4-benzodiazepin-3-yl)-2-(3,3,3-trifluoropropyl)succinamide (34); (2R,3S)—N-((3S)-2-oxo-5-phenyl-9-(trifluoromethyl)-2,3-dihydro-1H-1,4-benzodiazepin-3-yl)-3-propyl-2-(3,3,3-trifluoropropyl)succinamide (35); (2R,3S)-3-(cyclopropylmethyl)-N-((3S)-2-oxo-5-phenyl-9-(trifluoromethyl)-2,3-dihydro-1H-1,4-benzodiazepin-3-yl)-2-(3,3,3-trifluoropropyl)succinamide (36); (2R,3S)—N-((3S)-9-fluoro-2-oxo-5-phenyl-2,3-dihydro-1H-1,4-benzodiazepin-3-yl)-3-propyl-2-(3,3,3-trifluoropropyl)succinamide (37); (2R,3S)-3-(cyclopropylmethyl)-N-((3S)-9-methoxy-2-oxo-5-phenyl-2,3-dihydro-1H-1,4-benzodiazepin-3-yl)-2-(3,3,3-trifluoropropyl)succinamide (38); (2R,3S)—N-((3S)-8-bromo-9-methoxy-2-oxo-5-phenyl-2,3-dihydro-1H-1,4-benzodiazepin-3-yl)-3-propyl-2-(3,3,3-trifluoropropyl)succinamide (39); (2R,3S)—N-((3S)-9-methoxy-2-oxo-5-phenyl-2,3-dihydro-1H-1,4-benzodiazepin-3-yl)-3-propyl-2-(3,3,3-trifluoropropyl)succinamide (40); (2R,3S)—N-((3S)-9-hydroxy-2-oxo-5-phenyl-2,3-dihydro-1H-1,4-benzodiazepin-3-yl)-3-propyl-2-(3,3,3-trifluoropropyl)succinamide (41); (2R,3S)—N-((3S)-9-chloro-2-oxo-5-phenyl-2,3-dihydro-1H-1,4-benzodiazepin-3-yl)-3-(cyclopropylmethyl)-2-(3,3,3-trifluoropropyl)succinamide (42); (2R,3S)—N-((3S)-9-chloro-2-oxo-5-phenyl-2,3-dihydro-1H-1,4-benzodiazepin-3-yl)-3-propyl-2-(3,3,3-trifluoropropyl)succinamide (43); ((3S)-3-(((2R)-2-((1S)-2-amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl (4-(phosphonooxy)phenyl)acetate (44); ((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl dihydrogen phosphate (45); ((3S)-3-(((2R)-2-((1S)-1-amino-3-cyclopropyl-1-oxopropan-2-yl)-5,5,5-trifluoropentanoyl)amino)-9-fluoro-2-oxo-5-phenyl-2,3-dihydro-1H-1,4-benzodiazepin-1-yl)methyl 3-((phosphonooxy)methyl)benzoate (46); ((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl 5-((phosphonooxy)methyl)-2-pyridinecarboxylate (47); ((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H- 1,4-benzodiazepin-1-yl)methyl 3-(2,4-dimethyl-6-(phosphonooxy)phenyl)-3-methylbutanoate (48); S-4(2S,3R)-2-(Cyclopropylmethyl)-6,6,6-trifluoro-3-(((3S)-9-fluoro-2-oxo-5-phenyl-2,3-dihydro-1H-1,4-benzodiazepin-3-yl)carbamoyl)hexanoyl)amino)-L-cysteine.TFA (49); (2S,3R)—N1-((2-Aminoethyl)sulfanyl)-2-(cyclopropylmethyl)-N4-((3S)-9-fluoro-2-oxo-5-phenyl-2,3-dihydro-1H-1,4-benzodiazepin-3-yl)-3-(3,3,3-trifluoropropyl)succinamide.TFA (50); Methyl S-(((2S,3R)-2-(cyclopropylmethyl)-6,6,6-trifluoro-3-(((3S)-9-fluoro-2-oxo-5-phenyl-2,3-dihydro-1H-1,4-benzodiazepin-3-yl)carbamoyl)hexanoyl)amino)-L-cysteinate.TFA (51); ((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl L-valinate (52); ((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl 1-aminocyclopropanecarboxylate (53); (2S,3R)-2-(Cyclopropylmethyl)-$N^4$-((3S)-9-fluoro-2-oxo-5-phenyl-2,3-dihydro-1H-1,4-benzodiazepin-3-yl)-$N^1$-(1-pyrrolidinylmethyl)-3-(3,3,3-trifluoropropyl)succinamide (54); ((3S)-3-(((2R)-2-((1S)-2-amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl 4-((phosphonooxy)methyl)benzoate (55); and salts thereof.

One embodiment provides a compound of Formula (I) selected from: (2R,3S)-3-(cyclopropylmethyl)-N-((3S)-9-fluoro-2-oxo-5-phenyl-2,3-dihydro-1H-1,4-benzodiazepin-3-yl)-2-(3,3,3-trifluoropropyl)succinamide (1); ((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl (4-(phosphonooxy)phenyl)acetate (44); ((3S)-3-(((2R)-2-((1S)-2-amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl dihydrogen phosphate (45); ((3S)-3-(((2R)-2-((1S)-1-amino-3-cyclopropyl-1-oxopropan-2-yl)-5,5,5-trifluoropentanoyl)amino)-9-fluoro-2-oxo-5-phenyl-2,3-dihydro-1H-1,4-benzodiazepin-1-yl)methyl 3-((phosphonooxy)methyl)benzoate (46); ((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl 5-((phosphonooxy)methyl)-2-pyridinecarboxylate (47); ((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl 3-(2,4-dimethyl-6-(phosphonooxy)phenyl)-3-methylbutanoate (48); S-(((2S,3R)-2-(cyclopropylmethyl)-6,6,6-trifluoro-3-(((3S)-9-fluoro-2-oxo-5-phenyl-2,3-dihydro-1H-1,4-benzodiazepin-3-yl)carbamoyl)hexanoyl)amino)-L-cysteine.TFA (49); (2S,3R)—N1-((2-aminoethyl)sulfanyl)-2-(cyclopropylmethyl)-N4-((3S)-9-fluoro-2-oxo-5-phenyl-2,3-dihydro-1H-1,4-benzodiazepin-3-yl)-3-(3,3,3-trifluoropropyl)succinamide.TFA (50); Methyl S-(((2S,3R)-2-(cyclopropylmethyl)-6,6,6-trifluoro-3-(((3S)-9-fluoro-2-oxo-5-phenyl-2,3-dihydro-1H-1,4-benzodiazepin-3-yl)carbamoyl)hexanoyl)amino)-L-cysteinate.TFA (51); ((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl L-valinate (52); ((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl 1-aminocyclopropanecarboxylate (53); (2S,3R)-2-(Cyclopropylmethyl)-$N^4$-((3S)-9-fluoro-2- oxo-5-phenyl-2,3-dihydro-1H-1,4-benzodiazepin-3-yl)-N$^1$-(1-pyrrolidinylmethyl)-3-(3,3,3-trifluoropropyl)succinamide (54); and ((3S)-3-(((2R)-2-((1S)-2-amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl 4-((phosphonooxy)methyl)benzoate (55); and salts thereof.

One embodiment provides at least one compound of Formula (I) in which $R_3$ is H or —$CH_3$; and $R_4$ is H; wherein the compound of Formula (I) has a metabolic half life value of at least 45 minutes as measured in the human metabolic stability half-life assay described herein.

One embodiment provides at least one compound of Formula (I) in which $R_3$ is H or —$CH_3$; and $R_4$ is H; wherein the compound of Formula (I) has a metabolic half life value of at least 60 minutes as measured in the human metabolic stability half-life assay described herein.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe addition more embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

The terms "halo" and "halogen", as used herein, refer to F, Cl, Br, or I.

The term "alkyl" as used herein, refers to both branched and straight chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salts formed with inorganic and/or organic acids and bases. In addition, the term "salt(s)" may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

The compound of Formula (I) and/or a salt thereof is intended to include solvates of compounds of Formula (I) and solvates of salts of the compounds of Formula (I).

Any compound that can be converted in vivo to provide the bioactive agent (i.e., the compound of Formula (I)) is a prodrug within the scope and spirit of the invention. The compounds of Formula (I) in which either $R_3$ is $R_x$ or $R_4$ is $R_y$, are useful as prodrugs of the compounds of Formula (I) in which $R_3$ is H or —$CH_3$ and $R_4$ is H.

Various forms of prodrugs are well known in the art and are described in:

a) Wermuth, C. G. et al., *The Practice of Medicinal Chemistry*, Chapter 31, Academic Press (1996);

b) Bundgaard, H. ed., *Design of Prodrugs*, Elsevier (1985);

c) Bundgaard, H., Chapter 5, "Design and Application of Prodrugs", Krogsgaard-Larsen, P. et al., eds., *A Textbook of Drug Design and Development*, pp. 113-191, Harwood Academic Publishers (1991); and d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to a NOTCH receptor, or effective to treat or prevent proliferative diseases such as cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Crystal Forms of the Compound of Example 1

In one embodiment, the compound of Example 1

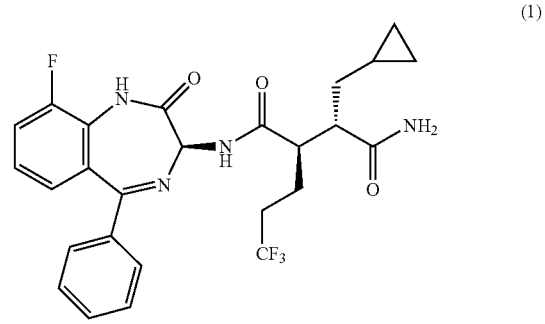 [SMILES: NC(=O)[C@@H](CC1CC1)[C@@H](CCC(F)(F)F)C(=O)N[C@H]1N=C(c2ccccc2)c2cccc(F)c2NC1=O]

(1)

is provided as a crystalline material comprising one or more crystalline forms. Examples of suitable crystalline forms of the compound of Example 1 include Forms M3-1, CA-2, SA-3, E2.5-4, and IPA2-5.

In one embodiment, the compound of Example 1 is provided as a crystalline material comprising the first crystalline form of Example 1. A first crystalline form of the compound of Example 1 comprises a crystalline form referred to herein as "Form M3-1" or "M3-1 Form". The M3-1 Form comprises about three methanol molecules for each molecule of Example 1.

In one embodiment, the M3-1 Form of the compound of Example 1 is characterized by unit cell parameters approximately equal to the following:

Unit Cell dimensions:
a=8.50 Å
b=17.55 Å
c=21.22 Å
α=90.0°
β=90.0°
γ=90.0°
Space group: P2(1)2(1)2(1)
Molecules of Example 1/asymmetric unit: 1
Volume=3166 Å$^3$
Density (calculated)=1.289 Mg/m$^3$, wherein the unit cell parameters of Form M3-1 are measured at a temperature of about −70° C.

Figure 6:
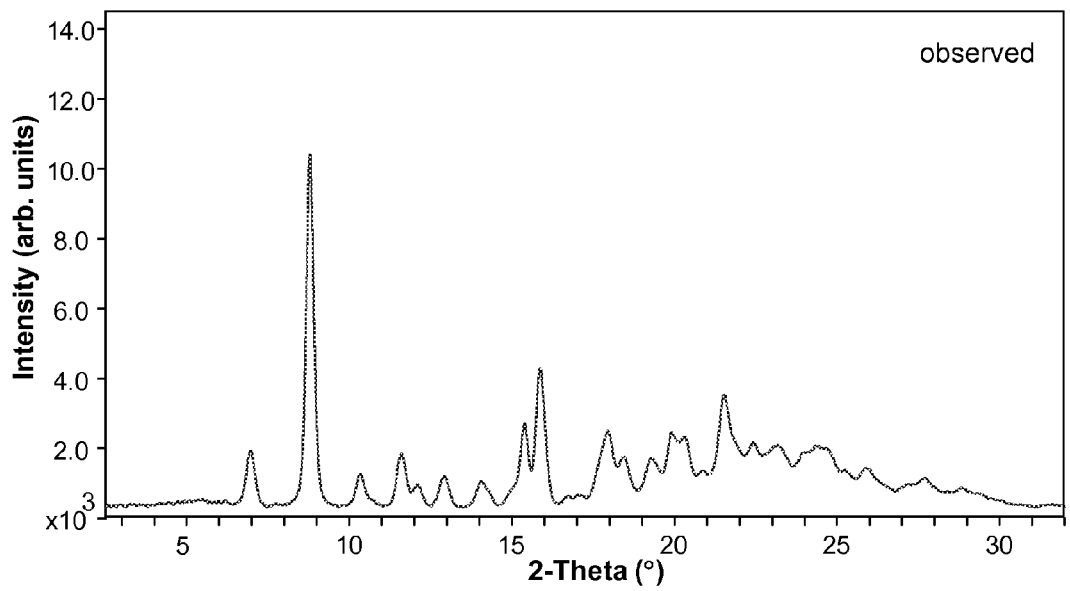
FIG. 6 shows the experimental (at approximately 25° C.) PXRD pattern (CuKα λ=1.5418 Å) of the P-1 Form of the compound of Example 1.

In another embodiment, the M3-1 Form of the compound of Example 1 is characterized by a simulated powder x-ray diffraction (PXRD) pattern substantially in accordance with the pattern shown in FIG. 6 and/or by an observed PXRD pattern substantially in accordance with the pattern shown in FIG. 6.

In yet another embodiment, the M3-1 Form of the compound of Example 1 is characterized by a PXRD pattern (CuKα λ=1.5418 Å at a temperature of about 25° C.) comprising four or more, preferably five or more, 2θ values selected from: 8.2±0.2; 9.6±0.2; 12.2±0.2; 14.4±0.2; 16.6±0.2; 19.1±0.2; 19.5±0.2, 20.2±0.2; 20.6±0.2; 21.4±0.2; 23.0±0.2; and 24.8±0.2, wherein the PXRD pattern of Form M3-1 is measured at a temperature of about 25° C.

In yet an even further embodiment, the M3-1 Form of Example 1 is characterized by fractional atomic coordinates substantially as listed in Table 1.

TABLE 1

Fractional Atomic Coordinates of Form M3-1 of Example 1 Calculated at a Temperature of about 25° C.; Atomic Coordinates (×$10^4$) and Equivalent Isotropic Displacement Parameters (Å$^2$ × $10^3$)

|       | x         | y        | z         | U(eq)* |
|-------|-----------|----------|-----------|--------|
| C(1)  | 4090(3)   | 11755(2) | 10464(2)  | 45(1)  |
| C(2)  | 4576(4)   | 11895(2) | 9843(2)   | 50(1)  |
| C(3)  | 4846(4)   | 12655(2) | 9650(2)   | 65(1)  |
| C(4)  | 4629(5)   | 13238(2) | 10056(3)  | 81(2)  |
| C(5)  | 4109(5)   | 13117(2) | 10668(3)  | 80(2)  |
| C(6)  | 3861(4)   | 12376(2) | 10851(2)  | 58(1)  |
| C(7)  | 4758(3)   | 11267(2) | 9386(2)   | 42(1)  |
| C(8)  | 4143(4)   | 11357(2) | 8731(2)   | 53(1)  |
| C(9)  | 4706(5)   | 10896(3) | 8248(2)   | 71(1)  |
| C(10) | 4079(7)   | 10926(3) | 7658(2)   | 94(2)  |
| C(11) | 2845(7)   | 11410(3) | 7532(2)   | 94(2)  |
| C(12) | 2295(6)   | 11876(3) | 7984(2)   | 81(1)  |
| C(13) | 2902(4)   | 11850(2) | 8600(2)   | 62(1)  |
| C(14) | 4650(3)   | 10396(2) | 10602(1)  | 34(1)  |
| C(15) | 6040(3)   | 10520(2) | 10150(1)  | 36(1)  |
| C(16) | 8211(3)   | 9745(2)  | 10527(1)  | 34(1)  |
| C(17) | 9055(3)   | 8985(2)  | 10489(1)  | 32(1)  |
| C(18) | 8786(4)   | 8576(2)  | 11119(1)  | 40(1)  |
| C(19) | 7077(4)   | 8350(2)  | 11215(2)  | 47(1)  |
| C(20) | 6760(5)   | 8039(2)  | 11853(2)  | 75(1)  |
| C(21) | 10825(3)  | 9091(2)  | 10359(1)  | 34(1)  |
| C(22) | 11197(4)  | 9600(2)  | 9784(2)   | 47(1)  |
| C(23) | 10606(6)  | 9326(3)  | 9180(2)   | 85(2)  |
| C(26) | 11589(4)  | 8316(2)  | 10262(1)  | 38(1)  |
| F(1)  | 3365(3)   | 12236(1) | 11445(1)  | 76(1)  |
| F(2)  | 5283(3)   | 7760(2)  | 11895(2)  | 104(1) |
| F(3)  | 6905(4)   | 8556(2)  | 12304(1)  | 118(1) |
| F(4)  | 7725(4)   | 7471(2)  | 12003(2)  | 130(2) |
| N(1)  | 5401(3)   | 10625(1) | 9517(1)   | 40(1)  |
| N(2)  | 3752(3)   | 11021(1) | 10698(1)  | 41(1)  |
| N(3)  | 7037(3)   | 9855(1)  | 10131(1)  | 34(1)  |
| N(4)  | 13115(3)  | 8289(1)  | 10387(2)  | 52(1)  |
| O(1)  | 4344(2)   | 9778(1)  | 10831(1)  | 41(1)  |
| O(3)  | 10849(2)  | 7755(1)  | 10073(1)  | 44(1)  |
| O(2)  | 8593(3)   | 10228(1) | 10927(1)  | 50(1)  |
| C(1S) | 10744(12) | 6386(4)  | 11270(3)  | 162(4) |
| C(2S) | 733(7)    | 1177(3)  | 2070(2)   | 94(2)  |
| C(3S) | 5998(10)  | 915(5)   | 2115(3)   | 137(3) |
| O(1S) | 11267(4)  | 6386(1)  | 10659(1)  | 65(1)  |
| O(2S) | 1159(3)   | 839(1)   | 1494(1)   | 77(1)  |
| O(3S) | 6691(6)   | 1278(2)  | 1564(2)   | 117(1) |
| C(24) | 10987(6)  | 9728(3)  | 8580(2)   | 87(1)  |
| C(25) | 11505(17) | 8922(4)  | 8692(4)   | 128(5) |
| C(25A)| 9304(6)   | 9559(8)  | 8765(4)   | 95(4)  |

*U(eq) is defined as one third of the trace of the orthogonalized U$^{ij}$ tensor.

In still yet an even further embodiment, the M3-1 form of the compound of Example 1 is substantially pure.

In still yet another embodiment, the M3-1 form of the compound of Example 1 contains at least about 90 wt. %, preferably at least about 95 wt. %, and more preferably at least about 99 wt. %, based on weight of the Form M3-1 of the compound of Example 1.

In yet another embodiment, a substantially pure Form M3-1 of the compound of Example 1 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially pure crystalline Form M3-1 has substantially pure phase homogeneity with less than about 1% of the total peak area of the experimentally measured PXRD pattern arising from peaks that are absent from the simulated PXRD pattern.

In another embodiment, the crystalline form of the compound of Example 1 consists essentially of Form M3-1. The crystalline form of this embodiment may comprise at least about 90 wt. %, preferably at least about 95 wt. %, and more preferably at least about 99 wt. %, based on the weight of the crystalline form, Form M3-1 of the compound of Example 1.

In yet another embodiment, a pharmaceutical composition is provided comprising Form M3-1 of the compound of Example 1; and at least one pharmaceutically-acceptable carrier and/or diluent.

In still another embodiment, a pharmaceutical composition comprises substantially pure Form M3-1 of compound of Example 1; and at least one pharmaceutically-acceptable carrier and/or diluent.

In still an even further embodiment, a therapeutically effective amount of Form M3-1 of the compound of Example 1 is combined with at least one pharmaceutically acceptable carrier and/or diluent to provide at least one pharmaceutical composition.

In one embodiment, the compound of Example 1 is provided in a second crystalline form of Example 1. The second crystalline form is a hydrated crystalline form referred to herein as "Form CA-2" or "CA-2 Form". The CA-2 Form is a hydrate with solvated channels.

In one embodiment, the CA-2 Form is characterized by unit cell parameters approximately equal to the following:

Unit cell dimensions:
 a=15.85 Å
 b=34.41 Å
 c=4.91 Å
 α=90.0°
 β=90.0°
 γ=90.0°
Space group: P2(1)2(1)2
Molecules of Example 1/asymmetric unit: 1
Volume=2679 Å$^3$
Density (calculated)=1.352 Mg/m$^3$, wherein the unit cell parameters of Form CA-2 are measured at a temperature of about −70° C.

Figure 7:
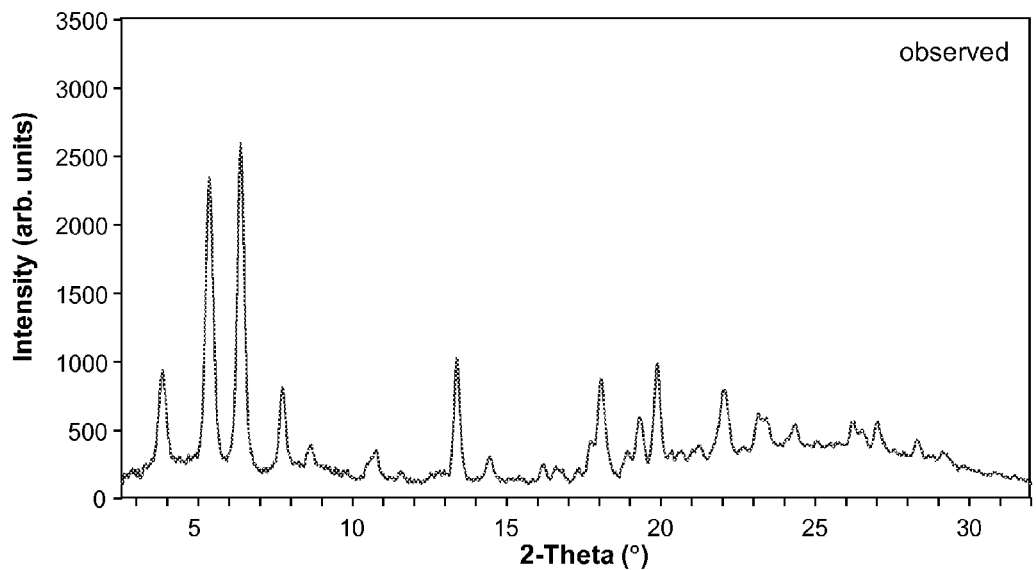
FIG. 7 shows the experimental (at approximately 25° C.) PXRD pattern (CuKα λ=1.5418 Å) of the P-4 Form of the compound of Example 1.

In another embodiment, the CA-2 Form is characterized by a simulated powder x-ray diffraction (PXRD) pattern in accordance with the pattern shown in FIG. 7 and/or by an observed PXRD pattern in accordance with the pattern shown in FIG. 7.

In yet another embodiment, the CA-2 Form of the compound of Example 1 is characterized by a PXRD pattern (CuKα λ=1.5418 Å at a temperature of about 25° C.) comprising four or more, preferably five or more, 2θ values selected from: 6.1±0.2; 9.5±0.2; 12.3±0.2; 13.5±0.2; 14.0±0.2; 15.4±0.2; 18.1±0.2, 19.6±0.2; 22.1±0.2; 23.7±0.2; 24.8±0.2 and 25.9±0.2, wherein the PXRD pattern of Form CA-2 is measured at a temperature of about 25° C.

In yet an even further embodiment, the CA-2 Form of Example 1 is characterized by fractional atomic coordinates substantially as listed in Table 2.

TABLE 2

Fractional Atomic Coordinates of Form CA-2 of Example 1 Calculated at a Temperature of about 25° C.; Atomic Coordinates ($\times 10^4$) and Equivalent Isotropic Displacement Parameters ($Å^2 \times 10^3$)

| | x | y | z | U(eq)* |
|---|---|---|---|---|
| O(2S) | 5000 | 0 | 2550(140) | 145(19) |
| F(1) | 8966(3) | −413(1) | 3824(9) | 48(1) |
| F(2) | 13136(4) | 710(2) | 1909(13) | 75(2) |
| F(3) | 13573(4) | 1291(2) | 1689(16) | 90(2) |
| F(4) | 13094(4) | 1059(2) | 5456(14) | 84(2) |
| O(1) | 10069(4) | 561(2) | −1313(13) | 44(2) |
| O(2) | 10210(4) | 1484(2) | 5676(13) | 46(2) |
| O(3) | 11706(4) | 2444(2) | −731(12) | 46(2) |
| N(1) | 8557(5) | 1083(2) | 1788(13) | 34(2) |
| N(2) | 9103(4) | 268(2) | 1341(13) | 34(2) |
| N(3) | 10020(4) | 1239(2) | 1468(13) | 30(2) |
| N(4) | 12041(5) | 2634(2) | 3511(15) | 46(2) |
| C(1) | 8539(6) | 240(2) | 3557(17) | 32(2) |
| C(2) | 8000(5) | 533(2) | 4412(18) | 32(2) |
| C(3) | 7449(6) | 455(2) | 6581(17) | 37(2) |
| C(4) | 7411(6) | 101(3) | 7806(19) | 49(3) |
| C(5) | 7925(6) | −204(3) | 6942(19) | 44(2) |
| C(6) | 8469(6) | −120(3) | 4830(20) | 39(3) |
| C(7) | 7939(6) | 906(2) | 2862(16) | 31(2) |
| C(8) | 7077(5) | 1076(2) | 2469(17) | 34(2) |
| C(9) | 6990(6) | 1482(3) | 2340(20) | 52(3) |
| C(10) | 6198(6) | 1639(3) | 1800(20) | 66(3) |
| C(11) | 5510(7) | 1403(3) | 1410(30) | 81(4) |
| C(12) | 5583(6) | 1004(3) | 1560(30) | 71(4) |
| C(13) | 6361(6) | 841(3) | 2120(20) | 52(3) |
| C(14) | 9558(6) | 584(3) | 561(18) | 32(2) |
| C(15) | 9416(5) | 946(2) | 2279(17) | 27(2) |
| C(16) | 10382(5) | 1488(2) | 3184(19) | 29(2) |
| C(17) | 11048(5) | 1752(2) | 2053(17) | 31(2) |
| C(18) | 11918(5) | 1616(2) | 3019(18) | 39(2) |
| C(19) | 12118(5) | 1201(2) | 2060(20) | 50(3) |
| C(20) | 12972(7) | 1074(3) | 2760(20) | 57(3) |
| C(21) | 10022(5) | 2319(2) | 1745(18) | 42(2) |
| C(22) | 9756(6) | 2701(3) | 2789(19) | 55(3) |
| C(23) | 8842(6) | 2822(3) | 2549(18) | 56(3) |
| C(24) | 9215(7) | 2737(3) | 5330(20) | 61(3) |
| C(25) | 10879(5) | 2172(2) | 2896(17) | 33(2) |
| C(26) | 11582(5) | 2429(2) | 1730(20) | 40(2) |
| O(1S) | 8456(4) | 1747(2) | 7615(13) | 63(2) |
| O(3S) | 5000 | 0 | 150(120) | 136(18) |
| O(4S) | 4800(30) | 181(13) | 5550(110) | 151(18) |

*U(eq) is defined as one third of the trace of the orthogonalized $U^{ij}$ tensor.

In still yet an even further embodiment, the CA-2 form of the compound of Example 1 is substantially pure.

In still yet another embodiment, the CA-2 form of the compound of Example 1 contains at least about 90 wt. %, preferably at least about 95 wt. %, and more preferably at least about 99 wt. %, based on weight of the second crystalline form, Form CA-2.

In yet another embodiment, a substantially pure second crystalline form has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, a substantially pure second crystalline form has substantially pure phase homogeneity with less than about 1% of the total peak area of the experimentally measured PXRD pattern arising from peaks that are absent from the simulated PXRD pattern.

In another embodiment, the second crystalline form of the compound of Example 1 consists essentially of Form CA-2. The second crystalline form of this embodiment may comprise at least about 90 wt. %, preferably at least about 95 wt. %, and more preferably at least about 99 wt. %, based on the weight of the second crystalline form, Form CA-2.

In one embodiment, the compound of Example 1 is provided in a third crystalline form of Example 1. The third crystalline form is a dimethanolate monohydrate crystalline form referred to herein as "Form SA-3" or "SA-3 Form". The SA-3 Form comprises about two methanol molecules and one water molecule for each molecule of Example 1.

In one embodiment, the SA-3 Form is characterized by unit cell parameters approximately equal to the following:
Unit cell dimensions:
a=8.50 Å
b=17.55 Å
c=21.22 Å
α=90.0°
β=90.0°
γ=90.0°
Space group: P2(1)2(1)2(1)
Molecules of Compound Example 1/asymmetric unit: 1
Volume=3166 $Å^3$
Density (calculated)=1.289 $Mg/m^3$,
wherein the unit cell parameters of Form SA-3 are measured at a temperature of about −70° C.

Figure 8:
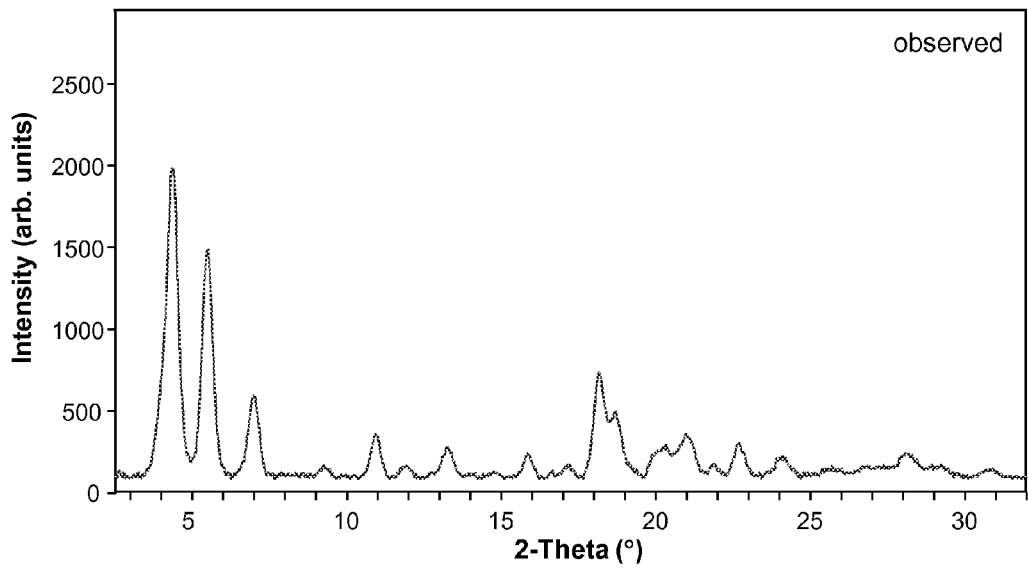
FIG. 8 shows the experimental (at approximately 25° C.) PXRD pattern (CuKα λ=1.5418 Å) of the P-5 Form of the compound of Example 1.

In another embodiment, the SA-3 Form of the compound of Example 1 is characterized by a simulated powder x-ray diffraction (PXRD) pattern in accordance with the pattern shown in FIG. 8 and/or by an observed PXRD pattern in accordance with the pattern shown in FIG. 8.

In yet another embodiment, the SA-3 Form of the compound of Example 1 is characterized by a PXRD pattern (CuKα λ=1.5418 Å at a temperature of about 25° C.) comprising four or more, preferably five or more, 2θ values selected from: 8.2±0.2; 9.6±0.2; 12.2±0.2; 14.4±0.2; 16.6±0.2; 19.1±0.2; 19.5±0.2, 20.2±0.2; 20.6±0.2; 21.4±0.2; 23.0±0.2; and 24.8±0.2, wherein the PXRD pattern of Form SA-3 is measured at a temperature of about 25° C.

In yet an even further embodiment, the SA-3 Form of Example 1 is characterized by fractional atomic coordinates substantially as listed in Table 3.

TABLE 3

Fractional Atomic Coordinates of Form SA-3 of Example 1 Calculated at a Temperature of about 25° C.; Atomic Coordinates ($\times 10^4$) and Equivalent Isotropic Displacement Parameters ($Å^2 \times 10^3$)

| | x | y | z | U(eq)* |
|---|---|---|---|---|
| C(1) | 4090(3) | 11755(2) | 10464(2) | 45(1) |
| C(2) | 4576(4) | 11895(2) | 9843(2) | 50(1) |
| C(3) | 4846(4) | 12655(2) | 9650(2) | 65(1) |
| C(4) | 4629(5) | 13238(2) | 10056(3) | 81(2) |
| C(5) | 4109(5) | 13117(2) | 10668(3) | 80(1) |
| C(6) | 3861(4) | 12376(2) | 10851(2) | 58(1) |
| C(7) | 4758(3) | 11267(2) | 9386(2) | 42(1) |
| C(8) | 4143(3) | 11357(2) | 8731(2) | 53(1) |
| C(9) | 4706(5) | 10896(3) | 8248(2) | 71(1) |
| C(10) | 4079(7) | 10926(3) | 7658(2) | 94(2) |
| C(11) | 2845(7) | 11410(3) | 7532(2) | 94(2) |
| C(12) | 2295(6) | 11876(3) | 7984(2) | 81(2) |
| C(13) | 2902(4) | 11850(2) | 8600(2) | 62(1) |
| C(14) | 4650(3) | 10396(2) | 10602(1) | 34(1) |
| C(15) | 6040(4) | 10520(2) | 10150(1) | 36(1) |
| C(16) | 8211(3) | 9745(2) | 10527(1) | 34(1) |
| C(17) | 9055(3) | 8985(2) | 10489(1) | 32(1) |
| C(18) | 8786(4) | 8576(2) | 11119(1) | 40(1) |
| C(19) | 7077(4) | 8350(2) | 11215(2) | 47(1) |
| C(20) | 6760(5) | 8039(3) | 11853(2) | 75(1) |
| C(21) | 10825(3) | 9091(2) | 10359(1) | 34(1) |
| C(22) | 11197(4) | 9600(2) | 9784(2) | 47(1) |
| C(23) | 10606(6) | 9326(3) | 9180(2) | 85(2) |
| C(26) | 11589(4) | 8316(2) | 10262(1) | 38(1) |
| F(1) | 3365(3) | 12236(1) | 11445(1) | 76(1) |
| F(2) | 5283(3) | 7760(2) | 11895(2) | 104(1) |
| F(3) | 6905(4) | 8556(2) | 12304(1) | 118(2) |
| F(4) | 7725(4) | 7471(2) | 12003(2) | 130(2) |
| N(1) | 5401(3) | 10625(1) | 9517(1) | 40(1) |

TABLE 3-continued

Fractional Atomic Coordinates of Form SA-3 of Example 1 Calculated at a Temperature of about 25° C.; Atomic Coordinates (×10⁴) and Equivalent Isotropic Displacement Parameters (Å² × 10³)

| | x | y | z | U(eq)* |
|---|---|---|---|---|
| N(2) | 3752(3) | 11021(1) | 10698(1) | 41(1) |
| N(3) | 7037(3) | 9855(1) | 10131(1) | 34(1) |
| N(4) | 13115(3) | 8289(2) | 10387(2) | 52(1) |
| O(1) | 4344(2) | 9778(1) | 10831(1) | 41(1) |
| O(3) | 10849(2) | 7755(1) | 10073(1) | 44(1) |
| O(2) | 8593(3) | 10228(1) | 10927(1) | 50(1) |
| C(1S) | 10744(12) | 6386(4) | 11270(3) | 162(4) |
| C(2S) | 733(7) | 1177(3) | 2070(2) | 94(2) |
| C(3S) | 5998(10) | 915(5) | 2115(3) | 137(3) |
| O(1S) | 11267(4) | 6386(1) | 10659(1) | 65(1) |
| O(2S) | 1159(3) | 839(2) | 1494(1) | 77(1) |
| O(3S) | 6691(6) | 1278(2) | 1564(2) | 117(1) |
| C(24) | 10987(6) | 9728(3) | 8580(2) | 87(1) |
| C(25) | 11505(17) | 8922(4) | 8692(4) | 128(5) |
| C(25A) | 9304(6) | 9559(8) | 8765(4) | 95(4) |

*U(eq) is defined as one third of the trace of the orthogonalized U$^{ij}$ tensor.

In still yet an even further embodiment, the SA-3 form of the compound of Example 1 is substantially pure.

In still yet another embodiment, the SA-3 form of the compound of Example 1 contains at least about 90 wt. %, preferably at least about 95 wt. %, and more preferably at least about 99 wt. %, based on weight of the third crystalline form, Form SA-3.

In yet another embodiment, a substantially pure Form SA-3 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially crystalline Form SA-3 has substantially pure phase homogeneity with less than about 1% of the total peak area of the experimentally measured PXRD pattern arising from peaks that are absent from the simulated PXRD pattern.

In another embodiment, the third crystalline form of the compound of Example 1 consists essentially of Form SA-3. The third crystalline form of this embodiment may comprise at least about 90 wt. %, preferably at least about 95 wt. %, and more preferably at least about 99 wt. %, based on the weight of the third crystalline form, Form SA-3.

In one embodiment, the compound of Example 1 is provided as a crystalline material comprising the fourth crystalline form of Example 1. A fourth crystalline form of the compound of Example 1 comprises a crystalline form referred to herein as "Form E2.5-4" or "E2.5-4 Form". The E2.5-4 Form comprises about 2.5 ethanol molecules for each molecule of Example 1.

In one embodiment, the E2.5-4 Form of the compound of Example 1 is characterized by unit cell parameters approximately equal to the following:

Unit cell dimensions:
a=8.61 Å
b=11.40 Å
c=17.24 Å
α=85.9°
β=89.1°
γ=78.2°
Space group: P1
Molecules of Example 1/asymmetric unit: 2
Volume=1652 Å³
Density (calculated)=1.260 Mg/m³, wherein the unit cell parameters of Form E2.5-4 are measured at a temperature of about –70° C.

Figure 9:
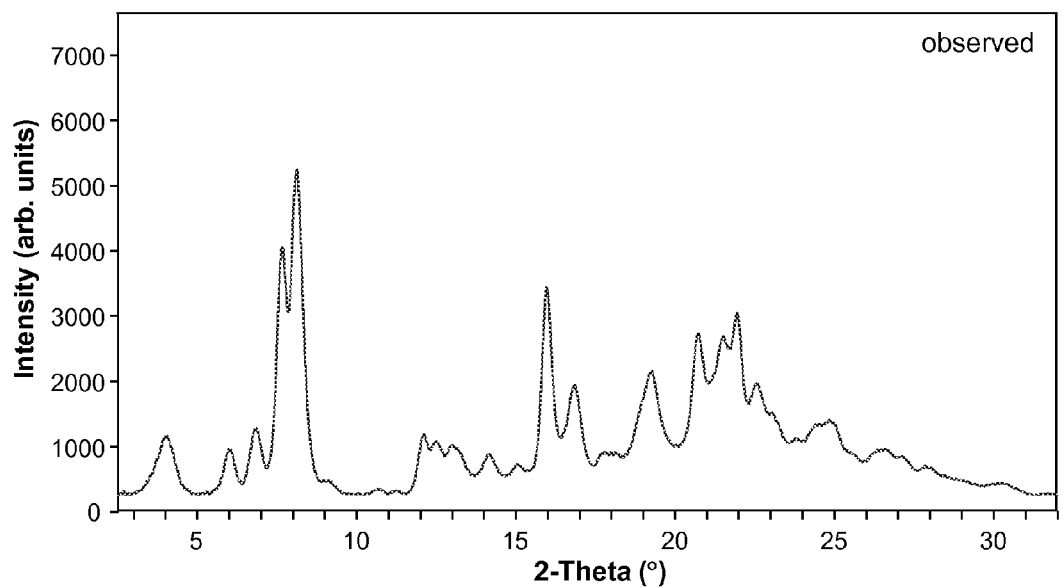
FIG. 9 shows the experimental (at approximately 25° C.) PXRD pattern (CuKα λ=1.5418 Å) of the P-6 Form of the compound of Example 1.

In another embodiment, the E2.5-4 Form of the compound of Example 1 is characterized by a simulated powder x-ray diffraction (PXRD) pattern substantially in accordance with the pattern shown in FIG. 9 and/or by an observed PXRD pattern substantially in accordance with the pattern shown in FIG. 9.

In yet another embodiment, the E2.5-4 Form of the compound of Example 1 is characterized by a PXRD pattern (CuKα λ=1.5418 Å at a temperature of about 25° C.) comprising four or more, preferably five or more, 2θ values selected from: 5.0±0.2; 7.8±0.2; 9.0±0.2; 14.5±0.2; 16.8±0.2; 20.7±0.2 and 21.4±0.2, wherein the PXRD pattern of Form E2.5-4 is measured at a temperature of about 25° C.

In yet an even further embodiment, the E2.5-4 Form of Example 1 is characterized by fractional atomic coordinates substantially as listed in Table 4.

TABLE 4

Fractional Atomic Coordinates of Form E2.5-4 of Example 1 Calculated at a Temperature of about 25° C.; Atomic Coordinates (×10⁴) and Equivalent Isotropic Displacement Parameters (Å² × 10³)

| | x | y | z | U(eq)* |
|---|---|---|---|---|
| C(1) | −3063(8) | 1770(7) | 2975(3) | 44(2) |
| C(2) | −2268(7) | 572(7) | 2927(4) | 42(2) |
| C(3) | −1890(8) | 138(7) | 2190(4) | 56(2) |
| C(4) | −2321(9) | 889(10) | 1517(4) | 67(3) |
| C(5) | −3135(9) | 2061(9) | 1553(4) | 62(2) |
| C(6) | −3485(9) | 2452(8) | 2286(4) | 55(2) |
| C(7) | −1828(7) | −224(6) | 3631(4) | 42(2) |
| C(8) | −2025(7) | −1506(6) | 3650(4) | 42(2) |
| C(9) | −1107(9) | −2384(8) | 4123(4) | 60(2) |
| C(10) | −1338(11) | −3525(8) | 4191(5) | 69(2) |
| C(11) | −2525(12) | −3834(9) | 3800(6) | 79(3) |
| C(12) | −3459(11) | −2983(9) | 3301(6) | 74(2) |
| C(13) | −3225(8) | −1820(8) | 3212(4) | 60(2) |
| C(14) | −2620(7) | 2155(6) | 4330(4) | 43(2) |
| C(15) | −1023(7) | 1320(6) | 4268(3) | 38(2) |
| C(16) | 1572(7) | 2206(6) | 5794(3) | 39(2) |
| C(17) | 938(7) | 3424(6) | 6129(4) | 45(2) |
| C(18) | −823(8) | 3583(7) | 6305(4) | 56(2) |
| C(19) | −1508(10) | 4747(9) | 6636(6) | 71(2) |
| C(20) | 3399(8) | 1985(7) | 5694(4) | 50(2) |
| C(21) | 4100(9) | 944(6) | 5193(4) | 54(2) |
| C(22) | 3757(9) | −206(7) | 5491(4) | 58(2) |
| C(23) | 4847(11) | −1351(8) | 5196(5) | 80(3) |
| C(24) | 4939(12) | −1000(9) | 6014(6) | 87(3) |
| C(25) | 4204(8) | 1791(6) | 6492(4) | 45(2) |
| C(26) | 2230(7) | −256(6) | 1683(4) | 38(2) |
| C(27) | 2532(7) | 810(5) | 1949(3) | 35(2) |
| C(28) | 2777(8) | 885(6) | 2740(4) | 43(2) |
| C(52) | 765(8) | 2200(7) | 5001(4) | 45(2) |
| C(29) | 2696(8) | −54(7) | 3270(4) | 51(2) |
| C(30) | 2361(8) | −1119(7) | 3033(4) | 51(2) |
| C(31) | 2136(8) | −1169(6) | 2253(4) | 44(2) |
| C(32) | 2531(7) | 1863(5) | 1389(4) | 33(1) |
| C(33) | 1706(7) | 3052(6) | 1648(4) | 40(2) |
| C(34) | 2252(8) | 4087(6) | 1376(4) | 50(2) |
| C(35) | 1451(10) | 5210(7) | 1579(5) | 64(2) |
| C(36) | 145(10) | 5300(7) | 2057(5) | 66(2) |
| C(37) | −400(9) | 4292(7) | 2317(5) | 64(2) |
| C(38) | 390(8) | 3169(6) | 2116(4) | 49(2) |
| C(39) | 2724(7) | −64(7) | 294(4) | 38(2) |
| C(40) | 3988(7) | 665(5) | 485(3) | 34(2) |
| C(41) | 6235(7) | 98(6) | −379(4) | 39(2) |
| C(42) | 6982(7) | 293(6) | −1161(3) | 38(2) |
| C(43) | 7179(7) | −898(6) | −1572(4) | 45(2) |
| C(44) | 5565(9) | −1233(7) | −1731(4) | 56(2) |
| C(45) | 5720(11) | −2470(8) | −1951(5) | 68(2) |
| C(46) | 8528(8) | 715(7) | −1072(4) | 51(2) |
| C(47) | 8149(13) | 1984(11) | −705(5) | 108(4) |
| C(48) | 9339(13) | 2399(10) | −347(6) | 97(3) |
| C(49) | 9025(15) | 3716(9) | −205(7) | 104(4) |
| C(50) | 9333(8) | 867(6) | −1848(4) | 41(2) |
| C(51) | 10292(19) | 3183(12) | −764(9) | 143(5) |
| F(1) | −4260(5) | 3611(4) | 2334(2) | 68(1) |

TABLE 4-continued

Fractional Atomic Coordinates of Form E2.5-4 of Example 1 Calculated at a Temperature of about 25° C.; Atomic Coordinates (×10⁴) and Equivalent Isotropic Displacement Parameters (Å² × 10³)

|  | x | y | z | U(eq)* |
|---|---|---|---|---|
| F(2) | −1420(8) | 5690(5) | 6174(4) | 120(2) |
| F(3) | −3047(6) | 4833(5) | 6823(4) | 110(2) |
| F(4) | −780(8) | 4921(6) | 7279(4) | 122(2) |
| F(5) | 1772(5) | −2200(4) | 2004(2) | 64(1) |
| F(6) | 6344(8) | −3300(5) | −1380(3) | 114(2) |
| F(7) | 4345(7) | −2740(5) | −2135(3) | 107(2) |
| F(8) | 6688(7) | −2712(4) | −2554(3) | 91(2) |
| N(1) | −1262(6) | 84(5) | 4251(3) | 46(1) |
| N(2) | −3557(6) | 2291(5) | 3688(3) | 42(1) |
| N(3) | −64(6) | 1362(5) | 4942(3) | 38(1) |
| N(4) | 5662(6) | 1985(5) | 6498(3) | 52(2) |
| N(5) | 3162(6) | 1832(4) | 716(3) | 36(1) |
| N(6) | 1939(6) | −434(5) | 907(3) | 38(1) |
| N(7) | 4914(6) | 860(5) | −207(3) | 38(1) |
| N(8) | 10901(7) | 639(5) | −1848(3) | 53(2) |
| O(1) | −3101(5) | 2649(4) | 4919(3) | 51(1) |
| O(2) | 886(5) | 2956(4) | 4462(3) | 56(1) |
| O(3) | 3536(5) | 1473(4) | 7092(2) | 47(1) |
| O(4) | 2506(5) | −294(4) | −371(3) | 51(1) |
| O(5) | 6856(5) | −759(4) | 85(3) | 46(1) |
| O(6) | 8557(5) | 1202(4) | −2450(2) | 45(1) |
| O(1S) | 1(7) | 8052(5) | 10391(4) | 76(2) |
| C(1S) | 845(15) | 7396(9) | 9716(9) | 136(5) |
| C(2S) | 30(20) | 6394(10) | 9572(5) | 196(8) |
| O(2S) | −355(7) | 9858(5) | 6302(3) | 77(2) |
| C(3S) | −456(9) | 8668(9) | 6328(5) | 103(3) |
| C(4S) | 928(15) | 7890(10) | 6746(16) | 316(19) |
| O(3S) | 3877(6) | 2552(5) | 8472(3) | 68(1) |
| C(5S) | 3755(16) | 3824(10) | 8298(7) | 108(3) |
| C(6S) | 3987(18) | 4373(13) | 9018(10) | 148(5) |
| O(4S) | 3396(6) | 3697(5) | 3736(3) | 63(1) |
| C(7S) | 3168(10) | 4985(7) | 3678(4) | 66(2) |
| C(8S) | 3421(11) | 5437(7) | 4451(3) | 92(3) |
| O(5S) | 5633(10) | 7871(6) | 1299(3) | 82(3) |
| C(9S) | 5980(30) | 6598(7) | 1235(11) | 157(9) |
| C(10S) | 5290(30) | 6190(20) | 540(10) | 188(11) |

*U(eq) is defined as one third of the trace of the orthogonalized $U^{ij}$ tensor.

In still yet an even further embodiment, the E2.5-4 form of the compound of Example 1 is substantially pure.

In still yet another embodiment, the E2.5-4 form of the compound of Example 1 contains at least about 90 wt. %, preferably at least about 95 wt. %, and more preferably at least about 99 wt. %, based on weight of the fourth crystalline form, Form E2.5-4.

In yet another embodiment, a substantially pure Form E2.5-4 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially crystalline Form E2.5-4 has substantially pure phase homogeneity with less than about 1% of the total peak area of the experimentally measured PXRD pattern arising from peaks that are absent from the simulated PXRD pattern.

In another embodiment, the fourth crystalline form of the compound of Example 1 consists essentially of Form E2.5-4. The fourth crystalline form of this embodiment may comprise at least about 90 wt. %, preferably at least about 95 wt. %, and more preferably at least about 99 wt. %, based on the weight of the fourth crystalline form, Form E2.5-4.

In one embodiment, the compound of Example 1 is provided as a crystalline material comprising the fifth crystalline form of Example 1. A fifth crystalline form of the compound of Example 1 comprises a crystalline form referred to herein as "Form IPA2-5" or "IPA2-5 Form". The IPA2-5 Form comprises about 2.5 ethanol molecules for each molecule of Example 1.

In one embodiment, the E2.5-4 Form of the compound of Example 1 is characterized by unit cell parameters approximately equal to the following:
Unit cell dimensions:
a=11.77 Å
b=8.58 Å
c=17.34 Å
α=90.0°
β=106.1°
γ=90.0°
Space group: P2(1)
Molecules of Example 1/asymmetric unit: 1
Volume=1683 Å³
Density (calculated)=1.260 Mg/m³,
wherein the unit cell parameters of Form IPA2-5 are measured at a temperature of about −70° C.

Figure 10:
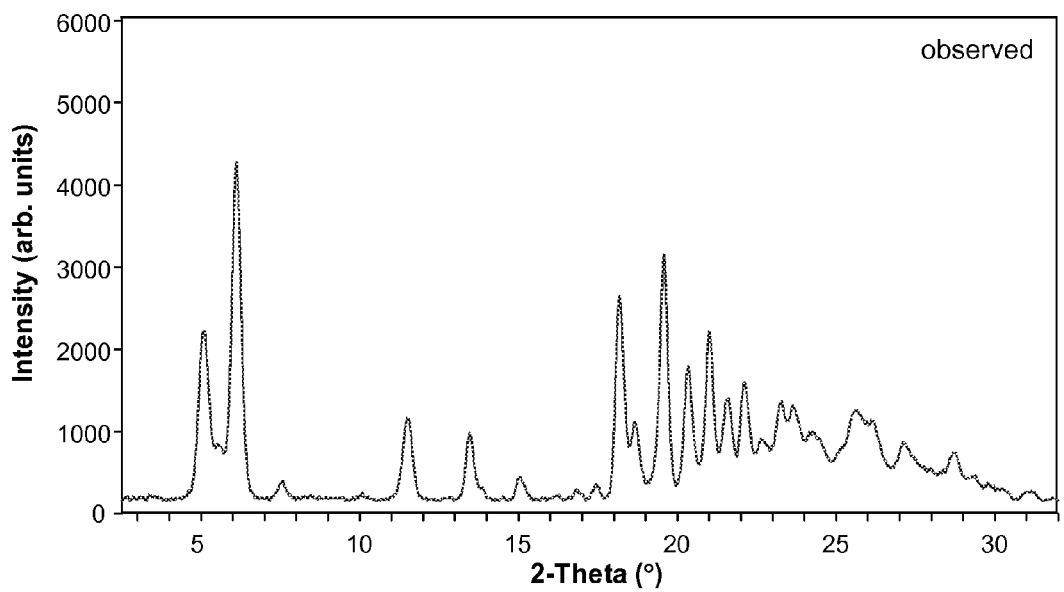
FIG. 10 shows the experimental (at approximately 25° C.) PXRD pattern (CuKα λ=1.5418 Å) of the P-7 Form of the compound of Example 1.

In another embodiment, the IPA2-5 Form of the compound of Example 1 is characterized by a simulated powder x-ray diffraction (PXRD) pattern substantially in accordance with the pattern shown in FIG. 10 and/or by an observed PXRD pattern substantially in accordance with the pattern shown in FIG. 10.

In yet another embodiment, the IPA2-5 Form of the compound of Example 1 is characterized by a PXRD pattern (CuKα λ=1.5418 Å at a temperature of about 25° C.) comprising four or more, preferably five or more, 2θ values selected from: 7.7±0.2; 13.0±0.2; 14.7±0.2; 15.2±0.2; 18.1±0.2; 19.2±0.2; 21.5±0.2, 22.1±0.2; 23.2±0.2; and 25.6±0.2, wherein the PXRD pattern of Form IPA2-5 is measured at a temperature of about 25° C.

In yet an even further embodiment, the IPA2-5 Form of Example 1 is characterized by fractional atomic coordinates substantially as listed in Table 5.

TABLE 5

Fractional Atomic Coordinates of Form IPA2-5 of Example 1 Calculated at a Temperature of about 25° C.; Atomic Coordinates (×10⁴) and Equivalent Isotropic Displacement Parameters (Å² × 10³)

|  | x | y | z | U(eq) |
|---|---|---|---|---|
| C(1) | 9227(5) | 7107(7) | 4208(3) | 36(1) |
| C(2) | 10306(5) | 6550(7) | 4690(3) | 38(1) |
| C(3) | 10424(5) | 6205(7) | 5497(3) | 43(2) |
| C(4) | 9487(6) | 6434(7) | 5815(3) | 48(2) |
| C(5) | 8423(6) | 6991(8) | 5357(3) | 52(2) |
| C(6) | 8318(5) | 7322(7) | 4570(3) | 42(2) |
| C(7) | 9417(5) | 6721(7) | 2846(3) | 38(1) |
| C(8) | 10120(4) | 5233(7) | 3171(3) | 32(1) |
| C(9) | 11329(4) | 6328(7) | 4365(3) | 36(1) |
| C(10) | 12527(5) | 6800(8) | 4870(3) | 43(2) |
| C(11) | 13525(5) | 6015(9) | 4816(4) | 58(2) |
| C(12) | 14632(5) | 6482(10) | 5283(4) | 66(2) |
| C(13) | 14745(6) | 7749(10) | 5789(4) | 66(2) |
| C(14) | 13757(6) | 8555(9) | 5838(4) | 62(2) |
| C(15) | 12650(5) | 8074(8) | 5382(3) | 51(2) |
| C(16) | 9476(5) | 3227(7) | 2178(3) | 35(1) |
| C(17) | 9527(4) | 2579(6) | 1369(3) | 33(1) |
| C(18) | 8267(4) | 2651(7) | 793(3) | 35(1) |
| C(19) | 7769(5) | 4300(8) | 740(3) | 48(2) |
| C(20) | 6630(5) | 4483(9) | 114(4) | 57(2) |
| C(21) | 10057(5) | 930(7) | 1496(3) | 36(1) |
| C(22) | 11411(4) | 1058(7) | 1884(3) | 42(2) |
| C(23) | 12042(5) | −447(8) | 2142(3) | 53(2) |
| C(24) | 13213(5) | −453(9) | 2754(4) | 70(2) |
| C(25) | 12173(6) | −1028(10) | 2954(4) | 80(2) |
| C(26) | 9873(5) | 49(8) | 715(3) | 37(1) |
| F(1) | 7273(3) | 7894(5) | 4103(2) | 61(1) |
| F(2) | 6154(4) | 5892(6) | 99(2) | 89(1) |

TABLE 5-continued

Fractional Atomic Coordinates of Form IPA2-5 of Example 1 Calculated at a Temperature of about 25° C.; Atomic Coordinates (×10$^4$) and Equivalent Isotropic Displacement Parameters (Å$^2$ × 10$^3$)

| | x | y | z | U(eq) |
|---|---|---|---|---|
| F(3) | 5816(4) | 3486(7) | 188(3) | 101(2) |
| F(4) | 6746(3) | 4254(6) | −621(2) | 85(1) |
| N(1) | 11283(4) | 5716(6) | 3673(3) | 41(2) |
| N(2) | 9033(4) | 7533(5) | 3398(2) | 37(1) |
| N(3) | 10270(4) | 4352(6) | 2502(2) | 37(1) |
| N(4) | 9587(4) | −1424(6) | 723(3) | 46(1) |
| O(1) | 9200(3) | 7129(5) | 2148(2) | 49(1) |
| O(2) | 8732(3) | 2782(5) | 2505(2) | 42(1) |
| O(3) | 10019(3) | 700(4) | 105(2) | 42(1) |
| C(1S) | 2899(5) | 5429(8) | 1490(3) | 53(2) |
| C(2S) | 3576(6) | 4954(11) | 2340(4) | 77(2) |
| C(3S) | 3261(6) | 4485(10) | 870(4) | 76(2) |
| O(1S) | 1680(3) | 5244(6) | 1427(2) | 52(1) |
| O(2S) | 7632(3) | 10054(5) | 2719(3) | 62(1) |
| C(4S) | 6465(7) | 9852(11) | 2207(8) | 142(5) |
| C(5S) | 5773(6) | 11252(10) | 2053(5) | 82(2) |
| C(6S) | 6096(7) | 8316(11) | 2042(5) | 100(3) |

*U(eq) is defined as one third of the trace of the orthogonalized U$^{ij}$ tensor.

In still yet an even further embodiment, the IPA2-5 form of the compound of Example 1 is substantially pure.

In still yet another embodiment, the IPA2-5 form of the compound of Example 1 contains at least about 90 wt. %, preferably at least about 95 wt. %, and more preferably at least about 99 wt. %, based on weight of the fifth crystalline form, Form IPA2-5.

In yet another embodiment, a substantially pure Form IPA2-5 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially crystalline Form IPA2-5 has substantially pure phase homogeneity with less than about 1% of the total peak area of the experimentally measured PXRD pattern arising from peaks that are absent from the simulated PXRD pattern.

In another embodiment, the fifth crystalline form of the compound of Example 1 consists essentially of Form IPA2-5. The fifth crystalline form of this embodiment may comprise at least about 90 wt. %, preferably at least about 95 wt. %, and more preferably at least about 99 wt. %, based on the weight of the fifth crystalline form, Form IPA2-5.

In one embodiment, the compound of Example 1 is provided in a sixth crystalline form. The sixth crystalline form is referred to herein as "Form P-1" or "P-1 Form".

Figure 11:
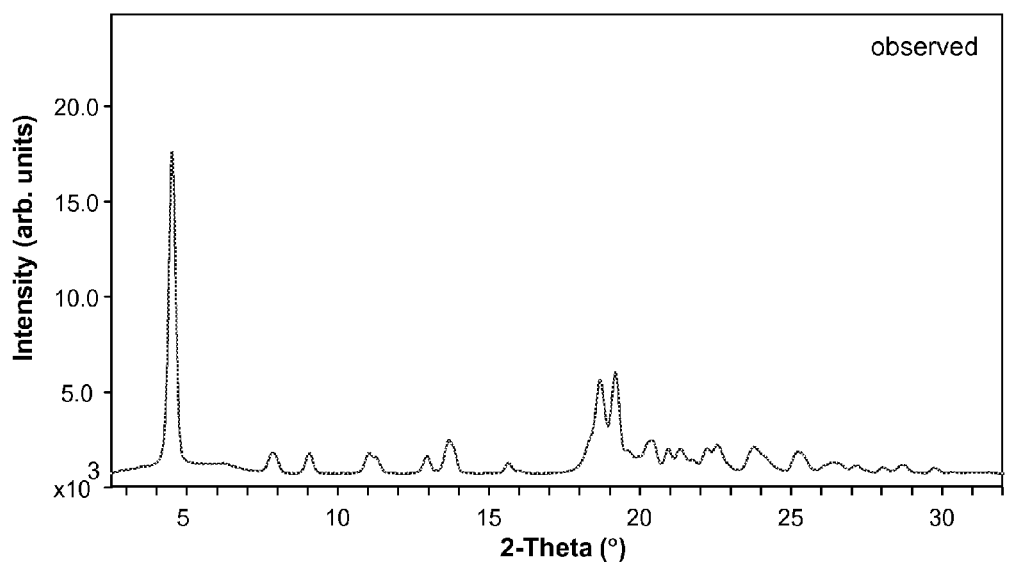
FIG. 11 shows the experimental (at approximately 25° C.) PXRD pattern (CuKα λ=1.5418 Å) of the P-9 Form of the compound of Example 1.

In another embodiment, the P-1 Form is characterized by an observed PXRD pattern in accordance with the pattern shown in FIG. 11.

The P-1 Form of the compound of Example 1 is characterized by a PXRD pattern (CuKα λ=1.5418 Å at a temperature of about 25° C.) comprising four or more, preferably five or more, 2θ values selected from: 7.0±0.2; 8.8±0.2; 10.3±0.2; 11.6±0.2; 12.9±0.2; 15.4±0.2; 15.9±0.2; 17.9±0.2 and 21.5±0.2, wherein the PXRD pattern of Form P-1 is measured at a temperature of about 25° C.

In one embodiment, the compound of Example 1 is provided in a seventh crystalline form. The seventh crystalline form is referred to herein as "Form P-4" or "P-4 Form".

Figure 12:
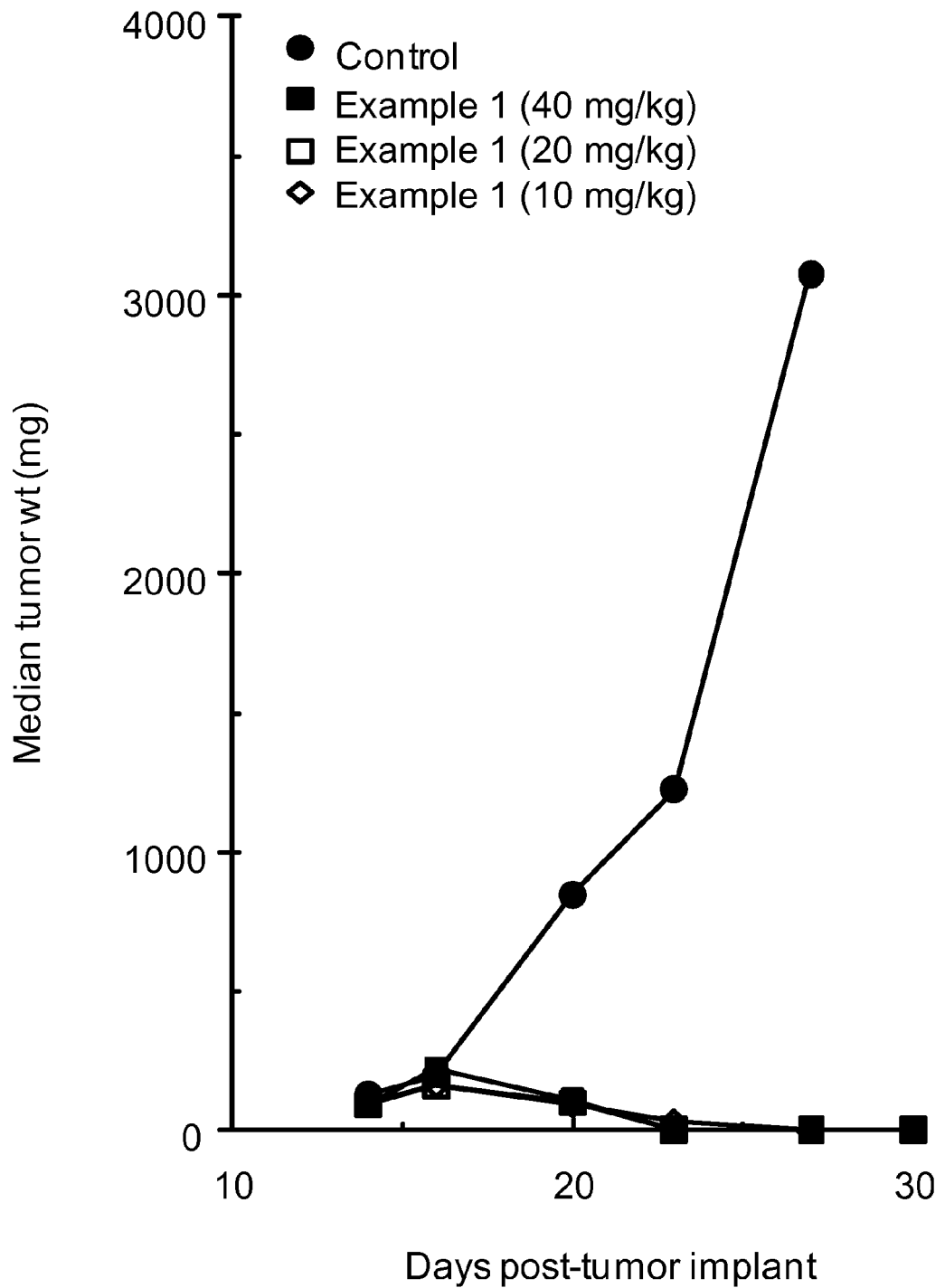
FIG. 12 shows the in vivo activity of Example 1 in Human T-cell acute lymphoblastic leukemia cell line TALL-1. Dosed orally; PO, QDx10. Each symbol represents the median tumor burden of a group of 8 mice. (●) Control; (0) Example 1, 10 mg/kg; (□) Example 1, 20 mg/kg; (■) Example 1, 40 mg/kg.

In another embodiment, the P-4 Form is characterized by an observed PXRD pattern in accordance with the pattern shown in FIG. 12.

The P-4 Form of the compound of Example 1 is characterized by a PXRD pattern (CuKα λ=1.5418 Å at a temperature of about 25° C.) comprising four or more, preferably five or more, 2θ values selected from: 3.8±0.2; 5.4±0.2; 6.4±0.2; 7.7±0.2; 13.4±0.2; 18.1±0.2; 19.3±0.2; 19.9±0.2 and 22.1±0.2, wherein the PXRD pattern of Form P-4 is measured at a temperature of about 25° C.

In one embodiment, the compound of Example 1 is provided in a eighth crystalline form. The eighth crystalline form is referred to herein as "Form P-5" or "P-5 Form".

Figure 13:
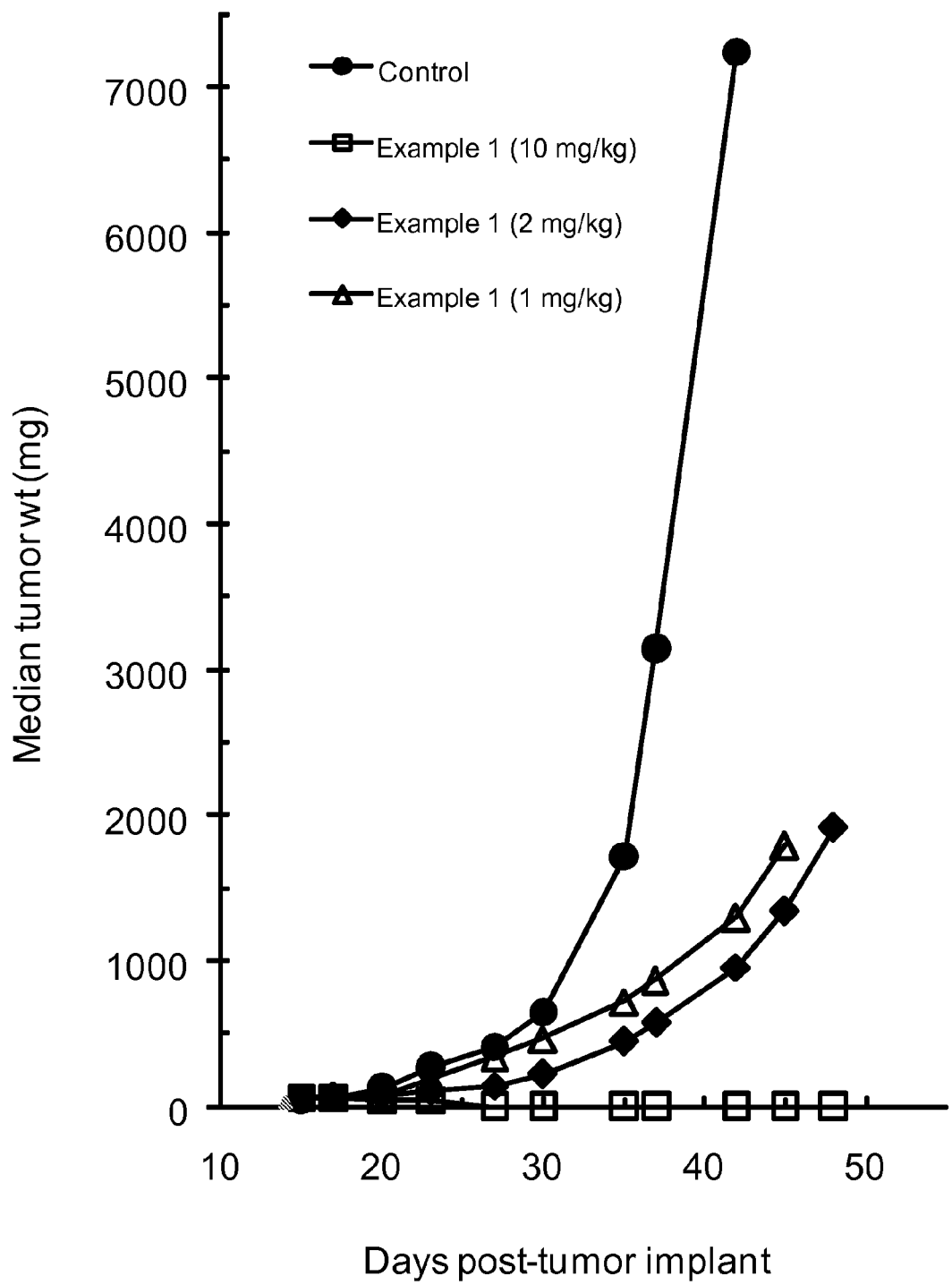
FIG. 13 shows the in vivo activity of Example 1 in Human T-cell acute lymphoblastic leukemia cell line TALL-1. Dosed orally; PO, QDx10. Each symbol represents the median tumor burden of a group of 8 mice. (●) Control; (Δ) Example 1, 1 mg/kg; (♦) Example 1, 2 mg/kg; (□) Example 1, 10 mg/kg.

In another embodiment, the P-5 Form is characterized by an observed PXRD pattern in accordance with the pattern shown in FIG. 13.

The P-5 Form of the compound of Example 1 is characterized by a PXRD pattern (CuKα λ=1.5418 Å at a temperature of about 25° C.) comprising four or more, preferably five or more, 2θ values selected from: 4.4±0.2; 5.5±0.2; 7.0±0.2; 10.9±0.2; 13.2±0.2; 18.2±0.2; 18.7±0.2 and 22.7±0.2, wherein the PXRD pattern of Form P-5 is measured at a temperature of about 25° C.

In one embodiment, the compound of Example 1 is provided in a ninth crystalline form. The ninth crystalline form is referred to herein as "Form P-6" or "P-6 Form".

Figure 14:
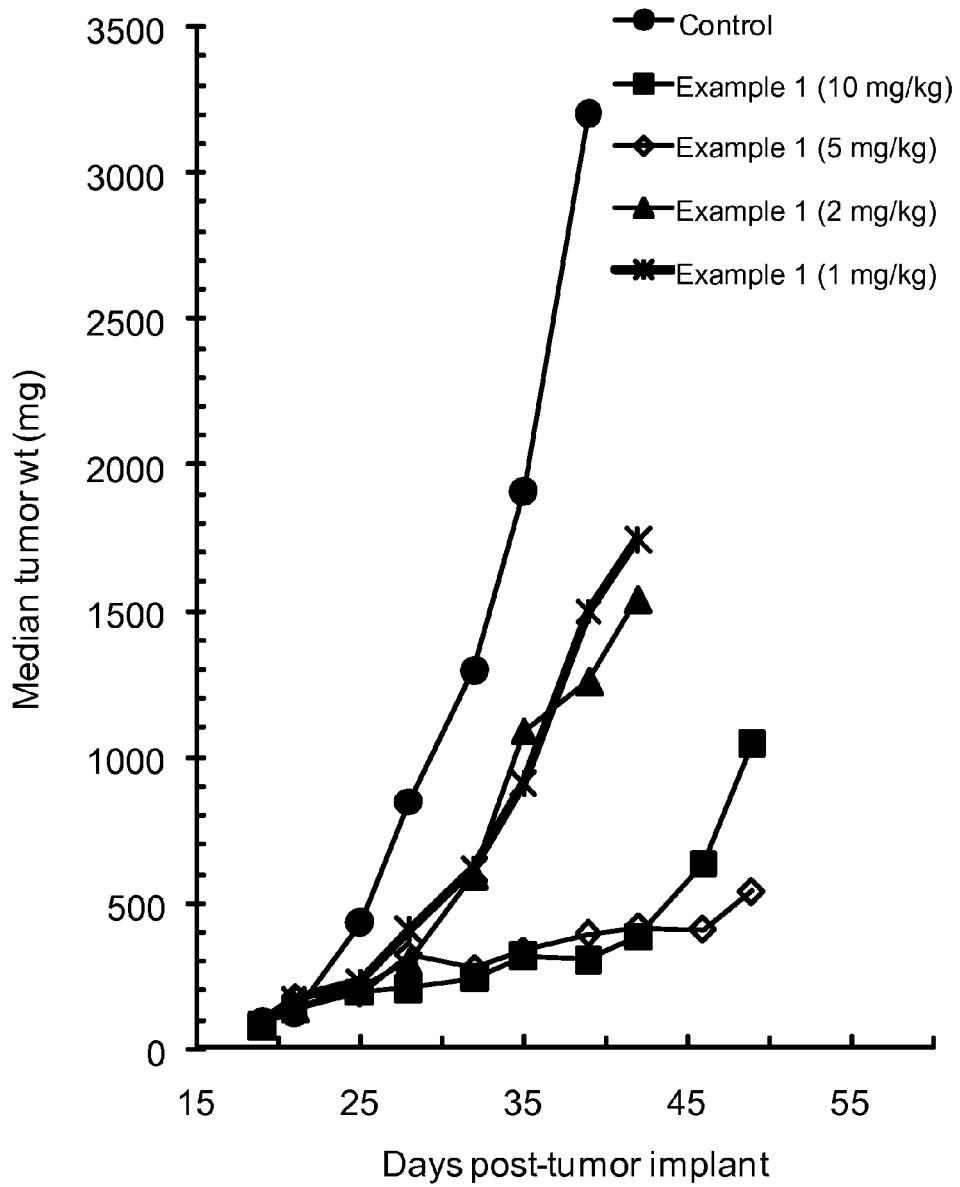
FIG. 14 shows the in vivo activity of Example 1 in human triple negative breast carcinoma cell line MDA-MB-157. Dosed orally; PO, QDx15 (10 day on-2 day off-5 day on). Each symbol represents the median tumor burden of a group of 8 mice. (●) Control; (*) Example 1, 1 mg/kg; (▲) Example 1, 2 mg/kg; (◇) Example 1, 5 mg/kg; (■) Example 1, 10 mg/kg.

In another embodiment, the P-6 Form is characterized by an observed PXRD pattern in accordance with the pattern shown in FIG. 14.

The P-6 Form of the compound of Example 1 is characterized by a PXRD pattern (CuKα λ=1.5418 Å at a temperature of about 25° C.) comprising four or more, preferably five or more, 2θ values selected from: 4.0±0.2; 6.0±0.2; 6.8±0.2; 7.7±0.2; 8.1±0.2; 16.0±0.2; 16.8±0.2; 19.3±0.2; 20.7±0.2 and 21.9±0.2, wherein the PXRD pattern of Form P-6 is measured at a temperature of about 25° C.

In one embodiment, the compound of Example 1 is provided in a tenth crystalline form. The tenth crystalline form is referred to herein as "Form P-7" or "P-7 Form".

Figure 15:
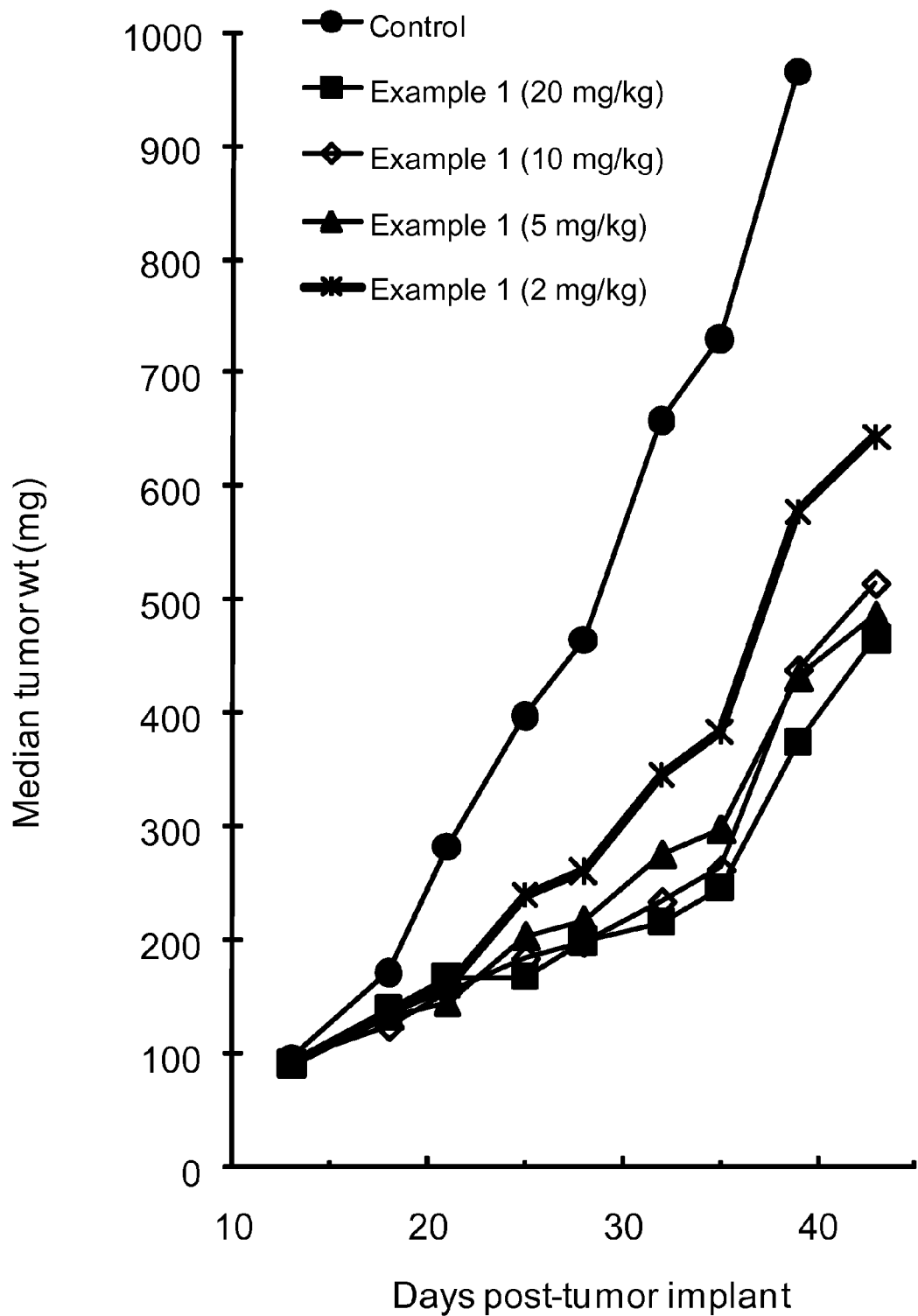
FIG. 15 shows the in vivo activity of Example 1 in human triple negative breast carcinoma cell line MDA-MB-468. Dosed orally; PO, QDx15 (10 day on-2 day off-5 day on). Each symbol represents the median tumor burden of a group of 8 mice. (●) Control; (*) Example 1, 2 mg/kg; (▲) Example 1, 5 mg/kg; (◇) Example 1, 10 mg/kg; (■) Example 1, 20 mg/kg.

In another embodiment, the P-7 Form is characterized by an observed PXRD pattern in accordance with the pattern shown in FIG. 15.

The P-7 Form of the compound of Example 1 is characterized by a PXRD pattern (CuKα λ=1.5418 Å at a temperature of about 25° C.) comprising four or more, preferably five or more, 2θ values selected from: 5.1±0.2; 6.1±0.2; 11.5±0.2; 13.5±0.2; 18.2±0.2; 19.6±0.2; 20.4±0.2; 21.0±0.2; 21.6±0.2 and 22.1±0.2, wherein the PXRD pattern of Form P-7 is measured at a temperature of about 25° C.

In one embodiment, the compound of Example 1 is provided in an eleventh crystalline form. The eleventh crystalline form is referred to herein as "Form P-9" or "P-9 Form".

Figure 16:
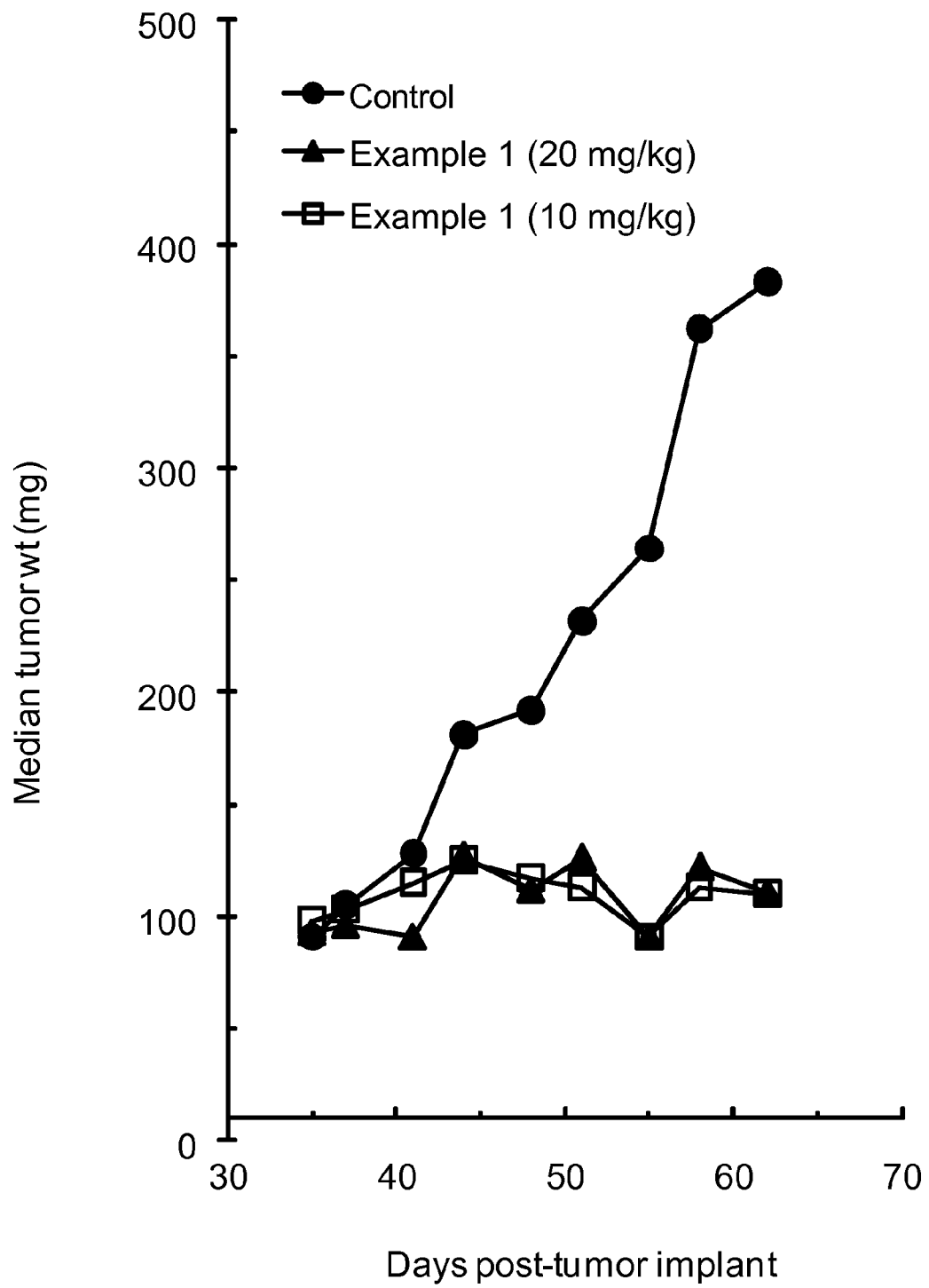
FIG. 16 shows the in vivo activity of Example 1 in human PAT70 pancreatic carcinoma cell line. Dosed orally; PO, QDx15 (10 day on-2 day off-5 day on). Each symbol represents the median tumor burden of a group of 8 mice. (●) Control; (□) Example 1, 10 mg/kg; (▲) Example 1, 20 mg/kg.

In another embodiment, the P-9 Form is characterized by an observed PXRD pattern in accordance with the pattern shown in FIG. 16.

The P-9 Form of the compound of Example 1 is characterized by a PXRD pattern (CuKα λ=1.5418 Å at a temperature of about 25° C.) comprising four or more, preferably five or more, 2θ values selected from: 4.5±0.2; 7.9±0.2; 9.1±0.2; 12.9±0.2; 13.7±0.2; 18.7±0.2 and 19.2±0.2, wherein the PXRD pattern of Form P-9 is measured at a temperature of about 25° C.

Compounds in accordance with Formula (I) and/or salts thereof can be administered by any means suitable for the condition to be treated, which can depend on the need for site-specific treatment or quantity of Formula (I) compound to be delivered.

Also embraced within this invention is a class of pharmaceutical compositions comprising the compound of Formula (I) and/or salt thereof; and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 1 to 2000 mg, preferably from about 1 to 500 mg, and more preferably from about 5 to 150 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethylcellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise the compound of Formula (I) and optionally an additional agent selected from any pharmaceutically acceptable carrier, adjuvant, and vehicle. Alternate compositions of this invention comprise a compound of the Formula (I) described herein and a pharmaceutically acceptable carrier, adjuvant, or vehicle.

Utility

The compounds of Formula (I) are useful for the treatment of cancer, for example, cancers dependent upon Notch activation. Notch activation has been implicated in the pathogenesis of various solid tumors including ovarian, pancreatic, as well as breast cancer and hematologic tumors such as leukemias, lymphomas, and multiple myeloma.

In one embodiment, a method is provided for treating cancer comprising administering to a mammal in need thereof a compound of Formula (I) and/or a salt thereof. The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. For example, the method of this embodiment is used to treat breast cancer, colon cancer, or pancreatic cancer. Preferably, the mammal is a human. For example, a therapeutically effective amount for treating cancer may be administered in the method of the present embodiment.

Routes of administration in the present embodiment include parenteral administration and oral administration.

In one embodiment, a method is provided for treating cancer comprising administering to a mammal in need thereof at least one compound of Formula (I) and/or at least one salt thereof, wherein said cancer is colorectal cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) and/or at least one salt thereof, wherein said cancer is triple negative breast cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) and/or at least one salt thereof, wherein said cancer is non-small cell lung cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) and/or at least one salt thereof, wherein said cancer is pancreatic cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) and/or at least one salt thereof, wherein said cancer is ovarian cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) and/or at least one salt thereof, wherein said cancer is melanoma. Preferably, the mammal is a human. For example, a therapeutically effective amount for treating cancer may be administered in the method of the present embodiment. Routes of administration in the present embodiment include parenteral administration and oral administration.

In one embodiment, the use of at least one compound of Formula (I) and/or at least one salt thereof, in the manufacture of a medicament for the treatment of cancer is provided. Preferably, in the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Suitable medicaments of the present embodiment include medicaments for parenteral administration, such as, for example, solutions and suspensions and medicaments for oral administration, such as, for example, tablets, capsules, solutions, and suspensions.

One embodiment at least one compound of Formula (I) and/or at least one salt thereof, for use in therapy in treating cancer. In the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma.

In one embodiment, a method is provided for treating cancer in a mammal wherein the cancer is dependent upon Notch activation, comprising administering to the patient at least one compound of Formula (I) and/or at least one salt thereof. The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Preferably, the method of this embodiment is used to treat breast cancer, colon cancer, or pancreatic cancer. Preferably, the mammal is a human. For example, a therapeutically effective amount for treating cancer may be administered in the method of the present embodiment. Suitable routes of administration include parenteral administration and oral administration.

In treating cancer, a combination of chemotherapeutic agents and/or other treatments (e.g., radiation therapy) is often advantageous. The second (or third) agent may have the same or different mechanism of action than the primary therapeutic agent. For example, drug combinations may be employed wherein the two or more drugs being administered act in different manners or in different phases of the cell cycle, and/or where the two or more drugs have nonoverlapping toxicities or side effects, and/or where the drugs being combined each has a demonstrated efficacy in treating the particular disease state manifested by the patient.

In one embodiment, a method is provided for treating cancer comprising administering to a mammal in need thereof at least one compound of Formula (I) and/or at least one salt thereof; and administering one or more additional anticancer agents.

The phrase "additional anticancer agent" refers to a drug selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/ anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MET inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Accordingly, the compounds of the present invention may be administered in combination with other anti-cancer treatments useful in the treatment of cancer or other proliferative diseases. The invention herein further comprises use of at least one compound of Formula (I) and/or at least one salt thereof in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of at least one compound of Formula (I) and/or at least one salt thereof; and one or more additional agents in kit form, e.g., where they are packaged together or placed in separate packages to be sold together as a kit, or where they are packaged to be formulated together.

In one embodiment, a method is provided for treating cancer comprising administering to a mammal in need thereof at least one compound of Formula (I) and/or at least one salt thereof; administering dasatinib; and optionally, one or more additional anticancer agents.

In one embodiment, a method is provided for treating cancer comprising administering to a mammal in need thereof at least one compound of Formula (I) and/or at least one salt thereof; administering paclitaxel; and optionally, one or more additional anticancer agents.

In one embodiment, a method is provided for treating cancer comprising administering to a mammal in need thereof at least one compound of Formula (I) and/or at least one salt thereof; administering tamoxifen; and optionally, one or more additional anticancer agents.

In one embodiment, a method is provided for treating cancer comprising administering to a mammal in need thereof at least one compound of Formula (I) and/or at least one salt thereof; administering a glucocorticoid; and optionally, one or more additional anticancer agents. An example of a suitable glucocorticoid is dexamethasone.

In one embodiment, a method is provided for treating cancer comprising administering to a mammal in need thereof at least one compound of Formula (I) and/or at least one salt thereof; administering carboplatin; and optionally, one or more additional anticancer agents.

The compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

In one embodiment, pharmaceutical compositions are provided comprising at least one compound of Formula (I) and/ or at least one salt thereof; one or more additional agents selected from a kinase inhibitory agent (small molecule, polypeptide, and antibody), an immunosuppressant, an anti-cancer agent, an anti-viral agent, antiinflammatory agent, antifungal agent, antibiotic, or an anti-vascular hyperproliferation compound; and any pharmaceutically acceptable carrier, adjuvant or vehicle.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The specific dose level and frequency of dosage for any particular subject however, may be varied and generally depends on a variety of factors, including, but not limited to, for example, the bioavailability of the specific compound of Formula (I) in the administered form, metabolic stability and length of action of the specific compound of Formula (I), species, body weight, general health, sex, diet of subject, mode and time of administration, rate of excretion, drug combination, and severity of the particular condition. For example, a daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

The administration can be continuous, i.e., every day, or intermittently. The terms "intermittent" or "intermittently" as used herein mean stopping and starting at either regular or irregular intervals. For example, intermittent administration includes administration one to six days per week; administration in cycles (e.g., daily administration for two to eight consecutive weeks followed by a rest period with no administration for up to one week); or administration on alternate days.

In one embodiment, the at least one compound of Formula (I) and/or at least one salt thereof is administered continuously to a patient in need thereof, one or more times daily. For example, a therapeutically effective amount of the compound of Formula (I) is administered to a patient in need thereof, one or more times daily for continuous days.

In one embodiment, the at least one compound of Formula (I) and/or at least one salt thereof is administered intermittently to a patient in need thereof, one or more times daily. For example, a therapeutically effective amount of the compound of Formula (I) is administered to a patient in need thereof, one or more times daily according to an intermittent schedule.

In one embodiment, the at least one compound of Formula (I) and/or at least one salt thereof is administered to a patient in need thereof, one or more times daily for continuous days followed by one or more days without administration. Preferably, a therapeutically effective amount of the compound of Formula (I) is administered. Examples of continuous dosing with a drug holiday are cycles of: 7 days on treatment followed by 7 days off treatment; 14 days on treatment followed by 7 days off treatment; and 7 days on treatment followed by 14 days off treatment. A cycle of on treatment/off treatment can be repeated multiple times as required to treat a patient.

In one embodiment, the at least one compound of Formula (I) and/or at least one salt thereof is administered to a patient in need thereof, according to an intermittent dosing schedule. Intermittent dosing schedules are repeating schedules including days in which the patient is administered the compound of Formula (I) and days in which the patient is not administered the compound of Formula (I). Examples of intermittent dosing schedules are: dosing four days each week for three continuous weeks followed by a week without dosing, and repeating on a four week interval; dosing five days each week for two continuous weeks followed by a week without dosing, and repeating on a three week interval; and dosing four days each week for one week followed by two weeks without dosing, and repeating on a three week interval. Preferably, a therapeutically effective amount of the compound of Formula (I) is administered.

In one embodiment, at least one compound of Formula (I) and/or at least one salt thereof is administered on one day, followed by 6 days of rest, and repeated on a weekly schedule.

In one embodiment, at least one compound of Formula (I) and/or at least one salt thereof is administered on one day, followed by 6 days of rest, and repeated on a weekly schedule for 1 to 4 weeks, and then followed by one week or rest. For example, the compound of Formula (I) is administered on one day, followed by 6 days of rest for three weeks, and then followed by one week of rest. This four week cycle can be repeated one or more times.

In one embodiment, at least one compound of Formula (I) and/or at least one salt thereof is administered on two consecutive days, followed by 5 days of rest, and repeated on a weekly schedule.

In one embodiment, at least one compound of Formula (I) and/or at least one salt thereof is administered on three consecutive days followed by four days of rest, and repeated on a weekly schedule.

In one embodiment, at least one compound of Formula (I) and/or at least one salt thereof is administered on one day, followed by 10 to 13 days of rest.

In one embodiment, at least one compound of Formula (I) and/or at least one salt thereof is administered once each day (QD). This embodiment include once daily oral administration.

In one embodiment, at least one compound of Formula (I) and/or at least one salt thereof is administered twice each day (BID). This embodiment include twice daily oral administration.

In one embodiment, at least one compound of Formula (I) and/or at least one salt thereof is administered on alternate days: one day on followed by one day of rest. This two day cycle can be repeated one or more times.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

The synthesis of the compounds of Formula (I) can be made using the methods summarized in Schemes 1 to 10. The synthesis of aminobenzophenone intermediate i may be accomplished by several methods skilled to one in the art, summarized in Schemes 1 to 6.

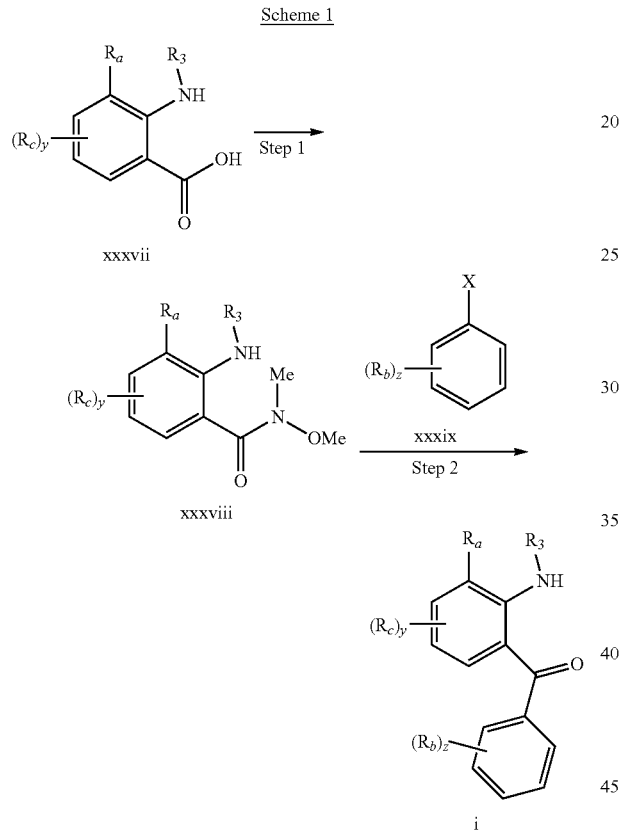

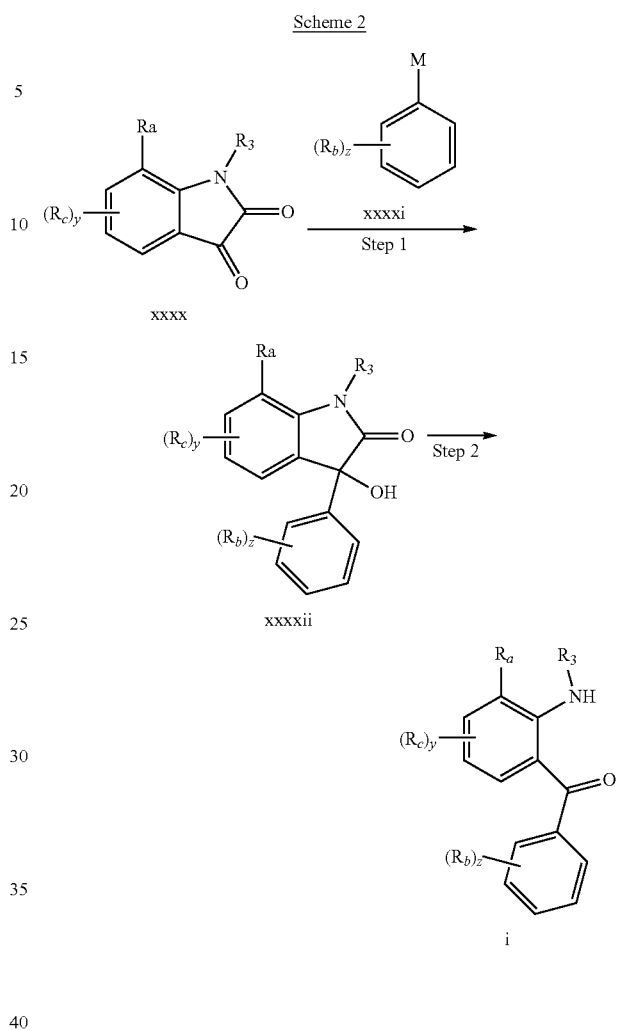

Step 1: The first step of Scheme 1 may be accomplished by coupling of a suitably substituted anthranilic acid (xxxvii), readily available to one skilled in the art, with a suitable dimethyl hydroxylamine equivalent under standard amide coupling conditions. For example, intermediate (xxxvii) may be treated with N,O-dimethylhydroxylamine hydrochloride in the presence of EDC and HOBt and a base such as triethylamine in a solvent such as DMF to form intermediate (xxxviii).

Step 2: Intermediate (xxxviii) may be transformed to the aminobenzophenone intermediate i by reaction with a suitable organometallic reagent (xxxix). For example, intermediate (xxxviii) may be treated with a preformed organolithium reagent (xxxix) (X=Li) in a solvent such as THF to form aminobenzophenone (i). Alternatively, an arylhalide (xxxix) (X=Cl, Br, or I) may be treated with an alkyllithium reagent such as butyllithium and the aryllithium reagent formed thereby may be used to effect the transformation of (xxxviii) to (i).

Step 1: The first step of Scheme 2 may be accomplished by addition of a suitably substituted organometallic reagent (xxxxi) to a suitably substituted isatin xxxx, readily available to one skilled in the art. For example, isatin (xxxx) may be treated with a Grignard reagent (xxxxi) (M=MgCl or MgBr) in a solvent such as THF at a suitable temperature such as 0° C. to give intermediate (xxxxii).

Step 2: The second step of Scheme 2 may be accomplished by treating intermediate (xxxxii) with a reagent such as potassium ferricyanide in the presence of bases such as sodium hydroxide and sodium bicarbonate in a suitable solvent mixture, such as DMF and water at a suitable temperature such as 110° C. to give aminobenzophenone intermediate (i).

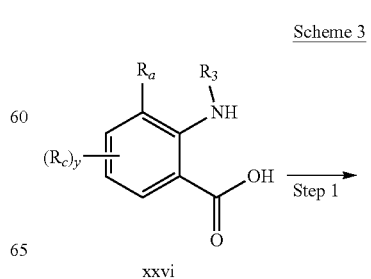

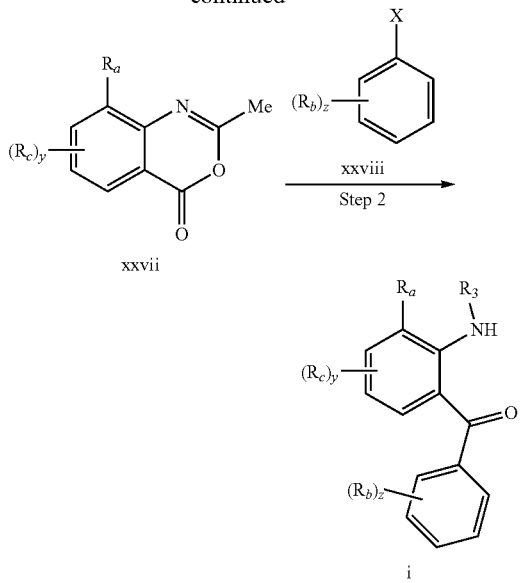

Step 1 of Scheme 3 may be accomplished by treatment of a suitably functionalized anthranilic acid (xxvi), readily available to one skilled in the art, with acetic anhydride at a suitable temperature, such as 180° C., to give intermediate (xxvii).

Step 2: Intermediate (xxvii) may be transformed to aminobenzophenone i by treatment with a functionalized organometallic reagent (xxviii). For example, intermediate xxvii may be treated with a Grignard reagent (xxviii) (M=MgBr or MgCl) in a solvent such as diethyl ether to give acetylated aminobenzophenone (i) ($R_3$=Ac). The acetyl group may then be removed by many methods known to one skilled in the art, such as treatment with HCl in a solvent such as ethanol at a suitable temperature, such as 100° C., to give aminobenzophenone (i).

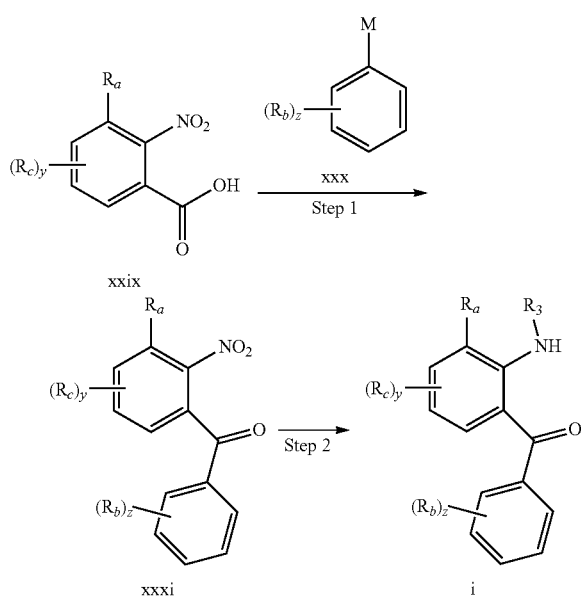

Step 1 of Scheme 4 may be accomplished by a number of methods known to one skilled in the art. For example, nitrobenzoic acid (xxix) may be converted to an acid chloride by a number of means, such as treatment with thionyl chloride at an appropriate temperature, such as 80° C. to give an acid chloride. This acid chloride may be treated with a suitable organometallic reagent (xxx), such as a Grignard reagent (M=MgBr or MgCl), in a solvent such as THF to give intermediate (xxxi).

Step 2: Conversion of intermediate (xxxi) to aminobenzophenone intermediate (i) may be accomplished by a number of methods known to one skilled in the art. For example, treatment of intermediate (xxxi) with zinc and ammonium chloride in a mixture of solvents such as ethanol and water can effect the transformation of intermediate (xxxi) to aminobenzophenone (i).

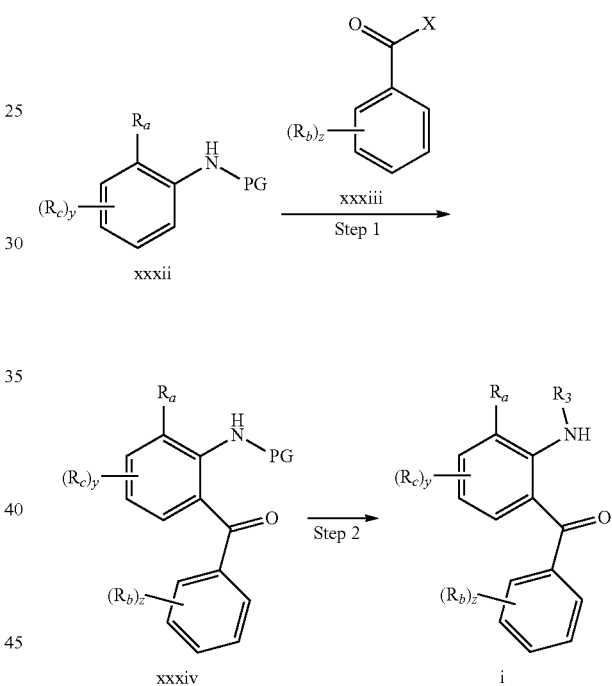

Step 1 of Scheme 5 may be accomplished by a number of methods known to one skilled in the art. For example, treatment of a suitably protected aniline (xxxii), where PG represents a suitable directing group, such as an amide or carbonate, with a base such as BuLi or t-BuLi in a solvent such as diethyl ether at an appropriate temperature such as −23° C. gives the dianion of intermediate xxxii, which may be treated with a suitable acylating agent (xxxiii), such as an ester (X=OEt), to give intermediate (i).

Step 2: The removal of the protecting group PG from intermediate (xxxiv) may be accomplished by a number of methods known to one skilled in the art. For example for PG=Boc, treatment of intermediate a in with an acid such as TFA in a solvent such as DCM effects the transformation of intermediate (xxxiv) to aminobenzophenone (i).

Scheme 6

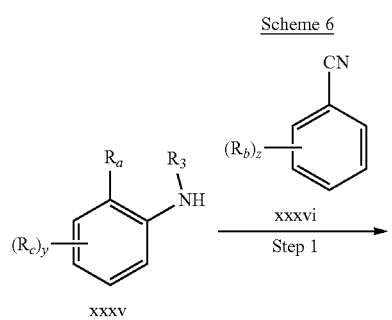

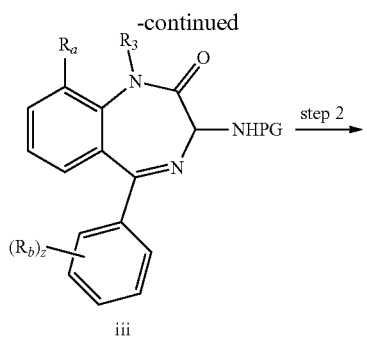

Step 1 of Scheme 6 may be accomplished by a number of methods known to one skilled in the art. For example, treatment of a suitably functionalized aniline (xxxv), readily available to one skilled in the art, with a suitable Lewis acid such as boron trichloride, followed by treatment with another Lewis acid, such as aluminum trichloride, and a suitably functionalized nitrile (xxxvi) in an appropriate solvent such as toluene at an appropriate temperature such as 60° C. gives an imine intermediate, which forms aminobenzophenone (i) upon treatment under appropriate hydrolysis conditions, such as treatment with hydrochloric acid.

Scheme 7

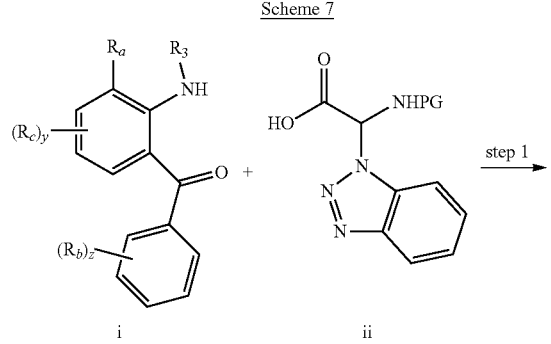

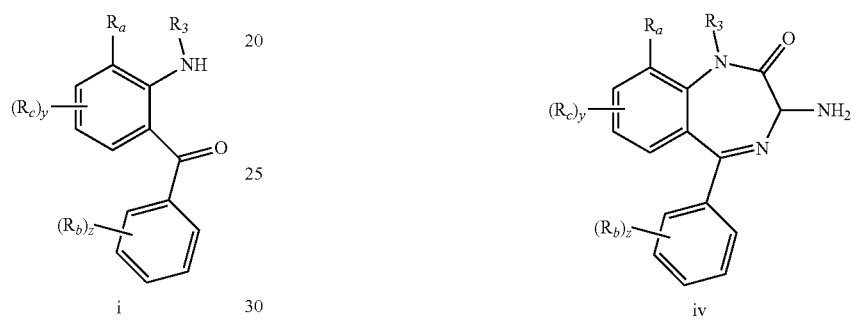

The preparation of benzodiazepinone (iv) may be accomplished in multitude of methods known to one skilled in the art. For example, as shown in Scheme 7, an appropriately substituted 2-aminobenzophenone (i) (for example, from Walsh, D. A., *Synthesis,* 677 (1980); and references cited therein, or other methods known to one skilled in the art) may be coupled to the protected glycine derivative (ii) (PG=protecting group, for example PG=CBz, see Katritzky, A. R. et al., *Org. Chem.,* 55:2206-2214 (1990), treated with a reagent such as ammonia and subjected to cyclization to afford the benzodiazepinone (iii), according to the procedure outlined in the literature (for example Sherrill, R. G. et al., *J. Org. Chem.,* 60:730 (1995); or other routes known to one skilled in the art). The resulting racemic mixture may be separated (using procedures known to one skilled in the art) to get the individual enantiomers, or used as a racemate. Also, if $R_3$ is H, (iii) may be, for example, treated with a reagent such as MeI and a base such as $K_2CO_3$ in a solvent such as DMF to prepare $R_3$ is methyl.

Step 2: The deprotection of (iii) may be accomplished in several ways known to one skilled in the art. For example, with PG=CBz, Compound (iii) may be treated with a reagent such as HBr in a solvent such as AcOH. Compound (iv) may be used as a racemate. Alternatively, compound (iv) may be subjected to enantiomeric resolution using standard methods (e.g., chiral preparative chromatography).

Scheme 8
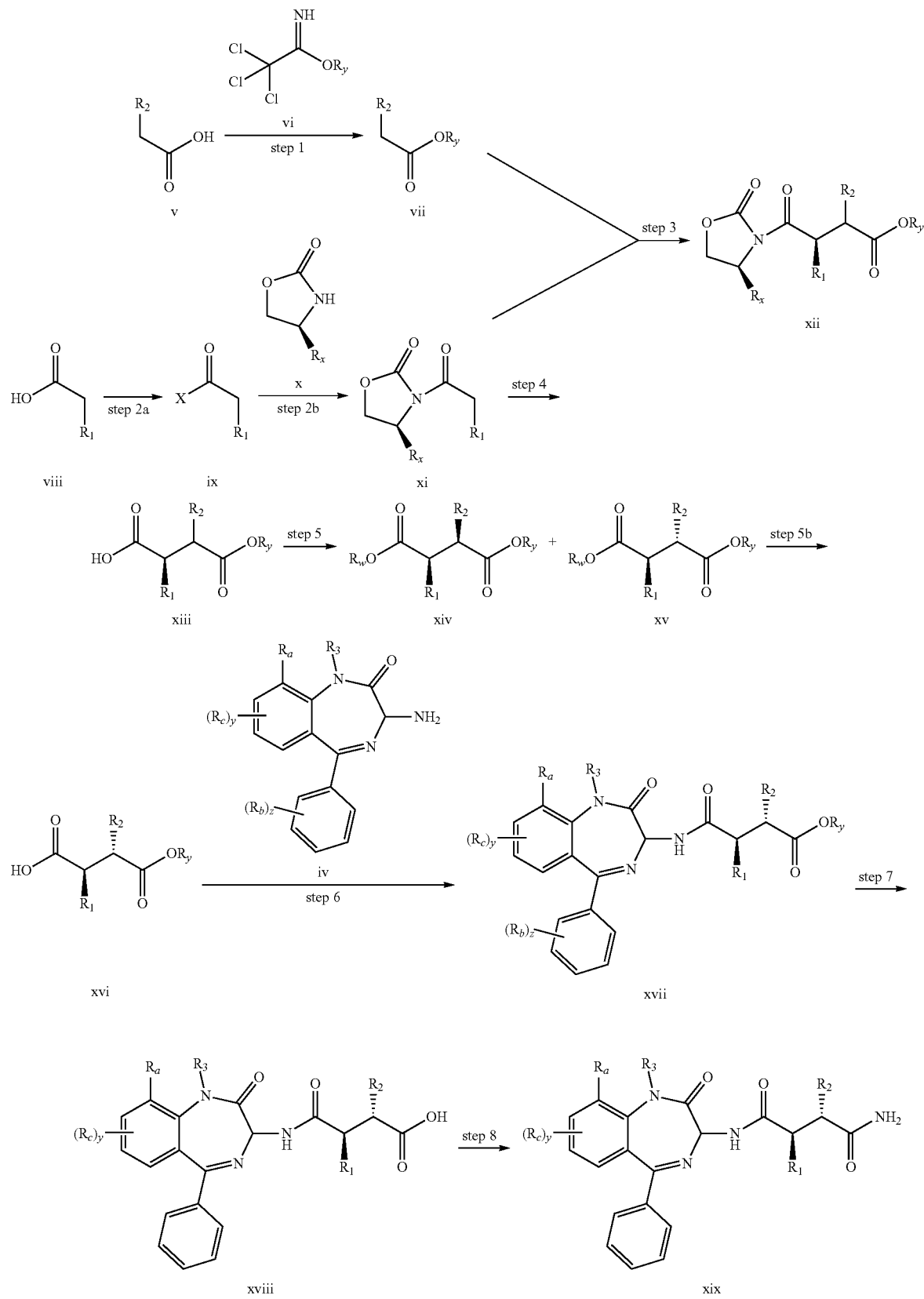

Step 1: The first step of Scheme 8 is accomplished by converting compound (v) to the ester (vii), employing one of the multiple ways known to one skilled in the art, such as treatment with a substituted acetimidate such as compound (vi) in the presence of a reagent such as boron trifluoride etherate at an appropriate temperature in a solvent such as THF.

Step 2: Acid (viii) can be converted to compound (ix) in multiple ways known to one skilled in the art. For example, treatment of acid (viii) with a reagent such as oxalyl chloride in a solvent such as DCM gives the acid chloride (ix, X=Cl). Compound (ix) can be treated with an oxazolidinone (x) under standard conditions to give compound (xi) (Evans, D. A. et al., *J. Am. Chem Soc.*, 112:4011 (1990)).

Step 3: Compound (xi) can be converted to compound (xii) in multiple ways (Baran, P. et al., *J. Am. Chem. Soc.*, 130(34): 11546 (2008)). For example, compound (vii) is treated with a base such as LDA in a solvent such as toluene, at low temperature such as −78° C. under an inert atmosphere such as $N_2$. The resulting mixture is added to a solution of compound (xi) treated with lithium chloride and a base such as LDA in a solvent such as toluene under an inert atmosphere such as $N_2$. To the resulting mixture of the enolates of compounds (vii) and (xi) is added bis(2-ethylhexanoyloxy) copper at a low temperature such as −78° C. under an inert atmosphere such as $N_2$ and warmed to room temperature to provide compound (xii).

Step 4: Conversion of compound (xii) to (xiii) may be accomplished by treating it with hydrogen peroxide and lithium hydroxide at an appropriate temperature using a mixture of solvents such as THF/water. If necessary, the diastereomers may be separated at this point via silica gel chromatography or preparative HPLC. Alternately, the mixture may be subjected to epimerization conditions, for example by treatment with LDA and diethylaluminum chloride followed by quenching with methanol or acetic acid to enrich the desired diastereomer.

Step 5: If desired, the desired (R,S)-diastereomer may be obtained in pure form by a series of steps involving protection of the carboxylic acid, separation of the diastereomers and deprotection, common steps known to one skilled in the art. For example, the mixture of diastereomers (xiii) can be protected as the benzyl ester by treating with a reagent such as benzyl bromide in the presence of base such as potassium carbonate in a solvent such as DMF. This diastereomeric mixture can then be subjected to purification procedures, for example preparative HPLC or silica gel chromatography. The diastereomerically pure material obtained can then be subjected to deprotection conditions (step 5b). For example, if R=Bn, the material can be treated under hydrogenation conditions using a catalyst such as palladium on carbon in a solvent such as MeOH under a hydrogen atmosphere.

Step 6: Benzodiazepinone (iv) may be coupled to either pure diastereomer compound (xvi) or diastereomeric mixture compound (xiii) in the presence of a coupling reagent such as TBTU and a base such as TEA, in a solvent such as DMF to provide compound (xvii) as either a diastereomerically pure compound or as a mixture of diastereoisomers, as appropriate. This mixture may be used as such in the subsequent step, or if desired, may be purified using an appropriate separation technique, such as chiral preparative chromatography to provide the diastereomerically pure compounds.

Step 7: Treatment of compound (xvii) with an acid such as TFA at an appropriate temperature such as 0° C., in a solvent such as DCM provides compound (xviii) as either a diastereomerically pure compound or as a mixture of diastereoisomers. This mixture may be used as such in the subsequent step, or if desired, may be purified using an appropriate separation technique, such as chiral preparative chromatography to provide the diastereomerically pure compounds.

Step 8: Conversion of compound (xviii) to compound (xix) may be accomplished via coupling of compound (xviii) with an appropriate amine source such as ammonium chloride, a carbodiimide such as EDC, HOBT and a base such as TEA in a solvent such as DMF. If necessary the diastereomeric mixture can be separated using an appropriate separation technique, such as chiral preparative chromatography.

Scheme 9

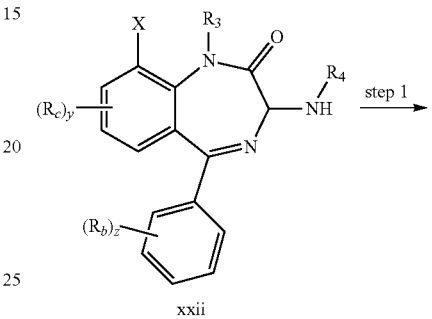

xxii

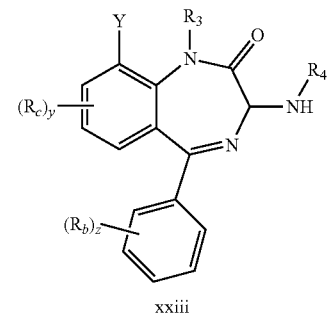

xxiii

Step 1: The first step of Scheme 9 is accomplished by cross coupling of intermediate (xxii) containing a halogen atom such as chlorine, bromine, or iodine (X=Cl, Br, or I) and where $R_4$ is a suitable group such as a carbamate or amide, with an appropriate coupling partner such as a boronic acid or organozinc compound under conditions known to one skilled in the art. For example, the coupling of the halogen containing moiety with a organozinc occurs in the presence of a catalyst such as tetrakis bis(tri-t-butylphosphine)palladium (0), zinc dust and a solvent such as DMF under an inert atmosphere such as $N_2$ to give intermediate (xiii), which may be employed as appropriate in Schemes 7 and 8.

Scheme 10

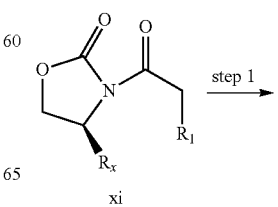

xi

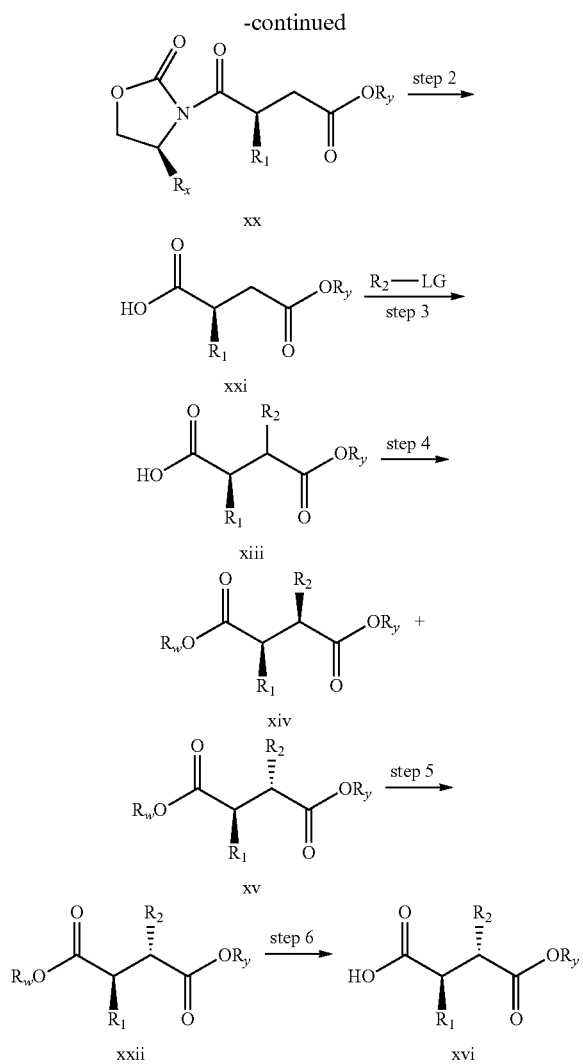

formed to another substituent. For example, using a different reactant ($R_2$-LG), such as allyl bromide, installs a suitable grouping for future modifications. Epimerization conditions, as noted above, may also be employed on this compound if desired.

Step 4: The fourth step of Scheme 10 is similar to that of step 5 in Scheme 8 and may be omitted if compound (xiii) will be used directly in, for example, step 6 of Scheme 8. However, if further manipulation of, for example, $R_2$ of compound (xiii) is desired, the carboxylic acid moiety of compound (xiii) may be protected with a suitable protecting group, for example a benzyl group. Hence, compound (xiii) may be treated with a reactant such as benzyl bromide, in the presence of a base such as potassium carbonate in a suitable solvent such as DMF. The resulting mixture of diastereoisomers may be separated if desired, employing suitable conditions such as preparative HPLC, preparative chiral HPLC or silica gel chromatography, and the resulting pure desired diastereoisomer compound (xv) used in the subsequent steps.

Step 5: If the $R_2$ group in compound (xv) is the desired moiety, then step 5 may be omitted. However, if the $R_2$ group is a moiety on which further modifications is desired, this may be done at this time. For example, if $R_2$=allyl, treatment of compound (xv) under cyclopropanation conditions may provide a functional group of a preferred embodiment. Consequently, compound (xv) where $R_2$=allyl may be treated with a reagent such as diazomethane, in the presence of a catalyst such as palladium acetate in a suitable solvent such as diethyl ether at a suitable temperature such as 0° C. to afford compound (xxii).

Step 6: The last step of Scheme 6 is a deprotection step, similar to step 5b of Scheme 8, and may be accomplished in several ways known to one skilled in the art. For example, for $R_w$=benzyl in compound (xxii), treatment under hydrogenation conditions using a catalyst such as palladium on carbon in a solvent such as MeOH under a hydrogen atmosphere may provide compound (xvi) that may subsequently be utilized, for example, in Step 6 of Scheme 8.

Compound (xiii) in Scheme 8 may also be prepared from compound (xi) by a synthetic sequence outlined in Scheme 10.

Step 1: The first step of Scheme 10 is accomplished by treating compound (xi) with a base such as sodium bis(trimethylsilyl)amide in a solvent such as THF at low temperature such as −78° C. under an inert atmosphere. To the resulting enolate of (xi) is treated with a reagent such as tert-butyl bromoacetate to provide compound (xx).

Step 2: Conversion of compound (xx) to (xxi) may be accomplished by treating compound (xx) with hydrogen peroxide and lithium hydroxide at an appropriate temperature using a mixture of solvents such as THF/water.

Step 3: Compound (xxi) can be converted to compound (xiii) by generating the enolate of (xxi) with a base such as LDA in a solvent such as THF at low temperature such as −78° C. under an inert atmosphere and further treatment with a reagent ($R_2$-LG) bearing an appropriate leaving group (e.g., LG=triflate). Compound (xiii) may then be utilized, for example, in step 6 of Scheme 8. Alternately, the mixture may be subjected to epimerization conditions, for example by treatment with LDA and diethylaluminum chloride followed by quenching with methanol or acetic acid to enrich the desired diastereomer. Moreover, a preferred embodiment entails the installation of a moiety that may later be trans- Abbreviations AcOH acetic acid
Boc tert-butoxycarbonyl
$Boc_2O$ di-tert-butyl dicarbonate
DCM dichloromethane
DMF dimethylformamide
DMSO dimethyl sulfoxide
dppf 1,1'-bis(diphenylphosphino)ferrocene
EDC 1-(3-dimethylaminopropyl)-3-ethylcarbodiimide hydrochloride
$Et_3N$ triethyl amine
$Et_2O$ diethyl ether
EtOH ethanol
EtOAc ethyl acetate
equiv. equivalents
g gram
h hour(s)
HPLC high pressure liquid chromatography
HOBt 1-hydroxybenzotriazole hydrate
KOtBu potassium tert-butoxide
LCMS Liquid Chromatography-Mass Spectroscopy
LDA lithium diisopropylamide
MeOH methanol
min minute(s)
mL milliliter
mmol millimolar
NaHMDS sodium bis(trimethylsilyl)amide n-BuLi n-butyl lithium
NH₄Oac ammonium acetate
Pd(OAc)₂ palladium acetate
pyBOP benzotriazol-1-yloxytripyrrolidino-phosphonium hexafluorophosphate
RT retention time
t-Bu tertiary butyl
tBuOH tertiary butyl alcohol
tBuOMe tert-butyl methyl ether
TBTU O-(1H-benzotriazol-1-yl)-N,N,N',N'-tetramethyluronium tetrafluoroborate
TEA triethylamine
TFA trifluoroacetic acid
THF tetrahydrofuran
TMEDA N,N,N',N'-tetramethylethylenediamine

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

Intermediate S1

(R)-2-((S)-1-tert-Butoxy-3-cyclopropyl-1-oxopropan-2-yl)-5,5,5-trifluoropentanoic acid

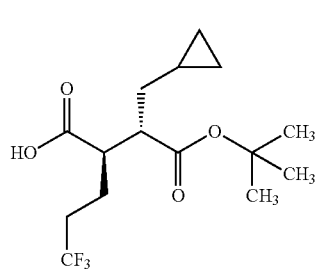

(S1)

Intermediate S1A (4S)-4-(Propan-2-yl)-3-(5,5,5-trifluoropentanoyl)-1,3-oxazolidin-2-one

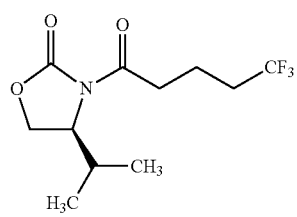

(S1A)

To a stirred solution of 5,5,5-trifluoropentanoic acid (5.04 g, 32.3 mmol) in DCM (50 mL) and DMF (3 drops) was added oxalyl chloride (3.4 mL, 38.8 mmol) dropwise over 5 min. The solution was stirred until all bubbling subsided. The reaction mixture was concentrated under reduced pressure to give a pale yellow oil. To a separate flask charged with a solution of (4S)-4-(propan-2-yl)-1,3-oxazolidin-2-one (4.18 g, 32.4 mmol) in THF (100 mL) at −78° C. was added n-BuLi (13.0 mL, 32.5 mmol, 2.5M in hexane) dropwise via syringe over 5 min. After stirring for 10 min, the above acid chloride dissolved in THF (20 mL) was added via cannula over 15 min. The reaction mixture was warmed to 0° C., and was allowed to warm to room temperature as the bath warmed and stirred overnight. To the reaction mixture was added saturated NH₄Cl, and then extracted with EtOAc (2×). The combined organics were washed with brine, dried (Na₂SO₄), filtered and concentrated under reduced pressure. The crude material was purified by silica gel chromatography (hexanes/EtOAc) to provide Intermediate S1A (7.39 g, 86%) as a colorless oil: $^1$H NMR (400 MHz, CDCl₃) δ 4.44 (1H, dt, J=8.31, 3.53 Hz), 4.30 (1H, t, J=8.69 Hz), 4.23 (1H, dd, J=9.06, 3.02 Hz), 2.98-3.08 (2H, m), 2.32-2.44 (1H, m, J=13.91, 7.02, 7.02, 4.03 Hz), 2.13-2.25 (2H, m), 1.88-2.00 (2H, m), 0.93 (3H, d, J=7.05 Hz), 0.88 (3H, d, J=6.80 Hz).

Intermediate S1B tert-Butyl 3-cyclopropylpropanoate

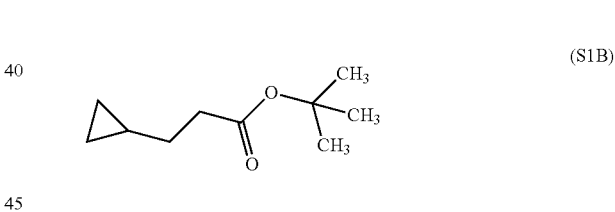

(S1B)

To a cool (0° C., precooled for at least 15 min), stirred solution of 3-cyclopropylpropanoic acid (5 g, 43.8 mmol) in hexane (30.0 mL) and THF (30 mL) under N₂ was added tert-butyl 2,2,2-trichloroacetimidate (15.7 mL, 88 mmol) portion wise over 5 min. The reaction mixture was stirred for 15 min. Boron trifluoride ether complex (0.555 mL, 4.38 mmol) was added and the reaction mixture was allowed to warm to room temperature as the bath warmed overnight. To the clear reaction mixture was added NaHCO₃ (5 g) and stirred for 60 min. The suspension was filtered through MgSO₄ and washed with 300 mL hexane. The filtrate was allowed to sit, then the resulting solid was filtered through the same MgSO₄ filter, washed with hexane (100 mL). The filtrate was concentrated under vacuo with the water bath not turned on. The residue was purified by silica gel chromatography (hexanes/EtOAc) to provide Intermediate S1B (6.05 g, 81%) as clear oil: $^1$H NMR (400 MHz, CDCl₃) δ 2.29 (2H, t, J=7.48 Hz), 1.35-1.54 (11H, m), 0.60-0.75 (1H, m), 0.29-0.46 (2H, m), −0.06-0.10 (2H, m).

Intermediate S1C (2S,3R)-tert-Butyl 2-(cyclopropylmethyl)-6,6,6-trifluoro-3-((S)-4-isopropyl-2-oxooxazolidine-3-carbonyl)hexanoate, and

Intermediate S1D (2R,3R)-tert-Butyl 2-(cyclopropylmethyl)-6,6,6-trifluoro-3-((S)-4-isopropyl-2-oxooxazolidine-3-carbonyl)hexanoate

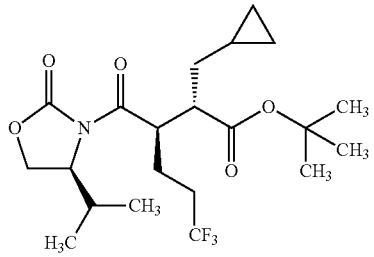
(S1C)

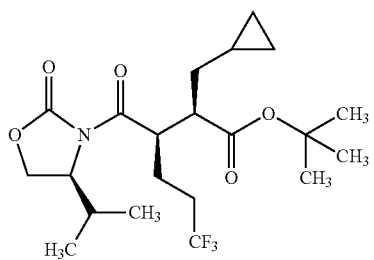
(S1D)

Diisopropylamine (6.64 ml, 46.6 mmol) was dissolved in 71.7 mL of THF and cooled to −78° C., then n-BuLi (18.0 mL, 44.9 mmol, 2.5M in hexane) was added dropwise over a period of 5 minutes. After 5 minutes, the resulting 0.5 M LDA solution was kept at 0° C.

In a separate flask, lithium chloride (2.62 g, 61.7 mmol) was dried under high vacuum with heating and cooled under nitrogen. Intermediate S1A (3.0 g, 11.23 mmol), azeotroped once with toluene, was transferred with 15.0 mL toluene to the flask containing LiCl, and cooled to −78° C. To this stirring suspension was added LDA (25.83 mL, 12.91 mmol, 1.15 equiv., 0.5M LDA) dropwise via syringe over 5 min. The reaction mixture was stirred at −78° C. for 15 minutes, then at 0° C. for 10 minutes and cooled to −78° C.

In a separate flask, Intermediate S1B (3.44 g, 20.21 mmol) was dissolved in 15.0 mL toluene under $N_2$ and cooled to −78° C. To this solution was added LDA (46.48 mL, 23.24 mmol, 1.15 equiv., 0.5M LDA) dropwise and stirred at −78° C. for 30 minutes, at which time this solution was added via cannula (fast negative pressure, all added within 30 seconds) to the LiCl/oxazolidone solution at −78° C. After 1 minute following transfer, solid bis(2-ethylhexanoyloxy)copper (10.80 g, 30.9 mmol) was added at −78° C., and the flask was transferred to 40° C. water bath and swirled vigorously for 15 minutes, and quenched over 5% $NH_4OH$ solution (20 mL saturated $NH_4OH$ and 100 mL water), and extracted with ethyl acetate (2×100 mL). The pooled organic phases were washed with brine, dried ($Na_2SO_4$), filtered, concentrated and purified by silica gel chromatography (hexanes/EtOAc) to afford a mixture of Intermediate S1C and Intermediate S1D (1.58 g, 32% yield) as an oil. $^1$H NMR showed this material to be a 1.5:1 mixture of S1C:S1D, by integration of the t-Bu peaks: $^1$H NMR of diastereoisomer mixture (400 MHz, CDCl$_3$) δ 4.53-4.41 (m, 2H), 4.39-4.19 (m, 5H), 4.10-4.01 (m, 1H), 2.89-2.77 (m, 2H), 2.47-2.26 (m, 2H), 2.16-1.72 (m, 8H), 1.47 (s, 9H, t-Bu of S1C, integrates for relative intensity of 1.5), 1.46 (s, 9H, t-Bu of S1D, integrates for relative intensity of 1), 0.98-0.86 (m, 16H), 0.78-0.64 (m, 2H), 0.56-0.37 (m, 4H), 0.14-0.01 (m, 4H).

Intermediate S1

(R)-2-((S)-1-tert-Butoxy-3-cyclopropyl-1-oxopropan-2-yl)-5,5,5-trifluoropentanoic acid, and

Intermediate S1E (R)-2-((R)-1-tert-Butoxy-3-cyclopropyl-1-oxopropan-2-yl)-5,5,5-trifluoropentanoic acid

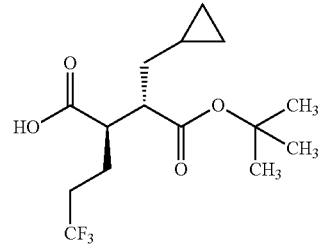
(S1)

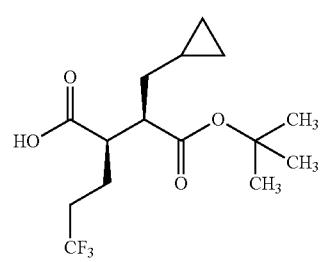
(S1E)

To a cool (0° C.), stirred solution of a mixture of Intermediates S1C:S1D (3.4 g, 7.81 mmol) in THF (60 mL) and water (20 mL) was added 30% $H_2O_2$ (4.82 mL, 79 mmol) followed by LiOH (0.567 g, 23.66 mmol). The reaction mixture was allowed to gradually warm up to room temperature and stirred at room temperature for 3 h. To the reaction mixture was added saturated $Na_2SO_3$ (20 mL) and saturated $NaHCO_3$ (40 mL), and then stirred for 5 min. The reaction mixture was partially concentrated and extracted with DCM (80 mL). The aqueous phase was acidified to pH ~2, saturated with NaCl, extracted with EtOAc (2×). The combined extracts were dried (MgSO$_4$), filtered and concentrated to provide a mixture of Intermediate S1 and Intermediate S1E (2.01 g, 79%). $^1$H NMR showed this material to be a 1.4:1 mixture of S1:S1E, by integration of the t-Bu peaks: $^1$H NMR of mixture of diastereomers (400 MHz, CDCl$_3$) δ 2.82-2.59 (m, 4H), 2.31-2.03 (m, 4H), 1.95-1.52 (m, 7H), 1.44 (s, 9H, t-Bu of S1, integrates for relative intensity of 1.4), 1.42 (s, 9H, t-Bu of S1E, integrates for relative intensity of 1), 0.93 (d, J=6.6 Hz, 1H), 0.88 (d, J=6.8 Hz, 1H), 0.74-0.57 (m, 2H), 0.43 (t, J=6.8 Hz, 3H), 0.11--0.04 (m, 3H).

Intermediate S1

(R)-2-((S)-1-tert-Butoxy-3-cyclopropyl-1-oxopropan-2-yl)-5,5,5-trifluoropentanoic acid, and Intermediate S1E (R)-2-((R)-1-tert-Butoxy-3-cyclopropyl-1-oxopropan-2-yl)-5,5,5-trifluoropentanoic acid, an enriched mixture

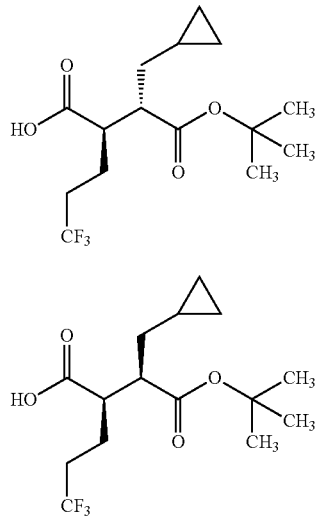

(S1)

(S1E)

To a cold (−78° C.), stirred solution of a 1.4:1 mixture of Intermediate S1 and S1E (2.00 g, 6.17 mmol) in THF (30 mL) under $N_2$ was added LDA (7.54 mL, 13.57 mmol, 1.8M) via syringe over 5 min, stirred for 15 min, warmed to room temperature (24° C. water bath), stirred for 15 min, cooled to −78° C. for 15 min. To the reaction mixture was added diethylaluminum chloride (12.95 mL, 12.95 mmol, 1M in hexane) via syringe, stirred for 10 min, warmed to room temperature (24° C. bath) for 15 min then back to −78° C. for 25 min. MeOH (38.9 mL, 962 mmol) was rapidly added, removed from bath then ice and 1N HCl (55.5 mL, 55.5 mmol) was gradually added was added slowly. Once gas evolution subsided, the mixture was extracted with EtOAc (2×), the combined organics washed with a solution of potassium fluoride (3.26 g, 56.2 mmol) in water (106 mL, 5895 mmol) and 1N HCl (15.72 mL, 15.72 mmol), brine then dried ($Na_2SO_4$). The mixture was subsequently filtered and concentrated to afford a~2:1 (S1:S1E, as determined by integration of the t-Bu peaks in the $^1$H NMR) enriched mixture of Intermediate S1 and Intermediate S1E (1.79 g, 90%). $^1$H NMR of mixture of diastereomers (400 MHz, $CDCl_3$) δ 2.87-2.57 (m, 2H), 2.36-2.06 (m, 2H), 1.97-1.81 (m, 2H), 1.81-1.70 (m, 1H), 1.70-1.56 (m, 1H), 1.47 (s, 9H, t-Bu of S1, integrates for relative intensity of 2.0), 1.45 (s, 9H, t-Bu of S1E, integrates for relative intensity of 1), 0.99-0.87 (m, 1H), 0.77-0.61 (m, 1H), 0.54-0.38 (m, 2H), 0.16--0.01 (m, 2H).

Intermediate S1F (2R,3S)-1-Benzyl 4-tert-butyl 3-(cyclopropylmethyl)-2-(3,3,3-trifluoropropyl)succinate, and Intermediate S1G (2R,3R)-1-Benzyl 4-tert-butyl 3-(cyclopropylmethyl)-2-(3,3,3-trifluoropropyl)succinate

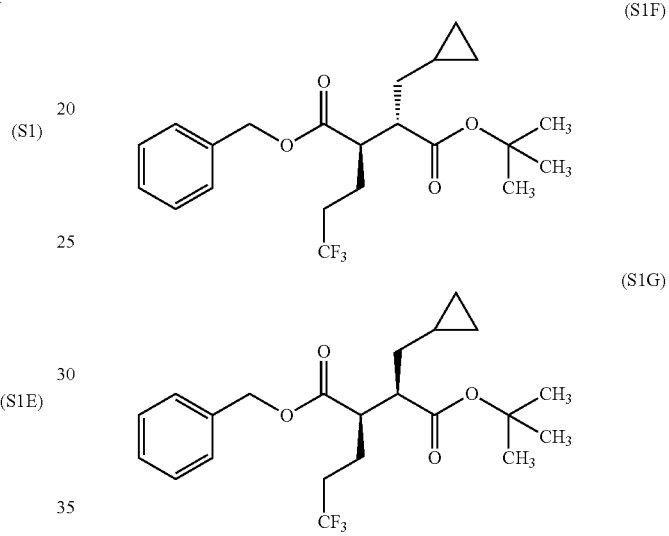

To a stirred solution of a 2.15:1 mixture of Intermediates S1 and S1E (2.22 g, 6.84 mmol) and benzyl bromide (0.98 ml, 8.24 mmol) in DMF (25 ml) was added potassium carbonate (1.41 g, 10.20 mmol). The reaction mixture was then stirred for 5.5 h. The reaction mixture was diluted with EtOAc (300 mL), washed with 10% LiCl (3×100 mL), saturated NaCl, then dried ($Na_2SO_4$), filtered and concentrated. The residue was purified by silica gel chromatography (hexane:toluene) to give Intermediate S1F (1.5 g, 53%) and Intermediate S1G (0.778 g, 27%). Intermediate S1F: $^1$H NMR (400 MHz, $CDCl_3$) δ 7.43-7.31 (m, 29H), 5.17 (d, J=11.9 Hz, 6H), 5.13 (d, J=11.9 Hz, 6H), 2.75-2.64 (m, 11H), 2.19-1.94 (m, 12H), 1.93-1.81 (m, 6H), 1.79-1.69 (m, 6H), 1.63-1.56 (m, 4H), 1.46 (s, 47H), 1.14 (ddd, J=13.8, 7.2, 3.5 Hz, 6H), 0.68-0.55 (m, 6H), 0.45-0.37 (m, 11H), −0.02--0.11 (m, 6H). Intermediate S1G: $^1$H NMR (400 MHz, $CDCl_3$) δ 7.40-7.32 (m, 5H), 5.16 (d, J=12.3 Hz, 1H), 5.13 (d, J=12.1 Hz, 1H), 2.88-2.79 (m, 1H), 2.74 (ddd, J=8.8, 7.3, 4.4 Hz, 1H), 2.18-1.93 (m, 2H), 1.90-1.79 (m, 2H), 1.70-1.59 (m, 1H), 1.44 (s, 9H), 1.31 (ddd, J=14.1, 7.3, 4.5 Hz, 1H), 0.73-0.61 (m, 1H), 0.49-0.38 (m, 2H), 0.10-0.03 (m, 1H), −0.01--0.07 (m, 1H).

Intermediate S1

Intermediate S1F (2.80 g, 6.76 mmol) was dissolved in ethyl acetate (26.0 mL) and methanol (26.0 mL). Palladium on carbon (10% wet Degussa, 0.539 g, 0.507 mmol) was added, then the atmosphere was exchanged for $H_2$ three times. The reaction mixture was stirred about 2 h, then filtered with MeOH washes. The filtrate was concentrated to give Intermediate S1 (2.19 g, 100% yield): $^1$H NMR (400 MHz, CDCl$_3$) δ 2.79-2.67 (m, 2H), 2.36-2.21 (m, 1H), 2.18-2.03 (m, 1H), 1.94 (dtd, J=14.6, 9.8, 4.8 Hz, 1H), 1.78 (ddd, J=11.1, 5.3, 3.0 Hz, 1H), 1.63 (ddd, J=13.9, 9.2, 7.0 Hz, 1H), 1.49 (s, 9H), 1.35 (ddd, J=13.8, 7.0, 3.9 Hz, 1H), 0.77-0.63 (m, 1H), 0.48 (dq, J=8.1, 1.7 Hz, 2H), 0.15-0.02 (m, 2H).

An alternate method to prepare Intermediate S1F, and hence Intermediate S1:

Intermediate S1H (S)-4-Benzyl-3-(5,5,5-trifluoropentanoyl)oxazolidin-2-one

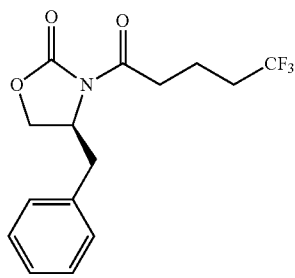

(S1H)

To a stirring solution of 5,5,5-trifluoropentanoic acid (71.4 g, 457 mmol) in DCM (315 mL) and 5 drops of DMF was added oxalyl chloride (229 mL, 457 mmol). The reaction mixture was then stirred until gas evolution subsided. The reaction mixture was concentrated, and the material was used below.

A separate flask was charged with (S)-4-benzyloxazolidin-2-one (60 g, 339 mmol) and THF (315 mL), cooled to −78° C., followed by the dropwise addition of n-butyl lithium (183 mL, 2.5M, 457 mmol). A heavy suspension resulted during addition, therefore additional THF (315 mL) was added. Once the addition of BuLi was ended, to the reaction mixture was added a solution of the above acid chloride in THF (150 mL) dropwise, stir for 10 minutes at −78° C., then allowed to warm to room temperature. The reaction mixture was quenched with aqueous saturated NH$_4$Cl solution at 0-5° C. The reaction mixture was extracted with EtOAc, washed with water, brine, dried (Na$_2$SO$_4$), filtered and concentrated. The residue was purified by silica gel chromatography (hexane/EtOAc) to provide Intermediate S1H (87 g, 81%): $^1$H NMR (400 MHz, CDCl$_3$) δ 7.32-7.39 (2H, m), 7.30 (1H, d, J=7.05 Hz), 7.18-7.25 (2H, m), 4.64-4.74 (1H, m), 4.17-4.27 (2H, m), 3.31 (1H, dd, J=13.35, 3.27 Hz), 3.00-3.11 (2H, m), 2.79 (1H, dd, J=13.35, 9.57 Hz), 2.16-2.28 (2H, m), 1.93-2.04 (2H, m).

Intermediate S1I tert-Butyl (3R)-3-(((4S)-4-benzyl-2-oxo-1,3-oxazolidin-3-yl)carbonyl)-6,6,6-trifluorohexanoate

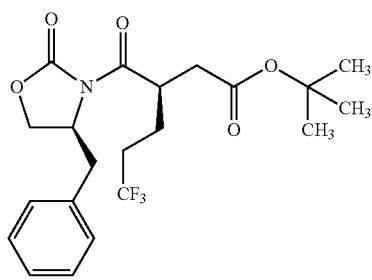

(S1I)

To a cold (−78° C.), stirred solution of Intermediate S1H (43 g, 136 mmol) in THF (150 mL) was added NaHMDS (150 mL, 1.0M in THF, 150 mmol) under nitrogen atmosphere. After 2 hours, tert-butyl 2-bromoacetate (53.2 g, 273 mmol) in THF (100 mL) was added at −78° C. and stirring was maintained at the same temperature. After 6 hours, the reaction mixture was warmed to room temperature. The reaction mixture was partitioned between saturated NH$_4$Cl and EtOAc. The organic phase was separated, and the aqueous layer was extracted with EtOAc (3×). The combined organics were washed with brine, dried (Na$_2$SO$_4$), filtered and concentrated under reduced pressure. The residue was purified by silica gel chromatography (hexane/EtOAc) to provide Intermediate S1I (37 g, 63%): $^1$H NMR (400 MHz, CDCl$_3$) δ 7.34 (2H, d, J=7.30 Hz), 7.24-7.32 (3H, m), 4.62-4.75 (1H, m, J=10.17, 6.89, 3.43, 3.43 Hz), 4.15-4.25 (3H, m), 3.35 (1H, dd, J=13.60, 3.27 Hz), 2.84 (1H, dd, J=16.62, 9.57 Hz), 2.75 (1H, dd, J=13.35, 10.07 Hz), 2.47 (1H, dd, J=16.62, 4.78 Hz), 2.11-2.23 (2H, m), 1.90-2.02 (1H, m), 1.72-1.84 (1H, m), 1.44 (9H, s).

Intermediate S1J (2R)-2-(2-tert-Butoxy-2-oxoethyl)-5,5,5-trifluoropentanoic acid

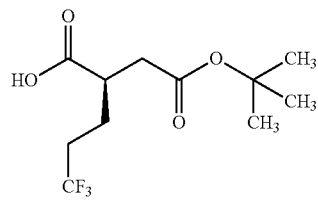

(S1J)

To a cool (0° C.), stirred solution of Intermediate S1I (26 g, 60.5 mmol) in THF (390 mL) and water (104 mL) was added H$_2$O$_2$ (24.1 mL, 236 mmol) followed by LiOH (2.75 g, 115 mmol) as a solution in water (28 mL). The reaction mixture was allowed to gradually warm to room temperature and stirred at room temperature for 3 h. The reaction mixture was cooled to 0° C., then saturated Na$_2$SO$_3$ and saturated NaHCO$_3$ were added. The reaction mixture was stirred for 5 min, and then partially concentrated and extracted with DCM (20 ml). The aqueous phase was acidified to pH ~3, extracted with EtOAc. The extract was dried (Na$_2$SO$_4$), filtered and concentrated to obtain Intermediate S1J (15 g, 92%): $^1$H NMR (400 MHz, CDCl$_3$) δ 2.83-2.95 (1H, m), 2.62-2.74 (1H, m), 2.45 (1H, dd, J=16.62, 5.79 Hz), 2.15-2.27 (2H, m), 1.88-2.00 (1H, m), 1.75-1.88 (1H, m), 1.45 (9H, s).

Intermediate S1K (2R,3S)-3-(tert-Butoxycarbonyl)-2-(3,3,3-trifluoropropyl)hex-5-enoic acid, and Intermediate S1L (2R,3R)-3-(tert-Butoxycarbonyl)-2-(3,3,3-trifluoropropyl)hex-5-enoic acid

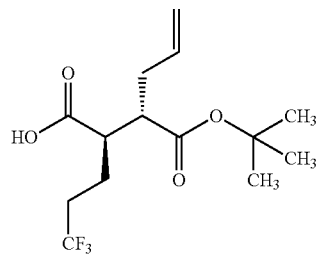

(S1K)

-continued

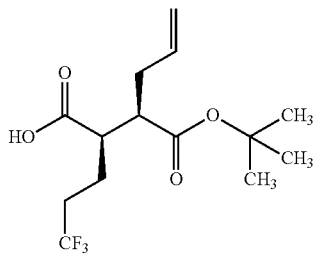
(S1L)

A flask was charged with THF (150 ml), then cooled to −20° C., then with stirring n-butyllithium (53.9 ml, 2.5 M in hexane, 135 mmol) was added, followed by diisopropylamine (19.4 ml, 137 mmol) over 55 min while maintaining the internal temperature at less than −8.5° C. After the addition was complete, the solution was stirred at 0° C. for 45 min, and then cooled to −78° C. To this was added a solution of Intermediate S1J (14.56 g, 53.9 mmol) in THF (15.0 ml) over 20 min, while maintaining internal temperature at less than −72° C. After addition was complete, the mixture was stirred at −78° C. for 100 min. To this was added 3-bromoprop-1-ene (6.38 ml, 75 mmol) over 10 min. The reaction mixture was stirred allowed to slowly warm to room temperature as bath warmed, and stirred overnight. To the solution was added ice and 1N HCl (215 mL) to pH about 1, then the solution was saturated with NaCl. The layers were separated. The aqueous layer was extracted with EtOAc (1×250 mL, 1×150 mL). The combined organic phases were washed with brine (1×300 mL), dried (MgSO$_4$), filtered, and evaporated. The residue was treated with benzene (50 mL) and evaporated twice, dried in vacuo to give a mixture of Intermediate S1K and Intermediate S1L (16.8 g, 100%). $^1$H NMR indicated a ratio 1:2 for S1K:S1L. $^1$H NMR of diastereoisomer mixture (400 MHz, CDCl$_3$) δ 5.81-5.66 (m, 1H), 5.17-5.04 (m, 2H), 2.81-2.62 (m, 2H), 2.45-2.38 (m, 2H), 2.33-2.03 (m, 3H), 1.96-1.83 (m, 2H), 1.45 (s, 9H, t-Bu of S1K, integrates for relative intensity of 1), 1.44 (s, 9H, t-Bu of S1L, integrates for relative intensity of 2).

Intermediate S1K (2R,3S)-3-(tert-Butoxycarbonyl)-2-(3,3,3-trifluoropropyl)hex-5-enoic acid, and Intermediate S1L (2R,3R)-3-(tert-Butoxycarbonyl)-2-(3,3,3-trifluoropropyl)hex-5-enoic acid, an enriched mixture

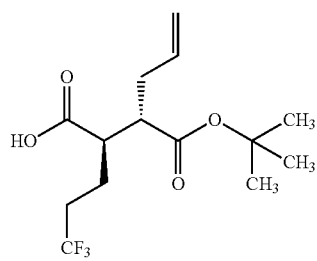
(S1K)

-continued

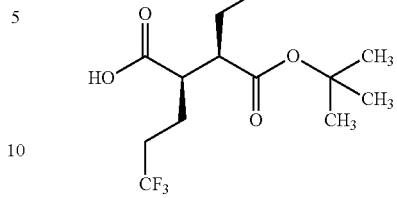
(S1L)

To a cold (−78° C.) stirred solution of a mixture of Intermediate S1K and Intermediate S1L (10 g, 32.2 mmol) in THF (150 mL) was slowly added LDA (39.4 mL, 70.9 mmol, 1.8M in heptane/THF/ethylbenzene). After stirring for 15 min the reaction mixture was placed in a room temperature water bath. After 15 min the reaction mixture was placed back in a −78° C. bath, stirred for 15 min then diethylaluminum chloride (81 mL, 81 mmol, 1M in hexane) was added via addition funnel. The reaction mixture was stirred at −78° C. After 10 min the reaction mixture was placed in a room temperature water bath for 15 min and then cooled back to −78° C. for 15 min. Meanwhile, a separate flask was charged MeOH (300 mL) and cooled to −78° C. The reaction mixture was then transferred to the cold and rapidly stirring MeOH via cannula by nitrogen pressure. After the transfer was complete ice (86 g) was added to the reaction mixture followed by slow addition of 1N HCl (300 mL). The reaction mixture was stirred until all gas evolution subsided. EtOAc (400 mL) was added, the phases separated, and the aqueous phase was extracted with EtOAc (300 mL). The combined EtOAc layers were washed with a mixture of potassium fluoride (17 g) in 600 mL H$_2$O and 1N HCl (86 mL), followed by brine. The organic phase was dried (Na$_2$SO$_4$), filtered and concentrated under reduced pressure to provide a 7:1 (S1K:S1L) enriched mixture of Intermediate S1K and Intermediate S1L (10.0 g, 100%): $^1$H NMR of diastereoisomer mixture (400 MHz, CDCl$_3$) δ 5.81-5.66 (m, 1H), 5.17-5.04 (m, 2H), 2.81-2.62 (m, 2H), 2.45-2.38 (m, 2H), 2.33-2.03 (m, 3H), 1.96-1.83 (m, 2H), 1.45 (s, 9H, t-Bu of S1K, integrates for relative intensity of 7), 1.44 (s, 9H, t-Bu of S1L, integrates for relative intensity of 1).

Intermediate S1M (2S,3R)-4-Benzyl 1-tert-butyl 2-allyl-3-(3,3,3-trifluoropropyl) succinate

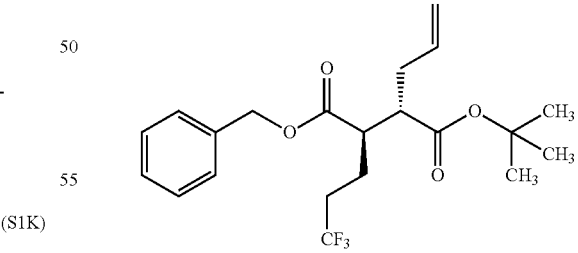
(S1M)

To a stirred solution of a 7:1 enriched mixture of Intermediate S1K and Intermediate S1L (10 g, 32.2 mmol) in DMF (100 ml) was added benzyl bromide (4.6 ml, 38.7 mmol) and potassium carbonate (6.68 g, 48.3 mmol). The reaction mixture was stirred for two hours at room temperature. To the reaction mixture was added Et$_3$N (9.0 mL. 64.5 mmol), followed by stirring for 60 min. The reaction mixture was diluted with Et$_2$O, washed with 10% LiCl (3×100 mL), brine (100 mL), and then dried (Na$_2$SO$_4$), filtered and concentrated. The residue was purified by silica gel chromatography (hexane/toluene) to provide Intermediate S1M (8.7 g, 67%): $^1$H NMR (400 MHz, CDCl$_3$) δ 7.40-7.31 (m, 5H), 5.70 (ddt, J=16.9, 10.2, 7.1 Hz, 1H), 5.19-5.11 (m, 2H), 5.09-5.02 (m, 2H), 2.83-2.68 (m, 2H), 2.43-2.32 (m, 2H), 2.19-1.94 (m, 2H), 1.91-1.81 (m, 2H), 1.42 (s, 9H).

Intermediate S1F (2R,3S)-1-Benzyl 4-tert-butyl 3-(cyclopropylmethyl)-2-(3,3,3-trifluoropropyl)succinate

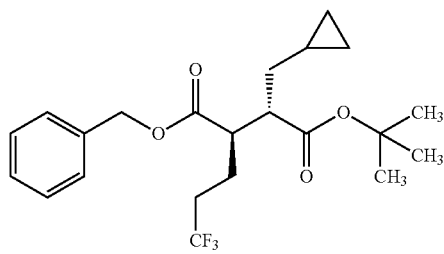
(S1F)

To a mixture of 40% KOH [KOH (6 g, 107 mmol) in water (9 mL)] and Et$_2$O (60 mL) cooled to 0° C. was added 1-methyl-3-nitro-1-nitrosoguanidine (1.5 g, 10.20 mmol) portion wise. The obtained solution was swirled several times. The ether layer (yellow solution) was pipetted to a mixture of Intermediate S1M (450 mg, 1.124 mmol) and Pd(OAc)$_2$ (25 mg, 0.11 mmol) in Et$_2$O (18 mL) at 0° C. The mixture was stirred at 0° C. for 3 h, and then the reaction mixture was quenched with several drops of acetic acid. The resulting mixture was washed with saturated NaHCO$_3$ and brine, dried over MgSO$_4$, filtered and concentrated. The above oil was purified by silica gel chromatography (hexane/EtOAc) to give Intermediate S1F (377 mg, 81%) as a colorless oil: HPLC: RT=3.790 min (H$_2$O/MeOH with TFA, CHROMOLITH® SpeedROD, 4.6×50 mm, gradient=4 min, wavelength=220 nm); MS(ES): m/z=415 [M+H$^+$]; $^1$H NMR (400 MHz, CDCl$_3$) δ 7.43-7.31 (m, 5H), 5.21-5.07 (m, 2H), 2.76-2.62 (m, 2H), 2.18-1.66 (m, 4H), 1.58-1.54 (m, 1H), 1.46 (s, 9H), 1.14 (ddd, J=13.8, 7.1, 3.5 Hz, 1H), 0.71-0.53 (m, 1H), 0.47-0.34 (m, 2H), 0.05-0.10 (m, 2H).

Intermediate S2

(2R,3S)-3-(tert-Butoxycarbonyl)-2-(3,3,3-trifluoropropyl)hexanoic acid

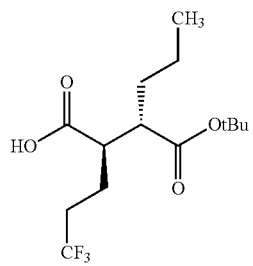
(S2)

Intermediate S1M (0.8 g, 1.998 mmol) was dissolved in MeOH (15.37 ml). Palladium on Carbon (Degussa, 10%) (0.053 g, 0.050 mmol) was added, then the atmosphere was exchanged with H$_2$ three times. The reaction mixture was stirred for about 6 hours, then filtered with EtOAc rinses. The filtrate was concentrated to give Intermediate S2 (627 mg, 100%): $^1$H NMR (400 MHz, chloroform-d) δ 2.72-2.65 (m, 1H), 2.64-2.56 (m, 1H), 2.34-2.04 (m, 2H), 1.98-1.86 (m, 1H), 1.82-1.59 (m, 2H), 1.47 (s, 9H), 1.44-1.23 (m, 3H), 0.99-0.86 (m, 3H).

Intermediate S3

(R)-2-((S)-1-(tert-Butoxy)-3-(1-methylcyclopropyl)-1-oxopropan-2-yl)-5,5,5-trifluoropentanoic acid

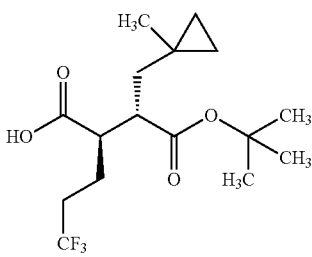
(S3)

Intermediate S3A (2R,3S)-3-(tert-Butoxycarbonyl)-5-methyl-2-(3,3,3-trifluoropropyl) hex-5-enoic acid, and Intermediate S3B (2R,3R)-3-(tert-Butoxycarbonyl)-5-methyl-2-(3,3,3-trifluoropropyl)hex-5-enoic acid

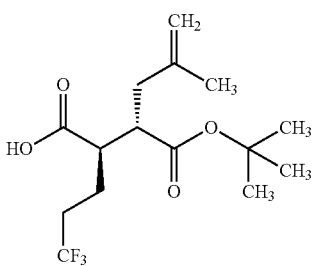
(S3A)

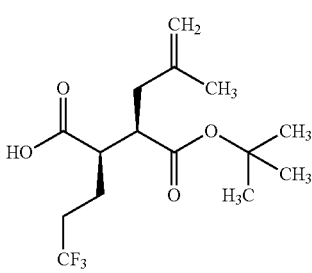
(S3B)

Intermediate S3A and Intermediate S3B were prepared from Intermediate S1J (3 g, 11.1 mmol) and 3-bromo-2- methylprop-1-ene (2.248 g, 16.65 mmol) according to the general procedure shown for Intermediate S1K and S1L. A 1:2 mixture of Intermediate S3A and Intermediate S3B (3.293 g, 91%) was obtained as a 2:1 mixture of 2R,3R and 2R,3S diastereomers and used without purification in the next step. MS(ES): m/z=323 [M–H⁻].

Intermediate S3A (2R,3S)-3-(tert-Butoxycarbonyl)-5-methyl-2-(3,3,3-trifluoropropyl)hex-5-enoic acid, and Intermediate S3B (2R,3R)-3-(tert-Butoxycarbonyl)-5-methyl-2-(3,3,3-trifluoropropyl)hex-5-enoic acid, an enriched mixture An enriched mixture of Intermediate S3A and Intermediate S3B was prepared from a 1:2 mixture of Intermediate S3A and Intermediate S3B (2.214 g, 6.83 mmol) according to the general procedure shown for Intermediate S1K and Intermediate S1L. A 1.8:1 mixture of Intermediate S3A and Intermediate S3B (1.165 g, 52.6%) was obtained. MS(ES): m/z=323 [M–H]⁻.

Intermediate S3C (2R,3S)-1-Benzyl 4-tert-butyl 3-(2-methylallyl)-2-(3,3,3-trifluoropropyl)succinate

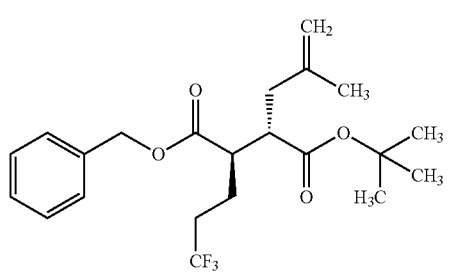

(S3C)

Intermediate S3C was prepared from a mixture of Intermediate S1A and Intermediate S3B (1.16 g, 3.58 mmol) according to the general procedure shown for Intermediate S1M. Intermediate S3C (0.571 g, 38.5%) was obtained. HPLC: RT=3.990 min (H₂O/MeOH with TFA, CHROMOLITH® ODS S5 4.6×50 mm, gradient=4 min, wavelength=220 nm). ¹H NMR (400 MHz, chloroform-d) δ 7.43-7.32 (m, 4H), 7.22-7.12 (m, 1H), 5.23-5.10 (m, 2H), 4.81-4.68 (m, 2H), 2.86 (ddd, J=10.0, 9.0, 5.3 Hz, 1H), 2.66 (td, J=9.3, 3.2 Hz, 1H), 2.39-2.30 (m, 2H), 2.10-1.84 (m, 3H), 1.81-1.73 (m, 1H), 1.69 (s, 3H), 1.44-1.39 (m, 9H).

Intermediate S3D (2R,3S)-1-Benzyl 4-tert-butyl 3-((1-methylcyclopropyl)methyl)-2-(3,3,3-trifluoropropyl)succinate

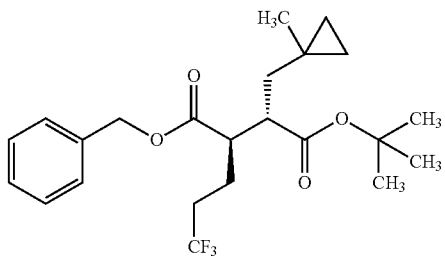

(S3D)

A solution of diethylzinc, 1M in hexane (18.63 mL, 18.63 mmol) in DCM (28 mL) was cooled in an ice/water bath. After 10 min a solution of trifluoroacetic acid (1.435 mL, 18.63 mmol) in DCM (14 mL) was added dropwise over a 8 min period and the reaction formed a white slurry which was stirred in the ice/water bath an additional 20 min. Diiodomethane (1.503 mL, 18.63 mmol) in DCM (7 mL) was added to the white slurry over 1 min; when complete all the solid dissolved to give a clear colorless solution. The reaction mixture was stirred in the ice/water bath for 20 min, then Intermediate S3C in DCM (7 mL) was added, the ice/water bath was removed, and the reaction mixture was allowed to warm to room temperature. After stirring 2 hours at room temperature the reaction mixture was washed with aqueous 1N HCl and the aqueous layer was back extracted with DCM. The combined organic layers were washed with saturated aqueous NaHCO₃. The organic layer was treated with activated charcoal, dried over MgSO₄, filtered and concentrated to give Intermediate S3D (1.9 g, 95%). HPLC: RT=4.011 min (H₂O/MeOH with TFA, CHROMOLITH® ODS S5 4.6×50 mm, gradient=4 min, wavelength=220 nm); ¹H NMR (400 MHz, chloroform-d) δ 7.42-7.32 (m, 5H), 5.23-5.09 (m, 2H), 2.87-2.73 (m, 1H), 2.63 (td, J=9.7, 3.4 Hz, 1H), 2.18-1.80 (m, 3H), 1.78-1.66 (m, 1H), 1.47 (s, 10H), 1.39-1.31 (m, 1H), 1.01 (s, 3H), 0.35-0.28 (m, 1H), 0.24-0.12 (m, 3H).

Intermediate S3

(R)-2-((S)-1-(tert-Butoxy)-3-(1-methylcyclopropyl)-1-oxopropan-2-yl)-5,5,5-trifluoropentanoic acid Intermediate S3 was prepared from Intermediate S3D (389 mg, 0.908 mmol) according to the general procedure shown for Intermediate S1. Intermediate S3 (297 mg, 97%) was obtained. HPLC: RT=3.469 min (H₂O/MeOH with TFA, CHROMOLITH® ODS S5, 4.6×50 mm, gradient=4 min, wavelength=220 nm); MS(ES): m/z=323[M–H⁻]

Intermediate A-1

(2-Amino-3-cyclopropoxyphenyl)(3-fluorophenyl)methanone

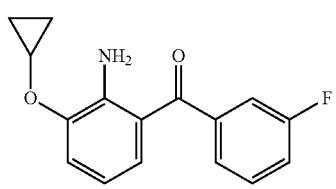

(A1)

Intermediate A1A

Methyl 2-nitro-3-(vinyloxy)benzoate

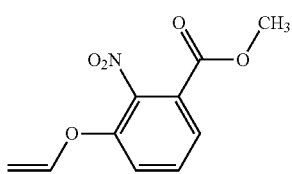

(A1A)

A mixture of copper (II) acetate (11.98 g, 65.9 mmol) and dichloromethane (80 mL) was stirred at room temperature for 10 minutes, before the addition of 2,4,6-trivinyl-1,3,5,2,4,6-trioxatriborinane compound with pyridine (1:1) (10.63 g, 44.2 mmol, 0.67 eq), methyl 3-hydroxy-2-nitrobenzoate (U.S. Publication No. 2012/0035194 A1 [0202]) (13 g, 65.9 mmol), pyridine (26.7 mL, 330 mmol), and molecular sieves (1 g). The resulting deep blue mixture was stirred at room temperature for 5 days, with the reaction mixture opened to the air. The reaction mixture was filtered through a pad of CELITE®, washing with dichloromethane. The filtrate was washed with 3M aqueous ammonium acetate (2×), water, and brine, and then dried and concentrated in vacuo. The crude product mixture was purified via silica gel chromatography (hexanes/EtOAc) to give Intermediate A1A (7.42 g, 33.2 mmol, 50.4% yield). HPLC: RT=2.487 min (H$_2$O/MeOH with TFA, SunFire C18 3.5 μm, 2.1×30 mm, gradient=4 min, wavelength=220 nm); MS(ES): m/z=246 [M+Na]$^+$; $^1$H NMR (400 MHz, chloroform-d) δ 7.77 (dd, J=7.8, 1.2 Hz, 1H), 7.55 (t, J=8.1 Hz, 1H), 7.38 (dd, J=8.4, 1.3 Hz, 1H), 6.61 (dd, J=13.6, 5.9 Hz, 1H), 4.95 (dd, J=13.6, 2.4 Hz, 1H), 4.69 (dd, J=5.9, 2.4 Hz, 1H), 3.93 (s, 3H), 1.56 (s, 1H), 0.03 (s, 1H).

Intermediate A-1B

Methyl 3-cyclopropoxy-2-nitrobenzoate

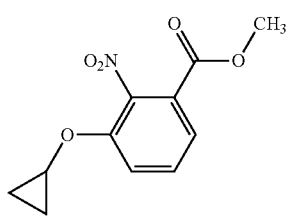

(A1B)

In a 3 necked, 500 mL flask, a solution of 2,2,2-trichloroacetic acid (16.30 g, 100 mmol) in dichloromethane (100 mL) was slowly added via an addition funnel to a −10° C. solution of diethylzinc (1M hexanes, 100 mL, 100 mmol) under a nitrogen atmosphere. The reaction mixture was stirred for 10 min. Next, diiodomethane (8 mL, 100 mmol) was dropwise added by syringe, and the reaction solution was stirred 10 min. A solution of Intermediate A1A (7.42 g, 33.2 mmol) in dichloromethane (20 mL) was added slowly via an addition funnel. The solution was allowed to warm to room temperature overnight. The reaction mixture was cooled to 0° C. and quenched with 1M HCl. The reaction solution was transferred to a separatory funnel, and the aqueous layer extracted with dichloromethane (3×). The combined extracts were washed with saturated sodium bicarbonate, water and brine, dried over anhydrous sodium sulfate, filtered and concentrated. The crude product mixture was purified by silica gel chromatography (hexanes/EtOAc) to Intermediate A1B (4.7 g, 19.81 mmol, 60.0% yield). HPLC: RT=2.66 min (H$_2$O/MeOH with TFA, SunFire C18 3.5 μm, 2.1×30 mm, gradient=4 min, wavelength=220 nm); MS(ES): m/z=260 [M+Na]$^+$; $^1$H NMR (400 MHz, chloroform-d) δ 7.68-7.57 (m, 2H), 7.57-7.41 (m, 1H), 4.03-3.82 (m, 4H), 0.94-0.78 (m, 4H).

Intermediate A1C

3-Cyclopropoxy-2-nitrobenzoic acid

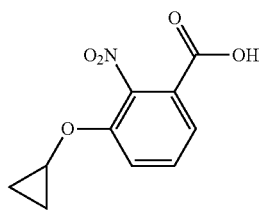

(A1C)

A solution of Intermediate A1B (4.7 g, 19.81 mmol) in THF (30 mL) and MeOH (30 mL) was treated with a solution of lithium hydroxide (2.88 g, 120 mmol) in water (15 mL, 833 mmol). The mixture was stirred at room temperature for 2 hours. The organic solvents were removed under reduced pressure. The resulting aqueous slurry was diluted with water, acidified with 1M HCl and extracted with ethyl acetate (3×). The extracts were combined and washed with brine, dried over anhydrous sodium sulfate, filtered and concentrated to provide Intermediate A1C (4.35 g, 19.8 mmol, 98% yield) as a yellowish solid. HPLC: RT=2.186 min (H$_2$O/MeOH with TFA, SunFire C18 3.5 μm, 2.1×30 mm, gradient=4 min, wavelength=220 nm); MS(ES): m/z=246 [M+Na]$^+$; $^1$H NMR (400 MHz, chloroform-d) δ 7.76 (dd, J=7.7, 1.8 Hz, 1H), 7.68-7.46 (m, 2H), 4.02 (tt, J=6.0, 2.9 Hz, 1H), 1.00-0.52 (m, 4H).

Intermediate A1D

2-Amino-3-cyclopropoxybenzoic acid

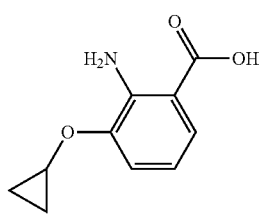

(A1D)

A 50 mL round bottom flask was charged with Intermediate A1C (205 mg, 0.919 mmol), 10% Pd/C (25 mg, 0.919 mmol) and methanol (6 mL). The flask was vacuum flushed with nitrogen (3×) followed by a vacuum flush with a hydrogen balloon (3×). The resulting suspension was stirred under a balloon of hydrogen at room temperature over night. The solution was filtered through CELITE®, washing with methanol, and the filtrate was concentrated to provide a reddish oil. The crude material was azeotroped with toluene (2×) and dried under vacuum to provide crude Intermediate A1D (175 mg, 0.906 mmol, 99% yield) as a reddish solid. The product was used without further purification in the next reaction. HPLC: RT=2.31 min (H$_2$O/MeOH with TFA, SunFire C18 3.5 μm, 2.1×30 mm, gradient=4 min, wavelength=220 nm); MS(ES): m/z=194.12 [M+H]$^+$.

Intermediate A1E

2-Amino-3-cyclopropoxy-N-methoxy-N-methylbenzamide

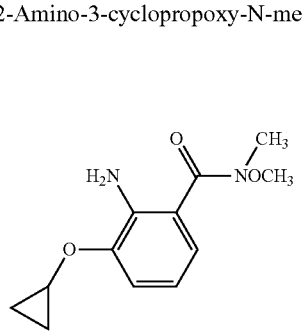

(A1E)

To a solution of Intermediate A1D (6.61 g, 34.2 mmol) N,O-dimethylhydroxylamine hydrochloride (10.01 g, 103 mmol), N-ethyl-N'-(3-dimethylaminopropyl)carbodiimide hydrochloride (7.87 g, 41.1 mmol) and 1-hydroxybenzotriazole hydrate (6.29 g, 41.1 mmol) in 50 ml of DMF was added triethylamine (19.07 mL, 137 mmol). The reaction solution was stirred at 60° C. overnight and then cooled to room temperature. The reaction mixture was partitioned between water and ethyl acetate and transferred to a separatory funnel and washed with 10% LiCl, water, and brine. The organic phase was dried over anhydrous sodium sulfate, filtered and concentrated to provide a dark oil. The crude product mixture was purified via silica gel chromatography (hexanes/EtOAc) to give Intermediate A1E (5.2 g, 22.01 mmol, 64.3% yield). HPLC: RT=1.975 min (H$_2$O/MeOH with TFA, SunFire C18 3.5 μm, 2.1×30 mm, gradient=4 min, wavelength=220 nm); MS(ES): m/z=237.12 [M+H]$^+$; $^1$H NMR (400 MHz, chloroform-d) δ 7.17 (dd, J=8.0, 1.2 Hz, 1H), 7.02 (dd, J=7.9, 1.3 Hz, 1H), 6.67 (t, J=7.9 Hz, 1H), 4.78 (br. s., 2H), 3.88-3.73 (m, 1H), 3.69-3.56 (m, 3H), 3.36 (s, 3H), 0.92-0.72 (m, 4H)).

Intermediate A1

A solution of 1-fluoro-3-iodobenzene (1.009 mL, 8.59 mmol) in tetrahydrofuran (100 mL) was cooled to −78° C. in a dry ice/acetone bath under nitrogen. Then a solution of n-BuLi (1.8 M in hexanes, 5.37 mL, 8.59 mmol) was added via syringe over 15 minutes and stirred for 60 minutes to give gave a dark-yellow suspension. Then a solution of Intermediate A1E (0.58 g, 2.455 mmol) in 10 mL of THF was added via syringe and the reaction mixture was stirred for 40 minutes at −78° C. After 40 minutes the mixture was poured into a mixture of ice and 1N HCl and extracted into ethyl acetate to give a light-yellow solution. The organic layer was washed with water and brine and concentrated to give a dark-yellow oil residue. The crude product mixture was purified via ISCO (0%-100% of EtOAC/heptane in 15 minutes, 40 g column) to give the pure product Intermediate A1 (0.46 g, 1.696 mmol, 69.1% yield). HPLC: RT=3.481 min (H$_2$O/MeOH with TFA, SunFire C18 3.5 μm, 2.1×30 mm, gradient=4 min, wavelength=220 nm); MS(ES): m/z=272.16 [M+H]$^+$; $^1$H NMR (400 MHz, chloroform-d) δ 7.48-7.40 (m, 2H), 7.36 (ddd, J=9.3, 1.9, 1.1 Hz, 1H), 7.27-7.18 (m, 2H), 7.08 (dd, J=8.3, 1.2 Hz, 1H), 6.58 (t, J=8.0 Hz, 1H), 6.39 (br. s., 2H), 3.83 (t, J=4.5 Hz, 1H), 0.86 (d, J=4.4 Hz, 4H).

The aminobenzophenones in Table 6 were prepared according to the general procedure given for Intermediate A1, starting from the appropriately substituted benzoic acid.

TABLE 6

| No. | Aminobenzophenone | Name | HPLC RT (min) | LC/MS |
|---|---|---|---|---|
| A2 | ![structure] | (2-amino-3-chlorophenyl)(3-fluoro-5-methylphenyl)methanone | 1.15[a] | 264 |
| A3 | ![structure] | (2-amino-3-cyclopropoxyphenyl)(phenyl)methanone | 3.318[b] | 254 |

TABLE 6-continued
| No. | Amino-benzophenone | Name | HPLC RT (min) | LC/MS |
|---|---|---|---|---|
| A4 | 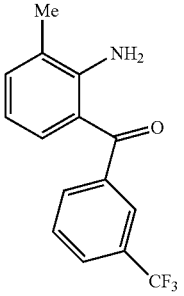 [SMILES: Cc1cccc(C(=O)c2cccc(C(F)(F)F)c2)c1N] | (2-amino-3-methylphenyl)(3-(trifluoromethyl)phenyl)methanone | 1.09$^a$ | 280 |
| A5 | 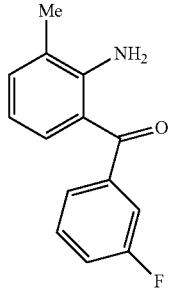 [SMILES: Cc1cccc(C(=O)c2cccc(F)c2)c1N] | (2-amino-3-methylphenyl)(3-fluorophenyl)methanone | 2.835$^c$ | 230 |
| A6 | 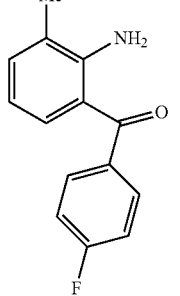 | (2-amino-3-methylphenyl)(4-fluorophenyl)methanone | 2.08$^d$ | 230.09 |
| A7 | 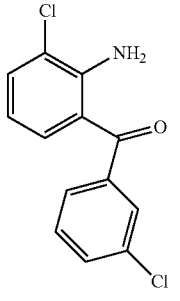 [SMILES: Nc1c(Cl)cccc1C(=O)c1cccc(Cl)c1] | (2-amino-3-chlorophenyl)(3-chlorophenyl)methanone | 2.24$^b$ | 266 |
| A8 | 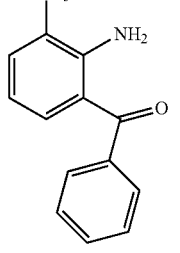 | (2-amino-3-(trifluormethyl)phenyl)(phenyl)methanone | 4.221$^e$ | 266 |

TABLE 6-continued

| No. | Amino-benzophenone | Name | HPLC RT (min) | LC/MS |
|---|---|---|---|---|
| A9 | (structure: 2-amino-3-methoxyphenyl with CF3-phenyl methanone) | (2-amino-3-methoxyphenyl)(3-(trifluoromethyl)phenyl)methanone | 1.08[a] | 296 |
| A10 | (structure: 2-amino-3-methoxyphenyl with 3-fluorophenyl methanone) | (2-amino-3-methoxyphenyl)(3-fluorophenyl)methanone | 3.29[f] | 246 |

[a]H$_2$O/MeOH with TFA, BEH C18 1.7 μm, 2.1 × 50 mm, gradient = 2 min, wavelength = 220 nm.
[b]H$_2$O/MeOH with TFA, SunFire C18 3.5 μm, 2.1 × 30 mm, gradient = 4 min, wavelength = 254 nm.
[c]H$_2$O/MeOH with TFA, CHROMOLITH® ODS S5, 4.6 × 50 mm, gradient = 4 min, wavelength = 220 nm.
[d]H$_2$O/MeOH with TFA, PHENOMENEX® 2.5 μm, 2.0 × 30 mm, gradient = 2 min, wavelength = 220 nm.
[e]H$_2$O/MeOH with H$_3$PO$_4$, SunFire C18 5 μm, 4.6 × 50 mm, gradient = 4 min, wavelength = 220 nm.
[f]H$_2$O/MeOH with H$_3$PO$_4$, YMC S5 ODS, 4.6 × 50 mm, gradient = 4 min, wavelength = 220 nm.

Intermediate A11

(2-Amino-3-fluorophenyl)(phenyl)methanone

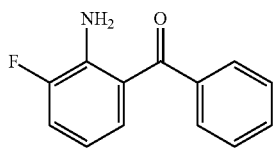

(A11)

Intermediate A11A

7-Fluoro-3-hydroxy-3-phenylindolin-2-one

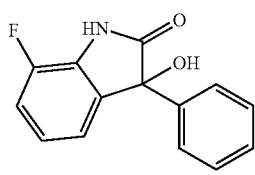

(A11A)

To a stirring solution of 7-fluoroindoline-2,3-dione (12.22 g, 74 mmol) in THF (40 mL) at 0° C. was added phenylmagnesium bromide (148 mL, 148 mmol) dropwise. The reaction mixture was allowed to stir at room temperature after addition was completed. The reaction mixture was judged complete by HPLC after 15 min. The reaction mixture was quenched with saturated NH$_4$Cl and extracted with EtOAc. The combined extracts were washed with brine, dried (Na$_2$SO$_4$), filtered and concentrated. The residue was purified by silica gel chromatography (EtOAc/hexane) to afford Intermediate A11A (18.84 g, 88%) as yellow solid: HPLC: RT=1.810 min (H$_2$O/MeOH with TFA, CHROMOLITH® SpeedROD, 4.6×50 mm, gradient=4 min, wavelength=220 nm); MS(ES): m/z=226 [M+H$^+$—H$_2$O]; $^1$H NMR (400 MHz, DMSO-d$_6$) δ 10.92 (s, 1H), 7.37-7.25 (m, 5H), 7.19 (ddd, J=10.4, 8.1, 1.3 Hz, 1H), 7.04-6.92 (m, 2H).

Intermediate A11

To a stirring solution of potassium ferrocyanide (20.87 g, 56.7 mmol), sodium bicarbonate (4.94 g, 58.8 mmol) and NaOH (0.959 g, 23.97 mmol) in water (100 mL) at 110-120° C. was added a solution of Intermediate A11A (5.3 g, 21.79 mmol) in DMF (12 mL) dropwise over 10 min. After refluxing for 1.5 hr, the reaction mixture was cooled to room temperature. The mixture was extracted twice with DCM. The combined extracts were washed with water and 10% LiCl, dried (MgSO$_4$), filtered and concentrated. The residue was purified by silica gel chromatography (EtOAc/hexane) to give Intermediate A11 (2.97 g, 63%) as yellow solid: HPLC: RT=2.513 min (H$_2$O/MeOH with TFA, CHROMOLITH® SpeedROD, 4.6×50 mm, gradient=4 min, wavelength=220 nm); MS(ES): m/z=216 [M+H]$^+$; $^1$H NMR (400 MHz, CDCl$_3$) δ 7.63-7.71 (2H, m), 7.54-7.60 (1H, m), 7.45-7.53 (2H, m), 7.25-7.31 (1H, m), 7.17 (1H, ddd, J=11.11, 7.81, 1.32 Hz), 6.56 (1H, td, J=8.03, 5.06 Hz), 6.12 (2H, br. s.).

The aminobenzophenones in Table 7 were prepared according to the general procedure given for Intermediate A11, starting from the appropriately substituted indoline-2,3-dione as known to one skilled in the art.

TABLE 7

| No. | Aminobenzophenone | Name | HPLC RT (min) | LC/MS |
|---|---|---|---|---|
| A12 | | (2-amino-3-chlorophenyl)(o-tolyl)methanone | 2.308$^a$ | 246 |
| A13 | | (2-amino-3-fluorophenyl)(m-tolyl)methanone | 2.07$^c$ | 230 |
| A14 | | (2-amino-3-fluorophenyl)(3-methoxyphenyl)methanone | 3.943$^e$ | 246 |
| A15 | | (2-amino-3-fluorophenyl)(3-fluorophenyl)methanone | 2.567$^b$ | 234 |
| A16 | | (2-amino-3-bromophenyl)(phenyl)methanone | 2.072$^f$ | 276 |

TABLE 7-continued

| No. | Amino-benzophenone | Name | HPLC RT (min) | LC/MS |
|---|---|---|---|---|
| A17 | 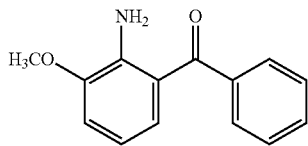 | (2-amino-3-chlorophenyl)(3-chlorophenyl)methanone | 2.24[b] | 266 |

[a]H$_2$O/MeOH with TFA, CHROMOLITH® ODS S5, 4.6 × 50 mm, gradient = 4 min, wavelength = 220 nm.
[b]H$_2$O/MeOH with TFA, CHROMOLITH® SpeedROD, 4.6 × 50 mm, gradient = 4 min, wavelength = 220 nm.
[c]H$_2$O/MeOH with TFA, SunFire C18 2.5 μm, 2.1 × 30 mm, gradient = 3 min, wavelength = 220 nm.
[d]H$_2$O/MeCN with NH$_4$OAc, PUROSPHER® Star C18 3 μm, 4 × 55 mm, gradient = 4 min, wavelength = 220 nm.
[e]H$_2$O/MeOH with H$_3$PO$_4$, SunFire C18 5 μm, 4.6 × 50 mm, gradient = 4 min, wavelength = 220 nm.
[f]H$_2$O/MeCN with ammonium formate, Ascentis Express C18 2.7 μm, 2.1 × 50 mm, gradient = 4 min, wavelength = 220 nm.

Intermediate A18

(2-Amino-3-methoxyphenyl)(phenyl)methanone

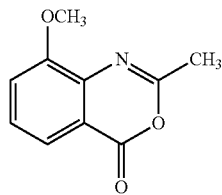 (A18)

Intermediate A18A

8-Methoxy-2-methyl-4H-benzo[d][1,3]oxazin-4-one (A18A)

2-Amino-3-methoxybenzoic acid (10.1 g, 60.4 mmol) was suspended in acetic anhydride (50 ml, 530 mmol). The mixture was heated to 140° C. with stirring for 180 min. The reaction mixture was cooled to room temperature and concentrated to provide Intermediate A18A (11.51 g, 100%): HPLC: RT=0.795 min (H$_2$O/MeOH with TFA, SunFire C18 2.5 μM, 2.1×30 mm, gradient=2 min, wavelength=220 nm); MS(ES): m/z=292 [M+H]$^+$; $^1$H NMR (400 MHz, DMSO-d$_6$) δ 7.59 (dd, J=6.9, 2.3 Hz, 1H), 7.52-7.42 (m, 2H), 3.89 (s, 3H), 2.39 (s, 3H).

Intermediate A18

A 100 mL round-bottomed flask containing Intermediate A18A (1 g, 5.23 mmol) in diethyl ether (20 mL), toluene (10 mL) and THF (10 mL) was cooled to 0° C. Phenyl magnesium bromide (1.9 mL, 5.75 mmol, 3M in Et$_2$O) was added in one portion. The reaction mixture was allowed to warm to room temperature and stirred overnight. The reaction mixture was cooled to 0° C. and 30 g crushed ice and 25 ml 6N HCl were added. The reaction mixture was allowed to slowly warm to room temperature. The reaction mixture was partitioned with ethyl acetate (100 mL) and brine (50 mL). The aqueous phase was separated and extracted with ethyl acetate (1×100 mL). The combined organic layers were dried (MgSO$_4$), filtered and concentrated. The residue was purified by silica gel chromatography to provide 882 mg colorless solid. This material was dissolved in AcOH (10 mL) and treated with concentrated HCl (6 mL, 72.0 mmol), then heated to 100° C. with stirring overnight. The reaction mixture was cooled to room temperature, concentrated and dried under vacuum. The residue was diluted with ethyl acetate (100 mL), the pH was adjusted to pH 10 with saturated NaHCO$_3$, then the phases separated. The aqueous phase was extracted with ethyl acetate (2×50 mL). The combined organic phases were dried (MgSO$_4$), filtered and concentrated. The residue was purified by silica gel chromatography (EtOAc/hexane) to provide Intermediate A18 (370 mg, 31%): HPLC: RT=1.888 min (H$_2$O/MeOH with TFA, SunFire C18 2.5 μM, 2.1×30 mm, gradient=2 min, wavelength=220 nm); MS(ES): m/z=228 [M+H]$^+$; $^1$H NMR (400 MHz, DMSO-d$_6$) δ 9.43 (br. s., 2H), 7.70-7.63 (m, 1H), 7.33-7.22 (m, 5H), 7.10-7.03 (m, 1H), 6.91 (dd, J=6.7, 2.1 Hz, 1H), 3.87 (s, 3H).

The aminobenzophenones in Table 8 were prepared according to the general procedure given for Intermediate A18, starting from the appropriately substituted anthranilic acid as known to one skilled in the art.

TABLE 8

| No. | Aminobenzophenone | Name | HPLC RT (min) | LC/MS |
|---|---|---|---|---|
| A19 | ![structure with OMe, NH2, C=O, Cl] | (2-amino-3-methoxyphenyl)(4-chlorophenyl)methanone | 2.143[a] | 262 |
| A20 | ![structure with Br, OMe, NH2, C=O, phenyl] | (2-amino-4-bromo-3-methoxyphenyl)(phenyl)methanone | 2.187[b] | 306 |

[a] H$_2$O/MeCN with NH$_4$OAc, PUROSPHER® Star C18 3 μm, 4 × 55 mm, gradient = 4 min, wavelength = 220 nm.
[b] H$_2$O/MeCN with NH$_4$OAc, PUROSPHER® Star C18 3 μm, 4 × 55 mm, gradient = 3 min, wavelength = 220 nm.

Intermediate A21

(2-Amino-3-chlorophenyl)(phenyl)methanone

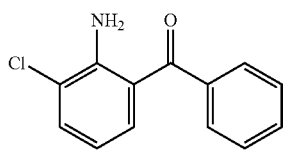

(A21)

Intermediate A21A (3-Chloro-2-nitrophenyl)(phenyl)methanone

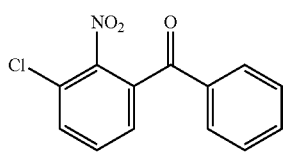

(A21A)

3-Chloro-2-nitrobenzoic acid (10 g, 49.6 mmol) was heated with thionyl chloride (30 mL) at 80° C. for 2 hours. The reaction mixture was concentrated to dryness, and the solid was dried under high vacuum for 15 minutes, dissolved in THF (120 mL) and cooled to −15° C. in a methanol/ice bath. To this solution was added phenylmagnesium bromide (49.6 mL, 49.6 mmol, 1M in THF) dropwise over a period of 15 minutes. After the addition was complete, the reaction flask was removed from the bath and stirred at room temperature overnight. The reaction mixture was quenched with addition of 1N HCl (100 mL). The reaction mixture was extracted with ethyl acetate (3×100 mL), dried (Na$_2$SO$_4$), concentrated and purified by silica gel chromatography (EtOAc/hexane) to afford Intermediate A21A (4.03 g, 31%) as an amber oil: HPLC: RT=1.96 min (H$_2$O/MeOH with TFA, PHENOMENEX® Luna C18 5 μM, 4.6×30 mm, gradient=4 min, wavelength=220 nm); MS(ES): m/z=262 [M+H]$^+$; $^1$H NMR (400 MHz, CDCl$_3$) δ 7.77-7.87 (2H, m), 7.63-7.76 (2H, m), 7.44-7.62 (4H, m).

Intermediate A21

A solution of Intermediate A21A (4.03 g, 15.40 mmol), zinc (10.07 g, 154 mmol) and ammonium chloride (8.24 g, 154 mmol) in EtOH (30 mL) and water (15 mL) was heated to reflux, and then cooled and stirred 1 h at room temperature. The mixture was filtered through CELITE® and concentrated, then the residue was partitioned between water/DCM, extracted with DCM (3×30 mL), dried (Na$_2$SO$_4$), filtered and concentrated to isolate Intermediate A21 (1.17 g, 33%) as a yellow oil: HPLC: RT=1.05 min (H$_2$O/MeOH with TFA, PHENOMENEX® Luna C18 5 μM, 4.6×30 mm, gradient=4 min, wavelength=220 nm); MS(ES): m/z=232 [M+H]$^+$; $^1$H NMR (400 MHz, CDCl$_3$) δ 7.68-7.61 (m, 2H), 7.59-7.52 (m, 1H), 7.51-7.38 (m, 4H), 6.67-6.51 (m, 3H).

The aminobenzophenones in Table 9 were prepared according to the general procedure given for Intermediate A21, starting from the appropriately substituted benzoic acid as known to one skilled in the art.

TABLE 9

| No. | Aminobenzophenone | Name | HPLC RT (min) | LC/MS |
|---|---|---|---|---|
| A22 | 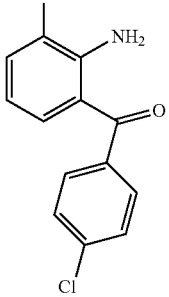 | (2-amino-3-chlorophenyl)(4-chlorophenyl)methanone | 2.157[a] | 266 |
| A23 | 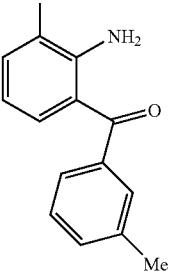 | (2-amino-3-chlorophenyl)(m-tolyl)methanone | 1.848[b] | 272 |
| A24 | 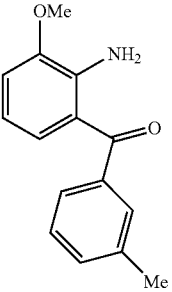 [SMILES: COc1cccc(C(=O)c2cccc(C)c2)c1N] | (2-amino-3-methoxyphenyl)(m-tolyl)methanone | 1.07[c] | 242 |

[a]$H_2O$/MeOH with TFA, ZORBAX® SB C18 5 μm, 4.6 × 55 mm, gradient = 4 min, wavelength = 220 nm.
[b]$H_2O$/MeOH with TFA, SunFire C18 2.5 μm, 2.1 × 30 mm, gradient = 2 min, wavelength = 220 nm.
[c]$H_2O$/MeOH with TFA, BEH C18 1.7 μm, 2.1 × 50 mm, gradient = 2 min, wavelength = 220 nm.
[d]$H_2O$/MeOH with TFA, PHENOMENEX® Luna C18 5 μm, 4.6 × 30 mm, gradient = 3 min, wavelength = 254 nm.

Intermediate A25

(2-Amino-3,4-dichlorophenyl)(phenyl)methanone

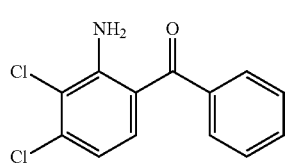
(A25)

Intermediate A25A

N-(6-Benzoyl-2,3-dichlorophenyl)pivalamide

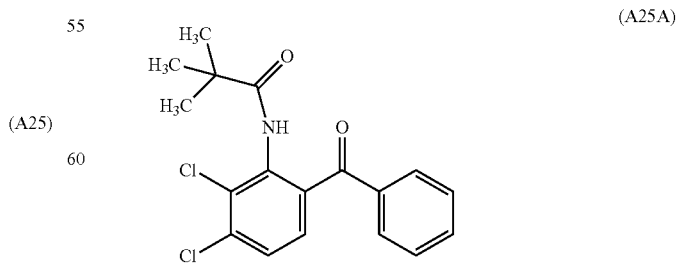

To a cool (−23° C.), stirred solution of N-(2,3-dichlorophenyl)pivalamide (Shimada, I. et al., *Bioorganic & Medicinal*

Chemistry, 16:1966-1982 (2008)), compound #12; 2.10 g, 8.53 mmol) and TMEDA (1.0 ml, 6.63 mmol) in t-BuOMe (21 ml) under $N_2$ was added n-BuLi (7.9 ml, 19.75 mmol, 2.5M in pentane) via syringe over 15 min. The reaction mixture was stirred for 90 min. To the cool reaction mixture was added a solution of N-methoxy-N-methylbenzamide (2.46 g, 14.89 mmol) in t-BuOMe (11 ml) via cannula over 30 min, then the reaction mixture was allowed to warm to room temperature as the bath warmed. To the reaction mixture was added saturated $NH_4Cl$, then the precipitated solid was collected by filtration, washed with water, and air dried overnight to afford Intermediate A25A (2.75 g, 88%) as a pale yellow solid: $^1$H NMR (400 MHz, $CDCl_3$) δ 8.04 (1H, br. s.), 7.76-7.83 (2H, m), 7.54-7.62 (1H, m), 7.43-7.49 (2H, m), 7.41 (1H, d, J=7.7 Hz), 7.35 (1H, d, J=7.7 Hz), 1.14 (9H, s).

Intermediate A25

To a stirred suspension of Intermediate A25A (2.75 g, 7.85 mmol) in EtOH (25 mL) was added 5N HCl (75 mL, 375 mmol). The reaction mixture was heated to 100° C. for 5.5 h. LCMS showed no conversion. The reaction mixture was cooled to room temperature, EtOH (75 mL) was added, and the mixture was reheated overnight. LCMS showed partial conversion. MeOH (25 mL) and concentrated HCl (25 mL) were added, heating continued overnight. LCMS showed ~30% completion. The reaction mixture was concentrated. The solid residue was dissolved in MeOH (75 mL), conc. HCl (40 mL) was added to the solution with stirring, then the solution was reheated to 100° C. for 3 h. Additional concentrated HCl (40 mL) was added, and heating continued overnight. The reaction mixture was cooled to room temperature and concentrated. The residue was dissolved in DCM, washed with saturated $NaHCO_3$, dried ($MgSO_4$), filtered and concentrated. After the residue was purified by silica gel chromatography (EtOAc/hexane), Intermediate A25A (1.38 g, 50%) was recovered and Intermediate A25 (596.6 mg, 29%) was obtained. HPLC: RT=2.26 min ($H_2O$/MeOH with TFA, SunFire C18 2.5 μm, 2.1×30 mm, gradient=4 min, wavelength=220 nm); MS(ES): m/z=266 [M+H]$^+$; $^1$H NMR (400 MHz, $CDCl_3$) δ 7.60-7.65 (2H, m), 7.53-7.59 (1H, m), 7.45-7.52 (2H, m), 7.35 (1H, d, J=8.8 Hz), 6.84 (2H, br. s.), 6.73 (1H, d, J=8.8 Hz).

Intermediate A26

(2-Amino-3-fluoro-4-methoxyphenyl)(phenyl)methanone

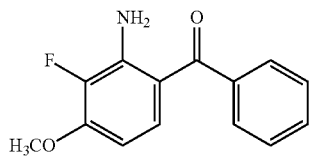

(A26)

To boron trichloride (11.69 ml, 11.69 mmol, 1.0 M heptane) at 0° C. was added dropwise a solution of 2-fluoro-3-methoxyaniline (1.50 g, 10.63 mmol) in toluene (5.31 ml). A solid formed upon addition, then partially dissolved. Benzonitrile (2.170 ml, 21.26 mmol) and aluminum chloride (1.559 g, 11.69 mmol) were added, and the reaction mixture was stirred for 30 min at 0° C. The ice bath was then removed and the reaction mixture was heated to 70° C. for 16 hours. The reaction mixture was cooled to room temperature, then 3N HCl (35.4 ml, 106 mmol) was added. The reaction mixture was then reheated to 70° C. After about 2 hours, a second portion of 3N HCl (35.4 ml, 106 mmol) was added. When the reaction was complete, the reaction mixture was cooled to room temperature, then basified to pH ca. 10 by addition of 1N NaOH. The reaction mixture was extracted four times with DCM, then the combined organic layers were washed with brine, dried ($Na_2SO_4$), filtered and evaporated. The residue was purified by silica gel chromatography (EtOAc/hexane) to give Intermediate A26 (0.979 g, 38%): HPLC: RT=1.827 min ($H_2O$/MeOH with TFA, SunFire C18 2.5 μm, 2.1×30 mm, gradient=2 min, wavelength=220 nm); MS(ES): m/z=246 [M+H]$^+$; $^1$H NMR (400 MHz, $CDCl_3$) δ 7.65-7.59 (m, 2H), 7.57-7.50 (m, 1H), 7.49-7.42 (m, 2H), 7.24 (d, J=2.0 Hz, 1H), 6.27 (dd, J=9.0, 7.7 Hz, 1H), 3.94 (s, 3H).

The aminobenzophenones in Table 10 were prepared according to the general procedure given for Intermediate A26, starting from the appropriately aniline and benzonitrile as known to one skilled in the art.

TABLE 10

| No. | Amino-benzophenone | Name | HPLC RT (min) | LC/MS |
|---|---|---|---|---|
| A27 | (structure) | (2-amino-3-methylphenyl)(phenyl)methanone | 1.00$^a$ | 212 |

TABLE 10-continued

| No. | Amino-benzophenone | Name | HPLC RT (min) | LC/MS |
|---|---|---|---|---|
| A28 | (structure: 3-fluoro-5-methyl-2-aminophenyl phenyl ketone) | (2-amino-3-fluoro-5-methylphenyl)(phenyl)methanone | 2.046[b] | 230 |
| A29 | (structure: 3-fluoro-4-methyl-2-aminophenyl phenyl ketone) | (2-amino-3-fluoro-4-methylphenyl)(phenyl)methanone | 2.041[b] | 230 |
| A30 | (structure: 2-amino-3-fluorophenyl 3-chlorophenyl ketone) | ((2-amino-3-fluorophenyl)(3-chlorophenyl)methanone | 2.059[d] | 250 |
| A31 | (structure: 2-amino-3-bromophenyl 4-chlorophenyl ketone) | (2-amino-3-bromophenyl)(4-chlorophenyl)methanone | 2.638[e] | 310 |

[a] $H_2O$/MeOH with TFA, BEH C18 1.7 μm, 2.1 × 50 mm, gradient = 2 min, wavelength = 220 nm.
[b] $H_2O$/MeCN with NH$_4$OAc, PUROSPHER ® Star C18 3 μm, 4 × 55 mm, gradient = 4 min, wavelength = 220 nm.
[c] $H_2O$/MeOH with TFA, ZORBAX ® C18 5 μm, 4.6 × 50 mm, gradient = 4 min, wavelength = 220 nm.
[d] $H_2O$/MeCN with NH$_4$OAc, Ascentis Express C8 2.7 μm, 2.1 × 50 mm, gradient = 4 min, wavelength = 220 nm.
[e] $H_2O$/MeCN with TFA, BEH C18 2.5 μm, 2.1 × 50 mm, gradient = 4 min, wavelength = 220 nm.

Intermediate A32

(2-Amino-3-fluorophenyl)(p-tolyl)methanone

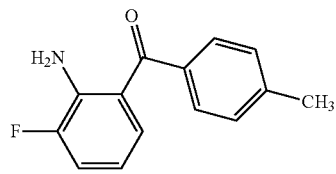

(A32)

Intermediate A32 was synthesized from 2-fluoroaniline and 4-methylbenzonitrile by the general procedure shown for Intermediate A26. Intermediate A32: NMR (400 MHz, CDCl$_3$) δ 7.57 (2H, d, J=1.6 Hz), 7.27-7.25 (3H, m), 57 (2H, d, J=7.04 Hz), 7.16-7.10 (1H, m), 6.00 (2H, br s), 2.43 (3H, s).

Intermediate B1

3-Amino-9-fluoro-5-phenyl-1H-benzo[e][1,4]diazepin-2(3H)-one

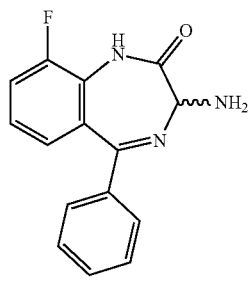

(B1)

Intermediate B1A

Benzyl 9-fluoro-2-oxo-5-phenyl-2,3-dihydro-1H-benzo[e][1,4]diazepin-3-ylcarbamate

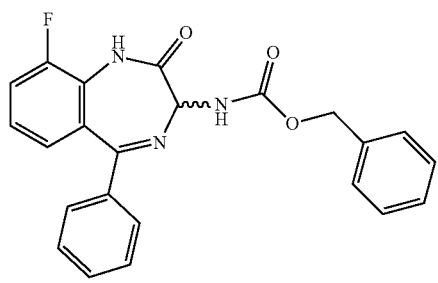

(B1A)

To a solution of 2-(1H-benzo[d][1,2,3]triazol-1-yl)-2-(benzyloxycarbonylamino)acetic acid (6.06 g, 18.59 mmol) in THF (40 mL) cooled at 0° C. was added oxalyl chloride (1.627 mL, 18.59 mmol), followed by DMF (0.05 mL). The mixture was stirred at 0° C. for 1.5 h. A solution of Intermediate A11 (2 g, 9.29 mmol) and 4-methylmorpholine (3.06 mL, 27.9 mmol) in THF (15 mL) was added slowly. After the addition, the reaction mixture was warmed to room temperature and stirred overnight. The reaction mixture was filtered through CELITE® and washed with 40 ml THF. The filtrate was treated with 7N NH$_3$/MeOH (40 mL). The mixture was stirred at room temperature for 3 h. The reaction mixture was concentrated, the residue was taken into EtOAc (150 mL), washed with 1N NaOH (150 mL), the aqueous layer was extracted with EtOAc (2×125 mL). The combined extracts were washed with brine, dried (MgSO$_4$), filtered and concentrated. The residue was dissolved in acetic acid (13 mL, 227 mmol) and treated with ammonium acetate (3.58 g, 46.5 mmol). The mixture was stirred at room temperature overnight. The reaction mixture was concentrated, and suspended in saturated NaHCO$_3$, extracted thrice with DCM. The combined extracts were washed with brine, dried and concentrated. The residue was purified by silica gel chromatography (hexane/EtOAc) to give Intermediate B1A (3.0 g, 79%): HPLC: RT=2.780 min (H$_2$O/MeOH with TFA, CHROMOLITH® SpeedROD, 4.6×50 mm, gradient=4 min, wavelength=220 nm); MS(ES): m/z=404 [M+H$^+$]; $^1$H NMR (400 MHz, CDCl$_3$) δ 7.92 (1H, br. s.), 7.57 (2H, d, J=7.04 Hz), 7.46-7.53 (1H, m), 7.30-7.46 (8H, m), 7.15-7.23 (2H, m), 6.61 (1H, d, J=8.14 Hz), 5.42 (1H, d, J=8.36 Hz), 5.20 (2H, s).

Intermediate B1

A mixture of Intermediate B1A (9 g, 22.31 mmol) in 33% HBr in HOAc (29.4 ml, 178 mmol) was stirred at room temperature for 1.5 h. Ether was added, then the precipitate was collected by filtration and rinsed with ether. The solid was suspended in water (150 mL) and saturated NaHCO$_3$ was added while stirring. The solid was collected by filtration, rinsed with water, and dried under vacuum to give Intermediate B1 (5.69 g, 95%): HPLC: RT=1.227 min (H$_2$O/MeOH with TFA, CHROMOLITH® SpeedROD, 4.6×50 mm, gradient=4 min, wavelength=220 nm); MS(ES): m/z=270 [M+H$^+$]; $^1$H NMR (400 MHz, DMSO-d$_6$) δ 10.57 (br. s., 1H), 7.61-7.36 (m, 6H), 7.32-7.19 (m, 1H), 7.11 (d, J=7.9 Hz, 1H), 4.34 (s, 1H), 2.76-2.55 (m, 2H).

Intermediate B2

(S)-3-Amino-9-chloro-5-(4-chlorophenyl)-1H-benzo[e][1,4]diazepin-2(3H)-one

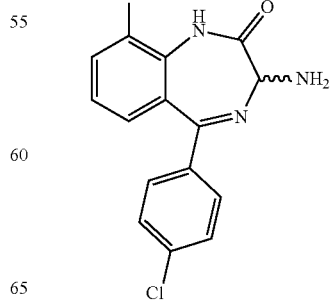

(B2)

Intermediate B2A

Benzyl 9-chloro-5-(4-chlorophenyl)-2-oxo-2,3-dihydro-1H-benzo[e][1,4]diazepin-3-ylcarbamate

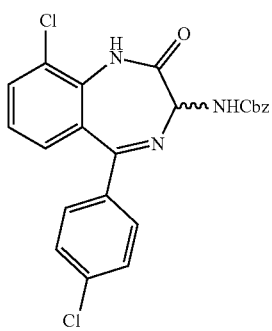

(B2A)

To a solution of 2-(1H-benzo[d][1,2,3]triazol-1-yl)-2-(((benzyloxy)carbonyl)amino)acetic acid (1.226 g, 3.76 mmol) in THF (30 mL), cooled to 0° C., under nitrogen atmosphere, was added oxalyl chloride (0.329 ml, 3.76 mmol) dropwise followed by DMF (0.01 mL, 0.129 mmol). The reaction mixture was stirred at 0° C. for two hours. A solution of Intermediate A22 (500 mg, 1.879 mmol) and 4-methylmorpholine (0.620 ml, 5.64 mmol) in THF (10 mL) was added dropwise to the acid chloride solution and stirred at room temperature for additional two hours. The reaction mixture was filtered through CELITE®, washed with THF (50 mL) and concentrated in vacuo to provide the crude intermediate (600 mg) that was subsequently taken as such to the next step: HPLC: RT=1.05 min (H$_2$O/MeCN with TFA, BEH C18 1.7 μm, 2.1×50 mm, gradient=4 min, wavelength=220 nm); MS(ES): m/z=455 [M−Bt]$^+$.

To a solution of the crude intermediate (600 mg, 1.05 mmol) in THF (40 mL) was added ammonia (30 mL, 2 M in methanol, 60.0 mmol) and stirred at room temperature for one hour. The reaction mixture was concentrated in vacuo, diluted with EtOAc (100 mL) and washed with aqueous 1N NaOH (2×50 mL). The organic layer was separated and the aqueous layer was extracted with EtOAc (3×100 mL). The combined organic layers were dried (anhydrous Na$_2$SO$_4$), filtered and concentrated in vacuo. The crude residue (2 g) was dissolved in glacial acetic acid (25 mL, 437 mmol) and the reaction mixture was stirred at room temperature for one hour and concentrated. The residue was slowly basified with ice-cold saturated aqueous NaHCO$_3$ (200 mL) and made alkaline (pH ~10) using aqueous 1N NaOH (10 mL). The aqueous phase was extracted with CH$_2$Cl$_2$ (3×100 mL), the organic layers were combined, dried (anhyd. Na$_2$SO$_4$), filtered and concentrated in vacuo. After addition of isopropanol (50 mL), the reaction mixture was stirred at room temperature for ten minutes. The solid formed was filtered and dried to provide Intermediate B2A (250 mg, 53%): HPLC: RT=2.095 min (H$_2$O/MeCN with NH$_4$OAc PUROSPHER® Star RP-18 3 μm, 4×55 mm, gradient=4 min, wavelength=254 nm); MS(ES): m/z=455 [M−Bt]$^+$; $^1$H NMR (400 MHz, DMSO-d$_6$) δ 8.42 (d, J=8.00 Hz, 1H), 7.82 (d, J=7.20 Hz, 1H), 7.53 (d, J=8.40 Hz, 3H), 7.40-7.25 (m, 7H), 5.08-5.01 (m, 3H).

Intermediate B2

To a 0° C. solution of Intermediate B2A (200 mg, 0.440 mmol) in DCM (15 mL) was added boron trichloride (1.761 mL, 1.761 mmol, 1M in DCM). After 15 min, the reaction mixture was partitioned between DCM (100 mL) and saturated NaHCO$_3$ (50 mL), then the aqueous layer was back extracted with ethyl acetate (2×75 mL). The combined organic layers were dried (Na$_2$SO$_4$), filtered and concentrated to afford Intermediate B2 (130 mg, 92%): HPLC: RT=1.46 min (H$_2$O/MeOH with TFA, Waters SunFire C18, 2.1×30 mm, gradient=2 min, wavelength=220 nm); MS(ES): m/z=320 [M+H$^+$]; $^1$H NMR (400 MHz, DMSO-d$_6$) δ 7.79 (dd, J=5.9, 3.3 Hz, 1H), 7.59-7.48 (m, 4H), 7.32-7.23 (m, 2H), 5.76 (s, 1H).

Intermediate B3

Benzyl (9-cyclopropyl-2-oxo-5-phenyl-2,3-dihydro-1H-benzo[e][1,4]diazepin-3-yl)carbamate

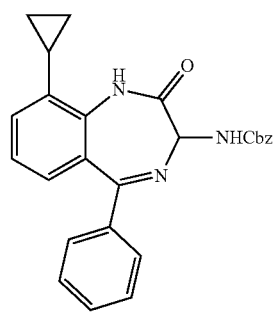

(B3)

Intermediate B3A

Benzyl (9-bromo-2-oxo-5-phenyl-2,3-dihydro-1H-benzo[e][1,4]diazepin-3-yl)carbamate

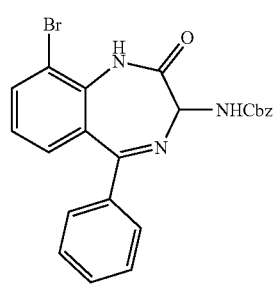

(B3A)

Intermediate B3A was prepared from Intermediate A16 by the general procedure given for Intermediate B1. Intermediate B3A: HPLC: RT=2.048 min (H$_2$O/MeOH with TFA, Ascentis Express C18 2.7 μm, 2.1×50 mm, gradient=4 min, wavelength=220 nm); MS(ES): m/z=464 [M+H$^+$].

Intermediate B3

To a stirred mixture of Intermediate B3A (2.00 g, 4.31 mmol), palladium dichloride dppf (946 mg, 1.29 mmol), potassium phosphate dibasic (2.25 g, 12.9 mmol) and cyclopropylboronic acid methyliminodiacetic acid ester (1.70 g, 8.61 mmol) in dioxane (12 mL) under nitrogen was added water (3 mL).

The reaction mixture was heated at 85° C. for 20 h and cooled to room temperature. The mixture was diluted with EtOAc and filtered through a pad of silica gel topped by CELITE®. This was further eluted with EtOAc. The filtrate was concentrated under reduced pressure and purified by silica gel chromatography (DCM/acetone) to give Intermediate B3 (1.20 g, 65%): HPLC: RT=3.246 min (H$_2$O/MeOH with TFA, CHROMOLITH® SpeedROD column 4.6×50 mm, gradient=4 min, wavelength=220 nm). MS(ES): m/z=426.1 [M+H$^+$]; $^1$H NMR (400 MHz, DMSO-d$_6$) δ 10.29 (s, 1H), 8.38 (d, J=8.6 Hz, 1H), 7.57-7.32 (m, 10H), 7.30 (d, J=7.5 Hz, 1H), 7.20 (t, J=7.6 Hz, 1H), 7.11 (d, J=7.3 Hz, 1H), 5.08 (s, 2H), 5.04 (d, J=8.4 Hz, 1H), 2.26-2.13 (m, 1H), 1.09-0.95 (m, 2H), 0.87-0.78 (m, 1H), 0.61-0.52 (m, 1H).

The substituted benzo[e][1,4]diazepin-2(3H)-one intermediates in Table 11 were prepared via HBr hydrolysis of their respective Cbz-protected precursors according to the general method shown for Intermediate B1, unless otherwise noted.

TABLE 11

| No. | Benzodiazepine | Starting material | Racemic/Chiral | HPLC RT | LC/MS | HPLC Conditions |
|---|---|---|---|---|---|---|
| B4 | (9-Cl, 5-(3-F,5-Me-phenyl)) | A2 | Racemic | 1.455$^e$ | 318 | (H$_2$O/MeOH with TFA, SunFire C18 2.5 μm, 2.1 × 30 mm, gradient = 3 min, wavelength = 220 nm) |
| B5 | (9-OMe, 5-(3-CF$_3$-phenyl)) | A9 | Racemic | 1.77$^f$ | 300.1 | (H$_2$O/MeOH with H$_3$PO$_4$, YMC S5 ODS, 4.6 × 50 mm, gradient = 4 min, wavelength = 220 nm) |
| B6 | (9-OMe, 5-(3-F-phenyl)) | A10 | Racemic | 2.11$^f$ | 350.1 | (H$_2$O/MeOH with H$_3$PO$_4$, YMC S5 ODS, 4.6 × 50 mm, gradient = 4 min, wavelength = 220 nm) |
| B7 | (9-O-CH$_2$-cyclopropyl, 5-(3-F-phenyl)) | A1 | Racemic | 2.253$^g$ | 326.15 (m + 1) | (H$_2$O/MeOH with TFA, SunFire C18 3.5 μm, 2.1 × 30 mm, gradient = 4 min, wavelength = 254 nm) |

TABLE 11-continued

| No. | Benzodiazepine | Starting material | Racemic/Chiral | HPLC RT | LC/MS | HPLC Conditions |
|---|---|---|---|---|---|---|
| B8 | (cyclopropyloxy-substituted benzodiazepine structure) | A3 | Racemic | 2.188$^g$ | 308.14 | (H$_2$O/MeOH with TFA, SunFire C18 3.5 µm, 2.1 × 30 mm, gradient = 4 min, wavelength = 254 nm) |
| B9$^a$ | (Me, 3-CF$_3$-phenyl benzodiazepine structure) | A4 | Racemic | 0.73$^h$ | 334 | H$_2$O/CH$_3$CN with 0.05% TFA, BEH C18 1.7 µm, 2.1 × 50 mm, gradient (2%-98%) = 1 min, wavelength = 220 |
| B10$^a$ | (Me, 3-F-phenyl benzodiazepine structure) | A5 | Racemic | 0.64$^h$ | 284 | H$_2$O/CH$_3$CN with 0.05% TFA, BEH C18 1.7 µm, 2.1 × 50 mm, gradient (2%-98%) = 1 min, wavelength = 220 |
| B11$^{b,r}$ | (Me, phenyl chiral benzodiazepine structure) | A27 | Chiral | 0.64$^h$ | 266 | (H$_2$O/MeOH with TFA, BEH C18 1.7 µm, 2.1 × 50 mm, gradient = 2 min, wavelength = 220 nm) |
| B12$^a$ | (Me, 4-F-phenyl benzodiazepine structure) | A6 | Racemic | 0.65$^h$ | 284 | H$_2$O/CH$_3$CN with 0.05% TFA, BEH C18 1.7 µm, 2.1 × 50 mm, gradient (2%-98%) = 1 min, wavelength = 220 |

TABLE 11-continued

| No. | Benzodiazepine | Starting material | Racemic/Chiral | HPLC RT | LC/MS | HPLC Conditions |
| --- | --- | --- | --- | --- | --- | --- |
| B13 | 9-Cl, 5-(2-methylphenyl) benzodiazepine structure | A12 | Racemic | 1.783$^i$ | 300 | (H$_2$O/MeOH with TFA, CHROMOLITH ® ODS S5, 4.6 × 50 mm, gradient = 4 min, wavelength = 220 nm) |
| B14 | 9-cyclopropyl, 5-phenyl benzodiazepine structure | B3 | Racemic | 2.09$^j$ | 292 | (H$_2$O/MeOH with TFA, CHROMOLITH ® SpeedROD, 4.6 × 50 mm, gradient = 4 min, wavelength = 220 nm) |
| B15 | 9-F, 5-(4-methylphenyl) benzodiazepine structure | A32 | Racemic | 0.69$^h$ | 284 | (H$_2$O/MeCN with TFA, BEH C18 1.7 µm, 2.1 × 50 mm, gradient = 2 min, wavelength = 220 nm) |
| B16 | 9-F, 7-Me, 5-phenyl benzodiazepine structure | A28 | Racemic | 0.62$^h$ | 284 | (H$_2$O/MeOH with TFA, BEH C18 1.7 µm, 2.1 × 50 mm, gradient = 2 min, wavelength = 220 nm) |
| B17 | 9-F, 8-Me, 5-phenyl benzodiazepine structure | A29 | Racemic | 1.370$^k$ | 284 | (H$_2$O/MeOH with TFA, SunFire C18 3.5 µm, 2.1 × 30 mm, gradient = 2 min, wavelength = 254 nm) |

TABLE 11-continued

| No. | Benzodiazepine | Starting material | Racemic/Chiral | HPLC RT | LC/MS | HPLC Conditions |
|---|---|---|---|---|---|---|
| B18 | (3-amino-9-fluoro-5-(3-methylphenyl)-benzodiazepinone) | A13 | Racemic | 0.61[h] | 284 | (H$_2$O/MeOH with TFA, BEH C18 1.7 μm, 2.1 × 50 mm, gradient = 2 min, wavelength = 220 nm) |
| B19[d] | (3-amino-9-methoxy-5-(4-chlorophenyl)-benzodiazepinone) | A19 | Racemic | 2.775[o] | 316 | (H$_2$O/MeOH with H$_3$PO$_4$, SunFire C18 5 μm, 4.6 × 50 mm, gradient = 4 min, wavelength = 220 nm) |
| B20 | (3-amino-9-fluoro-5-(3-methoxyphenyl)-benzodiazepinone) | A14 | Racemic | 2.262[o] | 300 | (H$_2$O/MeOH with H$_3$PO$_4$, SunFire C18 5 μm, 4.6 × 50 mm, gradient = 4 min, wavelength = 220 nm) |
| B21 | (3-amino-9-fluoro-5-(3-fluorophenyl)-benzodiazepinone) | A15 | Racemic | 1.302[j] | 288 | (H$_2$O/MeOH with TFA, CHROMOLITH ® SpeedROD 4.6 × 50 mm, gradient = 4 min, wavelength = 220 nm) |
| B22 | (3-amino-9-fluoro-5-(3-chlorophenyl)-benzodiazepinone) | A30 | Racemic | 1.393[m] | 304 | (H$_2$O/MeCN with NH$_4$OAc, PUROSPHER ® Star C18 3 μm, 4 × 55 mm, gradient = 4 min, wavelength = 220 and 254 nm) |

TABLE 11-continued

| No. | Benzodiazepine | Starting material | Racemic/Chiral | HPLC RT | LC/MS | HPLC Conditions |
|---|---|---|---|---|---|---|
| B23 | (9-Cl, 5-(3-chlorophenyl) 3-amino-1,3-dihydro-2H-1,4-benzodiazepin-2-one) | A17 | Racemic | 1.448[p] | 320 | (H$_2$O/MeOH with TFA, SunFire C18 2.5 µm, 2.1 × 30 mm, gradient = 2 min, wavelength = 220 nm) |
| B24 | (9-F, 8-MeO, 5-phenyl 3-amino-1,3-dihydro-2H-1,4-benzodiazepin-2-one) | A26 | Racemic | 0.60[h] | 300 | (H$_2$O/MeOH with TFA, BEH C18 1.7 µm, 2.1 × 50 mm, gradient = 2 min, wavelength = 220 nm) |
| B25[a] | (9-Cl, 5-(3-methylphenyl) 3-amino-1,3-dihydro-2H-1,4-benzodiazepin-2-one) | A23 | Racemic | 1.442[p] | 300 | (H$_2$O/MeOH with TFA, SunFire C18 2.5 µm, 2.1 × 30 mm, gradient = 2 min, wavelength = 220 nm) |
| B26 | (9-OMe, 5-(3-methylphenyl) 3-amino-1,3-dihydro-2H-1,4-benzodiazepin-2-one) | A24 | Racemic | 1.45[p] | 296 | (H$_2$O/CH$_3$CN with TFA, SunFire C18 3.5 µm, 2.1 × 30 mm, gradient = 2 min, wavelength = 220 nm) |
| B27[c] | (9-Br, 5-phenyl 3-amino-1,3-dihydro-2H-1,4-benzodiazepin-2-one) | A16 | Racemic | 1.89[p] | 330 | (H$_2$O/CH$_3$CN with TFA, SunFire C18 3.5 µm, 2.1 × 30 mm, gradient = 2 min, wavelength = 220 nm) |

TABLE 11-continued

| No. | Benzodiazepine | Starting material | Racemic/Chiral | HPLC RT | LC/MS | HPLC Conditions |
|---|---|---|---|---|---|---|
| B28[b,t] | 3-amino-9-methoxy-5-phenyl-1H-benzo[e][1,4]diazepin-2(3H)-one | A18 | chiral | 1.777[q] | 282 | (H$_2$O/MeOH with H3PO4, YMC ODS S5, 4.6 × 50 mm, gradient = 4 min, wavelength = 220 nm) |
| B29[a] | 3-amino-8,9-dichloro-5-phenyl-1H-benzo[e][1,4]diazepin-2(3H)-one | A25 | Racemic | 1.472[p] | 320 | (H$_2$O/MeOH with TFA, SunFire C18 2.5 µm, 2.1 × 30 mm, gradient = 2 min, wavelength = 220 nm) |
| B30 | 3-amino-5-phenyl-9-(trifluoromethyl)-1H-benzo[e][1,4]diazepin-2(3H)-one | A8 | Racemic | 2.323[o] | 320 | (H$_2$O/MeOH with H$_3$PO$_4$, SunFire C18 5 µm, 4.6 × 50 mm, gradient = 4 min, wavelength = 220 nm) |
| B31 | 3-amino-8-bromo-9-methoxy-5-phenyl-1H-benzo[e][1,4]diazepin-2(3H)-one | A20 | Racemic | 1.474[m] | 362 | (H$_2$O/MeCN with NH$_4$OAc, PUROSPHER ® Star C18 3 µm, 4 × 55 mm, gradient = 3 min, wavelength = 220 nm) |
| B32[b,u] | 3-amino-9-chloro-5-phenyl-1H-benzo[e][1,4]diazepin-2(3H)-one | A21 | Chiral | 0.61[h] | 286 | (H$_2$O/MeOH with TFA, BEH C18 1.7 µm, 2.1 × 50 mm, gradient = 2 min, wavelength = 220 nm) |

[a]This compound was isolated as its hydrobromide salt.
[b]This compound was prepared as a single enantiomer by separation of enantiomers of its benzyl carbamate by chiral SFC.
[c]This compound was isolated as its bis-hydrobromide salt.
[d]This compound was prepared by removal of the Cbz group with BCl$_3$ by the general procedure given for Intermediate B2.
[e]H$_2$O/MeOH with TFA, SunFire C18 2.5 µm, 2.1 × 30 mm, gradient = 3 min, wavelength = 220 nm.
[f]H$_2$O/MeOH with H$_3$PO$_4$, YMC S5 ODS, 4.6 × 50 mm, gradient = 4 min, wavelength = 220 nm.
[g]H$_2$O/MeOH with TFA, SunFire C18 2.5 µm, 2.1 × 30 mm, gradient = 4 min, wavelength = 220 nm.
[h]H$_2$O/MeOH with TFA, BEH C18 1.7 µm, 2.1 × 50 mm, gradient = 2 min, wavelength = 220 nm.
[i]H$_2$O/MeOH with TFA, CHROMOLITH ® ODS S5, 4.6 × 50 mm, gradient = 4 min, wavelength = 220 nm.

TABLE 11-continued

| No. | Benzodiazepine | Starting material | Racemic/Chiral | HPLC RT | LC/MS | HPLC Conditions |
|---|---|---|---|---|---|---|

[j]H₂O/MeOH with TFA, CHROMOLITH ® SpeedROD, 4.6 × 50 mm, gradient = 4 min, wavelength = 220 nm.
[k]H₂O/MeOH with TFA, SunFire C18 3.5 μm, 2.1 × 30 mm, gradient = 2 min, wavelength = 254 nm.
[l]H₂O/MeOH with TFA, ZORBAX C18 5 μm, 4.6 × 50 mm, gradient = 4 min, wavelength = 220 and 254 nm.
[m]H₂O/MeCN with NH₄OAc, PUROSPHER ® Star C18 3 μm, 4 × 55 mm, gradient = 4 min, wavelength = 220 nm.
[n]H₂O/MeCN with NH₄OAc, Ascentis Express C18 2.7 μm, 2.1 × 50 mm, gradient = 4 min, wavelength = 220 nm.
[o]H₂O/MeOH with H₃PO₄, SunFire C18 5 μm, 4.6 × 50 mm, gradient = 4 min, wavelength = 220 nm.
[p]H₂O/MeOH with TFA, SunFire C18 2.5 μm, 2.1 × 30 mm, gradient = 2 min, wavelength = 220 nm.
[q]H₂O/MeOH with H₃PO₄, YMC ODS S5, 4.6 × 50 mm, gradient = 4 min, wavelength = 220 nm.
[r]The (S)-enantiomer of this compound was obtained by preparative SFC chromatography of its benzyl carbamate (Thar 350, OJ-H 25 × 5 cm ID, 5 μm, 70/30 CO₂/MeOH, 300 mL/min).
[s]The (S)-enantiomer of this compound was obtained by preparative SFC chromatography (Thar 350 SFC, CHIRALPAK ® AS-H 25 × 5 cm ID, 5 μm, 86/14 CO₂/MeOH w/0.1% TEA, 290 mL/min).
[t]The (S)-enantiomer of this compound was obtained by preparative SFC chromatography (Berger SFC MG-II, CHIRALPAK ® AS 25 × 3 cm ID, 5 μm, 67/33 CO₂/MeOH w/0.1% diethylamine, 85 mL/min).
[u]The (S)-enantiomer of this compound was obtained by preparative SFC chromatography of its benzyl carbamate (Thar 350 SFC, AD-H 25 × 5 cm ID, 5 μm, 60/40 CO₂/MeOH, 280 mL/min).

Example 1

(2R,3S)-3-(Cyclopropylmethyl)-N-((3S)-9-fluoro-2-oxo-5-phenyl-2,3-dihydro-1H-1,4-benzodiazepin-3-yl)-2-(3,3,3-trifluoropropyl)succinamide (1)

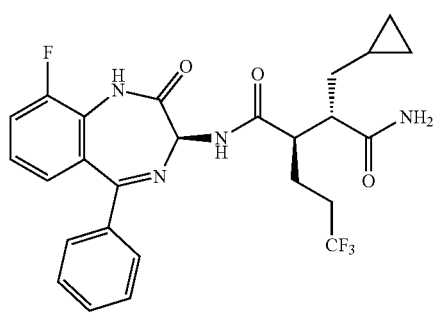

Preparation 1A (2S,3R)-tert-Butyl 2-(cyclopropylmethyl)-6,6,6-trifluoro-(3S)-((9-fluoro-2-oxo-5-phenyl-2,3-dihydro-1H-benzo[e][1,4]diazepin-3-yl)carbamoyl)hexanoate, and

Preparation 1B (2S,3R)-tert-Butyl 2-(cyclopropylmethyl)-6,6,6-trifluoro-(3R)-((9-fluoro-2-oxo-5-phenyl-2,3-dihydro-1H-benzo[e][1,4]diazepin-3-yl)carbamoyl)hexanoate (1A)

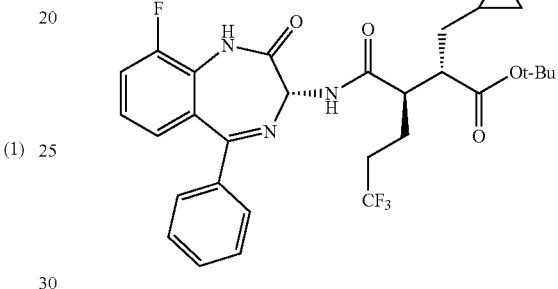

(1B)

To a mixture of Intermediate B1 (2.058 g, 7.64 mmol), Intermediate S1 (2.43 g, 7.49 mmol) and TBTU (2.77 g, 8.62 mmol) in DMF (15 mL) was added triethylamine (2.297 mL, 16.48 mmol). The mixture was stirred at room temperature for 1.5 h. The reaction mixture was pipetted into a mixture of water and 20% saturated NaHCO₃. The resulting mixture was stirred for 5 min. The solid was collected by filtration, washed with water, and dried. The solid was purified by silica gel chromatography (hexane/EtOAc) to give 1:1 mixture of Preparations 1A and 1B (3.94 g, 90%): HPLC: RT=3.441 min (H₂O/MeOH with TFA, CHROMOLITH® SpeedROD, 4.6× 50 mm, gradient=4 min, wavelength=220 nm); MS(ES): m/z=576 [M+H⁺].

Example 1 and Preparation 1C (2R,3S)-3-(Cyclopropylmethyl)-N1-((R)-9-fluoro-2-oxo-5-phenyl-2,3-dihydro-1H-benzo[e][1,4]diazepin-3-yl)-2-(3,3,3-trifluoropropyl)succinamide (1)

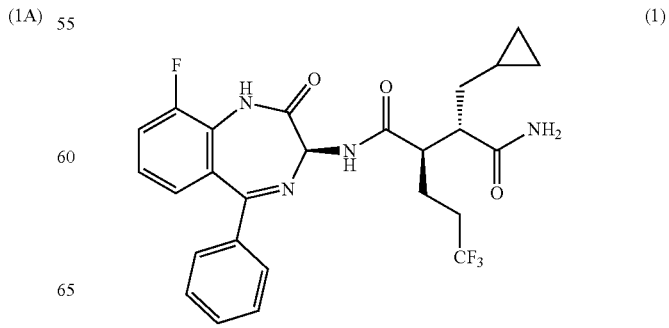

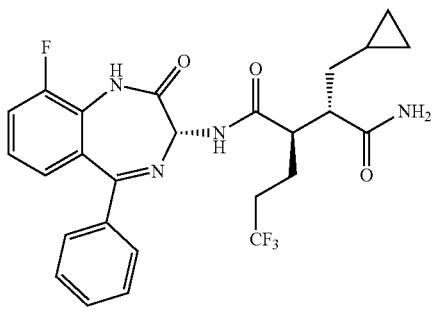

(1C)

To a suspension of a 1:1 mixture of Preparations 1A and 1B (3.94 g, 6.85 mmol) in DCM (20 mL) was added TFA (20 mL). The solution was stirred at room temperature for 1 h 50 min. Next, toluene was added. The solution was concentrated and the residue was azeotroped thrice with toluene/DCM. The yellow solid was dried under vacuum for 30 min. To a solution of the above solid carboxylic acid in THF (50 mL) was added HOBt (3.14 g, 20.54 mmol). The mixture was stirred for 5 min, and then EDC (3.94 g, 20.54 mmol) was added. After stirring another 5 min, the mixture was cooled to 8° C., and ammonia (20.54 mL, 41.1 mmol, 2M in IPA) was added. The mixture was stirred at room temperature overnight. The mixture was concentrated to a small volume. A solution of water and saturated NaHCO$_3$ (80/20) was added, and the solid was collected by filtration, washed by water and then dried. The solid was then triturated with Et$_2$O, then collected by filtration, rinsed with ether, and dried to give 3.49 g solid. The solid was then subjected SFC chiral separation [Lux-Cell4 (5×25 cm) 20% MeOH in CO$_2$, 320 mL/min, 254 nm, 40° C., 100 bars, 3.5 mL/3 min]. The second eluting fraction was concentrated, and the solid was sonicated with a small amount of MeOH, collected by filtration and dried to give Example 1 (1.25 g, 32%): HPLC: RT=2.555 min (H$_2$O/MeOH with TFA, CHROMOLITH® SpeedROD, 4.6×50 mm, gradient=4 min, wavelength=220 nm); MS(ES): m/z=519 [M+H$^+$]; $^1$H NMR (400 MHz, CD$_3$OD) δ 7.70-7.38 (m, 6H), 7.36-7.14 (m, 2H), 5.43 (s, 1H), 2.79-2.70 (m, 1H), 2.70-2.61 (m, 1H), 2.60-2.42 (m, 1H), 2.33-2.15 (m, 1H), 1.90-1.66 (m, 3H), 1.30 (ddd, J=13.6, 7.6, 3.4 Hz, 1H), 0.79-0.66 (m, 1H), 0.54-0.40 (m, 2H), 0.20-0.11 (m, 1H), 0.10-0.01 (m, 1H).

The first eluting fraction from the SFC purification was concentrated to give Preparation 1C (1.47 g, 38%): HPLC: RT=2.643 min (H$_2$O/MeOH with TFA, CHROMOLITH® SpeedROD, 4.6×50 mm, gradient=4 min, wavelength=220 nm); MS(ES): m/z=519 [M+H$^+$]; $^1$H NMR (400 MHz, CD$_3$OD) δ 7.62-7.40 (m, 1H), 7.28 (td, J=8.1, 5.0 Hz, 1H), 7.22-7.16 (m, 1H), 5.45 (s, 1H), 2.81-2.60 (m, 3H), 2.40-2.16 (m, 3H), 1.94-1.66 (m, 4H), 1.43 (ddd, J=13.8, 7.8, 3.5 Hz, 1H), 0.77-0.63 (m, 1H), 0.51-0.36 (m, 2H), 0.21-0.13 (m, 1H), 0.10-0.00 (m, 1H).

Crystal Form M3-1(tris-methanolate) was prepared by adding approximately 3 mg of Example 1 to approximately 0.7 mL of methanol solution. Colorless prism-like crystals were obtained after one day of slow evaporation of the solution at room temperature.

Crystal Form CA-2 (hydrate with solvated channels) was prepared by adding approximately 3 mg of Example 1 to approximately 0.7 mL of acetonitrile/water/acetic acid solution (5:2:1). Colorless needle crystals were obtained after three days of slow evaporation of the solution at room temperature.

Crystal Form SA-3 (di-methanolate monohydrate) was prepared by adding approximately 3 mg of Example 1 to approximately 0.7 mL of methanol/water solution (10:1). Colorless needle crystals were obtained after four days of slow evaporation of the solution at room temperature.

Crystal Form E2.5-4 (2.5 ethanolate) was prepared by adding approximately 5 mg of Example 1 to approximately 0.5 mL of absolute ethanol solution. Colorless needle crystals were obtained after one day of slow evaporation of the solution at room temperature.

Crystal Form IPA2-5 (di-isopropanolate) was prepared by adding approximately 3 mg of Example 1 to approximately 0.5 mL of isopropanol solution. Colorless needle crystals were obtained after 30 minutes of slow evaporation of the solution at room temperature.

Example 2

(2R,3S)-3-(Cyclopropylmethyl)-N-((3S)-9-methoxy-2-oxo-5-(3-(trifluoromethyl)phenyl)-2,3-dihydro-1H-1,4-benzodiazepin-3-yl)-2-(3,3,3-trifluoropropyl)succinamide

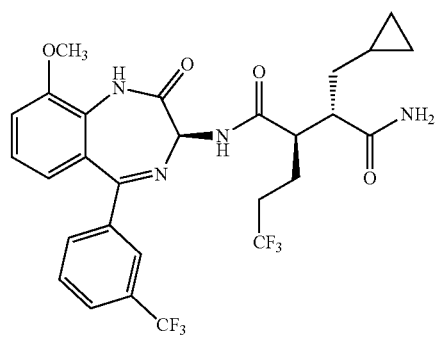

(2)

Preparation 2A (2S,3R)-tert-Butyl 2-(cyclopropylmethyl)-6,6,6-trifluoro-3-(((S)-9-methoxy-2-oxo-5-(3-(trifluoromethyl)phenyl)-2,3-dihydro-1H-benzo[e][1,4]diazepin-3-yl)carbamoyl)hexanoate, and Preparation 2B (2S,3R)-tert-Butyl 2-(cyclopropylmethyl)-6,6,6-trifluoro-3-(4R)-9-methoxy-2-oxo-5-(3-(trifluoromethyl)phenyl)-2,3-dihydro-1H-benzo[e][1,4]diazepin-3-yl)carbamoyl)hexanoate

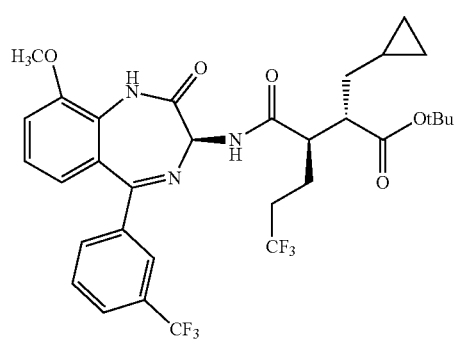

(2A)

-continued

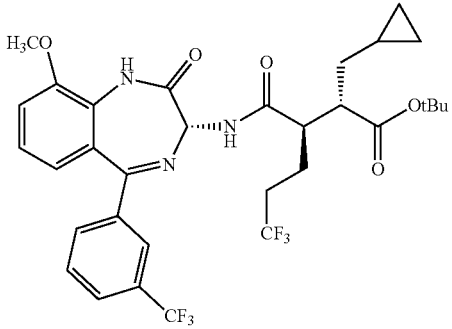

(2B)

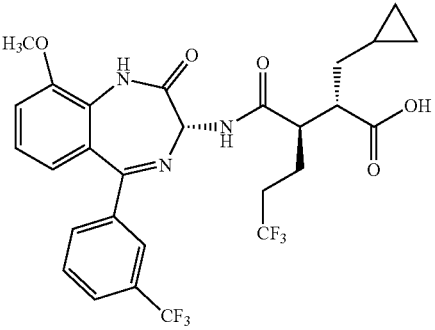

(2D)

To a solution of Intermediate B5 hydrobromide (100 mg, 0.263 mmol) in DMF (1 mL) at 0° C. was added Intermediate S1 (106 mg, 0.289 mmol), followed by TBTU (253 mg, 0.789 mmol) and triethylamine (0.220 mL, 1.578 mmol). The reaction mixture was stirred at room temperature for 1 h, then water was added and the mixture was stirred for 10 min. The solid was filtered off, then dissolved in EtOAc and diluted with water. The organic layer was separated, washed with brine, dried over MgSO$_4$, filtered and concentrated to give a crude mixture of Preparation 2A and Preparation 2B, which was used directly in the next reaction. HPLC: RT=3.901 min (H$_2$O/MeOH with H$_3$PO$_4$, YMC S5 ODS, 4.6×50 mm, gradient=4 min, wavelength=220 nm); MS(ES): m/z=648 [M+H$^+$].

Preparation 2C (2S,3R)-2-(Cyclopropylmethyl)-6,6,6-trifluoro-3-(((S)-9-methoxy-2-oxo-5-(3-(trifluoromethyl)phenyl)-2,3-dihydro-1H-benzo[e][1,4]diazepin-3-yl)carbamoyl) hexanoic acid, and Preparation 2D (2S,3R)-2-(Cyclopropylmethyl)-6,6,6-trifluoro-3-(((R)-9-methoxy-2-oxo-5-(3-(trifluoromethyl)phenyl)-2,3-dihydro-1H-benzo[e][1,4]diazepin-3-yl)carbamoyl)hexanoic acid

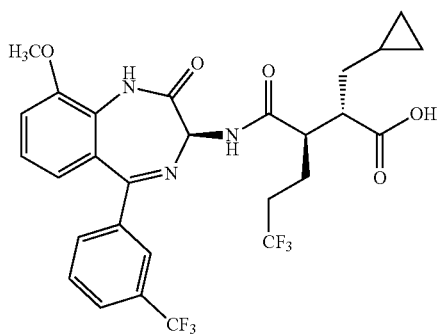

(2C)

The above mixture of Preparation 2A and Preparation 2B was dissolved in DCM (2 mL) and cooled to 0° C. TFA (1 mL) was added dropwise. The mixture was stirred at room temperature for 2 hours. The solvent was evaporated, then the residue was diluted with EtOAc and 1N NaOH. The organic layer was separated and discarded. The aqueous layer was adjusted to pH 1 with 1N HCl, then extracted with EtOAc. The organic layer was separated and washed with brine, dried over MgSO$_4$, filtered and concentrated to give a mixture of Preparation 2C and Preparation 2D (110 mg, 71%). HPLC: RT=3.461 min (H$_2$O/MeOH with H$_3$PO$_4$, YMC S5 ODS, 4.6×50 mm, gradient=4 min, wavelength=220 nm); MS(ES): m/z=592 [M+H$^+$].

Example 2

A mixture of Preparation 2C and Preparation 2D (75 mg, 0.125 mmol) was dissolved in THF (2 mL). EDC (48.0 mg, 0.250 mmol), 1-hydroxybenzotriazole (33.8 mg, 0.250 mmol), and ammonia (2M in iPrOH, 0.375 mL, 0.750 mmol) were added. The reaction mixture was stirred at room temperature for 24 hours, then water was added. The precipitated solid was filtered off, washed with water, and dried. This solid was dissolved in EtOAc and water. The organic layer was separated and washed with brine, dried over MgSO$_4$, filtered and concentrated. This material was purified by silica gel chromatography (DCM/EtOAc).

This solid was purified by preparative SFC chromatography (Berger SFC MGII, CHIRALPAK® AS 25×3 cm ID, 5 μm, 80/20 CO$_2$/MeOH, 85 mL/min) to give Example 2. HPLC: RT=11.1 min (H$_2$O/CH$_3$CN with TFA, SunFire C18 3.5 μm, 4.6×150 mm, gradient=15 min, wavelength=220 and 254 nm); MS(ES): m/z=599.3[M+H$^+$]; $^1$H NMR (400 MHz, methanol-d$_4$) δ 7.94 (s, 1H), 7.84-7.69 (m, 2H), 7.66-7.55 (m, 1H), 7.35-7.17 (m, 2H), 6.91 (dd, J=7.7, 1.3 Hz, 1H), 5.39 (s, 1H), 4.01 (s, 3H), 2.80-2.58 (m, 2H), 2.57-2.40 (m, 1H), 2.30-2.11 (m, 1H), 1.87-1.62 (m, 3H), 0.96-0.80 (m, 1H), 0.74-0.61 (m, 1H), 0.53-0.35 (m, 2H), 0.19-0.08 (m, 1H), 0.06-0.01 (m, 1H).

Example 3

(2R,3S)—N-((3S)-9-Chloro-5-(3-fluoro-5-meth-ylphenyl)-2-oxo-2,3-dihydro-1H-benzo[e][1,4]diaz-epin-3-yl)-3-(cyclopropylmethyl)-2-(3,3,3-trifluoro-propyl)succinamide

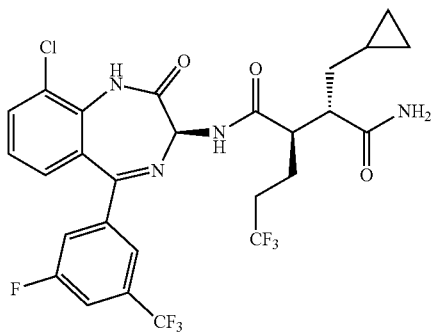

(3)

Example 3 was prepared from Intermediate B4 and Intermediate 51 according to the general procedure shown for Example 1. This solid was purified by preparative SFC chromatography (Berger SFC MGII, IC 4 25×3 cm ID, 5 μm, 85/15 CO$_2$/MeOH, 85 mL/min) to give Example 3. HPLC: RT=9.109 min (H$_2$O/CH$_3$CN with TFA, SunFire C18 3.5 μm, 4.6×150 mm, gradient=15 min, wavelength=220 and 254 nm); MS(ES): m/z=567 [M+H$^+$]; δ $^1$H NMR (400 MHz, methanol-d$_4$) δ 7.77 (dd, J=7.7, 1.5 Hz, 1H), 7.37-7.24 (m, 2H), 7.16 (s, 1H), 7.14-7.06 (m, 2H), 5.35 (s, 1H), 2.78-2.67 (m, 1H), 2.65-2.58 (m, 1H), 2.48 (d, J=11.7 Hz, 1H), 2.37 (s, 3H), 2.27-2.13 (m, 1H), 1.85-1.62 (m, 3H), 1.33-1.21 (m, 1H), 0.69 (d, J=7.0 Hz, 1H), 0.51-0.36 (m, 2H), 0.19-0.09 (m, 1H), 0.06--0.02 (m, 1H).

Example 4

(2R,3S)-3-(Cyclopropylmethyl)-N-((3S)-5-(3-fluo-rophenyl)-9-methoxy-2-oxo-2,3-dihydro-1H-1,4-benzodiazepin-3-yl)-2-(3,3,3-trifluoropropyl)succi-namide

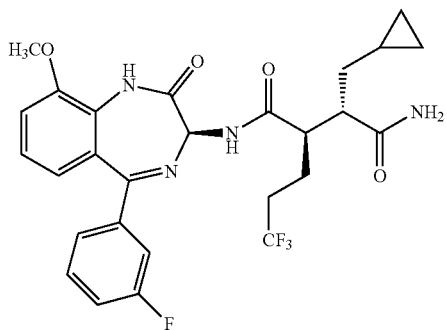

(4)

Example 4 was prepared from Intermediate B6 and Intermediate S1 according to the general procedure shown for Example 1. This solid was purified by preparative SFC chromatography (Berger SFC MGIII, CHIRALPAK® IC 25×3 cm ID, 5 μm, 90/10 CO$_2$/MeOH, 220 mL/min) to give Example 4. HPLC: RT=10.46 min (H$_2$O/CH$_3$CN with TFA, SunFire C18 3.5 μm, 4.6×150 mm, gradient=15 min, wavelength=220 and 254 nm); MS(ES): m/z=549.2[M+H$^+$]; $^1$H NMR (400 MHz, methanol-d$_4$) δ 7.47-7.19 (m, 7H), 6.93 (dd, J=7.7, 1.5 Hz, 1H), 5.36 (s, 1H), 4.00 (s, 3H), 2.78-2.57 (m, 2H), 2.54-2.35 (m, 1H), 2.31-2.11 (m, 1H), 1.84-1.62 (m, 3H), 1.37-1.27 (m, 1H), 0.76-0.61 (m, 1H), 0.50-0.34 (m, 2H), 0.17-0.10 (m, 1H), 0.08-0.01 (m, 1H).

Example 5

(2R,3S)-3-(Cyclopropylmethyl)-N-((3S)-9-(cyclo-propyloxy)-5-(3-fluorophenyl)-2-oxo-2,3-dihydro-1H-1,4-benzodiazepin-3-yl)-2-(3,3,3-trifluoropropyl)succinamide

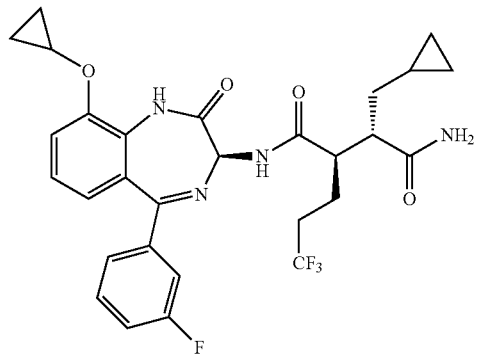

(5)

Example 5 was prepared from Intermediate B7 and Intermediate S1 according to the general procedure shown for Example 1. This solid was purified by preparative SFC chromatography (Berger SFC MGII, Regis Whelk-O R,R 25×3 cm ID, 5 μm, 83/17 CO$_2$/MeOH, 85 mL/min) to give Example 5. HPLC: RT=10.52 min (H$_2$O/CH$_3$CN with TFA, SunFire C18 3.5 μm, 4.6×150 mm, gradient=15 min, wavelength=220 and 254 nm); MS(ES): m/z=575.29 [M+H$^+$]; $^1$H NMR (400 MHz, methanol-d$_4$) δ 7.62 (dd, J=8.1, 1.1 Hz, 1H), 7.53-7.17 (m, 5H), 6.97 (dd, J=8.1, 1.1 Hz, 1H), 5.37 (s, 1H), 4.00 (t, J=4.4 Hz, 1H), 2.86-2.58 (m, 2H), 2.58-2.10 (m, 2H), 1.98-1.62 (m, 3H), 1.46-1.15 (m, 1H), 1.05-0.82 (m, 4H), 0.81-0.59 (m, 1H), 0.58-0.36 (m, 2H), 0.25-0.10 (m, 2H).

Example 6

(2R,3S)-3-(Cyclopropylmethyl)-N-((3S)-9-(cyclo-propyloxy)-2-oxo-5-phenyl-2,3-dihydro-1H-1,4-benzodiazepin-3-yl)-2-(3,3,3-trifluoropropyl)succi-namide

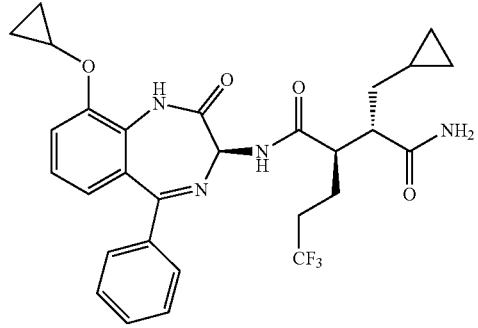

(6)

Example 6 was prepared from Intermediate B8 and Intermediate S1 according to the general procedure shown for Example 1. This solid was purified by preparative SFC chromatography (Berger SFC MGII, IC, 25×3 cm ID, 5 μm, 82/18 $CO_2$/MeOH, 85 mL/min) to give Example 6. HPLC: RT=9.07 min ($H_2O$/$CH_3CN$ with TFA, SunFire C18 3.5 μm, 4.6×150 mm, gradient=15 min, wavelength=220 and 254 nm); MS(ES): m/z=557.6 [M+H$^+$]; $^1$H NMR (400 MHz, methanol-$d_4$) δ 7.69-7.34 (m, 1H), 7.24 (t, J=8.0 Hz, 1H), 6.94 (dd, J=7.9, 1.1 Hz, 1H), 5.37 (s, 1H), 4.10-3.86 (m, 1H), 2.91-2.60 (m, 2H), 2.60-2.09 (m, 2H), 1.99-1.61 (m, 3H), 1.57-1.19 (m, 2H), 1.10-0.83 (m, 4H), 0.80-0.61 (m, 1H), 0.57-0.34 (m, 2H), 0.22--0.05 (m, 2H).

Example 7

(2R,3S)—N-((3S)-5-(4-Chlorophenyl)-9-cyclopropyl-2-oxo-2,3-dihydro-1H-1,4-benzodiazepin-3-yl)-3-(cyclopropylmethyl)-2-(3,3,3-trifluoropropyl)succinamide

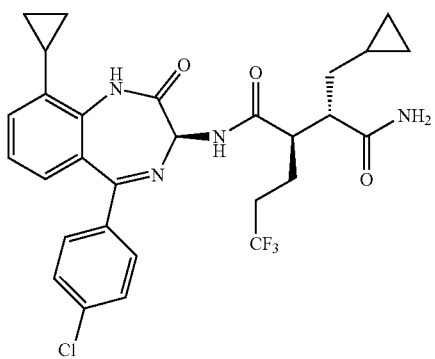

(7)

Preparation 7A

9-Bromo-5-(4-chlorophenyl)-1H-benzo[e][1,4]diazepin-2(3H)-one

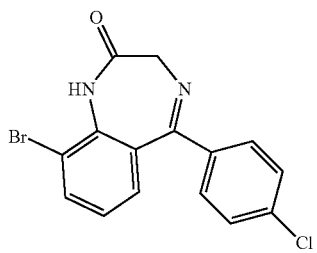

(7A)

To a stirred solution of Intermediate A31 (6.5 g, 20.93 mmol) in DCM (70.00 mL) was added pyridine (2.031 mL, 25.1 mmol) in one portion followed by bromoacetyl bromide (3.64 mL, 41.9 mmol) dropwise at 0° C. The reaction mixture was allowed to stir for 1 h at room temperature, then the reaction mixture was diluted with DCM (50 ml) and washed with water twice, then brine. The organic layer was dried over $Na_2SO_4$, filtered and concentrated to afford crude 2-bromo-N-(2-bromo-6-(4-chlorobenzoyl)phenyl)acetamide. This material was dissolved in 2M ammonia in MeOH (80.00 ml, 160 mmol) and stirred for 16 h at room temperature. The reaction mixture was concentrated and the residue was purified by silica gel chromatography (hexanes/EtOAc) to give Preparation 7A (2.1 g, 31.6% yield): HPLC: RT=2.029 min ($H_2O$/$CH_3CN$ with TFA, BEH C18 2.5 μm, 2.1×50 mm, gradient=4 min, wavelength=220 nm); MS(ES): m/z=349 [M+H$^+$].

Preparation 7B

9-Bromo-5-(4-chlorophenyl)-1-(4-methoxybenzyl)-1H-benzo[e][1,4]diazepin-2(3H)-one

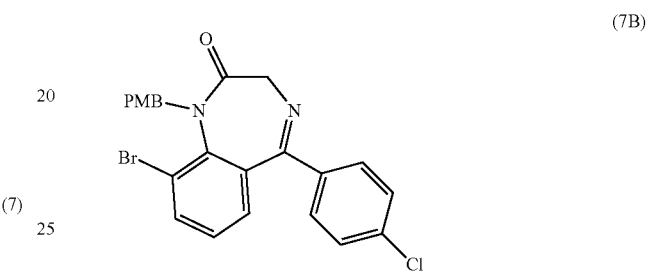

(7B)

To a stirred solution of Preparation 7A (1.5 g, 4.29 mmol) in DMF (25.00 mL) was added $K_2CO_3$ (1.779 g, 12.87 mmol) followed by 1-(chloromethyl)-4-methoxybenzene (0.873 mL, 6.44 mmol) in one portion. The reaction mixture was allowed to stir for 2 h at room temperature, then the reaction mixture was diluted with EtOAc and washed with water and brine. The organic layer was dried over $Na_2SO_4$, filtered and was concentrated. The crude material was purified by silica gel chromatography (hexanes/EtOAc) to give Preparation 7B (1.1 g, 54.6% yield): MS(ES): m/z=469 [M+H$^+$].

Preparation 7C

3-Azido-9-bromo-5-(4-chlorophenyl)-1-(4-methoxybenzyl)-1H-benzo[e][1,4]diazepin-2(3H)-one

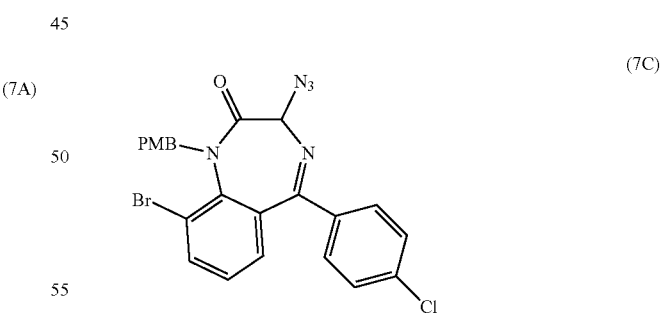

(7C)

To a stirred solution of Preparation 7B (1.00 g, 2.129 mmol) in THF (50.00 mL) at −78° C., was added LDA in THF (2.129 ml, 4.26 mmol) dropwise over 15 seconds. The reaction mixture was allowed to stir for 2 h at −78° C., then 2,4,6-triisopropylbenzenesulfonyl azide (1.317 g, 4.26 mmol) in THF (50.00 mL) was added. The reaction mixture was allowed to stir for 2 h at −78° C., then AcOH (0.3 ml, 5.24 mmol) was added dropwise. The reaction mixture was allowed to warm to room temperature and stirred for 16 h. The reaction was quenched with 10% $NaHCO_3$(aq) (50 ml). The mixture was extracted three times with EtOAC. The combined organic layers were washed with brine, dried over Na₂SO₄, filtered and concentrated. The crude material was purified by silica gel chromatography to give Preparation 7C (0.6 g, 1.175 mmol, 55.2% yield): MS(ES): m/z=510 [M+H⁺].

Preparation 7D

3-Amino-9-bromo-5-(4-chlorophenyl)-1-(4-methoxybenzyl)-1H-benzo[e][1,4]diazepin-2(3H)-one

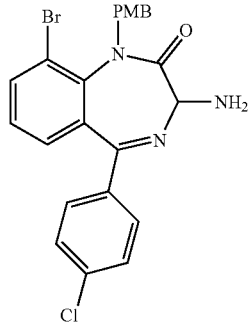

(7D)

To a stirred solution of Preparation 7C (0.550 g, 1.077 mmol) in THF (5.00 mL) and water (5.00 mL) was added triphenylphosphine (0.282 g, 1.077 mmol) in one portion. The reaction mixture was allowed to stir for 3 h at room temperature. The reaction mixture was diluted water and extracted three times with EtOAc, The combined organic layers were washed with brine, dried over Na₂SO₄, filtered and concentrated. The crude material was purified by silica gel chromatography (hexanes/EtOAc) to give Preparation 7D (0.480 g, 0.495 mmol, 46.0% yield): MS(ES): m/z=484 [M+H⁺].

Preparation 7E

3-Amino-9-bromo-5-(4-chlorophenyl)-1H-benzo[e][1,4]diazepin-2(3H)-one

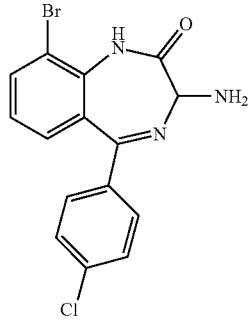 [SMILES: Cc1ccc(C2=NC(N)C(=O)Nc3c(F)cccc32)cc1]

(7E)

To a stirred solution of Preparation 7D (0.480 g, 0.990 mmol) in TFA (10.00 mL, 130 mmol) was added anisole (1.082 mL, 9.90 mmol) followed by triflic acid (4.40 µl, 0.050 mmol) in one portion. The reaction mixture was allowed to stir for 16 h at room temperature, then concentrated. The solid was basified to the pH-8-9 with aqueous 10% NaHCO₃ solution and extracted three times with EtOAC. The combined organic layers were washed with brine, dried over Na₂SO₄, filtered and concentrated. The crude material was purified by crystallization from EtOAC (10 ml). The solid was filtered and dried under vacuum to get Preparation 7E (0.170 g, 0.466 mmol, 47.1% yield): HPLC: RT=1.680 min (H₂O/CH₃CN with TFA, BEH C18 2.5 µm, 2.1×50 mm, gradient=4 min, wavelength=220 nm); MS(ES): m/z=364[M+H⁺].

Preparation 7F (2S,3R)-tert-Butyl 3-((9-bromo-5-(4-chlorophenyl)-2-oxo-2,3-dihydro-1H-benzo[e][1,4]diazepin-3-yl)carbamoyl)-2-(cyclopropylmethyl)-6,6,6-trifluorohexanoate

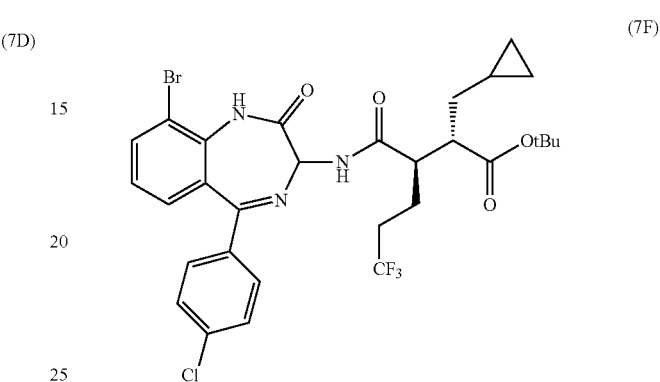

(7F)

To a stirred solution of Preparation 7E (0.120 g, 0.329 mmol) and Intermediate S1 (0.128 g, 0.395 mmol) in DMF (1.2 mL) was added TBTU (0.116 g, 0.362 mmol) in one portion followed by TEA (0.138 mL, 0.987 mmol) dropwise over 15 seconds. The reaction mixture was stirred at room temperature for 1 h, then water was added to the reaction mixture. The solid formed was stirred for 10 minutes, filtered, and dried under vacuum. The crude material was purified by silica gel chromatography (hexanes/EtOAc) to give Preparation 7F (0.160 g, 72.5% yield): HPLC: RT=3.017 min (H₂O/CH₃CN with TFA, BEH C18 2.5 µm, 2.1×50 mm, gradient=4 min, wavelength=220 nm); MS(ES): m/z=670 [M+H⁺].

Preparation 7F and Preparation 7G (2S,3R)-tert-Butyl 3-((3S)-(5-(4-chlorophenyl)-9-cyclopropyl-2-oxo-2,3-dihydro-1H-benzo[e][1,4]diazepin-3-yl)carbamoyl)-2-(cyclopropylmethyl)-6,6,6-trifluorohexanoate and (2S,3R)-tert-Butyl 3-((3R)-(5-(4-chlorophenyl)-9-cyclopropyl-2-oxo-2,3-dihydro-1H-benzo[e][1,4]diazepin-3-yl)carbamoyl)-2-(cyclopropylmethyl)-6,6,6-trifluorohexanoate

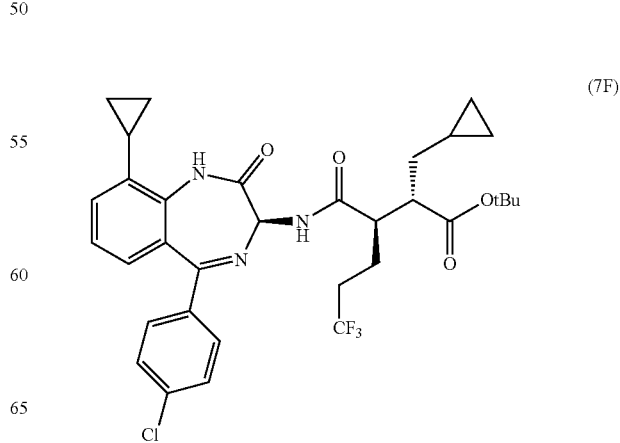

(7F)

-continued

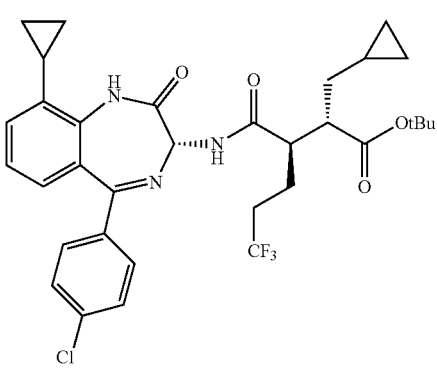

(7G)

A stirred solution of Preparation 7E (0.16 g, 0.238 mmol), cyclopropylboronic acid (0.041 g, 0.477 mmol), tripotassium phosphate (0.202 g, 0.954 mmol) and tricyclohexylphosphine (6.69 mg, 0.024 mmol) in toluene (0.3 mL) and water (0.100 mL) was degassed twice and heated to 90° C. Palladium(II) acetate (6.96 mg, 0.031 mmol) was added, and the reaction mixture was heated at 100° C. for 3 h. The reaction mixture was cooled to room temperature and extracted three times with EtOAc. The combined organic layers were washed with brine, dried over $Na_2SO_4$, filtered and concentrated. The crude material was purified by silica gel chromatography (hexanes/EtOAc) to give a mixture of starting material and product.

A stirred solution of a portion of this material (0.09 g, 0.134 mmol), cyclopropylboronic acid (0.012 g, 0.134 mmol), tripotassium phosphate (0.114 g, 0.537 mmol), tricyclohexylphosphine (3.76 mg, 0.013 mmol) in toluene (2.0 mL) and water (0.667 mL) was degassed twice and heated to 90° C. Palladium(II) acetate (3.91 mg, 0.017 mmol) was added and the reaction mixture was heated to 100° C. for 2 h. The reaction mixture was cooled to room temperature and was extracted with three times with EtOAc. The combined organic layers were washed with brine, dried over $Na_2SO_4$, filtered and concentrated. The crude material was purified by silica gel chromatography (hexanes/EtOAc).

This material was purified by SFC (CHIRALPAK® IA, 250×4.6 mm ID, 5 µm, 75/25 $CO_2$/MeOH, 3 mL/min) to give Preparation 7G (0.04 g, 0.063 mmol, 26% yield) and Preparation 7F (0.045 g, 0.071 mmol, 30% yield).

Preparation 7F (2nd peak from SFC): HPLC: RT=3.064 min ($H_2O$/$CH_3CN$ with TFA, BEH C18 2.5 µm, 2.1×50 mm, gradient=4 min, wavelength=220 nm); MS(ES): m/z=632 [M+H$^+$]; Chiral HPLC: RT=3.90 min ($CO_2$/MeOH, CHIRALPAK® IA 5 µm, 4.6×250 mm, gradient=9 min, wavelength=223 nm).

Preparation 7G (1st peak from SFC): HPLC: RT=3.064 min ($H_2O$/$CH_3CN$ with TFA, BEH C18 2.5 µm, 2.1×50 mm, gradient=4 min, wavelength=220 nm); MS(ES): m/z=632 [M+H$^+$]; Chiral HPLC: RT=2.72 min ($CO_2$/MeOH, CHIRALPAK® IA 5 µm, 4.6×250 mm, gradient=9 min, wavelength=223 nm).

Preparation 7H (2S,3R)-3-(((3S)-5-(4-Chlorophenyl)-9-cyclopropyl-2-oxo-2,3-dihydro-1H-benzo[e][1,4]diazepin-3-yl)carbamoyl)-2-(cyclopropylmethyl)-6,6,6-trifluorohexanoic acid

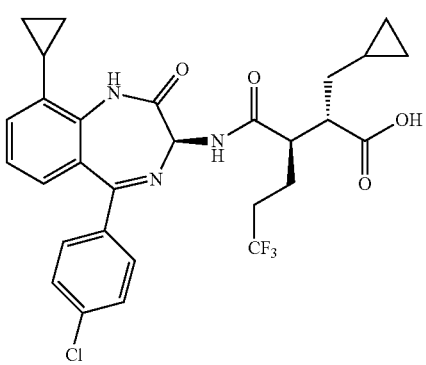

(7H)

To a stirred solution of Preparation 7F (0.045 g, 0.071 mmol) in DCM (0.5 mL) was added TFA (0.225 ml, 2.92 mmol) in one portion. The reaction mixture was allowed to stir for 2 hours at room temperature, then concentrated. Water was added and stirred for 10 minutes, the solid was filtered and dried under vacuum to get Preparation 7H (0.030 g, 73.2% yield): HPLC: RT=2.582 min ($H_2O$/$CH_3CN$ with TFA, BEH C18 2.5 µm, 2.1×50 mm, gradient=4 min, wavelength=220 nm); MS(ES): m/z=576 [M+H$^+$].

Example 7

To a stirred solution of Preparation 7H (30.5 mg, 0.053 mmol) in THF (0.40 mL) under $N_2$ was added EDC (25.4 mg, 0.132 mmol), HOBt (25.9 mg, 0.169 mmol), and ammonia (2M in IPA) (0.164 mL, 0.328 mmol). The reaction mixture was stirred for 3.5 h, then diluted with 10 mL of water and filtered. The solid was rinsed with water, then dried under vacuum. The material was purified by silica gel chromatography (hexanes/EtOAc) to give Example 7 (12.8 mg, 41.2%): HPLC: RT=12.09 min ($H_2O$/$CH_3CN$ with TFA, SunFire C18 3.5 µm, 4.6×150 mm, gradient=15 min, wavelength=220 and 254 nm); MS(ES): m/z=575.1 [M+H$^+$]; $^1$H NMR (400 MHz, MeOD) δ 7.60-7.54 (m, 2H), 7.46-7.41 (m, 2H), 7.40-7.35 (m, 1H), 7.25-7.14 (m, 2H), 5.32 (s, 1H), 2.76-2.67 (m, 1H), 2.65-2.58 (m, 1H), 2.56-2.42 (m, 1H), 2.31-2.16 (m, 1H), 2.10 (tt, J=8.4, 5.5 Hz, 1H), 1.87-1.73 (m, 2H), 1.72-1.61 (m, 1H), 1.36-1.20 (m, 2H), 1.18-1.03 (m, 2H), 0.83-0.76 (m, 1H), 0.74-0.64 (m, 1H), 0.50-0.36 (m, 2H), 0.17-0.07 (m, 1H), 0.05--0.05 (m, 1H).

Example 8

(2R,3S)-3-(Cyclopropylmethyl)-N-((3S)-9-hydroxy-5-(3-methylphenyl)-2-oxo-2,3-dihydro-1H-1,4-benzodiazepin-3-yl)-2-(3,3,3-trifluoropropyl)succinamide (8)

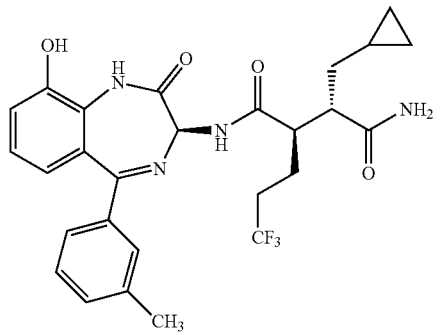

A solution of Example 31, (50 mg, 0.092 mmol) in DCM (10 mL) was cooled to 0° C. BBr$_3$ (1M in DCM, 0.459 mL, 0.459 mmol) was added. The reaction mixture was removed from the cooling bath and warmed to room temperature. After 1 h, the reaction mixture was partitioned between ethyl acetate and water. The aqueous layer was extracted twice more with ethyl acetate. The organic layer was dried with Na$_2$SO$_4$, filtered and concentrated. The crude material was purified by silica gel chromatography (hexanes/EtOAc). This solid was purified by preparative SFC chromatography (Berger SFC MGII, AC-H 250×30 mm ID, 5 μm, 85/15 CO$_2$/MeOH, 85 mL/min) to give Example 8 (18 mg, 36%). HPLC: RT=8.00 min (H$_2$O/CH$_3$CN with TFA, SunFire C18 3.5 μm, 4.6×150 mm, gradient=15 min, wavelength=220 and 254 nm); MS(ES): m/z=531 [M+H$^+$]; $^1$H NMR (400 MHz, DMSO-d$_6$) δ 9.29 (d, J=7.3 Hz, 1H), 7.59 (br. s., 1H), 7.40 (s, 1H), 7.34 (d, J=5.1 Hz, 2H), 7.30-7.22 (m, 1H), 7.15-7.02 (m, 2H), 6.96 (br. s., 1H), 6.71 (d, J=7.0 Hz, 1H), 5.19 (d, J=7.0 Hz, 1H), 3.18 (s, 3H), 2.75-2.64 (m, 2H), 2.25 (br. s., 1H), 1.72-1.43 (m, 3H), 1.11-0.99 (m, 1H), 0.57 (d, J=7.0 Hz, 1H), 0.39-0.27 (m, 2H), 0.10--0.14 (m, 2H).

Example 9

(2R,3S)-3-(Cyclopropylmethyl)-N-((3S)-9-methyl-2-oxo-5-(3-(trifluoromethyl)phenyl)-2,3-dihydro-1H-1,4-benzodiazepin-3-yl)-2-(3,3,3-trifluoropropyl)succinamide (9)

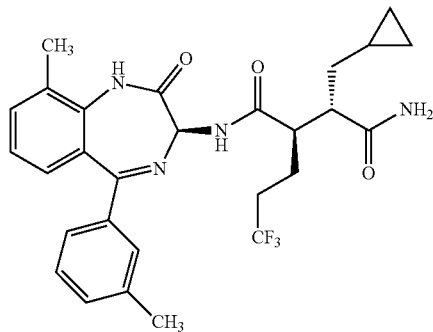

Example 9 was prepared from Intermediate B9 and Intermediate S1 according to the general procedure shown for Example 1. After separation of the diastereomers by preparative SFC chromatography (Instrument: Berger SFC MGII, Column: PHENOMENEX® Lux Cellulose 2 25×3 cm, 5 μm; Mobile Phase: 88/12 CO$_2$/MeOH Flow rate: 85 mL/min; Detection at 220 nm), Example 9 was obtained. HPLC: RT=9.269 min (H$_2$O/CH$_3$CN with TFA, SunFire C18 3.5 μm, 3.0×150 mm, gradient=15 min, wavelength=220 and 254 nm); MS(ES): m/z=583.1 [M+H$^+$]; $^1$H NMR (400 MHz, methanol-d$_4$) δ 7.98 (s, 1H), 7.82 (d, J=7.9 Hz, 1H), 7.77 (d, J=7.9 Hz, 1H), 7.67-7.60 (m, 1H), 7.59-7.53 (m, 1H), 7.27-7.17 (m, 2H), 5.38 (s, 1H), 2.80-2.71 (m, 1H), 2.71-2.61 (m, 1H), 2.59-2.47 (m, 4H), 2.29-2.17 (m, 1H), 1.90-1.65 (m, 3H), 1.30 (ddd, J=13.5, 7.5, 3.4 Hz, 1H), 0.77-0.66 (m, 1H), 0.52-0.38 (m, 2H), 0.19-0.09 (m, 1H), 0.08--0.02 (m, 1H).

Example 10

(2R,3S)-3-(Cyclopropylmethyl)-N-((3S)-5-(3-fluorophenyl)-9-methyl-2-oxo-2,3-dihydro-1H-1,4-benzodiazepin-3-yl)-2-(3,3,3-trifluoropropyl)succinamide (10)

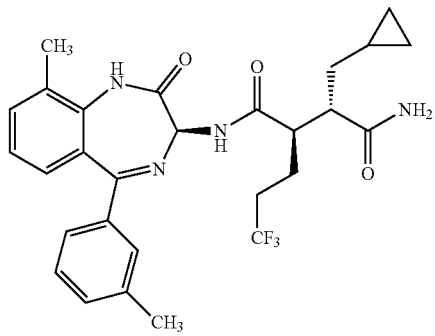

Example 10 was prepared from Intermediate B10 and Intermediate S1 according to the general procedure shown for Example 1. After separation of the diastereomers by preparative SFC chromatography (Instrument: Berger SFC MGII, Column: Chiral IC 25×3 cm, 5 μm; Mobile Phase: 85/15 CO$_2$/MeOH Flow rate: 85 mL/min; Detection at 220 nm.), Example 10 was obtained. HPLC: RT=8.688 min (H$_2$O/CH$_3$CN with TFA, SunFire C18 3.5 μm, 3.0×150 mm, gradient=15 min, wavelength=220 and 254 nm); MS(ES): m/z=533.1 [M+H$^+$]; $^1$H NMR (400 MHz, methanol-d$_4$) δ 7.76-7.59 (m, 1H), 7.53 (dd, J=5.5, 3.5 Hz, 1H), 7.48-7.35 (m, 2H), 7.32 (d, J=7.7 Hz, 1H), 7.28-7.19 (m, 3H), 5.34 (s, 1H), 4.22 (dd, J=5.6, 1.9 Hz, 1H), 2.78-2.68 (m, 1H), 2.67-2.58 (m, 1H), 2.56-2.43 (m, 4H), 2.28-2.16 (m, 1H), 1.86-1.65 (m, 3H), 1.47-1.41 (m, 1H), 0.76-0.63 (m, 1H), 0.50-0.40 (m, 2H), 0.18-0.09 (m, 1H), 0.07--0.01 (m, 1H).

Example 11

(2R,3S)-3-(Cyclopropylmethyl)-N-((3S)-9-methyl-2-oxo-5-phenyl-2,3-dihydro-1H-1,4-benzodiazepin-3-yl)-2-(3,3,3-trifluoropropyl)succinamide

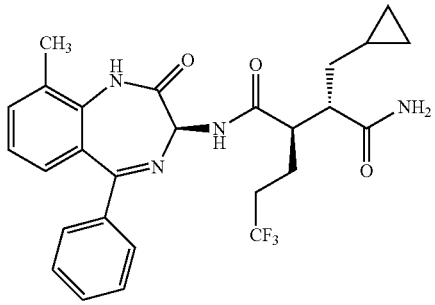

(11)

Example 11 was prepared from Intermediate B11 and Intermediate S1 according to the general procedure shown for Example 1. After separation of the diastereomers, Example 11 was obtained. This solid was purified by preparative SFC chromatography (Berger SFC MGII, Chiral IC 250×30 mm ID, 5 μm, 85/15 $CO_2$/MeOH, 85 mL/min) to give Example 11. HPLC: RT=7.673 min ($H_2O$/$CH_3CN$ with TFA, SunFire C18 3.5 μm, 4.6×150 mm, gradient=15 min, wavelength=220 and 254 nm); MS(ES): m/z=515 [M+H$^+$ ]; $^1$H NMR (400 MHz, methanol-$d_4$) δ 7.62-7.56 (m, 2H), 7.55-7.48 (m, 2H), 7.47-7.39 (m, 2H), 7.23-7.16 (m, 2H), 5.35 (s, 1H), 2.80-2.70 (m, 1H), 2.67 (dd, J=10.7, 3.4 Hz, 1H), 2.49 (s, 4H), 2.35-2.14 (m, 1H), 1.91-1.65 (m, 3H), 1.35-1.24 (m, 1H), 0.78-0.64 (m, 1H), 0.53-0.39 (m, 2H), 0.14 (br. s., 1H), 0.05 (d, J=4.2 Hz, 1H).

Example 12

(2R,3S)-3-(Cyclopropylmethyl)-N-((3S)-5-(4-fluorophenyl)-9-methyl-2-oxo-2,3-dihydro-1H-1,4-benzodiazepin-3-yl)-2-(3,3,3-trifluoropropyl)succinamide

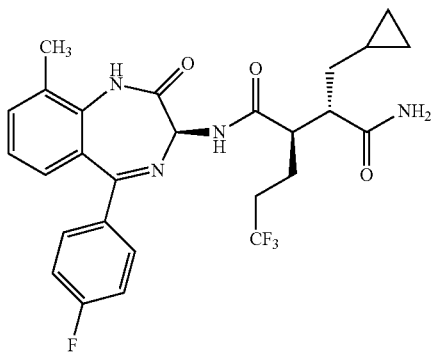

(12)

Example 12 was prepared from Intermediate B12 and Intermediate S1 according to the general procedure shown for Example 1. After separation of the diastereomers by preparative SFC chromatography (Instrument: Berger SFC MGII, Column: Chiral OD 25×3 cm, 5 μm; Mobile Phase: 85/15 $CO_2$/MeOH Flow rate: 85 mL/min; Detection at 220 nm.), Example 12 was obtained. HPLC: RT=8.744 min ($H_2O$/$CH_3CN$ with TFA, SunFire C18 3.5 μm, 3.0×150 mm, gradient=15 min, wavelength=220 and 254 nm); MS(ES): m/z=533.1[M+H$^+$]; $^1$H NMR (400 MHz, methanol-$d_4$) δ 7.65-7.59 (m, 2H), 7.51 (dd, J=5.6, 3.0 Hz, 1H), 7.24-7.11 (m, 4H), 4.22 (dd, J=5.7, 1.8 Hz, 1H), 2.76-2.66 (m, 1H), 2.66-2.58 (m, 1H), 2.55-2.43 (m, 4H), 2.22 (td, J=10.2, 5.7 Hz, 1H), 1.78 (ddd, J=15.8, 11.1, 4.6 Hz, 2H), 1.73-1.68 (m, 1H), 1.47-1.41 (m, 1H), 0.74-0.63 (m, 1H), 0.51-0.37 (m, 2H), 0.16-0.08 (m, 1H), 0.06--0.02 (m, 1H).

Example 13

(2R,3S)—N-((3S)-9-Chloro-5-(2-methylphenyl)-2-oxo-2,3-dihydro-1H-1,4-benzodiazepin-3-yl)-3-(cyclopropylmethyl)-2-(3,3,3-trifluoropropyl)succinamide

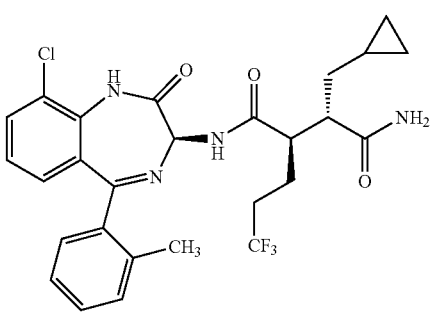

(13)

Example 13 was prepared from Intermediate B13 and Intermediate S1 according to the general procedure shown for Example 1. This solid was purified by preparative SFC chromatography (Berger SFC MGII, Chiral IC 25×3 cm ID, 5 mm, 80/20 $CO_2$/MeOH, 85 mL/min) to give Example 13. HPLC: RT=10.699 min ($H_2O$/$CH_3CN$ with TFA, SunFire C18 3.5 μm, 4.6×150 mm, gradient=15 min, wavelength=220 and 254 nm); MS(ES): m/z=549[M+H$^+$]; $^1$H NMR (500 MHz, methanol-$d_4$) δ 7.72 (dd, J=7.9, 1.5 Hz, 1H), 7.41-7.33 (m, 1H), 7.30-7.23 (m, 3H), 7.18 (t, J=7.9 Hz, 1H), 7.08 (dd, J=7.9, 1.5 Hz, 1H), 5.42 (s, 1H), 2.75-2.67 (m, 1H), 2.66-2.59 (m, 1H), 2.50-2.33 (m, 1H), 2.29-2.11 (m, 1H), 2.04 (s, 3H), 1.87-1.71 (m, 2H), 1.67 (ddd, J=13.7, 10.8, 6.4 Hz, 1H), 1.25 (ddd, J=13.6, 7.6, 3.5 Hz, 1H), 0.76-0.62 (m, 1H), 0.50-0.36 (m, 2H), 0.13-0.06 (m, 1H), 0.04--0.05 (m, 1H).

Example 14

(2R,3S)-3-(Cyclopropylmethyl)-N-(9-cyclopropyl-2-oxo-5-phenyl-2,3-dihydro-1H-1,4-benzodiazepin-3-yl)-2-(3,3,3-trifluoropropyl)succinamide

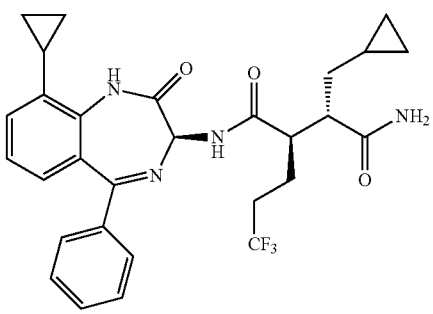

(14)

Example 14 was prepared from Intermediate B14 and Intermediate S1 according to the general procedure shown for Example 1. After separation of the diastereomers (Preparative SFC Chromatography, Berger SFC MGII, CHIRALPAK® OD 250×21 mm ID, 5 µm, 86/14 CO$_2$/MeOH, 85 mL/min), Example 14 was obtained. HPLC: RT=11.10 min (H$_2$O/CH$_3$CN with TFA, SunFire C18 3.5 µm, 4.6×150 mm, gradient=15 min, wavelength=220 and 254 nm); MS(ES): m/z=541.2 [M+H$^+$]; $^1$H NMR (400 MHz, DMSO-d$_6$) δ 10.26 (s, 1H), 9.28 (d, J=7.0 Hz, 1H), 7.57 (br. s., 1H), 7.55-7.50 (m, 3H), 7.48-7.41 (m, 2H), 7.30-7.25 (m, 1H), 7.19 (t, J=7.7 Hz, 1H), 7.13-7.09 (m, 1H), 6.96 (br. s., 1H), 5.18 (d, J=7.0 Hz, 1H), 2.75-2.63 (m, 2H), 2.27-2.11 (m, 2H), 1.66-1.58 (m, 3H), 1.55-1.47 (m, 1H), 1.12-1.00 (m, 3H), 0.79 (td, J=5.4, 3.6 Hz, 1H), 0.66 (td, J=5.5, 3.7 Hz, 1H), 0.60-0.50 (m, 1H), 0.40-0.29 (m, 2H), 0.07--0.02 (m, 1H), –0.06--0.16 (m, 1H).

Example 15

(2R,3S)—N-((3S)-9-Methyl-2-oxo-5-phenyl-2,3-dihydro-1H-1,4-benzodiazepin-3-yl)-3-propyl-2-(3,3-trifluoropropyl)succinamide

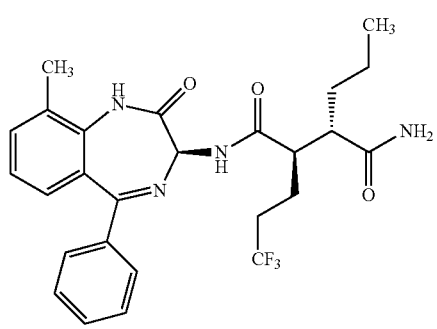

(15)

Example 15 was prepared from Intermediate B11 and Intermediate S2 according to the general procedure shown for Example 1. This solid was purified by preparative SFC chromatography (Berger SFC MGII, Chiral IC 25×3 cm ID, 5 µm, 85/15 CO$_2$/MeOH, 85 mL/min) to give Example 15. HPLC: RT=8.414 min (H$_2$O/CH$_3$CN with TFA, SunFire C18 3.5 µm, 4.6×150 mm, gradient=15 min, wavelength=220 and 254 nm); MS(ES): m/z=[M+H$^+$]; $^1$H NMR (400 MHz, methanol-d$_4$) δ 7.64-7.56 (m, 2H), 7.54-7.47 (m, 2H), 7.46-7.35 (m, 2H), 7.20-7.14 (m, 2H), 5.35 (s, 1H), 2.78-2.66 (m, 1H), 2.52 (m, 2H), 2.47 (s, 3H), 2.22 (d, J=11.4 Hz, 1H), 1.89-1.70 (m, 2H), 1.65 (d, J=8.1 Hz, 1H), 1.51-1.19 (m, 3H), 0.99-0.86 (m, 3H).

Example 16

(2R,3S)-3-(Cyclopropylmethyl)-N-((3S)-9-fluoro-5-(4-methylphenyl)-2-oxo-2,3-dihydro-1H-1,4-benzodiazepin-3-yl)-2-(3,3,3-trifluoropropyl)succinamide

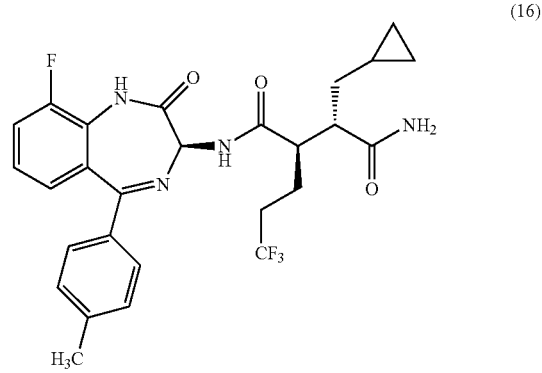 [SMILES: Cc1ccc(C2=N[C@H](NC(=O)[C@H](CCC(F)(F)F)[C@H](CC3CC3)C(N)=O)C(=O)Nc3c(F)cccc32)cc1]

(16)

Preparation 16A (2S,3R)-tert-Butyl 2-(cyclopropylmethyl)-6,6,6-trifluoro-3-(((S)-9-fluoro-2-oxo-5-(p-tolyl)-2,3-dihydro-1H-benzo[e][1,4]diazepin-3-yl)carbamoyl)hexanoate, and Preparation 16B (2S,3R)-tert-Butyl 2-(cyclopropylmethyl)-6,6,6-trifluoro-3-(((R)-9-fluoro-2-oxo-5-(p-tolyl)-2,3-dihydro-1H-benzo[e][1,4]diazepin-3-yl)carbamoyl)hexanoate

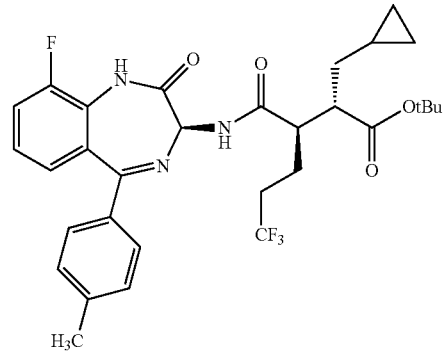

(16A)

-continued (16B)
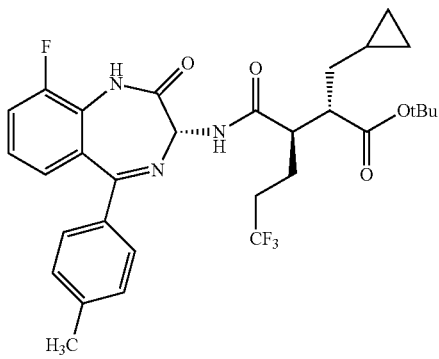

-continued (16D)
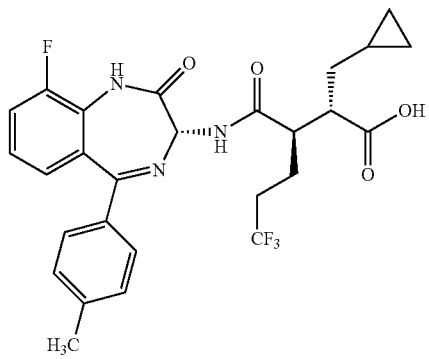

A mixture of Preparation 16A and Preparation 16B was prepared from Intermediate B15 (220 mg, 0.777 mmol) and Intermediate S1 (277 mg, 0.854 mmol) according to the general procedure shown for Preparation 1A and Preparation 1B. A mixture of Preparation 16A and Preparation 16B (400 mg, 87%) was obtained. HPLC: RT=2.228 min ($H_2O$/MeOH with TFA, ZORBAX® SBC18 5 µm, 4.6×50 mm, gradient=3 min, wavelength=220 nm); MS(ES): m/z=590 [M+H$^+$].

Preparation 16C (2S,3R)-2-(Cyclopropylmethyl)-6,6,6-trifluoro-3-(((S)-9-fluoro-2-oxo-5-(p-tolyl)-2,3-dihydro-1H-benzo[e][1,4]diazepin-3-yl)carbamoyl)hexanoic acid, and Preparation 16D (2S,3R)-2-(Cyclopropylmethyl)-6,6,6-trifluoro-3-(((R)-9-fluoro-2-oxo-5-(p-tolyl)-2,3-dihydro-1H-benzo[e][1,4]diazepin-3-yl)carbamoyl)hexanoic acid (16C)
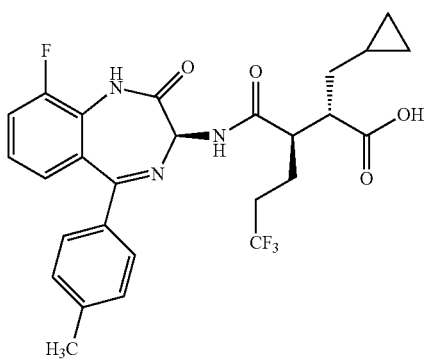

A mixture of Preparation 16A and Preparation 16B (400 mg, 0.678 mmol) was dissolved in DCM (8 mL) and cooled to 0° C. TFA (4 mL, 52 mmol) was added, then the reaction mixture was allowed to warm to room temperature. After 4 hours, the reaction mixture was concentrated. Ice water was added, then the precipitated solid was filtered off and washed with water. The solid was dried to give a mixture of Preparation 16C and Preparation 16D (250 mg, 69%). HPLC: RT=0.98 min ($H_2O$/MeCN with TFA, Acquity BEH C-18 1.7 µm, 2.1×50 mm, gradient=2 min, wavelength=220 nm); MS(ES): m/z=534 [M+H$^+$].

Example 16

A mixture of Preparation 16C and Preparation 16D (0.1 g, 0.187 mmol) was dissolved in DMSO (1 mL) and cooled to 0° C. Ammonium chloride (0.080 g, 1.499 mmol), diisopropylethylamine (0.098 mL, 0.562 mmol) and PyBOP (0.161 g, 0.309 mmol) were added, and the reaction mixture was allowed to stir at room temperature overnight. The reaction mixture was diluted with water, then the solid was filtered and dried. The solid was dissolved in DCM (50 mL), and washed with water (10 mL), then brine (10 mL). The organic layer was dried over sodium sulfate and concentrated. The crude material was purified by silica gel chromatography (chloroform/methanol).

After purification by preparative HPLC (CHIRALPAK® AD-H 250×4.6 mm, 5 µm, 70/30 hexanes/EtOH, 1 mL/min), Example 16 was obtained. HPLC: RT=9.342 min ($H_2O$/$CH_3CN$ with TFA, XBridge 3.5 µm, 4.6×150 mm, gradient=15 min, wavelength=220 and 254 nm); MS(ES): m/z=533 [M+H$^+$]; $^1$H NMR (400 MHz, methanol-$d_4$) δ 9.38 (d, J=4 Hz, 1H), 7.45-7.50 (m, 3H), 7.19-7.30 (m, 4H), 5.41 (d, J=4 Hz, 1H), 2.62-2.72 (m, 2H), 2.48-2.52 (m, 1H), 2.42 (s, 3H), 2.21-2.26 (m, 1H), 1.68-1.85 (m, 3H), 1.28-1.34 (m, 1H), 0.70-0.73 (m, 1H), 0.43-0.49 (m, 2H), 0.11-0.12 (m, 1H), 0.01-0.11 (m, 1H).

Example 17

(2R,3S)-3-(Cyclopropylmethyl)-N-((3S)-9-fluoro-7-methyl-2-oxo-5-phenyl-2,3-dihydro-1H-1,4-benzodiazepin-3-yl)-2-(3,3,3-trifluoropropyl)succinamide

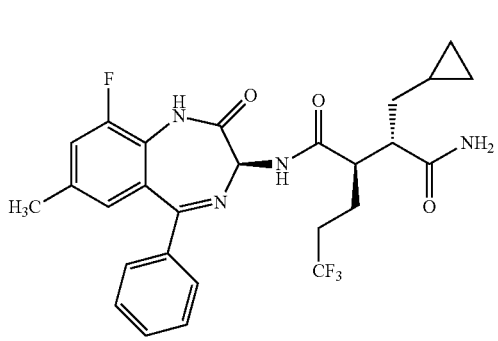

(17)

Example 17 was prepared from Intermediate B16 and Intermediate S1 according to the general procedure shown for Example 16. After purification by preparative HPLC (CHIRALPAK® AD-H 250×4.6 mm, 5 µm, 70/30 hexanes/EtOH, 1 mL/min), Example 17 was obtained. HPLC: RT=1.87 min (H$_2$O/MeOH with TFA, ZORBAX® 5 µm, C-18 4.6×50 mm, gradient=2 min, wavelength=220 nm); MS(ES): m/z=533 [M+H$^+$]; $^1$H NMR (400 MHz, methanol-d$_4$) δ 7.58-7.560 (m, 2H), 7.52-7.56 (m, 1H), 7.44-7.47 (m, 2H), 7.32-7.35 (dd, J=11.0, 1.4 Hz, 1H), 7.00 (br s, 1H), 5.43 (d, J=3.6 Hz, 1H), 2.62-2.74 (m, 2H), 2.42-2.58 (m, 1H), 2.36 (s, 3H), 2.18-2.31 (m, 1H), 1.68-1.85 (m, 3H), 1.27-1.32 (m, 1H), 0.71-0.74 (m, 1H), 0.44-0.50 (m, 2H), 0.10-0.19 (m, 1H), 0.04-0.08 (m, 1H).

Example 18

(2R,3S)-3-(Cyclopropylmethyl)-N-((3S)-9-fluoro-8-methyl-2-oxo-5-phenyl-2,3-dihydro-1H-1,4-benzodiazepin-3-yl)-2-(3,3,3-trifluoropropyl)succinamide

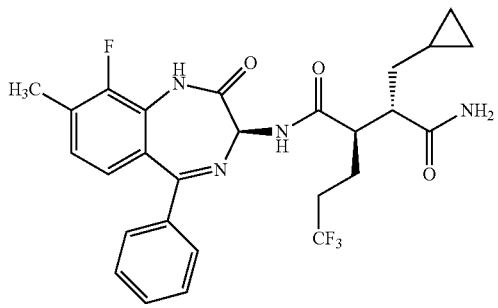

(18)

Example 18 was prepared from Intermediate B17 and Intermediate S1 according to the general procedure shown for Example 16. After purification by preparative HPLC (CHIRALPAK® AD-H 250×4.6 mm, 5 µm, 70/30 hexanes/EtOH, 1 mL/min), Example 18 was obtained. LCMS: RT=1.72 min (H$_2$O/MeCN with NH$_4$OAc, PUROSPHER® Star RP-18 3 µm, 4×55 mm, gradient=2 min, wavelength=220 nm); MS(ES): m/z=533 [M+H$^+$]; $^1$H NMR (400 MHz, methanol-d$_4$) δ 7.57-7.59 (m, 2H), 7.51-7.55 (m, 1H), 7.43-7.46 (m, 2H), 7.16 (t, J=7.6 Hz, 1H), 7.07-7.09 (m, 1H), 5.42 (s, 1H), 2.65-2.75 (m, 2H), 2.45-2.55 (m, 1H), 2.43 (s, 3H), 2.16-2.32 (m, 1H), 1.68-1.83 (m, 3H), 1.27-1.30 (m, 1H), 0.69-0.74 (m, 1H), 0.44-0.50 (m, 2H), 0.10-0.17 (m, 1H), 0.03-0.09 (m, 1H).

Example 19

(2R,3S)-3-(Cyclopropylmethyl)-N-((3S)-9-fluoro-5-(3-methylphenyl)-2-oxo-2,3-dihydro-1H-1,4-benzodiazepin-3-yl)-2-(3,3,3-trifluoropropyl)succinamide

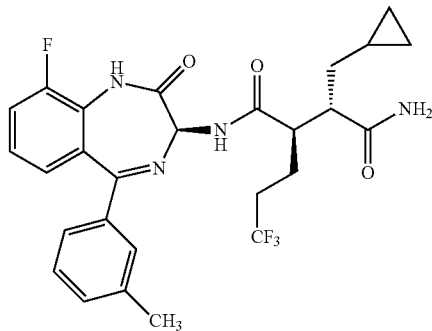

(19)

Example 19 was prepared from Intermediate B18 and Intermediate S1 according to the general procedure shown for Example 1. This solid was purified by preparative SFC chromatography (Berger SFC MGII, Chiral IC 25×3 cm ID, 5 µm, 88/12 CO$_2$/MeOH, 85 mL/min) to give Example 19. HPLC: RT=8.608 min (H$_2$O/CH$_3$CN with TFA, SunFire C18 3.5 µm, 4.6×150 mm, gradient=15 min, wavelength=220 and 254 nm); MS(ES): m/z=533 [M+H$^+$]; $^1$H NMR (400 MHz, methanol-d$_4$) δ 7.50-7.42 (m, 2H), 7.36-7.22 (m, 4H), 7.20-7.14 (m, 1H), 5.40 (s, 1H), 2.76-2.68 (m, 1H), 2.65 (dd, J=10.7, 3.4 Hz, 1H), 2.53-2.42 (m, 1H), 2.37 (s, 3H), 2.21 (d, J=10.6 Hz, 1H), 1.84-1.64 (m, 3H), 1.33-1.23 (m, 1H), 0.71 (s, 1H), 0.50-0.39 (m, 2H), 0.16-0.10 (d, J=4.2 Hz, 1H), 0.09-0.00 (m, 1H).

Example 20

(2R,3S)-3-(Cyclopropylmethyl)-N-((3S)-9-fluoro-1-methyl-2-oxo-5-phenyl-2,3-dihydro-1H-1,4-benzodiazepin-3-yl)-2-(3,3,3-trifluoropropyl)succinamide

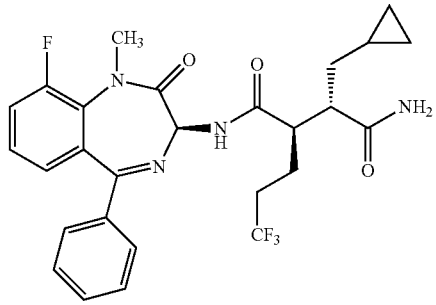

(20)

To a mixture of Example 1 (30 mg, 0.058 mmol) and Cs$_2$CO$_3$ (37.7 mg, 0.116 mmol) in DMF (0.6 mL) was added iodomethane (6.51 μl, 0.104 mmol). The mixture was stirred at room temperature for 15 min. Water was added and the resulting solid material was collected by filtration, rinsed with water and dried to give Example 20 (25 mg, 81%). HPLC: RT=2.735 min (CHROMOLITH® SpeedROD column 4.6× 50 mm, 10-90% aqueous methanol over 4 minutes containing 0.1% TFA, 4 mL/min, monitoring at 220 nm); MS(ES): m/z=533 [M+H]$^+$; $^1$H NMR (400 MHz, CD$_3$OD) δ 7.71-7.65 (m, 2H), 7.59-7.38 (m, 5H), 7.22 (d, J=7.7 Hz, 1H), 5.45 (s, 1H), 3.40 (d, J=4.0 Hz, 3H), 2.78-2.68 (m, 1H), 2.68-2.59 (m, 1H), 2.58-2.41 (m, 1H), 2.33-2.15 (m, 1H), 1.89-1.64 (m, 3H), 1.26 (ddd, J=13.6, 7.6, 3.4 Hz, 1H), 0.77-0.64 (m, 1H), 0.52-0.39 (m, 2H), 0.17-0.10 (m, 1H), 0.07--0.01 (m, 1H).

Example 21

(2R,3S)—N-((3S)-5-(4-Chlorophenyl)-9-methoxy-2-oxo-2,3-dihydro-1H-1,4-benzodiazepin-3-yl)-3-(cyclopropylmethyl)-2-(3,3,3-trifluoropropyl)succinamide

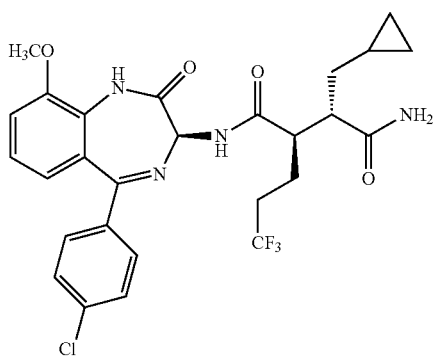

(21)

Example 21 was prepared from Intermediate B19 and Intermediate S1 according to the general procedure shown for Example 1. After separation of the diastereomers by preparative SFC chromatography (Instrument: Berger SFC MGII, Column: Chiral IA 25×2 cm, 5 μm; Mobile Phase: 85/15 CO$_2$/MeOH Flow rate: 60 mL/min; Detection at 220 nm), Example 21 was obtained. HPLC: RT=4.121 min (H$_2$O/MeOH with TFA, SunFire C18 3.5 μm, 4.6×50 mm, gradient=4 min, wavelength=220 nm); MS(ES): m/z=565 [M+H$^+$]; $^1$H NMR (400 MHz, DMSO-d$_6$) δ 10.08 (s, 1H), 9.34 (d, J=7.0 Hz, 1H), 7.64-7.48 (m, 5H), 7.35-7.28 (m, 1H), 7.27-7.18 (m, 1H), 6.95 (br. s., 1H), 6.91-6.84 (m, 1H), 5.17 (d, J=6.8 Hz, 1H), 3.92 (s, 3H), 2.75-2.60 (m, 2H), 2.57-2.53 (m, 1H), 2.30-2.14 (m, 1H), 1.67-1.56 (m, 2H), 1.56-1.43 (m, 1H), 1.09-0.96 (m, 1H), 0.64-0.46 (m, 1H), 0.39-0.25 (m, 2H), 0.00 (dd, J=7.6, 3.0 Hz, 1H), −0.07--0.18 (m, 1H).

Example 22

(2R,3S)-3-(Cyclopropylmethyl)-N-((3S)-9-fluoro-5-(3-methoxyphenyl)-2-oxo-2,3-dihydro-1H-1,4-benzodiazepin-3-yl)-2-(3,3,3-trifluoropropyl)succinamide

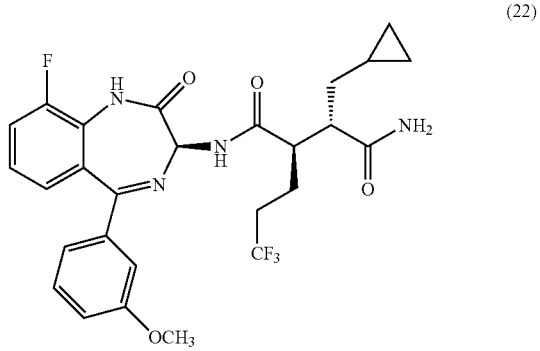 [SMILES: COc1cccc(C2=N[C@H](NC(=O)[C@H](CCC(F)(F)F)[C@H](CC3CC3)C(N)=O)C(=O)Nc3c(F)cccc32)c1]

(22)

Example 22 was prepared from Intermediate B20 and Intermediate S1 according to the general procedure shown for Example 1. After separation of the diastereomers by preparative SFC chromatography (Instrument: Berger SFC MGII, Column: Chiral OD-H 25×3 cm, 5 μm; Mobile Phase: 80/20 CO$_2$/MeOH Flow rate: 85 mL/min; Detection at 220 nm), Example 22 was obtained. HPLC: RT=3.806 min (SunFire C18, 5.0 um, 4.6 mm×50 mm, 10-90% aqueous methanol containing 0.2% H$_3$PO$_4$, 4 min gradient, monitored at 220 nm). MS(ES): m/z=549.4 [M+H$^+$]; $^1$H NMR (400 MHz, chloroform-d) δ 7.61-7.51 (m, 1H), 7.35 (s, 1H), 7.29 (d, J=8.1 Hz, 1H), 7.20 (s, 2H), 7.10 (s, 1H), 7.03 (dd, J=8.4, 2.6 Hz, 2H), 5.85 (br. s., 1H), 5.63 (br. s., 1H), 5.56 (d, J=7.7 Hz, 1H), 3.82 (s, 3H), 2.72 (s, 1H), 2.59 (s, 1H), 2.37-2.08 (m, 2H), 2.00-1.90 (m, 1H), 1.88-1.75 (m, 2H), 1.50-1.39 (m, 1H), 0.80-0.67 (m, 1H), 0.55-0.38 (m, 2H), 0.25-0.17 (m, 1H), 0.13-0.04 (m, 1H).

Example 23

(2R,3S)-3-(Cyclopropylmethyl)-N-((3S)-9-fluoro-5-(3-fluorophenyl)-2-oxo-2,3-dihydro-1H-1,4-benzodiazepin-3-yl)-2-(3,3,3-trifluoropropyl)succinamide

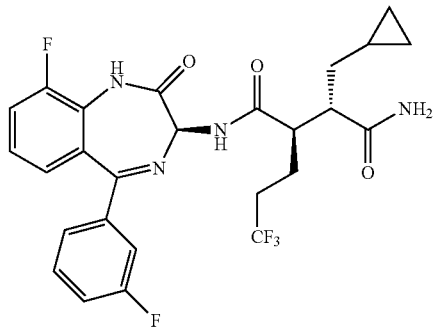

(23)

Example 23 was prepared from Intermediate B21 and Intermediate S1 according to the general procedure shown for Example 1. This solid was purified by preparative SFC chromatography (Berger SFC MGII, CHIRALPAK® IC 250×30 mm ID, 5 μm, 86/14 CO$_2$/MeOH, 85 mL/min) to give Example 23. HPLC: RT=2.630 min (H₂O/CH₃CN with TFA, CHROMOLITH® SpeedROD, 4.6×50 mm, gradient=4 min, wavelength=220 nm); MS(ES): m/z=537 [M+H⁺]; ¹H NMR (400 MHz, methanol-d₄) δ 7.54-7.37 (m, 3H), 7.37-7.25 (m, 3H), 7.25-7.20 (m, 1H), 5.44 (s, 1H), 2.79-2.61 (m, 2H), 2.59-2.41 (m, 1H), 2.33-2.14 (m, 1H), 1.90-1.65 (m, 3H), 1.31 (ddd, J=13.6, 7.5, 3.5 Hz, 1H), 0.78-0.65 (m, 1H), 0.53-0.40 (m, 2H), 0.19-0.11 (m, 1H), 0.09-0.01 (m, 1H).

Example 24

(2R,3S)—N-((3S)-5-(3-Chlorophenyl)-9-fluoro-2-oxo-2,3-dihydro-1H-1,4-benzodiazepin-3-yl)-3-(cyclopropylmethyl)-2-(3,3,3-trifluoropropyl)succinamide (24)

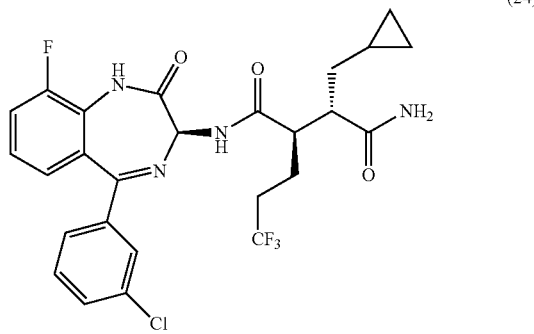

Example 24 was prepared from Intermediate B22 and Intermediate S1 according to the general procedure shown for Example 16. After purification by preparative HPLC (CHIRALPAK® IA 250×4.6 mm, 5 μm, 90/10 hexanes/EtOH, 1 mL/min), Example 24 was obtained. HPLC: RT=1.929 min (H₂O/MeOH with TFA, ZORBAX® SB C18 5 μm, 4.6×50 mm, gradient=4 min, wavelength=220 and 254 nm); MS(ES): m/z=553 [M+H⁺]; ¹H NMR (400 MHz, methanol-d₄) δ 7.68-7.68 (m, 1H), 7.48-7.57 (m, 2H), 7.43-7.44 (m, 2H), 7.31 (m, 1H), 7.22 (d, J=8.00 Hz, 1H), 5.44 (s, 1H), 2.65-2.74 (m, 2H), 2.45-2.55 (m, 1H), 2.20-2.29 (m, 1H), 1.68-1.85 (m, 3H), 1.28-1.28 (m, 1H), 0.71-0.74 (m, 1H), 0.44-0.50 (m, 2H), 0.12-0.18 (m, 1H), 0.04-0.07 (m, 1H).

Example 25

(2R,3S)—N-((3S)-5-(4-Chlorophenyl)-9-methoxy-2-oxo-2,3-dihydro-1H-1,4-benzodiazepin-3-yl)-3-propyl-2-(3,3,3-trifluoropropyl)succinamide (25)

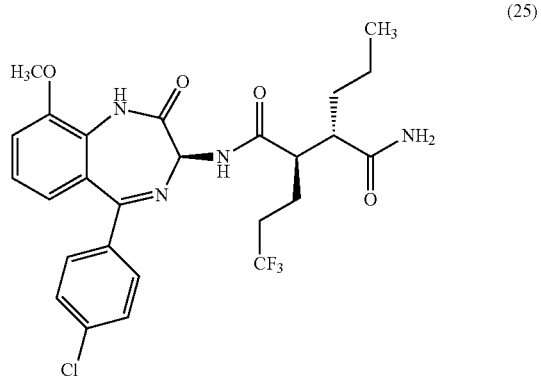 [SMILES: CCC[C@H](C(N)=O)[C@@H](CCC(F)(F)F)C(=O)N[C@H]1N=C(c2ccc(Cl)cc2)c2cccc(OC)c2NC1=O]

Example 25 was prepared from Intermediate B19 and Intermediate S2 according to the general procedure shown for Example 1. This solid was purified by preparative SFC chromatography (Berger SFC MGII, AS-H 250×30 mm ID, 5 μm, 88/12 CO₂/MeOH, 85 mL/min) to give Example 25. HPLC: RT=9.13 min (H₂O/CH₃CN with TFA, SunFire C18 3.5 μm, 4.6×150 mm, gradient=15 min, wavelength=220 and 254 nm); MS(ES): m/z=553 [M+H⁺]; ¹H NMR (400 MHz, DMSO-d₆) δ 10.09 (s, 1H), 9.40 (d, J=7.3 Hz, 1H), 7.56 (d, J=2.6 Hz, 4H), 7.37-7.31 (m, 1H), 7.30-7.17 (m, 2H), 6.97-6.85 (m, 2H), 5.21 (d, J=7.0 Hz, 1H), 4.04-3.82 (m, 3H), 2.74-2.61 (m, 2H), 2.44-2.35 (m, 1H), 2.24 (br. s., 1H), 1.68-1.42 (m, 3H), 1.31-1.07 (m, 3H), 0.81 (t, J=6.9 Hz, 3H).

Example 26

(2R,3S)—N-((3S)-9-Chloro-5-(3-chlorophenyl)-2-oxo-2,3-dihydro-1H-benzo[e][1,4]diazepin-3-yl)-3-(cyclopropylmethyl)-2-(3,3,3-trifluoropropyl)succinamide (26)

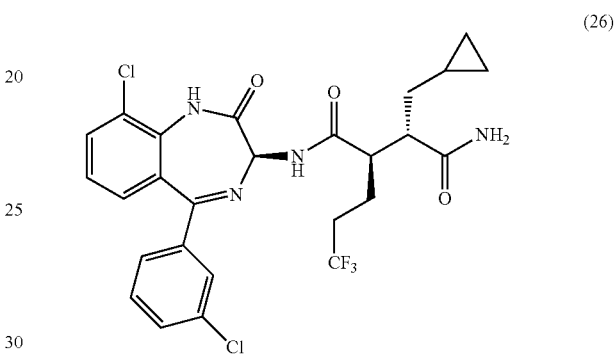

Example 26 was prepared from Intermediate B23 and Intermediate S1 according to the general procedure shown for Example 1. This solid was purified by preparative SFC chromatography (Berger SFC MGII, AS-H 250×30 mm ID, 5 μm, 82/18 CO₂/MeOH, 85 mL/min) to give Example 26. HPLC: RT=2.05 min (H₂O/MeOH with TFA, SunFire C18 2.5 μm, 2.1×30 mm, gradient=3 min, wavelength=220 nm); MS(ES): m/z=569 [M+H⁺]; ¹H NMR (400 MHz, DMSO-d₆) δ 7.65 (br. s., 1H), 7.60 (br. s., 1H), 7.50 (t, J=7.6 Hz, 1H), 7.40 (d, J=7.0 Hz, 2H), 7.33 (br. s., 1H), 7.10 (d, J=6.2 Hz, 1H), 6.97 (br. s., 1H), 2.64-2.54 (m, 2H), 2.25 (d, J=11.7 Hz, 1H), 1.70-1.57 (m, 2H), 1.54 (br. s., 1H), 1.25 (s, 1H), 1.09 (br. s., 1H), 0.58 (d, J=6.6 Hz, 1H), 0.41-0.27 (m, 2H), 0.02 (t, J=9.1 Hz, 1H), −0.09 (d, J=4.6 Hz, 1H).

Example 27

(2R,3S)—N-((3S)-9-Chloro-5-(4-chlorophenyl)-2-oxo-2,3-dihydro-1H-1,4-benzodiazepin-3-yl)-3-(cyclopropylmethyl)-2-(3,3,3-trifluoropropyl)succinamide (27)

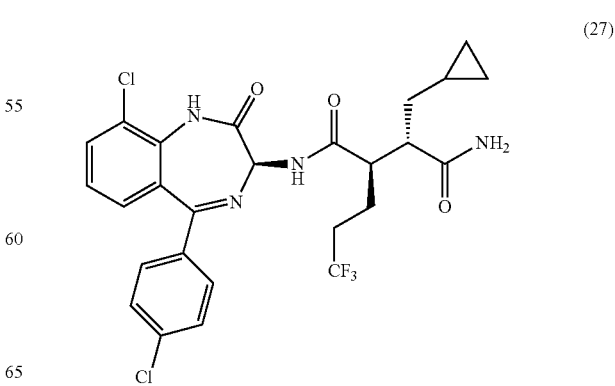

Example 27 was prepared from Intermediate B2 and Intermediate S1 according to the general procedure shown for Example 1. This solid was purified by preparative SFC chromatography (Berger SFC MGII, AS-H 250×30 mm ID, 5 μm, 88/12 CO$_2$/MeOH, 85 mL/min) to give Example 27. HPLC: RT=9.33 min (H$_2$O/CH$_3$CN with TFA, SunFire C18 3.5 μm, 4.6×150 mm, gradient=15 min, wavelength=220 and 254 nm); MS(ES): m/z=569 [M+H$^+$]; $^1$H NMR (400 MHz, DMSO-d$_6$) δ 10.49 (br. s., 1H), 9.37 (br. s., 1H), 7.83 (br. s., 1H), 7.68-7.49 (m, 4H), 7.32 (br. s., 1H), 6.97 (br. s., 1H), 5.20 (br. s., 1H), 2.79-2.57 (m, 2H), 2.36-2.29 (m, 1H), 2.25 (br. s., 1H), 1.71-1.57 (m, 2H), 1.57-1.41 (m, 1H), 1.06 (br. s., 1H), 0.57 (br. s., 1H), 0.43-0.24 (m, 2H), 0.12--0.05 (m, 1H), −0.05--0.22 (m, 1H).

Example 28

(2R,3S)—N-((3S)-9-Chloro-5-(4-chlorophenyl)-2-oxo-2,3-dihydro-1H-1,4-benzodiazepin-3-yl)-3-propyl-2-(3,3,3-trifluoropropyl)succinamide (28)

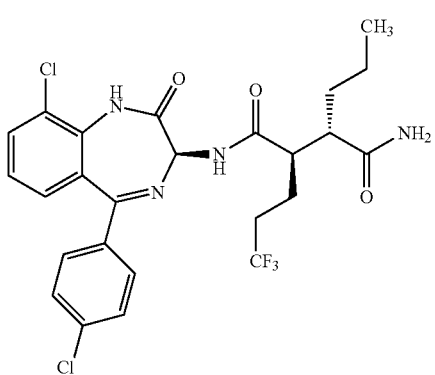

Example 28 was prepared from Intermediate B2 and Intermediate S2 according to the general procedure shown for Example 1. This solid was purified by preparative SFC chromatography (Berger SFC MGII, AS-H 250×30 mm ID, 5 μm, 82/18 CO$_2$/MeOH, 85 mL/min) to give Example 28. HPLC: RT=9.27 min (H$_2$O/CH$_3$CN with TFA, SunFire C18 3.5 μm, 4.6×150 mm, gradient=15 min, wavelength=220 and 254 nm); MS(ES): m/z=557[M+H$^+$]; $^1$H NMR (400 MHz, DMSO-d$_6$) δ 9.42 (br. s., 1H), 7.85 (d, J=6.8 Hz, 1H), 7.64-7.49 (m, 4H), 7.34 (br. s., 1H), 6.95 (s, 1H), 5.24 (br. s., 1H), 2.79-2.64 (m, 2H), 2.45-2.29 (m, 2H), 2.24 (br. s., 1H), 1.68-1.55 (m, 1H), 1.47 (d, J=8.8 Hz, 1H), 1.24 (br. s., 2H), 1.21-1.03 (m, 1H), 0.82 (t, J=6.9 Hz, 2H).

Example 29

(2R,3S)-3-(Cyclopropylmethyl)-N-((3S)-9-fluoro-8-methoxy-2-oxo-5-phenyl-2,3-dihydro-1H-1,4-benzodiazepin-3-yl)-2-(3,3,3-trifluoropropyl)succinamide (29)

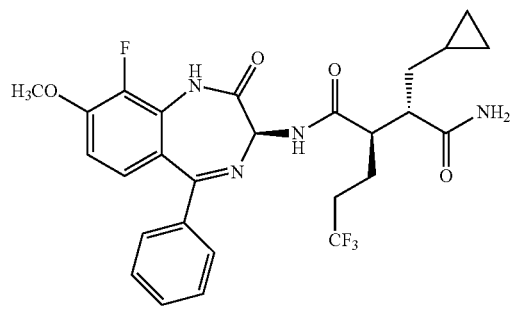

Example 29 was prepared from Intermediate B24 and Intermediate S1 according to the general procedure shown for Example 1. This solid was purified by preparative SFC chromatography (Berger SFC MGII, Chiral IC 25×3 cm ID, 5 μm, 83/17 CO$_2$/MeOH, 85 mL/min) to give Example 29. HPLC: RT=8.524 min (H$_2$O/CH$_3$CN with TFA, SunFire C18 3.5 μm, 3.0×150 mm, gradient=15 min, wavelength=220 nm); MS(ES): m/z=519 [M+H$^+$]; $^1$H NMR (400 MHz, methanol-d$_4$) δ 7.60-7.54 (m, 2H), 7.50 (d, J=7.5 Hz, 1H), 7.45-7.38 (m, 2H), 7.17-7.10 (m, 1H), 7.08-7.01 (m, 1H), 5.42 (s, 1H), 3.99 (s, 3H), 2.78-2.67 (m, 1H), 2.65 (dd, J=10.5, 3.4 Hz, 1H), 2.55-2.41 (m, 1H), 2.28-2.13 (m, 1H), 1.90-1.62 (m, 3H), 1.33-1.22 (m, 1H), 0.70 (br. s., 1H), 0.51-0.38 (m, 2H), 0.19-0.10 (m, 1H), 0.08--0.02 (m, 1H).

Example 30

(2R,3S)—N-((3S)-9-Chloro-5-(3-methylphenyl)-2-oxo-2,3-dihydro-1H-1,4-benzodiazepin-3-yl)-3-(cyclopropylmethyl)-2-(3,3,3-trifluoropropyl)succinamide (30)

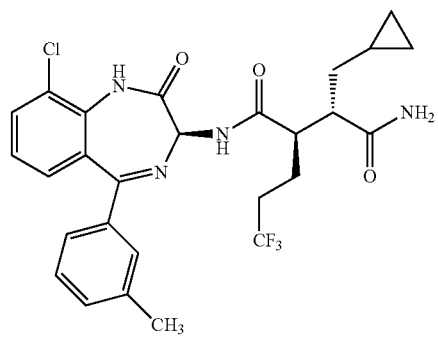

Example 30 was prepared from Intermediate B25 and Intermediate S1 according to the general procedure shown for Example 1. This solid was purified by preparative SFC chromatography (Berger SFC MGII, PHENOMENEX® Lux Cellulose-4-250×30 mm ID, 5 μm, 83/17 CO$_2$/MeOH, 85 mL/min) to give Example 30. HPLC: RT=2.03 min (H$_2$O/MeOH with TFA, SunFire C18 3.5 μm, 2.1×30 mm, gradient=4 min, wavelength=220 nm); MS(ES): m/z=549 [M+H$^+$]; $^1$H NMR (400 MHz, DMSO-d$_6$) δ 10.46 (br. s., 1H), 9.34 (br. s., 1H), 7.83 (t, J=4.5 Hz, 1H), 7.60 (br. s., 1H), 7.45-7.21 (m, 6H), 6.97 (br. s., 1H), 5.19 (d, J=5.7 Hz, 1H), 2.75-2.61 (m, 2H), 2.47 (d, J=3.5 Hz, 1H), 2.39-2.31 (m, 3H), 2.30-2.18 (m, 1H), 1.70-1.48 (m, 3H), 1.07 (ddd, J=13.3, 7.5, 3.4 Hz, 1H), 0.64-0.53 (m, 1H), 0.41-0.29 (m, 2H), 0.07--0.02 (m, 1H), −0.05--0.14 (m, 1H).

Example 31

(2R,3S)-3-(Cyclopropylmethyl)-N-((3S)-9-methoxy-5-(3-methylphenyl)-2-oxo-2,3-dihydro-1H-1,4-benzodiazepin-3-yl)-2-(3,3,3-trifluoropropyl)succinamide (31)

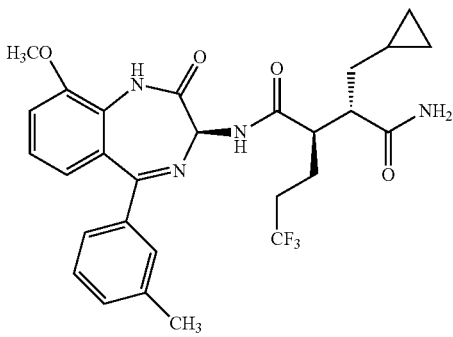

Example 31 was prepared from Intermediate B26 and Intermediate S1 according to the general procedure shown for Example 1. This solid was purified by preparative SFC chromatography (Berger SFC MGII, AS-H 250×30 mm ID, 5 µm, 80/20 CO$_2$/MeOH, 85 mL/min) to give Example 31. HPLC: RT=8.81 min (H$_2$O/CH$_3$CN with TFA, SunFire C18 3.5 µm, 4.6×150 mm, gradient=15 min, wavelength=220 and 254 nm); MS(ES): m/z=545 [M+H$^+$]; $^1$H NMR (400 MHz, DMSO-d$_6$) δ 10.04 (s, 1H), 9.32 (d, J=7.0 Hz, 1H), 7.59 (br. s., 1H), 7.39 (s, 1H), 7.37-7.22 (m, 6H), 6.96 (br. s., 1H), 6.87 (dd, J=7.9, 1.1 Hz, 1H), 5.18 (d, J=7.3 Hz, 1H), 3.93 (s, 3H), 2.75-2.60 (m, 2H), 2.35 (s, 3H), 2.30-2.15 (m, 1H), 1.71-1.46 (m, 3H), 1.05 (ddd, J=13.3, 7.4, 3.1 Hz, 1H), 0.67-0.50 (m, 1H), 0.42-0.24 (m, 2H), 0.08--0.02 (m, 1H), −0.05--0.16 (m, 1H).

Example 32

(2R,3S)—N-((3S)-9-Cyano-2-oxo-5-phenyl-2,3-dihydro-1H-1,4-benzodiazepin-3-yl)-3-propyl-2-(3,3,3-trifluoropropyl)succinamide (32)

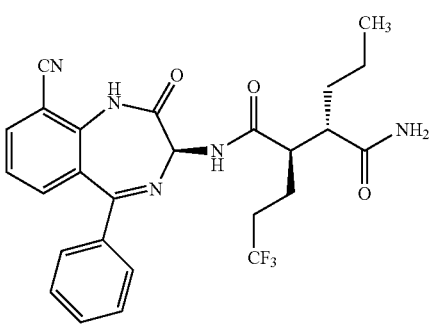

Preparation 32A ((2S,3R)-tert-Butyl 3-((9-bromo-2-oxo-5-phenyl-2,3-dihydro-1H-benzo[e][1,4]diazepin-3-yl)carbamoyl)-6,6,6-trifluoro-2-propylhexanoate (32A)

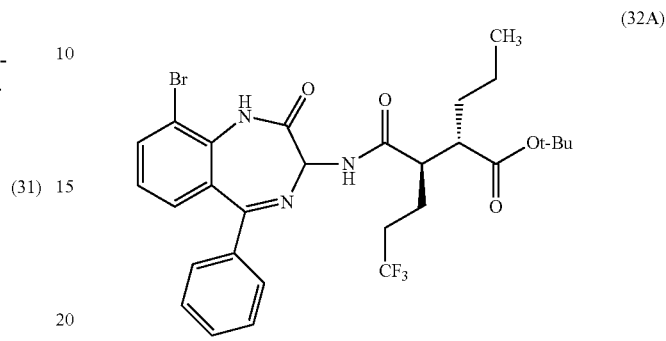

To a stirred solution of Intermediate B27 (412.9 mg, 0.839 mmol), Intermediate S2 (279.2 mg, 0.894 mmol) and TBTU (294.5 mg, 0.917 mmol) in DMF (3.4 mL) was added triethylamine (0.47 mL, 3.37 mmol). The reaction mixture was stirred overnight, then water was added. The precipitate was collected by filtration, washed with water, and air dried to give Preparation 32A (456 mg, 87% yield)): HPLC RT=2.292 min (MeOH/H$_2$O with TFA, Waters SunFire C18 2.1×30 mm, 2 min gradient, wavelength=254 nm); MS(ES): m/z=624 [M+H]$^+$.

Preparation 32B ((2S,3R)-tert-Butyl 3-((9-bromo-2-oxo-5-phenyl-1-((2-(trimethylsilyl)ethoxy)methyl)-2,3-dihydro-1H-benzo[e][1,4]diazepin-3-yl)carbamoyl)-6,6,6-trifluoro-2-propylhexanoate (32B)

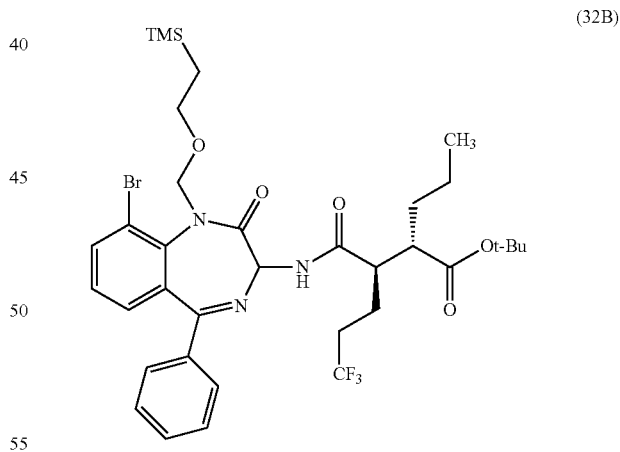

To a stirred solution of Preparation 32A (242.8 mg, 0.389 mmol) in DMF (4 mL) were added Cs$_2$CO$_3$ (638.3 mg, 1.959 mmol), 2-(trimethylsilyl)ethoxymethyl chloride (0.21 mL, 1.184 mmol), and tetrabutylammonium iodide (21.4 mg, 0.058 mmol). The reaction mixture was stirred overnight, then diluted with EtOAc, washed three times with 10% LiCl, washed with brine, dried with Na$_2$SO$_4$, filtered and concentrated. The residue was purified by silica gel chromatography (heptane/EtOAc) to give Preparation 32B (214.7 mg, 73.2% yield): LCMS: RT=2.542 min (MeOH/H$_2$O/ with TFA, Waters SunFire C18 2.1×30 mm, 2 min gradient, wavelength=254 nm); MS(ES): m/z=754 [M+H]$^+$.

Preparation 32C ((2S,3R)-tert-Butyl 3-((9-cyano-2-oxo-5-phenyl-1-((2-(trimethylsilyl)ethoxy)methyl)-2,3-dihydro-1H-benzo[e][1,4]diazepin-3-yl)carbamoyl)-6,6,6-trifluoro-2-propylhexanoate

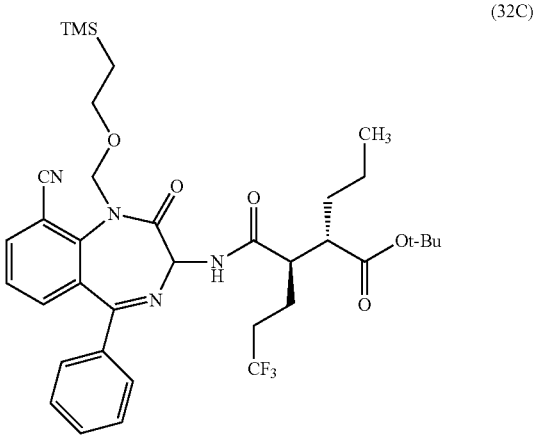 [SMILES: CCC[C@H](C(=O)OC(C)(C)C)[C@@H](CCC(F)(F)F)C(=O)NC1N=C(c2ccccc2)c2cccc(C#N)c2N(COCC[Si](C)(C)C)C1=O]

(32C)

A suspension of Preparation 32B (214.7 mg, 0.284 mmol), zinc cyanide (36.7 mg, 0.313 mmol) and zinc (18.60 mg, 0.284 mmol) in DMA (22 mL) was freeze/pump/thaw degassed three times. Bis(tri-t-butylphosphine)palladium(0) (29.1 mg, 0.057 mmol) was added, the flask was purged with nitrogen twice, then the reaction mixture was heated to 100° C. with stirring overnight. The reaction mixture was cooled to room temperature and filtered. The filtrate was diluted with EtOAc, washed three times with 10% LiCl, washed with brine, dried with Na$_2$SO$_4$, filtered and concentrated. The residue was purified by silica gel chromatography (heptanes/EtOAc) to give Preparation 32C (110.9 mg 55.6% yield): HPLC RT=2.408 min (MeOH/H$_2$O with TFA, Waters SunFire C18 2.1×30 mm, 2 min gradient, wavelength=254 nm); MS(ES): m/z=701 [M+H]$^+$; $^1$H NMR (400 MHz, chloroform-d) δ 7.94 (1H, dd, J=7.7, 1.3 Hz), 7.59-7.67 (3H, m), 7.38-7.55 (5H, m), 5.89 (1H, d, J=11.0 Hz), 5.57 (1H, dd, J=8.1, 3.7 Hz), 5.41 (1H, d, J=11.2 Hz), 3.16-3.31 (2H, m), 2.52-2.68 (2H, m), 2.09-2.48 (2H, m), 1.89-2.06 (1H, m), 1.57-1.87 (3H, m), 1.50 (9H, d, J=2.9 Hz), 1.22-1.48 (3H, m), 0.87-1.00 (3H, m), 0.68 (1H, ddd, J=13.5, 10.9, 6.4 Hz), 0.40-0.51 (1H, m), −0.30 (9H, d, J=0.4 Hz).

Preparation 32D ((2S,3R)-3-((9-Cyano-2-oxo-5-phenyl-2,3-dihydro-1H-benzo[e][1,4]diazepin-3-yl)carbamoyl)-6,6,6-trifluoro-2-propylhexanoic acid

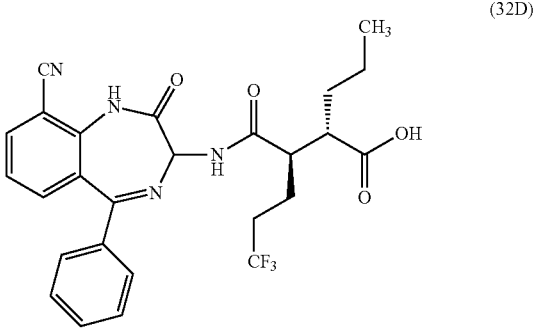 [SMILES: CCC[C@H](C(=O)O)[C@@H](CCC(F)(F)F)C(=O)NC1N=C(c2ccccc2)c2cccc(C#N)c2NC1=O]

(32D)

To a stirred Preparation 32C (110 mg, 0.157 mmol) in DCM (2 mL) under N$_2$ was added TFA (2 mL, 26.0 mmol). After 60 min, the reaction mixture was diluted with toluene, concentrated, and dried under vacuum overnight. The residue was purified by silica gel chromatography (DCM/EtOAc) to give Preparation 32D (67.0 mg, 83% yield): HPLC RT=1.877 min (MeOH/H$_2$O/ with TFA, Waters SunFire C18 2.1×30 mm, 2 min gradient, wavelength=254 nm); MS(ES): m/z=515 [M+H]$^+$.

Example 32

To a stirred suspension of Preparation 32D (70.7 mg, 1.322 mmol), ammonium chloride (70.7 mg, 1.322 mmol), EDC (84.1 mg, 0.439 mmol) and HOBt (58.1 mg, 0.379 mmol) in DMF (1.0 mL) was added triethylamine (0.27 mL, 1.937 mmol). The reaction mixture was stirred overnight, then water was added. The aqueous phase was extracted with EtOAc, the combined organics were dried with Na$_2$SO$_4$, filtered and concentrated. The material was purified by Preparative HPLC (Luna 5 μm C18 (30×100 mm), H$_2$O/MeOH w/ 0.1% TFA, 20 min gradient, 35-50% B, 220 nm). Fractions containing product were concentrated in a SPEEDVAC®, then diluted with DCM, washed with sat. NaHCO$_3$, dried with Na$_2$SO$_4$, filtered and concentrated. The solid was dissolved in MeCN, diluted with water, frozen, and lyophilized to give Example 32 (13.8 mg, 0.026 mmol, 20%): HPLC: RT=1.745 min (MeOH/H$_2$O/0.1% TFA, Waters SunFire C18 2.1×30 mm, 2 min gradient, wavelength=254 nm); MS(ES): m/z=514 [M+H]$^+$; $^1$H NMR (400 MHz, CD$_3$OD) δ 8.04 (1H, dd, J=7.7, 1.3 Hz), 7.66 (1H, dd, J=8.0, 1.4 Hz), 7.56-7.61 (2H, m), 7.49-7.56 (1H, m), 7.38-7.48 (3H, m), 5.43 (1H, s), 2.73 (1H, td, J=10.5, 3.7 Hz), 2.42-2.59 (2H, m), 2.14-2.34 (1H, m), 1.56-1.90 (3H, m), 1.19-1.52 (4H, m), 0.92 (3H, t, J=7.0 Hz).

Example 33

(2R,3S)—N-((3S)-9-Methoxy-2-oxo-5-phenyl-2,3-dihydro-1H-1,4-benzodiazepin-3-yl)-3-((1-methylcyclopropyl)methyl)-2-(3,3,3-trifluoropropyl)succinamide

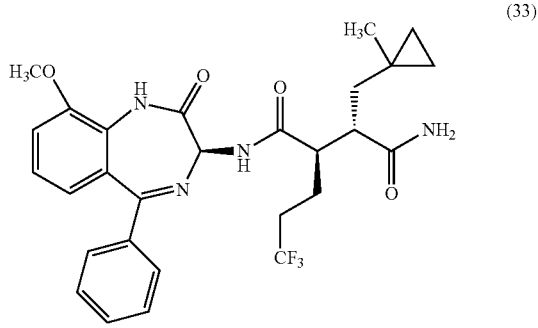 [SMILES: COc1cccc2c1NC(=O)[C@@H](NC(=O)[C@H](CCC(F)(F)F)[C@H](CC1(C)CC1)C(N)=O)N=C2c1ccccc1]

(33)

Example 33 was prepared from Intermediate B28 and Intermediate S3 according to the general procedure shown for Example 1. HPLC: RT=9.173 min (H$_2$O/CH$_3$CN with TFA, SunFire C18 3.5 μm, 4.6×150 mm, gradient=15 min, wavelength=220 and 254 nm); MS(ES): m/z=545[M+H]$^+$; $^1$H NMR (500 MHz, DMS-d$_6$) δ 10.05 (s, 1H), 9.31 (d, J=7.2 Hz, 1H), 7.64 (br. s., 1H), 7.56-7.50 (m, 3H), 7.49-7.43 (m, 2H), 7.34-7.29 (m, 1H), 7.24 (t, J=8.0 Hz, 1H), 6.94 (br. s., 1H), 6.87 (dd, J=7.8, 1.1 Hz, 1H), 5.20 (d, J=7.2 Hz, 1H), 3.93 (s, 3H), 2.59 (d, J=7.8 Hz, 2H), 2.29-2.16 (m, 1H), 1.61 (d, J=6.7 Hz, 2H), 1.47 (d, J=13.6 Hz, 1H), 1.28-1.19 (m, 1H), 0.96 (s, 3H), 0.37-0.30 (m, 1H), 0.18-0.06 (m, 3H).

Example 34

(2R,3S)-3-(Cyclopropylmethyl)-N-((3S)-8,9-dichloro-2-oxo-5-phenyl-2,3-dihydro-1H-1,4-benzodiazepin-3-yl)-2-(3,3,3-trifluoropropyl)succinamide

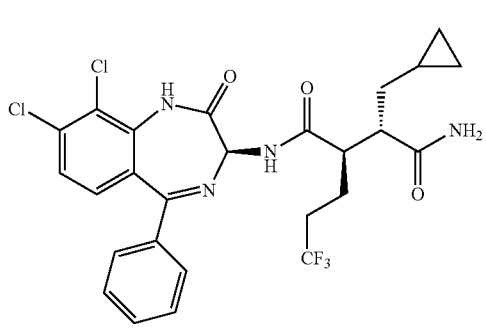

(34)

Example 34 was prepared from Intermediate B29 and Intermediate S1 according to the general procedure shown for Example 1. This solid was purified by preparative SFC chromatography (Berger SFC MGII, PHENOMENEX® Lux Cellulose-4 25×3 cm ID, 5 μm, 83/17 $CO_2$/MeOH, 85 mL/min) to give Example 34. HPLC: RT=2.080 min ($H_2O$/MeOH with TFA, SunFire C18 3.5 μm, 2.1×30 mm, gradient=2 min, wavelength=254 nm); MS(ES): m/z=569 [M+H$^+$]; $^1$H NMR (400 MHz, DMSO-$d_6$) δ 10.63 (1H, br. s.), 9.33 (1H, br. s.), 7.51-7.63 (5H, m), 7.43-7.51 (2H, m), 7.29 (1H, d, J=8.6 Hz), 6.96 (1H, br. s.), 5.24 (1H, br. s.), 2.67-2.76 (1H, m), 2.16-2.31 (1H, m), 1.58-1.66 (2H, m), 1.53 (1H, ddd, J=13.3, 10.6, 6.3 Hz), 1.07 (1H, ddd, J=13.1, 7.4, 3.2 Hz), 0.51-0.64 (1H, m), 0.27-0.40 (2H, m), −0.03-0.05 (1H, m), −0.15-−0.07 (1H, m).

Example 35

(2R,3S)—N-((3S)-2-Oxo-5-phenyl-9-(trifluoromethyl)-2,3-dihydro-1H-1,4-benzodiazepin-3-yl)-3-propyl-2-(3,3,3-trifluoropropyl)succinamide

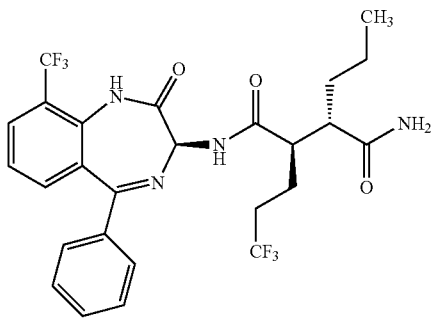

(35)

Example 35 was prepared from Intermediate B30 and Intermediate S2 according to the general procedure shown for Example 1. This solid was purified by preparative SFC chromatography (Berger SFC MGII, IC 250×30 mm ID, 5 μm, 85/15 $CO_2$/MeOH, 85 mL/min) to give Example 35. HPLC: RT=8.848 min ($H_2O$/$CH_3CN$ with TFA, SunFire C18 3.5 μm, 4.6×150 mm, gradient=15 min, wavelength=220 and 254 nm); MS(ES): m/z=557.1 [M+H$^+$]; $^1$H NMR (400 MHz, chloroform-d) δ 7.91 (s, 2H), 7.60 (t, J=8.3 Hz, 2H), 7.56-7.46 (m, 3H), 7.45-7.31 (m, 3H), 5.80 (br. s., 1H), 5.60 (d, J=7.9 Hz, 1H), 5.57 (br. s., 1H), 2.70 (td, J=9.9, 3.7 Hz, 1H), 2.50 (td, J=9.9, 3.7 Hz, 1H), 2.32-2.08 (m, 2H), 2.00-1.87 (m, 1H), 1.87-1.75 (m, 2H), 1.72-1.62 (m, 1H), 1.54-1.42 (m, 1H), 1.39-1.29 (m, 1H), 0.98 (t, J=7.3 Hz, 3H).

Example 36

(2R,3S)-3-(Cyclopropylmethyl)-N-((3S)-2-oxo-5-phenyl-9-(trifluoromethyl)-2,3-dihydro-1H-1,4-benzodiazepin-3-yl)-2-(3,3,3-trifluoropropyl)succinamide

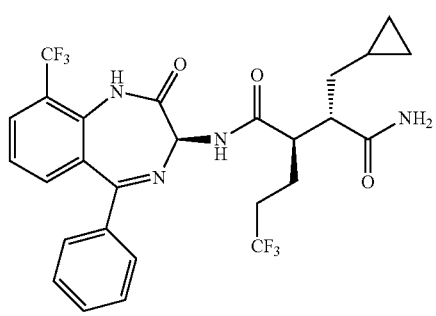

(36)

Example 36 was prepared from Intermediate B30 and Intermediate S1 according to the general procedure shown for Example 1. The solid was purified by preparative SFC chromatography (Berger SFC MGII, CHIRALPAK® IC 250×30 mm ID, 5 μm, 88/12 $CO_2$/MeOH, 85 mL/min) to give Example 36. HPLC: RT=3.391 min ($H_2O$/MeOH with $H_3PO_4$, SunFire C18 3.5 μm, 4.6×50 mm, gradient=15 min, wavelength=220 nm); MS(ES): m/z=569 [M+H$^+$]; $^1$H NMR (400 MHz, chloroform-d) δ 7.97 (br. s., 1H), 7.91 (d, J=7.0 Hz, 1H), 7.67-7.58 (m, 2H), 7.54-7.46 (m, 3H), 7.45-7.32 (m, 3H), 5.86 (br. s., 1H), 5.67 (br. s., 1H), 5.57 (d, J=7.9 Hz, 1H), 2.74 (td, J=9.8, 3.6 Hz, 1H), 2.59 (td, J=10.0, 3.5 Hz, 1H), 2.30-2.09 (m, 2H), 2.01-1.76 (m, 3H), 1.47 (ddd, J=13.6, 7.9, 3.5 Hz, 1H), 0.82-0.72 (m, 1H), 0.57-0.42 (m, 2H), 0.27-0.18 (m, 1H), 0.13 (dt, J=8.6, 4.4 Hz, 1H).

Example 37

(2R,3S)—N-((3S)-9-Fluoro-2-oxo-5-phenyl-2,3-dihydro-1H-1,4-benzodiazepin-3-yl)-3-propyl-2-(3,3,3-trifluoropropyl)succinamide

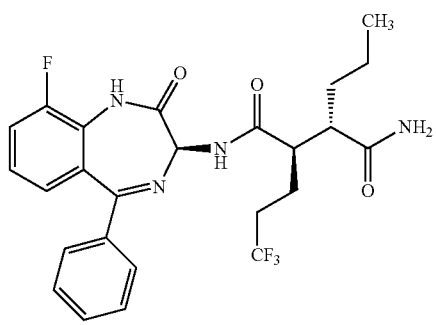

(37)

Example 37 was prepared from Intermediate B1 and Intermediate S2 according to the general procedure shown for Example 1. This solid was purified by preparative SFC chromatography (Berger SFC MGII, Chiral IC 250×30 mm ID, 5 μm, 82/18 $CO_2$/MeOH, 85 mL/min) to give Example 37. HPLC: RT=7.635 min ($H_2O$/$CH_3CN$ with TFA, SunFire C18 3.5 μm, 4.6×150 mm, gradient=15 min, wavelength=220 and 254 nm); MS(ES): m/z=507 [M+H⁺]; ¹H NMR (400 MHz, methanol-d₄) δ 7.58-7.64 (2H, m), 7.41-7.57 (4H, m), 7.29 (1H, td, J=8.09, 4.95 Hz), 7.18-7.24 (1H, m), 5.46 (1H, s), 2.75 (1H, td, J=10.51, 3.85 Hz), 2.43-2.59 (2H, m), 2.15-2.33 (1H, m), 1.59-1.93 (3H, m), 1.19-1.55 (5H, m), 0.91-1.00 (3H, m).

Example 38

(2R,3S)-3-(Cyclopropylmethyl)-N-((3S)-9-methoxy-2-oxo-5-phenyl-2,3-dihydro-1H-1,4-benzodiazepin-3-yl)-2-(3,3,3-trifluoropropyl)succinamide (38)

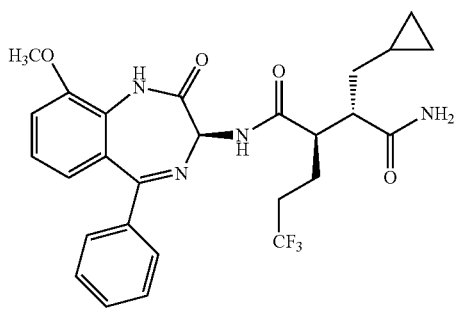

Example 38 was prepared from Intermediate B28 and Intermediate S1 according to the general procedure shown for Example 1. After separation of the diastereomers by preparative HPLC (YMC ODS-A 5 μm 30×250 mm, 10-90% aqueous methanol containing 0.1% TFA, 25 mL/min, 40 min gradient, monitored at 254 nm), Example 38 was obtained. HPLC: RT=3.846 min (H₂O/MeOH with H₃PO₄, SunFire C18 5 μm, 4.6×50 mm, gradient=4 min, wavelength=220 nm); MS(ES): m/z=531 [M+H⁺]; ¹H NMR (400 MHz, methanol-d₄) δ 7.52-7.58 (2H, m), 7.46-7.52 (1H, m), 7.37-7.44 (2H, m), 7.25-7.29 (1H, m), 7.22 (1H, t, J=8.03 Hz), 6.91 (1H, dd, J=7.81, 1.43 Hz), 5.36 (1H, s), 4.00 (3H, s), 2.68-2.76 (1H, m), 2.59-2.67 (1H, m), 2.37-2.54 (1H, m), 2.13-2.31 (2H, m), 1.64-1.88 (3H, m), 1.26-1.33 (1H, m), 0.63-0.77 (1H, m), 0.36-0.52 (2H, m), 0.11-0.18 (1H, m), −0.01-0.08 (1H, m).

Example 39

(2R,3S)—N-((3S)-8-Bromo-9-methoxy-2-oxo-5-phenyl-2,3-dihydro-1H-1,4-benzodiazepin-3-yl)-3-propyl-2-(3,3,3-trifluoropropyl)succinamide (39)

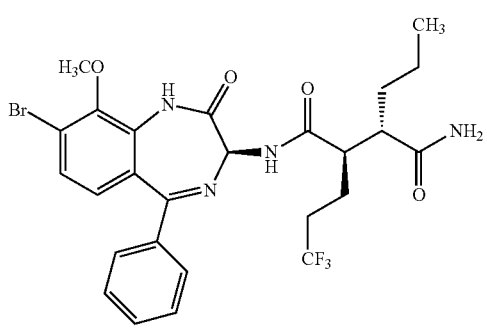

Example 39 was prepared from Intermediate B31 and Intermediate S2 according to the general procedure shown for Example 1. This solid was purified by preparative SFC chromatography (Berger SFC MGII, Chiral IC 250×30 mm ID, 5 μm, 85/15 CO₂/MeOH, 85 mL/min) to give Example 39. HPLC: RT=9.299 min (H₂O/CH₃CN with TFA, SunFire C18 3.5 μm, 4.6×150 mm, gradient=15 min, wavelength=220 and 254 nm); MS(ES): m/z=597.4 [M+H⁺]; ¹H NMR (400 MHz, DMSO-d₆) δ ppm 10.54 (1H, br. s.), 9.31 (1H, br. s.), 7.49-7.60 (4H, m), 7.46 (3H, t, J=7.26 Hz), 6.99 (1H, d, J=8.36 Hz), 6.94 (1H, br. s.), 5.20 (1H, br. s.), 3.86 (3H, s), 2.56-2.77 (2H, m), 2.40 (1H, t, J=9.90 Hz), 2.16-2.35 (1H, m), 1.55-1.69 (2H, m), 1.41-1.54 (1H, m), 1.04-1.32 (3H, m), 0.82 (3H, t, J=6.93 Hz).

Example 40

(2R,3S)—N-((3S)-9-Methoxy-2-oxo-5-phenyl-2,3-dihydro-1H-1,4-benzodiazepin-3-yl)-3-propyl-2-(3,3,3-trifluoropropyl)succinamide (40)

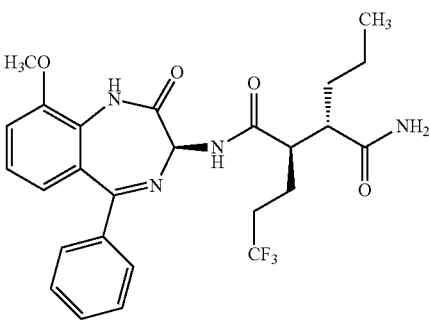

Example 40 was prepared from Intermediate B28 and Intermediate S2 according to the general procedure shown for Example 1. The diastereomers were separated by silica gel chromatography (hexanes/EtOAc) to afford Example 40. HPLC: RT=8.6 min (H₂O/CH₃CN with TFA, SunFire C18 3.5 μm, 4.6×150 mm, gradient=15 min, wavelength=220 and 254 nm); MS(ES): m/z=519.3[M+H⁺]; ¹H NMR (400 MHz, methanol-d₄) δ 7.61-7.55 (m, 2H), 7.52-7.47 (m, 1H), 7.46-7.36 (m, 2H), 7.32-7.18 (m, 2H), 6.92 (dd, J=7.8, 1.4 Hz, 1H), 5.39 (s, 1H), 4.01 (s, 3H), 2.73 (td, J=10.5, 3.9 Hz, 1H), 2.56-2.36 (m, 2H), 2.22 (d, J=11.4 Hz, 1H), 1.87-1.71 (m, 2H), 1.71-1.59 (m, 1H), 1.54-1.35 (m, 2H), 1.35-1.20 (m, 1H), 0.99-0.88 (m, 3H).

Example 41

(2R,3S)—N-((3S)-9-Hydroxy-2-oxo-5-phenyl-2,3-dihydro-1H-1,4-benzodiazepin-3-yl)-3-propyl-2-(3,3,3-trifluoropropyl)succinamide (41)

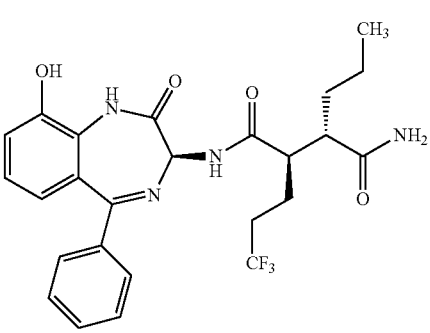

To a solution of Example 40 (100 mg, 0.193 mmol) in DCM (3 mL) at room temperature was added 1M BBr$_3$ in DCM (0.579 mL, 0.579 mmol) slowly. The reaction mixture was stirred at room temperature for 3 h, then MeOH was added and stirred for 30 min. The reaction mixture was concentrated and this process was repeated two more times. The reaction mixture was diluted with EtOAc and saturated aqueous NaHCO$_3$. The layers were separated and the organic layer was washed with brine, dried over MgSO$_4$, filtered and concentrated to give crude material. The crude material was purified by silica gel chromatography (hexanes/EtOAc). The material was then purified with preparative HPLC (H$_2$O/MeOH with TFA, Waters Xbridge C18 19×100 mm, gradient=12 min, wavelength=220 nm, RT=8.656 min). After concentration, Example 41 (28 mg, 30.8% yield) was obtained as light yellow solid; HPLC: RT=7.55 min (H$_2$O/CH$_3$CN with TFA, SunFire C18 3.5 μm, 4.6×150 mm, gradient=15 min, wavelength=220 and 254 nm); MS(ES): m/z=505.3[M+H$^+$]; $^1$H NMR (400 MHz, methanol-d$_4$) δ 7.60-7.54 (m, 2H), 7.49 (t, J=7.4 Hz, 1H), 7.40 (t, J=7.5 Hz, 2H), 7.14-7.04 (m, 2H), 6.81 (dd, J=7.2, 2.1 Hz, 1H), 5.41 (s, 1H), 2.72 (td, J=10.5, 4.0 Hz, 1H), 2.57-2.37 (m, 2H), 2.30-2.10 (m, 1H), 1.87-1.59 (m, 3H), 1.54-1.34 (m, 2H), 1.34-1.20 (m, 1H), 0.98-0.87 (m, 3H).

Example 42

(2R,3S)—N-((3S)-9-Chloro-2-oxo-5-phenyl-2,3-dihydro-1H-1,4-benzodiazepin-3-yl)-3-(cyclopropylmethyl)-2-(3,3,3-trifluoropropyl)succinamide

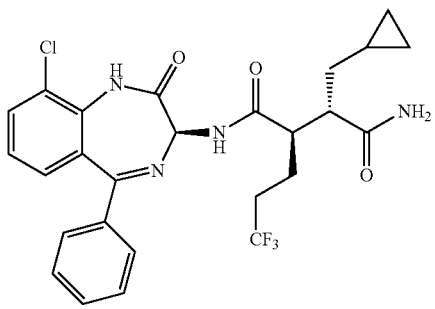

(42)

Example 42 was prepared from Intermediate B32 and Intermediate S1 according to the general procedure shown for Example 1. This solid was purified by preparative SFC chromatography (Berger SFC MGII, CHIRALPAK® IC 25×2.1 cm ID, 5 μm, 85/15 CO$_2$/MeOH, 45 mL/min) to give Example 42. HPLC: RT=0.88 min (H$_2$O/CH$_3$CN with TFA, BEH C18 1.7 μm, 2.1×50 mm, gradient=2 min, wavelength=254 nm); MS(ES): m/z=535 [M+H$^+$]; $^1$H NMR (400 MHz, methanol-d$_4$) δ 7.68-7.84 (1H, m), 7.50-7.66 (3H, m), 7.38-7.51 (2H, m), 7.22-7.40 (2H, m), 5.28-5.46 (1H, m), 2.60-2.82 (2H, m), 2.42-2.61 (1H, m), 2.09-2.35 (1H, m), 1.63-1.96 (3H, m), 1.21-1.38 (1H, m), 0.63-0.81 (1H, m), 0.36-0.56 (2H, m), 0.10-0.22 (1H, m), −0.10-0.11 (1H, m).

Example 43

(2R,3S)—N-((3S)-9-Chloro-2-oxo-5-phenyl-2,3-dihydro-1H-1,4-benzo diazepin-3-yl)-3-propyl-2-(3,3,3-trifluoropropyl)succinamide

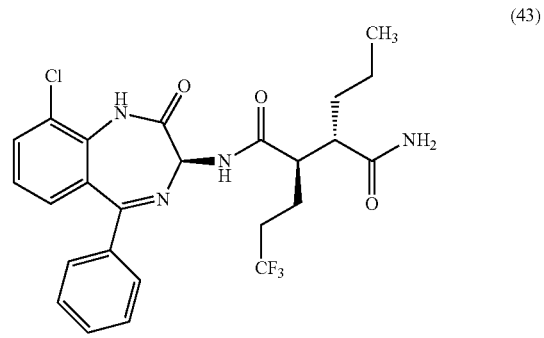 [SMILES: CCC[C@H](C(N)=O)[C@@H](CCC(F)(F)F)C(=O)N[C@H]1N=C(c2ccccc2)c2cccc(Cl)c2NC1=O]

(43)

Example 43 was prepared from Intermediate B32 and Intermediate S2 according to the general procedure shown for Example 1. The diastereomers were separated (Preparative SFC chromatography, Berger SFC MGII, Lux Cel2 250×30 mm ID, 5 μm, 80/20 CO$_2$/MeOH, 85 mL/min) to afford Example 43. HPLC: RT=8.95 min (H$_2$O/CH$_3$CN with TFA, SunFire C18 3.5 μm, 4.6×150 mm, gradient=15 min, wavelength=220 and 254 nm); MS(ES): m/z=523 [M+H$^+$]; $^1$H NMR (400 MHz, chloroform-d) δ 8.02 (s, 1H), 7.69 (dd, J=7.9, 1.5 Hz, 1H), 7.57-7.46 (m, 4H), 7.44-7.38 (m, 2H), 7.34 (dd, J=7.9, 1.3 Hz, 1H), 7.24-7.16 (m, 1H), 5.84 (br. s., 1H), 5.57 (d, J=7.9 Hz, 1H), 5.53 (br. s., 1H), 2.67 (td, J=9.8, 3.7 Hz, 1H), 2.53 (td, J=9.8, 3.6 Hz, 1H), 2.34-2.12 (m, 2H), 2.01-1.91 (m, 1H), 1.88-1.71 (m, 2H), 1.69-1.58 (m, 1H), 1.54-1.44 (m, 1H), 1.41-1.28 (m, 1H), 0.98 (t, J=7.3 Hz, 3H).

Example 44

((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl (4-(phosphonooxy)phenyl) acetate

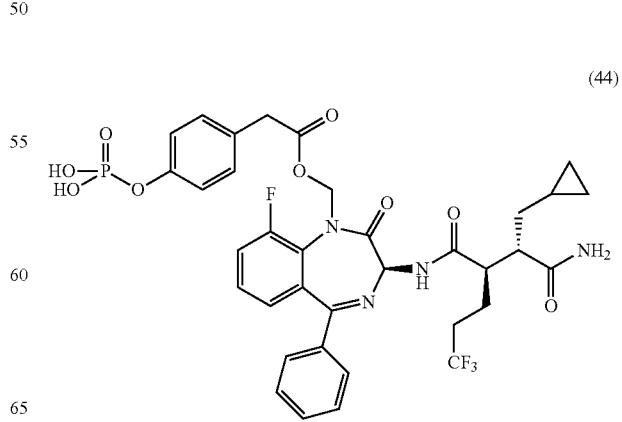

(44)

Preparation 44A (2R,3S)-3-(Cyclopropylmethyl)-N1-((S)-9-fluoro-1-(methylthiomethyl)-2-oxo-5-phenyl-2,3-dihydro-1H-benzo[e][1,4]diazepin-3-yl)-2-(3,3,3-trifluoropropyl)succinamide

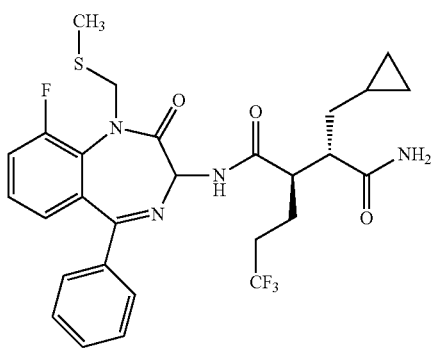

(44A)

To a 1:1 mixture of Example 1 and Preparation 1C (100 mg, 0.193 mmol) in DMF (2.00 mL) was added Cs$_2$CO$_3$ (170 mg, 0.521 mmol) and (chloromethyl)(methyl)sulfane (46.6 mg, 0.919 mmol) under nitrogen. This mixture was stirred at room temperature for 55 min, then diluted with water. The aqueous layer was extracted with EtOAc. The organic layer was washed with brine, then dried over anhydrous magnesium sulfate, filtered and concentrated under reduced pressure to give Preparation 44A (56.4 mg, 51%): HPLC: RT=3.825 min (H$_2$O/MeOH with TFA, CHROMOLITH® ODS, 4.6×50 mm, gradient=4 min, wavelength=220 nm); MS(ES): m/z=579 [M+H$^+$].

Preparation 44B

Methyl 2-(4-(di-tert-butoxyphosphoryloxy)phenyl)acetate

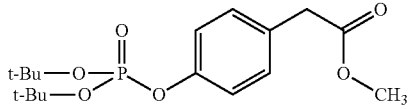

(44B)

To a stirred solution of methyl 2-(4-hydroxyphenyl)acetate (1.80 g, 10.83 mmol) in acetonitrile (35 mL) was added 1H-tetrazole (3% 1H-tetrazole in MeCN, 65.0 mL, 22.1 mmol), followed by di-tert-butyl diethylphosphoramidite (5.91 g, 23.70 mmol). The reaction mixture was stirred at room temperature for 35 min and concentrated to give a solid. To this solid in 50 mL of DCM was added 30% H$_2$O$_2$ (30 mL). The resulting mixture was stirred at room temperature for 30 min and diluted with DCM. The organic phase was separated, washed sequentially with water, saturated NaHCO$_3$ solution, and brine, then concentrated. The residue was purified by silica gel chromatography (hexane/EtOAc) to afford Preparation 44B (3.94 g, 100%). $^1$H NMR (400 MHz, CDCl$_3$) δ 7.25-7.14 (m, 4H), 3.69 (s, 3H), 3.59 (s, 2H), 1.51 (s, 18H).

Preparation 44C 2-(4-(Di-tert-butoxyphosphoryloxy)phenyl)acetic acid

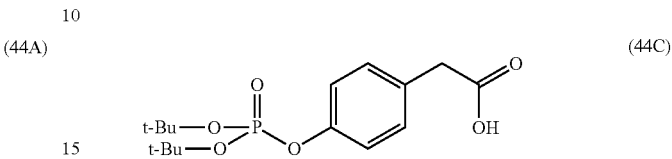

(44C)

To a stirred solution of Preparation 44B (0.635 g, 1.772 mmol) in THF (12.0 mL) and water (3.00 mL) was added lithium hydroxide (0.122 g, 2.14 mmol). The reaction mixture was stirred at room temperature for 2 h. The mixture was concentrated to remove organics and diluted with 10 mL of pH 4 phosphate solution. The aqueous phase was pH 6-7 by pH paper. The resulting mixture was extracted with EtOAc. The combined EtOAc extracts were washed with brine, dried (MgSO$_4$), filtered and concentrated to give Preparation 44C (0.462 g, 76%). $^1$H NMR (400 MHz, DMSO-d$_6$) δ 12.30 (br. s., 1H), 7.25 (d, J=8.4 Hz, 2H), 7.13-7.03 (m, 2H), 3.55 (s, 2H), 1.44 (s, 1H).

Preparation 44D ((S)-3-((R)-2-((S)-1-Amino-3-cyclopropyl-1-oxopropan-2-yl)-5,5,5-trifluoropentanamido)-2-oxo-5-phenyl-2,3-dihydro-1H-benzo[e][1,4]diazepin-1-yl)methyl 2-(4-(di-tert-butoxyphosphoryloxy)-2-fluorophenyl)acetate

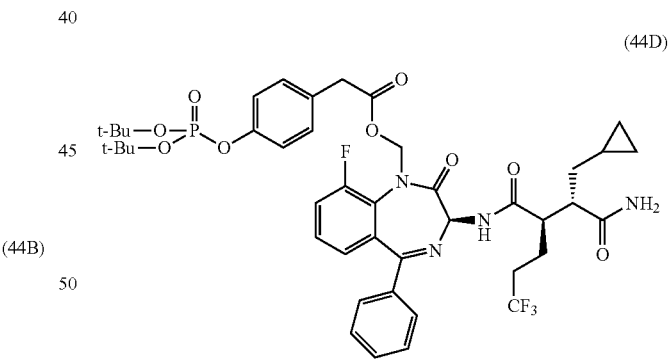

(44D)

To a stirred mixture of Preparation 44A (156 mg, 0.270 mmol) and triethylamine hydrochloride (74.2 mg, 0.539 mmol) in DCM (2.40 mL) under nitrogen was added sulfuryl chloride (0.033 mL, 0.404 mmol). The mixture was stirred at room temperature for 15 min and concentrated to dryness to give a yellow solid. Preparation 44C (187 mg, 0.543 mmol) and Cs$_2$CO$_3$ (372 mg, 1.141 mmol) were combined in DMF (1.00 mL) at room temperature under nitrogen. To this mixture was added a solution of the above yellow solid in DMF (2.00 mL). The resulting mixture was stirred at room temperature for 70 min, then diluted with water and EtOAc. The layers were separated and the organic layer was washed successively with 10% LiCl solution and brine. The organic layer was dried with anhydrous magnesium sulfate, filtered and concentrated. The crude material was purified by flash chromatography (Teledyne ISCO CombiFlash 0% to 100% solvent A/B=hexane/EtOAc, REDISEP® SiO$_2$ 40 g, detecting at 254 nM, and monitoring at 220 nM). Concentration of appropriate fractions provided a mixture of two diastereoisomers (143 mg). These diastereoisomers were then separated by preparative SFC chromatography (Berger SFC MGII, Regis Whelk-O R,R 25×3 cm ID, 5 μm, 80/20 CO$_2$/MeOH, 85 mL/min). Fractions containing product were concentrated, dried overnight under vacuum to give Preparation 44D (45.2 mg, 19.0%) as a colorless solid: Chiral HPLC: RT=12.519 min, Berger SFC, Regis Whelk-O R,R 250×4.6 mm ID, 5 μm, 80/20 CO$_2$/MeOH, 2.0 mL/min; HPLC: RT=3.680 min (H$_2$O/MeOH with TFA, CHROMOLITH® ODS, 4.6×50 mm, gradient=4 min, wavelength=220 nm); MS(ES): m/z=875 [M+H$^+$].

Example 44

To a stirred solution of preparation 44D (28.6 mg, 0.033 mmol) in DCM (1.00 mL) at 0° C. was added TFA (0.10 mL, 1.30 mmol). The reaction mixture was stirred at 0° C. for 15 min, then stirred at room temperature for 20 min. The mixture was concentrated under reduced pressure to give Example 44 (24.2 mg, 92%). HPLC: RT=2.760 min (H$_2$O/MeOH with TFA, CHROMOLITH® ODS, 4.6×50 mm, gradient=4 min, wavelength=220 nm); MS(ES): m/z=763 [M+H$^+$]; $^1$H NMR (400 MHz, CD$_3$OD) δ 7.63-7.49 (m, 4H), 7.48-7.37 (m, 3H), 7.15 (d, J=7.7 Hz, 1H), 7.01-6.91 (m, 2H), 6.87-6.82 (m, 2H), 6.07 (d, J=10.3 Hz, 1H), 5.68 (d, J=10.3 Hz, 1H), 5.46 (s, 1H), 3.41-3.32 (m, 2H), 2.78-2.67 (m, 1H), 2.61 (td, J=10.7, 3.4 Hz, 1H), 2.54-2.38 (m, 1H), 2.29-2.13 (m, 1H), 1.84-1.72 (m, 2H), 1.70-1.60 (m, 1H), 1.23-1.15 (m, 1H), 0.76-0.62 (m, 1H), 0.51-0.33 (m, 2H), 0.15-0.06 (m, 1H), 0.05--0.04 (m, 1H).

Example 45

((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl dihydrogen phosphate (45)

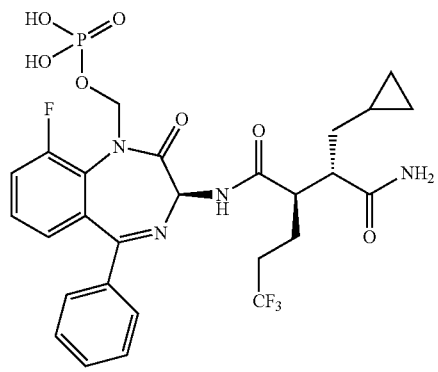

Preparation 45A ((S)-3-((R)-2-((S)-1-Amino-3-cyclopropyl-1-oxopropan-2-yl)-5,5,5-trifluoropentanamido)-9-fluoro-2-oxo-5-phenyl-2,3-dihydro-1H-benzo[e][1,4]diazepin-1-yl)methyl di-tert-butyl phosphate

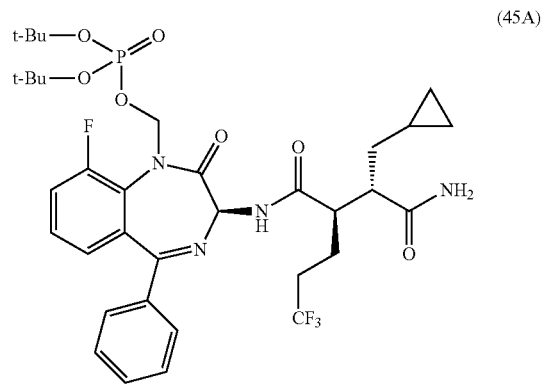 [SMILES: CC(C)(C)OP(=O)(OCN1C(=O)[C@@H](NC(=O)[C@H](CCC(F)(F)F)[C@H](CC2CC2)C(N)=O)N=C(c2ccccc2)c2cccc(F)c21)OC(C)(C)C]

(45A)

To a stirred mixture of Preparation 44A (174 mg, 0.301 mmol) and triethylamine hydrochloride (83.0 mg, 0.601 mmol) in DCM (3.00 mL) under nitrogen was added sulfuryl chloride (0.037 mL, 0.451 mmol). The mixture was stirred at room temperature for 50 min and concentrated to dryness to give a yellow solid. This yellow solid, tetrabutylammonium di-tert-butyl phosphate (325 mg, 0.719 mmol), and sodium iodide (43.1 mg, 0.287 mmol) were combined in THF (5.00 mL) at room temperature under nitrogen. This mixture was heated at 65° C. for 21 h and cooled to room temperature, then was diluted with EtOAc and washed sequentially with saturated NaHCO$_3$ solution and brine. The organic layer was dried with anhydrous MgSO$_4$, filtered and concentrated. The residue was purified by silica gel chromatography (hexane/EtOAc). The resulting mixture of two diastereoisomers were separated by preparative SFC chromatography (Berger SFC MGII, Chiral IC 25×3 cm ID, 5 μm, 85/15 CO$_2$/MeOH, 85 mL/min). Fractions containing product were concentrated and dried overnight under vacuum to afford Preparation 45A (59.0 mg, 27.7%) as a colorless solid: Chiral SFC: RT=3.478 min, Chiral IC 250×4.6 mm ID, 5 μm, 80/20 CO$_2$/MeOH, 2.0 mL/min; HPLC: RT=3.443 min (H$_2$O/MeOH with TFA, CHROMOLITH® ODS, 4.6×50 mm, gradient=4 min, wavelength=220 nm); MS(ES): m/z=741 [M+H$^+$].

Example 45

Preparation 45A (53.0 mg, 0.072 mmol) was dissolved in DCM (4.50 mL) in a 2 dram glass vial in an ice bath. TFA (0.45 mL, 5.84 mmol) was added through the side of the 2 dram vial. This mixture was stirred at 0° C. for 105 min, diluted with 30 mL of DCM and concentrated to give Example 45 (42.2 mg, 92%): HPLC: RT=2.432 min (H$_2$O/MeOH with TFA, CHROMOLITH® ODS, 4.6×50 mm, gradient=4 min, wavelength=220 nm); MS(ES): m/z=629 [M+H$^+$]; $^1$H NMR (400 MHz, CD$_3$OD) δ 7.73-7.66 (m, 2H), 7.57-7.49 (m, 2H), 7.47-7.38 (m, 3H), 7.17 (d, J=7.7 Hz, 1H), 6.18 (t, J=9.8 Hz, 1H), 5.48 (s, 1H), 5.42 (dd, J=9.8, 8.3 Hz, 1H), 3.27-3.24 (m, 1H), 2.75-2.66 (m, 1H), 2.65-2.56 (m, 1H), 2.55-2.38 (m, 1H), 2.29-2.12 (m, 1H), 1.86-1.71 (m, 2H), 1.66 (ddd, J=13.5, 10.7, 6.4 Hz, 1H), 1.22 (ddd, J=13.6, 7.7, 3.3 Hz, 1H), 0.74-0.62 (m, 1H), 0.50-0.35 (m, 2H), 0.17-0.06 (m, 1H).

Example 46

((3S)-3-(((2R)-2-((1S)-1-Amino-3-cyclopropyl-1-oxopropan-2-yl)-5,5,5-trifluoropentanoyl)amino)-9-fluoro-2-oxo-5-phenyl-2,3-dihydro-1H-1,4-benzodiazepin-1-yl)methyl 3-((phosphonooxy)methyl)benzoate (46)

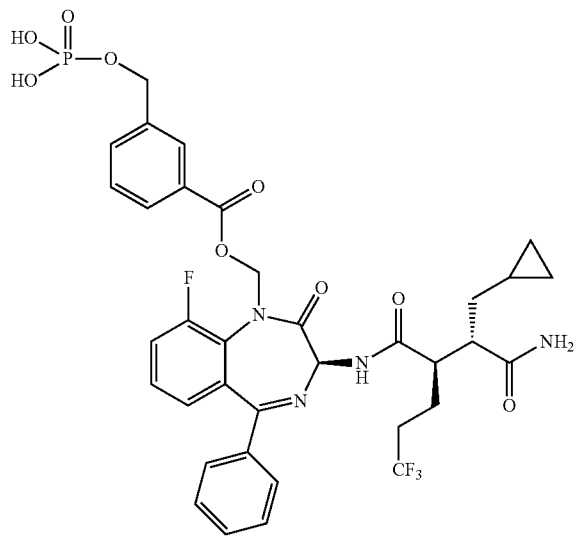

Preparation 46A

Methyl 3-((di-tert-butoxyphosphoryloxy)methyl)benzoate (46A)

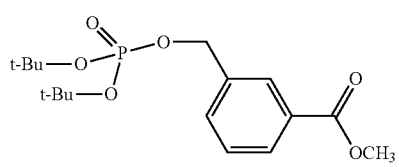

To a stirred mixture of methyl 3-(bromomethyl)benzoate (1.08 g, 4.71 mmol) in DMF (20 mL) was added tetrabutylammonium di-tert-butyl phosphate (2.34 g, 5.19 mmol). The mixture was stirred at room temperature for 1.5 h, then diluted with ether and washed sequentially with 10% LiCl solution and brine. The organic layers were dried over anhydrous magnesium sulfate, filtered and concentrated. The crude material was purified by flash chromatography (Teledyne ISCO CombiFlash 0% to 100% solvent A/B=hexane/EtOAc, REDISEP® SiO$_2$ 40 g, detecting at 254 nM, and monitoring at 220 nM). Concentration of appropriate fractions provided Preparation 46A (1.38 g, 82%): HPLC: RT=3.163 min (H$_2$O/MeOH with TFA, CHROMOLITH® ODS, 4.6×50 mm, gradient=4 min, wavelength=220 nm); MS(ES): m/z=359 [M+H$^+$]; $^1$H NMR (400 MHz, DMSO-d$_6$) δ 8.01 (s, 1H), 7.94-7.89 (m, 1H), 7.66 (d, J=7.9 Hz, 1H), 7.58-7.48 (m, 1H), 5.01 (d, J=8.4 Hz, 2H), 3.86 (s, 3H), 1.41 (s, 18H).

Preparation 46B 3-((Di-tert-butoxyphosphoryloxy)methyl)benzoic acid (46B)

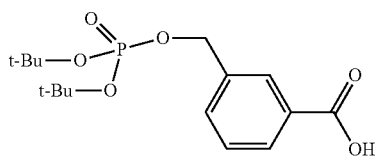

Preparation 46B was prepared from Preparation 46A (425 mg, 1.186 mmol) according to the general procedure shown for Preparation 44C. Preparation 46B (380 mg, 93%) was obtained. HPLC: RT=2.853 min (H$_2$O/MeOH with TFA, CHROMOLITH® ODS, 4.6×50 mm, gradient=4 min, wavelength=220 nm); MS(ES): m/z=345 [M+H$^+$]; $^1$H NMR (400 MHz, DMSO-d$_6$) δ 12.99 (br. s., 1H), 7.98 (d, J=1.5 Hz, 1H), 7.90 (dt, J=7.7, 1.4 Hz, 1H), 7.62 (d, J=8.1 Hz, 1H), 7.55-7.47 (m, 1H), 5.00 (d, J=8.4 Hz, 2H), 1.41 (s, 18H).

Preparation 46C ((S)-3-((R)-2-((S)-1-Amino-3-cyclopropyl-1-oxopropan-2-yl)-5,5,5-trifluoropentanamido)-9-fluoro-2-oxo-5-phenyl-2,3-dihydro-1H-benzo[e][1,4]diazepin-1-yl)methyl 3-((di-tert-butoxyphosphoryloxy)methyl)benzoate (46C)

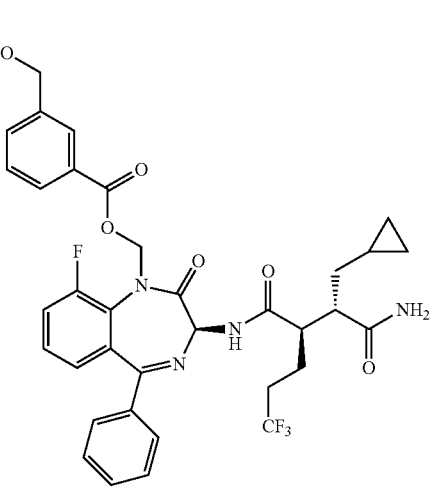

Preparation 46C was prepared from Preparation 46B (115 mg, 0.203 mmol) and Preparation 44A (116 mg, 0.200 mmol) according to the general procedure shown for Preparation 44D. A mixture of two diastereoisomers was obtained, which were separated by preparative SFC chromatography (Berger SFC MGII, Regis Whelk-O R,R 25×3 cm ID, 5 µm, 80/20 CO$_2$/MeOH, 85 mL/min). Fractions containing the desired product were concentrated and dried overnight under vacuum to afford Preparation 46C (59.0 mg, 27.7%) as a colorless solid: Chiral SFC: RT=12.331 min, Regis Whelk-O R,R 250×

4.6 mm ID, 5 μm, 80/20 CO₂/MeOH, 2.0 mL/min; HPLC: RT=3.67 min (H₂O/MeOH with TFA, CHROMOLITH® ODS, 4.6×50 mm, gradient=4 min, wavelength=220 nm); MS(ES): m/z=875 [M+H⁺].

Example 46

Example 46 as prepared from Preparation 46C (47.0 mg, 0.054 mmol) according to the general procedure shown for Example 44. Example 46 (39.7 mg, 95%) was obtained. HPLC: RT=2.898 min (H₂O/MeOH with TFA, CHROMOLITH® ODS, 4.6×50 mm, gradient=4 min, wavelength=220 nm); MS(ES): m/z=763 [M+H⁺]; ¹H NMR (400 MHz, CD₃OD) δ ppm 7.70 (s, 1H), 7.65-7.51 (m, 3H), 7.49-7.37 (m, 4H), 7.26 (q, J=7.7 Hz, 3H), 7.14 (d, J=7.9 Hz, 1H), 6.35 (d, J=10.3 Hz, 1H), 5.98 (d, J=10.6 Hz, 1H), 5.53 (s, 1H), 4.89-4.85 (m, 2H), 3.35 (d, J=1.8 Hz, 1H), 2.76-2.67 (m, 1H), 2.65-2.57 (m, 1H), 2.55-2.40 (m, 1H), 2.30-2.15 (m, 1H), 1.87-1.72 (m, 2H), 1.66 (ddd, J=13.6, 10.7, 6.7 Hz, 1H), 1.21 (ddd, J=13.6, 7.6, 3.4 Hz, 1H), 0.72-0.61 (m, 1H), 0.48-0.34 (m, 2H), 0.12-0.06 (m, 1H).

Example 47

((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl 5-((phosphonooxy)methyl)-2-pyridinecarboxylate

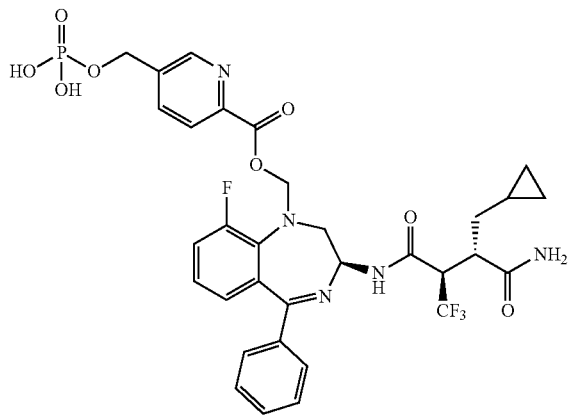

(47)

Preparation 47A 5-((tert-Butyldimethylsilyloxy)methyl)-2-chloropyridine

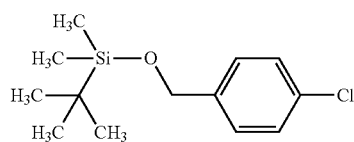

(47A)

To a stirred solution of (6-chloropyridin-3-yl)methanol (643 mg, 4.48 mmol) in DMF (15 mL) was added tert-butylchlorodimethylsilane (675 mg, 4.48 mmol) and imidazole (610 mg, 8.96 mmol). The reaction mixture was stirred at room temperature for 5 h, then diluted with 200 mL of ether, washed with saturated NaHCO₃ solution, 10% LiCl solution, and brine. The solution was dried with anhydrous MgSO₄, filtered and concentrated. The residue was purified by silica gel chromatography (hexane/EtOAc) to provide Preparation 47A (869 mg, 75%). HPLC: RT=3.623 min (H₂O/MeOH with TFA, CHROMOLITH® ODS, 4.6×50 mm, gradient=4 min, wavelength=220 nm); MS(ES): m/z=258 [M+H⁺]; ¹H NMR (400 MHz, DMSO-d₆) δ 8.35 (d, J=1.8 Hz, 1H), 7.77 (dd, J=8.1, 2.4 Hz, 1H), 7.50 (d, J=8.4 Hz, 1H), 4.75 (s, 2H), 0.93-0.86 (m, 9H), 0.12-0.06 (m, 6H).

Preparation 47B

Methyl 5-((tert-butyldimethylsilyloxy)methyl)picolinate

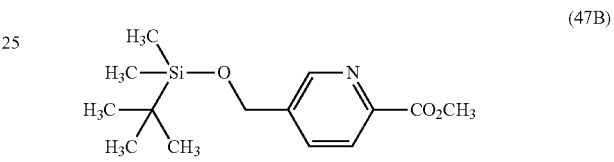

(47B)

To a stirred mixture of Preparation 47A (1.76 g, 6.83 mmol) in DMF (10.0 mL) and MeOH (10.0 mL) was added Et₃N (3.20 mL, 22.96 mmol) in a steel bomb. Then palladium (II) acetate (0.267 g, 1.189 mmol) and (S)-(−)-2,2'-bis(diphenylphosphino)-1,1'-binaphthyl (1.30 g, 2.088 mmol) were added. The steel bomb was evacuated and filled with carbon monoxide to 50 psi, then sealed and heated at 75° C. for 18.5 h and cooled to room temperature. This mixture was concentrated to remove MeOH. The mixture was diluted with 80 mL of water and extracted with ether. The ether extract was washed with 10% LiCl solution and brine, then dried with anhydrous MgSO₄, filtered and concentrated. The residue was purified by silica gel chromatography (hexane/EtOAc) to give Preparation 47B (1.47 g, 77%). HPLC: RT=3.400 min (H₂O/MeOH with TFA, CHROMOLITH® ODS, 4.6×50 mm, gradient=4 min, wavelength=220 nm); MS(ES): m/z=282 [M+H⁺]; ¹H NMR (400 MHz, DMSO-d₆) δ 8.72-8.54 (m, 1H), 8.05 (d, J=7.9 Hz, 1H), 7.89-7.82 (m, 1H), 4.85 (s, 2H), 3.87 (s, 3H), 0.99-0.81 (m, 9H), 0.19--0.07 (m, 6H).

Preparation 47C

Methyl 5-(hydroxymethyl)picolinate

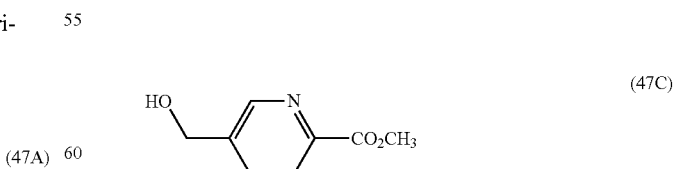

(47C)

To a stirred solution of Preparation 47B (1310 mg, 4.65 mmol) in anhydrous MeOH (95.00 mL) was added TFA (9.00 mL, 117 mmol). The mixture was stirred at room temperature for 3 days and concentrated. It was diluted with 20 mL of saturated NaHCO₃ solution, further saturated with solid NaHCO₃, and extracted with EtOAc. Combined EtOAc extracts were washed with brine, dried with anhydrous MgSO₄, filtered and concentrated and purified by silica gel chromatography (hexane/EtOAc) to afford Preparation 47C (496 mg, 64%): HPLC: RT=0.615 min (H₂O/MeOH with TFA, CHROMOLITH® ODS, 4.6×50 mm, gradient=4 min, wavelength=220 nm); MS(ES): m/z=168 [M+H⁺]; ¹H NMR (400 MHz, DMSO-d₆) δ 8.67-8.62 (m, 1H), 8.03 (d, J=8.1 Hz, 1H), 7.94-7.85 (m, 1H), 5.48 (t, J=5.7 Hz, 1H), 4.63 (d, J=5.5 Hz, 2H), 3.87 (s, 3H).

Preparation 47D

Methyl 5-((di-tert-butoxyphosphoryloxy)methyl)picolinate

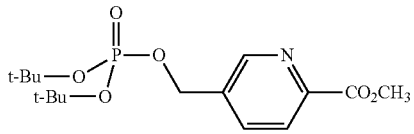

(47D)

Preparation 47D was prepared from Preparation 47C (208 mg, 1.244 mmol) according to the general procedure shown for Preparation 44B. Preparation 47D (196 mg, 43.8%) was obtained: HPLC: RT=2.633 min (H₂O/MeOH with TFA, CHROMOLITH® ODS, 4.6×50 mm, gradient=4 min, wavelength=220 nm); MS(ES): m/z=360 [M+H⁺]; ¹H NMR (400 MHz, DMSO-d₆) δ 8.72 (d, J=1.5 Hz, 1H), 8.09 (dd, J=8.0, 0.6 Hz, 1H), 7.99 (dd, J=8.1, 2.2 Hz, 1H), 5.08 (d, J=8.4 Hz, 2H), 3.89 (s, 3H), 1.40 (s, 18H).

Preparation 47E 5-((Di-tert-butoxyphosphoryloxy)methyl)picolinic acid

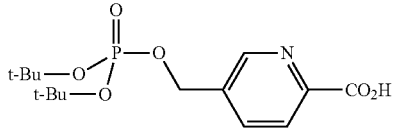

(47E)

Preparation 47E was prepared from Preparation 47D (55.0 mg, 0.153 mmol) according to the general procedure shown for Preparation 44C. Preparation 47E (35.5 mg, 67.2%) was obtained. HPLC: RT=2.185 min (H₂O/MeOH with TFA, CHROMOLITH® ODS, 4.6×50 mm, gradient=4 min, wavelength=220 nm); MS(ES): m/z=346 [M+H⁺]; ¹H NMR (400 MHz, DMSO-d₆) δ ppm 13.27 (br. s., 1H), 8.72 (d, J=1.5 Hz, 1H), 8.08 (d, J=8.1 Hz, 1H), 7.98 (dd, J=8.0, 2.1 Hz, 1H), 5.09 (d, J=8.6 Hz, 2H), 1.43 (s, 18H).

Preparation 47F ((S)-3-((R)-2-((S)-1-Amino-3-cyclopropyl-1-oxopropan-2-yl)-5,5,5-trifluoropentanamido)-9-fluoro-2-oxo-5-phenyl-2,3-dihydro-1H-benzo[e][1,4]diazepin-1-yl)methyl 6-((di-tert-butoxyphosphoryloxy)methyl)picolinate

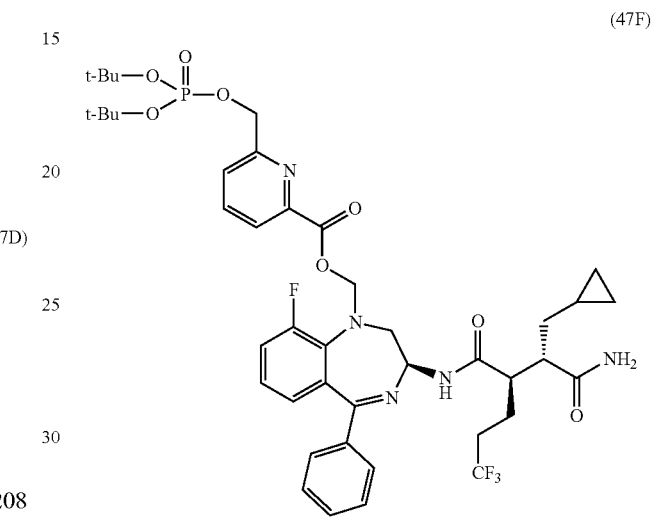

(47F)

Preparation 47F was prepared from Preparation 47E (33.0 mg, 0.096 mmol) and Preparation 44A (46.0 mg, 0.079 mmol) according to the general procedure shown for Preparation 44D to give a mixture of two diastereoisomers, which were separated by preparative SFC chromatography (Berger SFC MGII, PHENOMENEX® Lux Cellulose-4 25×3 cm ID, 5 μm, 75/25 CO₂/MeOH, 85 mL/min). Fractions containing the product were concentrated, dried overnight under vacuum to afford Preparation 47F (10.3 mg, 14.8%) as a colorless solid. Chiral HPLC: RT=7.494 min, Berger SFC, PHENOMENEX® Lux Cellulose-4 250×4.6 mm ID, 5 μm, 70/30 CO₂/MeOH, 2.0 mL/min; HPLC: RT=3.413 min (H₂O/MeOH with TFA, CHROMOLITH® ODS, 4.6×50 mm, gradient=4 min, wavelength=220 nm); MS(ES): m/z=876 [M+H⁺]; ¹H NMR (400 MHz, CD₃OD) δ 8.60 (s, 1H), 7.81-7.77 (m, 2H), 7.67-7.57 (m, 1H), 7.52-7.46 (m, 3H), 7.45-7.39 (m, 1H), 7.31-7.23 (m, 2H), 7.18 (d, J=7.7 Hz, 1H), 6.45 (d, J=10.6 Hz, 1H), 6.08 (d, J=10.3 Hz, 1H), 5.57 (s, 1H), 5.09 (d, J=8.4 Hz, 2H), 3.39-3.35 (m, 1H), 2.79-2.71 (m, 1H), 2.68-2.60 (m, 1H), 2.58-2.43 (m, 1H), 2.32-2.17 (m, 1H), 1.88-1.76 (m, 2H), 1.73-1.63 (m, 1H), 1.50 (s, 18H), 1.24 (ddd, J=13.7, 7.6, 3.5 Hz, 1H), 0.77-0.62 (m, 1H), 0.53-0.36 (m, 2H), 0.18-0.08 (m, 1H).

Example 47

Example 47 was prepared from Preparation 47F (10.3 mg, 0.012 mmol) according to the general procedure shown for Example 44. Example 47 (8.44 mg, 81%) was obtained. HPLC: RT=2.558 min (H₂O/MeOH with TFA, CHROMOLITH® ODS, 4.6×50 mm, gradient=4 min, wavelength=220 nm); MS(ES): m/z=764 [M+H⁺]; ¹H NMR (400 MHz, CD₃OD) δ 8.56 (s, 1H), 7.75 (s, 2H), 7.62-7.54 (m, 1H), 7.53-7.34 (m, 4H), 7.27-7.19 (m, 2H), 7.15 (d, J=7.7 Hz, 1H), 6.43 (d, J=10.3 Hz, 1H), 6.05 (d, J=10.6 Hz, 1H), 5.53 (s, 1H), 5.06 (d, J=7.7 Hz, 2H), 3.35 (br. s., 1H), 2.77-2.67 (m, 1H), 2.65-2.56 (m, 1H), 2.55-2.39 (m, 1H), 2.33-2.15 (m, 1H), 1.86-1.71 (m, 2H), 1.69-1.57 (m, 1H), 1.21 (ddd, J=13.5, 7.7, 3.2 Hz, 1H), 0.68 (d, J=6.6 Hz, 1H), 0.49-0.32 (m, 2H), 0.15-0.04 (m, 1H).

Example 48

((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl 3-(2,4-dimethyl-6-(phosphonooxy)phenyl)-3-methylbutanoate (48)

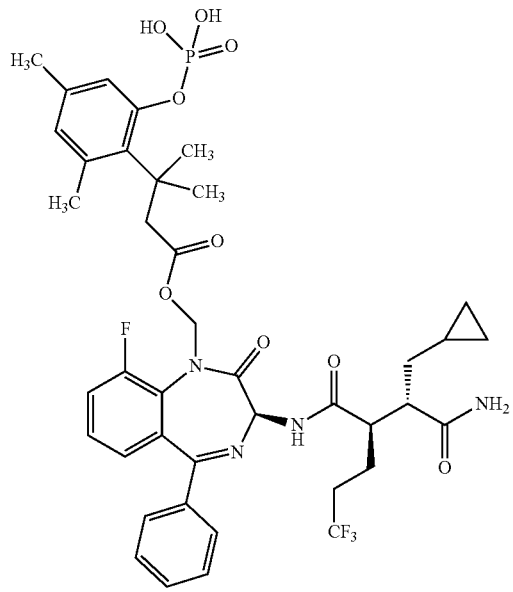

Preparation of 48A (2R,3S)—N1-(1-(Chloromethyl)-9-fluoro-2-oxo-5-phenyl-2,3-dihydro-1H-benzo[e][1,4]diazepin-3-yl)-3-(cyclopropylmethyl)-2-(3,3,3-trifluoropropyl)succinamide (48A)

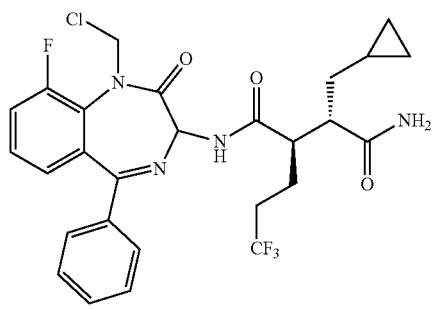

Preparation 44A (173 mg, 0.299 mmol) and triethylamine hydrochloride (123 mg, 0.897 mmol) in CH$_2$Cl$_2$ (5 mL) were added to a 100 mL round-bottomed flask. Sulfuryl chloride (0.036 mL, 0.448 mmol) was added, and the reaction mixture was stirred at room temperature for 30 min. Additional sulfuryl chloride (7.29 µl, 0.090 mmol) was added, and the reaction mixture was stirred for 15 min, then concentrated. The residue was dissolved in 2 mL CH$_2$Cl$_2$ and concentrated again, then dried under vacuum. Preparation 48A was obtained. HPLC: RT=3.138 min (CHROMOLITH® ODS 4.6×50 mm (4 min grad) eluting with 10-90% aqueous MeOH over 4 minutes containing TFA, 4 mL/min, monitoring at 220 nm).

Preparation 48B (3-((R)-2-((S)-1-Amino-3-cyclopropyl-1-oxopropan-2-yl)-5,5,5-trifluoropentanamido)-9-fluoro-2-oxo-5-phenyl-2,3-dihydro-1H-benzo[e][1,4]diazepin-1-yl) methyl 3-(2-(bis(benzyloxy)phosphoryloxy)-4,6-dimethylphenyl)-3-methylbutanoate (48B)

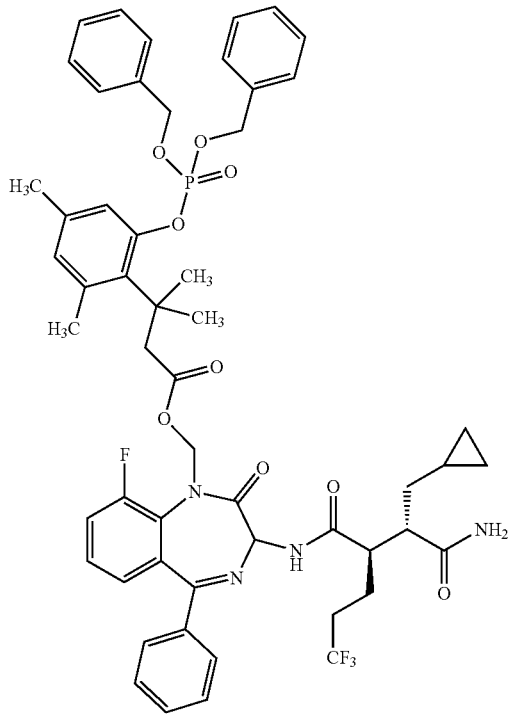

To a solution of 3-(2-((bis(benzyloxy)phosphoryl)oxy)-4,6-dimethylphenyl)-3-methylbutanoic acid (284 mg, 0.588 mmol) (J. Org. Chem., 61(24):8636 (1996)) in DMF (4 mL) was added Cs$_2$CO$_3$ (488 mg, 1.499 mmol). The mixture was stirred at room temperature for 1 min, and then Preparation 48A (170 mg, 0.300 mmol) in DMF (6 mL) was added dropwise. The reaction mixture was stirred at room temperature for 17 hr. The reaction mixture was then diluted with EtOAc and washed three times with aqueous 10% LiCl. The organic layer was dried over MgSO$_4$, filtered and concentrated. The crude material was then purified by silica gel chromatography (hexane/acetone). The product was collected and concentrated to give Preparation 48B (192.8 mg, 64%) as a 1:1 mixture of diastereomers. HPLC: RT=4.031 min (CHRO-MOLITH® ODS 4.6×50 mm (4 min grad) eluting with 10-90% aqueous MeOH over 4 minutes containing TFA, 4 mL/min, monitoring at 220 nm); MS(ES): m/z=1013 [M+H]⁺.

Example 48

To a solution of Preparation 48B (192.8 mg, 0.190 mmol) in EtOH (5 mL) was added 10% Pd/C (60.8 mg, 0.057 mmol). The atmosphere was exchanged 5 times with hydrogen. Next, the reaction mixture was stirred at room temperature under a hydrogen balloon. After stirring an additional 45 min, 10% Pd/C (60.8 mg, 0.057 mmol) was added and the resulting mixture was stirred under a hydrogen balloon. After stirring an additional 40 min, the reaction mixture was filtered through a 0.45 μm membrane with EtOH rinse. The mother liquor was concentrated and the mixture of diastereomers separated on preparative HPLC column (C18 Luna 30×100 eluting with a 12 min gradient from 55% B to 75% B (MeOH/H₂O/TFA) with a 30 min hold time in 3 injections). The product was collected and concentrated to give Example 48 (43.8 mg, 27%): ¹H NMR (500 MHz, CD₃OD) δ 7.73-7.64 (m, 2H), 7.59-7.39 (m, 5H), 7.19 (d, J=7.5 Hz, 1H), 7.04 (s, 1H), 6.64 (s, 1H), 5.95 (d, J=10.5 Hz, 1H), 5.50 (d, J=10.5 Hz, 1H), 2.77-2.66 (m, 3H), 2.61 (td, J=10.8, 3.5 Hz, 1H), 2.54-2.40 (m, 1H), 2.33 (s, 3H), 2.28-2.20 (m, 1H), 2.18 (s, 3H), 1.88-1.70 (m, 2H), 1.66 (ddd, J=13.7, 10.8, 6.5 Hz, 1H), 1.33 (s, 3H), 1.31 (s, 3H), 1.22 (ddd, J=13.7, 7.6, 3.6 Hz, 1H), 0.74-0.62 (m, 1H), 0.50-0.37 (m, 2H), 0.16-0.07 (m, 1H), 0.04--0.03 (m, 1H); HPLC: RT=3.391 min (CHRO-MOLITH® ODS 4.6×50 mm (4 min grad) eluting with 10-90% aqueous MeOH over 4 minutes containing 0.% TFA, 4 mL/min, monitoring at 220 nm); MS(ES): m/z=883 [M+H].

Example 49

S-(((2S,3R)-2-(Cyclopropylmethyl)-6,6,6-trifluoro-3-(((3S)-9-fluoro-2-oxo-5-phenyl-2,3-dihydro-1H-1,4-benzodiazepin-3-yl)carbamoyl)hexanoyl)amino)-L-cysteine.TFA (49)

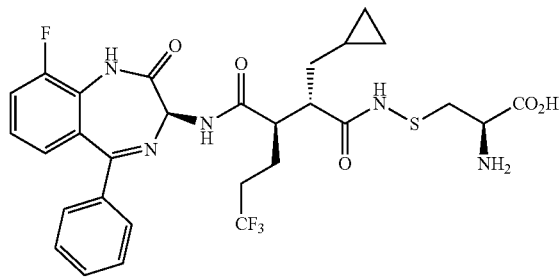

Preparation 49A (R)-tert-Butyl 2-((tert-butoxycarbonyl)amino)-3-(((2S,3R)-2-(cyclopropylmethyl)-6,6,6-trifluoro-3-(4S)-9-fluoro-2-oxo-5-phenyl-2,3-dihydro-1H-benzo[e][1,4]diazepin-3-yl)carbamoyl)hexanamido)thio)propanoate (49A)

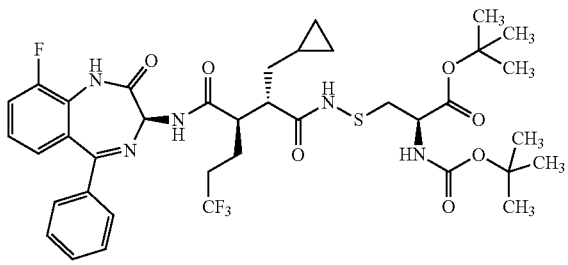

A solution of silver nitrate (131 mg, 0.771 mmol) in methanol (3 mL) was treated with (2R,2'R)-di-tert-butyl 3,3'-disulfanediylbis(2-((tert-butoxycarbonyl)amino)propanoate) (426 mg, 0.771 mmol). The mixture was stirred for 30 minutes and then treated with Example 1 (100 mg, 0.193 mmol) and TEA (0.108 mL, 0.771 mmol) to afford a light yellow solution. The reaction mixture was stirred at room temperature overnight and then concentrated to dryness. The crude product was dissolved in a small amount of CH₂Cl₂ and purified by silica gel chromatography (ethyl acetate/hexanes) to afford Preparation 49A (53 mg, 34.6%): HPLC: RT=4.508 min (SunFire C18, 5.0 μm, 4.6 mm×50 mm, 10-90% aqueous methanol containing 0.2% H₃PO₄, 4 min gradient, monitored at 220 nm); MS(ES): m/z=794.6 [M+H]⁺.

Example 49

A solution of Preparation 49A (7.8 mg, 9.83 μmol) in DCM (2 mL) at 0° C. was treated with TFA (0.2 mL, 2.60 mmol). The reaction mixture was slowly warmed to room temperature and stirred for six hours and then concentrated to dryness. The crude reaction product was dissolved in a small amount of MeOH and purified by reversed phase HPLC (YMC ODS-A 5 μm 30×250 mm, 10-90% aqueous methanol containing 0.1% TFA, 25 mL/min, 30 min gradient, monitored at 220 nm). The desired compound was lyophilized to dryness to afford Example 49.TFA (2.8 mg, 36.5%): ¹H NMR (400 MHz, CD₃OD) δ 7.60-7.54 (m, 2H), 7.53-7.49 (m, 1H), 7.48-7.40 (m, 3H), 7.27 (td, J=8.1, 5.0 Hz, 1H), 7.17 (d, J=7.9 Hz, 1H), 5.44-5.38 (m, 1H), 3.98 (dd, J=10.8, 3.7 Hz, 1H), 3.55 (dd, J=15.4, 3.7 Hz, 1H), 2.98-2.89 (m, 1H), 2.88-2.76 (m, 2H), 2.54-2.35 (m, 1H), 2.29-2.10 (m, 1H), 1.88-1.69 (m, 2H), 1.67-1.56 (m, 1H), 1.43 (ddd, J=13.8, 7.0, 3.4 Hz, 1H), 0.70-0.57 (m, 1H), 0.54-0.44 (m, 2H), 0.16-0.03 (m, 2H). HPLC: RT=3.350 min (SunFire C18, 5.0 μm, 4.6 mm×50 mm, 10-90% aqueous methanol containing 0.2% H₃PO₄, 4 min gradient, monitored at 220 nm); MS(ES): m/z=638.3 [M+H]⁺.

Example 50

(2S,3R)—N1-((2-Aminoethyl)sulfanyl)-2-(cyclopropylmethyl)-N4-((3S)-9-fluoro-2-oxo-5-phenyl-2,3-dihydro-1H-1,4-benzodiazepin-3-yl)-3-(3,3,3-trifluoropropyl)succinamide.TFA (50)

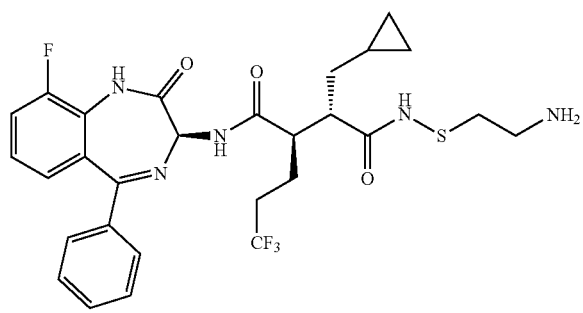

Preparation 50A tert-Butyl 2-((2S,3R)-2-(cyclopropylmethyl)-6,6,6-trifluoro-3-((S,Z)-9-fluoro-2-oxo-5-phenyl-2,3-dihydro-1H-benzo[e][1,4]diazepin-3-ylcarbamoyl)hexanamidothio)ethylcarbamate (50A)

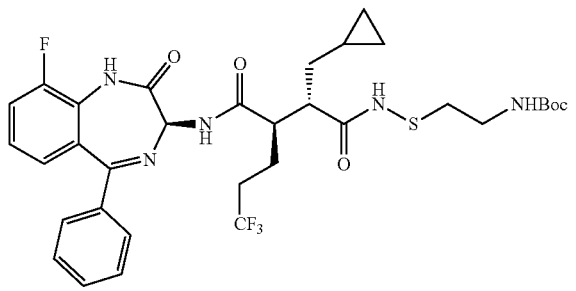

A slight suspension of silver nitrate (39.3 mg, 0.231 mmol) in methanol (1 mL) was treated with tert-butyl 2,2'-disulfanediylbis(ethane-2,1-diyl)dicarbamate (82 mg, 0.23 mmol). The mixture was stirred for 30 minutes and then Example 1 (30 mg, 0.058 mmol) and TEA (0.032 mL, 0.231 mmol) were added, resulting in a light yellow solution. The reaction mixture was stirred at room temperature over for 5 hours and then concentrated to dryness. The crude product was dissolved in a small amount of $CH_2Cl_2$ and purified by silica gel chromatography (ethyl acetate/hexanes) to afford Preparation 50A (21.8 mg, 54.3%). HPLC: RT=4.285 min (SunFire C18, 5.0 μm, 4.6 mm×50 mm, 10-90% aqueous methanol containing 0.2% $H_3PO_4$, 4 min gradient, monitored at 220 nm); MS(ES): m/z=694.4 $[M+H]^+$.

Example 50

A suspension of Preparation 50A (20 mg, 0.029 mmol) in DCM (2 mL) at 0° C. was treated with TFA (0.2 mL, 2.60 mmol) and slowly warmed to room temperature over 1 hour. The reaction mixture was then concentrated to dryness. The crude reaction product was dissolved in a small amount of MeOH and purified by reversed phase HPLC (YMC ODS-A 5 μm 30×250 mm, 10-90% aqueous methanol containing 0.1% TFA, 20 mL/min, 30 min gradient, monitored at 220 nm). The product (retention time=18.679 minutes) was isolated and lyophilized to dryness to afford Example 50.TFA (17.8 mg, 84%): $^1$H NMR (400 MHz, $CD_3OD$) δ 7.63-7.41 (m, 1H), 7.34-7.24 (m, 1H), 7.19 (d, J=7.9 Hz, 1H), 5.47-5.39 (m, 1H), 3.24-3.15 (m, 2H), 3.12-2.94 (m, 2H), 2.92-2.77 (m, 2H), 2.58-2.39 (m, 1H), 2.31-2.13 (m, 1H), 1.93-1.79 (m, 1H), 1.78-1.59 (m, 2H), 1.50-1.40 (m, 1H), 0.70-0.57 (m, 1H), 0.52-0.43 (m, 2H), 0.15-0.05 (m, 2H); HPLC: RT=3.135 min (SunFire C18, 5.0 μm, 4.6 mm×50 mm, 10-90% aqueous methanol containing 0.2% $H_3PO_4$, 4 min gradient, monitored at 220 nm); MS(ES): m/z=594.4 $[M+H]^+$.

Example 51

Methyl S-(((2S,3R)-2-(Cyclopropylmethyl)-6,6,6-trifluoro-3-(((3S)-9-fluoro-2-oxo-5-phenyl-2,3-dihydro-1H-1,4-benzodiazepin-3-yl)carbamoyl)hexanoyl)amino)-L-cysteinate.TFA (51)

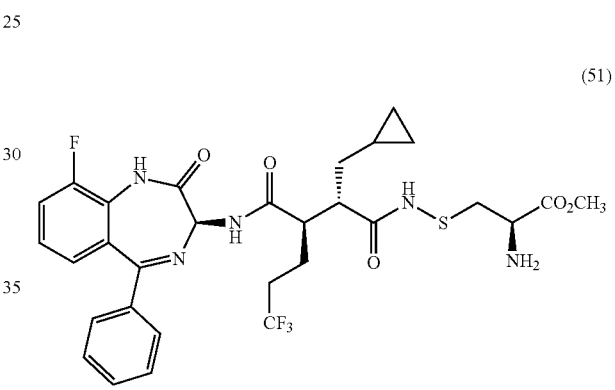

Preparation 51A (R)-Methyl 2-((tert-butoxycarbonyl)amino)-3-(((2S,3R)-2-(cyclopropylmethyl)-6,6,6-trifluoro-3-((S)-9-fluoro-2-oxo-5-phenyl-2,3-dihydro-1H-benzo[e][1,4]diazepin-3-yl)carbamoyl)hexanamido)thio)propanoate (51A)

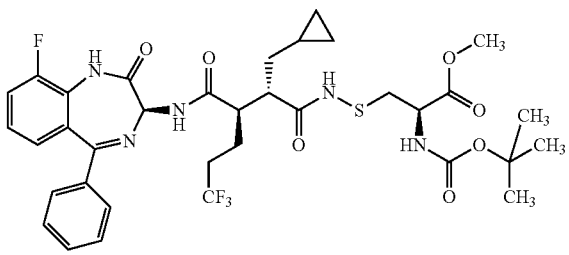

A slight suspension of silver nitrate (39.3 mg, 0.231 mmol) in methanol (1 mL) was treated with (2R,2'R)-dimethyl 3,3'-disulfanediylbis(2-((tert-butoxycarbonyl)amino)propanoate) (108 mg, 0.231 mmol). The mixture was stirred for 30 minutes and then Example 1 (30 mg, 0.058 mmol) and TEA (0.032 mL, 0.231 mmol) were added resulting in a light yellow solution. The mixture was stirred at room temperature 48 hours. The crude mixture was concentrated to dryness. The crude product was dissolved in a small amount of $CH_2Cl_2$ and purified by silica gel chromatography (ethyl acetate/hexanes) to afford Preparation 51A (15.2 mg, 34.9%): HPLC: RT=4.260 min (SunFire C18, 5.0 μm, 4.6 mm×50 mm, 10-90% aqueous methanol containing 0.2% $H_3PO_4$, 4 min gradient, monitored at 220 nm); MS(ES): m/z=752.31 $[M+H]^+$.

Example 51

A solution of Preparation 51A (15 mg, 0.020 mmol) in DCM (1 mL) at 0° C. was treated with TFA (100 μl, 1.298 mmol) and slowly warmed to room temperature. The starting material was consumed after 4 hours. The reaction mixture was concentrated to dryness. The crude reaction product was dissolved in a small amount of MeOH and purified by reversed phase HPLC (YMC ODS C18 5 μm 20×100 mm, 10-90% aqueous methanol containing 0.1% TFA, 20 mL/min, 30 min gradient, monitored at 220 nm). The product (retention time=19.644 minutes) was isolated and lyophilized to dryness to afford Example 51.TFA (3.2 mg, 20.4%): $^1$H NMR (400 MHz, DMSO-$d_6$) δ 10.82 (s, 1H), 9.56 (s, 1H), 9.45 (d, J=7.0 Hz, 1H), 8.59 (br. s., 3H), 7.64-7.56 (m, 1H), 7.56-7.52 (m, 2H), 7.50-7.44 (m, 2H), 7.31 (td, J=8.0, 5.1 Hz, 1H), 7.16 (d, J=7.9 Hz, 1H), 5.28 (d, J=7.0 Hz, 1H), 4.10 (dd, J=8.8, 4.2 Hz, 1H), 3.75 (s, 3H), 3.27 (dd, J=15.0, 4.2 Hz, 1H), 2.98 (dd, J=15.1, 9.1 Hz, 1H), 2.86-2.77 (m, 1H), 2.72 (dd, J=10.3, 3.3 Hz, 1H), 2.64-2.55 (m, 1H), 2.30-2.14 (m, 1H), 1.66-1.36 (m, 3H), 1.25 (ddd, J=13.5, 6.8, 3.2 Hz, 1H), 0.58-0.45 (m, 1H), 0.40-0.30 (m, 2H), 0.03--0.11 (m, 2H); HPLC: RT=3.175 min (SunFire C18, 5.0 μm, 4.6 mm×50 mm, 10-90% aqueous methanol containing 0.2% $H_3PO_4$, 4 min gradient, monitored at 220 nm); MS(ES): m/z=652.4 $[M+H]^+$.

Example 52

((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl L-valinate Preparation 52A (S)-Chloromethyl 2-((tert-butoxycarbonyl)amino)-3-methylbutanoate

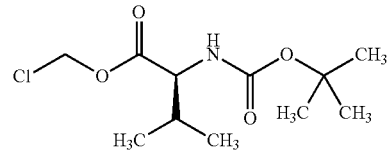

(52A)

To a stirred solution of (S)-2-((tert-butoxycarbonyl)amino)-3-methylbutanoic acid (1 g, 4.60 mmol), sodium carbonate (2.439 g, 23.01 mmol) and tetrabutylammonium hydrogen sulfate (0.313 g, 0.921 mmol) in a mixture of DCM (10 mL) and water (5 mL) at 0° C., was added chloromethyl chlorosulfate (1.519 g, 9.21 mmol). The reaction mixture was allowed to warm to room temperature overnight. The mixture was diluted with DCM and water, and the organic layer was separated, washed with a brine solution, and dried over $Na_2SO_4$. The solution was filtered and concentrated in vacuo and the residue obtained was purified by a flash chromatography ($SiO_2$, 0-10% EtOAc in hexane) to afford Preparation 52A (0.9 g, 73.6%) as a colorless oil. $^1$H NMR (400 MHz, $CDCl_3$) δ 0.93 (d, J=6.80 Hz, 3H), 1.00 (d, J=6.80 Hz, 3H), 1.43 (s, 9H), 2.17-2.18 (m, 1H), 4.25-4.27 (m, 1H), 4.96 (d, J=7.60 Hz, 1H), 5.62 (d, J=6.00 Hz, 1H), 5.88 (d, J=6.00 Hz, 1H).

Preparation 52B (S)—((S,Z)-3-((R)-2-((R)-1-Amino-3-cyclopropyl-1-oxopropan-2-yl)-5,5,5-trifluoropentanamido)-9-fluoro-2-oxo-5-phenyl-2,3-dihydro-1H-benzo[e][1,4]diazepin-1-yl)methyl 2-(tert-butoxycarbonylamino)-3-methylbutanoate, and Preparation 52C (S)—((R,Z)-3-((R)-2-((R)-1-Amino-3-cyclopropyl-1-oxopropan-2-yl)-5,5,5-trifluoropentanamido)-9-fluoro-2-oxo-5-phenyl-2,3-dihydro-1H-benzo[e][1,4]diazepin-1-yl)methyl 2-(tert-butoxycarbonylamino)-3-methylbutanoate

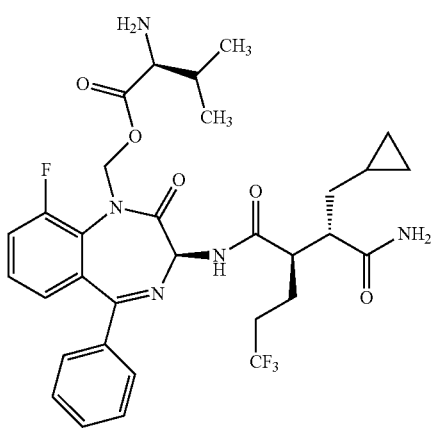

(52)

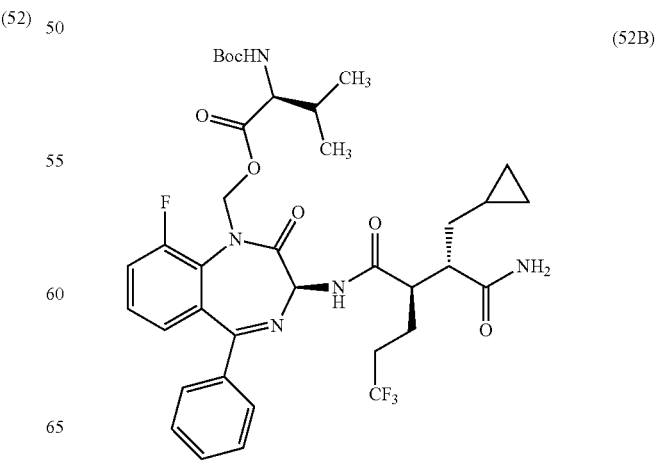

(52B)

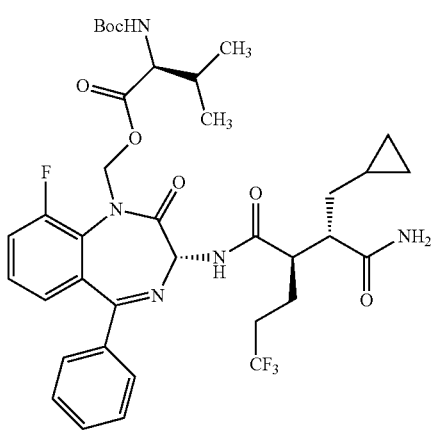

(52C)

To a stirred solution of Example 1 (30 mg, 0.058 mmol) in DMF (0.5 mL) was added K$_2$CO$_3$ (15.99 mg, 0.116 mmol) and the mixture was stirred for 10 minutes. Preparation 52A (77 mg, 0.289 mmol) was added and the reaction mixture was allowed to stir at room temperature overnight. The reaction mixture was concentrated under reduced pressure. The mixture was diluted with EtOAc and water, and the organic layer was separated, washed with brine solution, and dried over Na$_2$SO$_4$. The mixture was filtered and concentrated in vacuo and the residue obtained was purified by chromatography on Preparative TLC (SiO$_2$, 40% EtOAc in hexane) to afford a mixture of diastereomers Preparations 52B and 52C (20 mg, 46% yield) as off-white solid: HPLC RT=2.045 min (ZORBAX® SB C18 (4.6×50) mm, 5 μm, Positive mode; Mobile Phase A: 10% MeOH-90% H$_2$O-0.1% TFA, Mobile Phase B: 90% MeOH-10% H$_2$O-0.1% TFA, Flow: 5 ml/min; monitored at 220 nm); MS(ESI): m/z=748 [M+H]$^+$.

Example 52

To a stirred solution of a mixture of Preparations 52B and 52C (20 mg, 0.027 mmol) in DCM (0.5 mL) at 0° C. was added 4M HCl in dioxane (0.020 mL, 0.080 mmol). The reaction mixture was allowed to warm to room temperature for 2 h. The resulting mixture was concentrated under reduced pressure, and the solid obtained was dissolved in a mixture of water and diethyl ether. The aqueous layer was collected and lyophilized to dryness to afford a mixture of diastereomers. The mixture of diastereomers was separated by reversed-phase HPLC (SunFire C18 150×19 mm 5 g, Mobile Phase A: 0.1% TFA in water:CH$_3$CN (90:10), Mobile Phase B: Methanol, Flow: 15.0 ml/min). Lyophilization of appropriate fractions provided Example 52 (3 mg) as an off-white solid. $^1$H NMR (400 MHz, DMSO-d$_6$) δ ppm 9.47 (d, J=8.00 Hz, 1H), 8.2 (brs, 3H), 7.73-7.78 (ddd, J=11.6 Hz, 8.4 Hz and 1.2 Hz, 1H), 7.49-7.63 (m, 8H), 7.25 (d, J=8.00 Hz, 1H), 6.98 (s, 1H), 5.98 (d, J=12.00 Hz, 1H), 5.83 (d, J=12.00 Hz, 1H), 5.42 (d, J=8.00 Hz, 1H), 3.75-3.79 (m, 2H), 2.50-2.52 (td, underneath solvent peak J=6.8 Hz and J=3.2 Hz, 2H), 1.63 (A of AB, J$_{AB}$=7.6 Hz, 2H), 1.59 (B of AB, J$_{BA}$=7.6 Hz, 2H), 1.47-1.53 (m, 5H), 1.00-1.07 (m, 3H), 0.84-0.86 (m, 4H), 0.61 (d, J=8.00 Hz, 3H), 0.56 (d, J=8.00 Hz, 3H), 0.51 (t, J=8.00 Hz, 1H), 0.32-0.35 (m, 2H), −0.14-−0.11 (m, 1H); HPLC RT=6.198 min (Column: SunFire C18 (4.6×150) mm, 3.5 micron SC/862, Buffer: 0.05% TFA in water pH 2.5 adjusted with NH$_3$, Mobile Phase A: Buffer: Acetonitrile (95:5), Mobile Phase B: Acetonitrile: Buffer (95:5), Flow: 1 ml/min, monitored at 220 nm); MS(ESI): m/z=648 [M+H]$^+$.

Example 53

((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl 1-aminocyclopropanecarboxylate

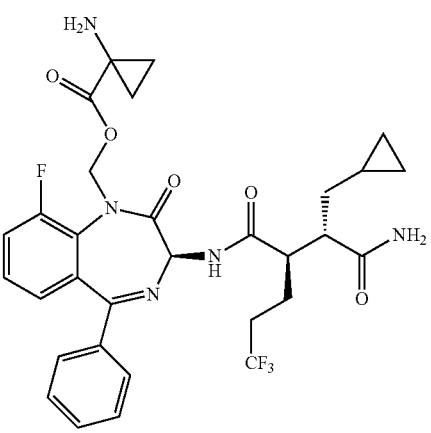

(53)

Preparation 53A

Chloromethyl 1-(tert-butoxycarbonylamino)cyclopropanecarboxylate

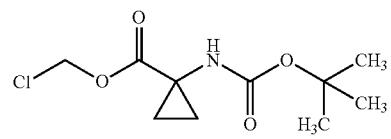

(53A)

To a stirred solution of 1-((tert-butoxycarbonyl)amino)cyclopropane-carboxylic acid (0.55 g, 2.73 mmol), sodium carbonate (1.449 g, 13.67 mmol) and tetrabutylammonium hydrogen sulfate (0.186 g, 0.547 mmol) in a mixture of DCM (10 mL) and water (5 mL) at 0° C., was added chloromethyl chlorosulfate (0.902 g, 5.47 mmol). The reaction mixture was allowed to warm to room temperature overnight. The mixture was diluted with DCM and water and the organic layer was separated, washed with a brine solution and dried over Na$_2$SO$_4$. The mixture was filtered and concentrated in vacuo and the residue obtained was purified by a flash chromatography (SiO$_2$, 0-10% EtOAc in hexane) to afford Preparation 53A (0.5 g, 73.3%) as an off-white solid: $^1$H NMR (400 MHz, CDCl$_3$) δ 1.24-1.26 (m, 2H), 1.46 (s, 9H), 1.60-1.61 (m, 2H), 5.13 (s, 1H), 5.71 (s, 2H).

Preparation 53B ((S)-3-((R)-2-((S)-1-Amino-3-cyclopropyl-1-oxopropan-2-yl)-5,5,5-trifluoropentanamido)-9-fluoro-2-oxo-5-phenyl-2,3-dihydro-1H-benzo[e][1,4]diazepin-1-yl)methyl 1-(tert-butoxycarbonylamino)cyclopropanecarboxylate (53B)

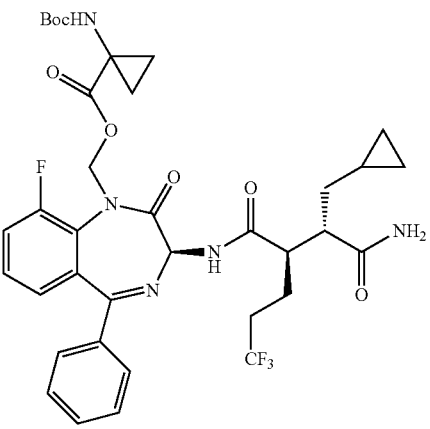

To a solution of Example 1 (0.040 g, 0.077 mmol) in DMF (1.2 mL), K$_2$CO$_3$ (0.021 g, 0.154 mmol) was added followed by the addition of Preparation 53A (0.096 g, 0.386 mmol). The reaction mixture was stirred at 24° C. for 5 h. Water (8 mL) was added to the reaction mixture, followed by extraction with EtOAc. The combined organic layers were dried with Na$_2$SO$_4$, filtered and concentrated to dryness. The crude material was purified by preparative-TLC (0-60% EtOAc/hexane) to afford Preparation 53B: (0.034 g, 60.2%): HPLC: RT=10.596 (Column: XBridge phenyl (4.6×150) mm, 3.5 micron, Buffer: 0.05% TFA in water pH 2.5 adjusted with dil.NH$_3$, Mobile Phase A: Buffer:Acetonitrile (95:5), Mobile Phase B: Acetonitrile: Buffer (95:5), Flow-1 mL/min, monitored at 220 nm); MS(ES): m/z=732 [M+H]$^+$.

Example 53

To a solution of Preparation 53B (0.034 g, 0.046 mmol) in DCM (2 mL) at 0° C., was added 4M HCl in dioxane (0.116 mL, 0.465 mmol) dropwise. The mixture was allowed to warm to room temperature and stirred at 24° C. for 4 h. The reaction mixture was then concentrated to dryness. The crude material was purified by preparative reversed-phase HPLC (Column: XTERRA® RP 18 (150×19 mm), Mobile Phase A: 0.1% TFA in water: ACN (90:10), Mobile Phase B: ACN, Flow rate: 15 mL/min) to afford Example 53 (0.0083 g, 28.3%). $^1$H NMR (400 MHz, DMSO-d$_6$) δ 9.41 (d, J=8.00 Hz, 1H), 8.58 (brs, 3H), 7.72-7.77 (ddd, J=11.6 Hz, 8.4 Hz and 1.2 Hz, 1H), 7.51-7.62 (m, 7H), 7.23 (d, J=8.00 Hz, 1H), 6.98 (s, 1H), 6.10 (d, J=12.00 Hz, 1H), 5.73 (d, J=12.00 Hz, 1H), 5.42 (d, J=8.00 Hz, 1H), 2.68-2.71 (m, 1H), 2.44-2.47 (td, underneath solvent peak J=6.8 Hz and J=3.2 Hz 2H), 2.33 (s, 1H), 1.64 (A of AB, J$_{AB}$=7.6 Hz, 2H), 1.60 (B of AB, J$_{BA}$=7.6 Hz, 2H), 1.49-1.50 (m, 1H), 1.00-1.08 (m, 3H), 0.93-0.98 (m, 1H), 0.82-0.86 (m, 1H), 0.55 (t, J=8.00 Hz, 1H), 0.33 (m, 2H), −0.14−−0.11 (m, 1H); HPLC: RT=6.272 min (SunFire C18 (4.6×150) mm, 3.5 micron, Buffer: 0.05% TFA in water pH 2.5 adjusted with NH$_3$, Mobile Phase A: Buffer: Acetonitrile (95:5), Mobile Phase B: Acetonitrile: Buffer (95:5), Flow rate: 1 mL/min, monitored at 220 nm); MS(ES): m/z=632 [M+H]$^+$.

Example 54

(2S,3R)-2-(Cyclopropylmethyl)-N$^4$-((3S)-9-fluoro-2-oxo-5-phenyl-2,3-dihydro-1H-1,4-benzodiazepin-3-yl)-N$^1$-(1-pyrrolidinylmethyl)-3-(3,3,3-trifluoropropyl)succinamide (54)

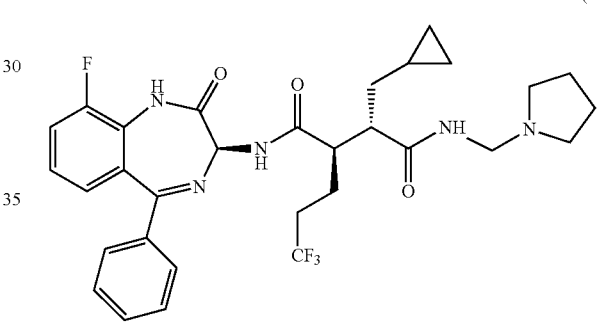

Example 1 (0.020 g, 0.039 mmol) was dissolved in a solution of formaldehyde (0.57 mL, 7.71 mmol) and pyrrolidine (0.549 g, 7.71 mmol) in MeOH (1.0 mL). The reaction mixture was stirred at 24° C. for 15 h and then concentrated to dryness under reduced pressure. The resulting residue was diluted with water (8 mL) and extracted with EtOAc. The combined organic layers were dried over Na$_2$SO$_4$, filtered and concentrated to dryness. The crude material was purified by preparative reversed-phase HPLC (Column: Symmetry C8 (250×20 mm), Mobile Phase A: 0.1% TFA in water: CH$_3$CN (90:10), Mobile Phase B: CH$_3$CN, Flow rate: 16.0 mL/min) to afford Example 54 (0.0128 g, 55.2%): $^1$H NMR (400 MHz, DMSO-d$_6$) δ 10.84 (s, 1H), 9.95 (s, 1H), 9.42-9.48 (m, 2H), 7.47-7.64 (m, 6H), 7.29-7.35 (m, 1H), 7.17 (d, J=8.00 Hz, 1H), 5.29 (d, J=8.00 Hz, 1H), 3.10-3.13 (m, 9H), 2.84 (t, J=5.6 Hz, 3H), 2.66 (m, 3H), 2.24-2.34 (m, 4H), 1.83-1.98 (m, 10H), 1.55-1.63 (m, 5H), 1.19-1.25 (m, 2H), 0.60 (brm, 1H), 0.37 (d, J=8.00 Hz, 2H), 0.008−−0.05; HPLC:RT=6.861 min (Column: SunFire C18 (4.6×150) mm, 3.5 micron, Buffer: 0.05% TFA in water pH 2.5 adjusted with NH$_3$, Mobile Phase A: Buffer: Acetonitrile (95:5), Mobile Phase B: Acetonitrile: Buffer (95:5), Flow rate: 1 mL/min, monitored at 220 nm); MS(ES): m/z=602 [M+H]$^+$.

Example 55

((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl 4-((phosphonooxy)methyl)benzoate (55)

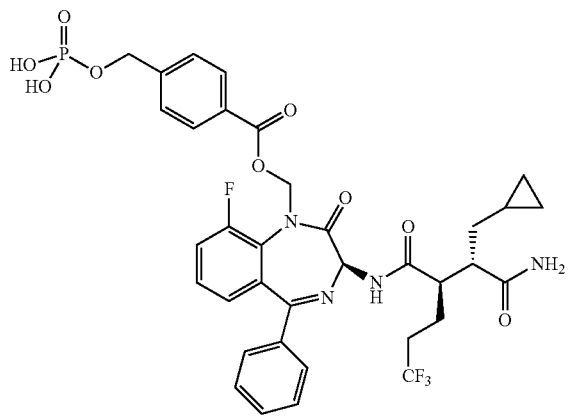

Preparation 55A

Methyl 4-((di-tert-butoxyphosphoryloxy)methyl)benzoate (55A)

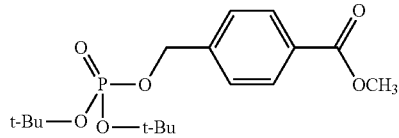

Methyl 4-(bromomethyl)benzoate (1200 mg, 5.24 mmol), potassium di-tert-butyl phosphate (1431 mg, 5.76 mmol) and sodium iodide (785 mg, 5.24 mmol) were combined in DMF (3.00 mL) under nitrogen. The reaction mixture was stirred at room temperature for 24 h. The reaction mixture was diluted with ether, washed with 10% LiCl solution and brine, then dried (MgSO₄), filtered and concentrated in vacuo. The residue was purified by silica gel chromatography (hexane/EtOAc) to provide Preparation 55A (571 mg, 1.593 mmol, 30%): $^1$H NMR (400 MHz, CDCl₃) δ 8.03 (d, J=8.4 Hz, 2H), 7.53-7.37 (m, 2H), 5.05 (d, J=7.5 Hz, 2H), 3.92 (s, 3H), 1.48 (d, J=0.4 Hz, 18H).

Preparation 55B 4-((di-tert-butoxyphosphoryloxy)methyl)benzoic acid (55B)

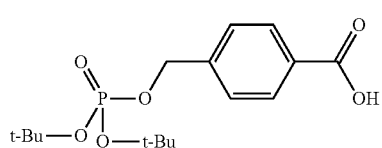

To a stirred solution of Preparation 55A (352 mg, 0.982 mmol) in THF (8.00 mL) and water (3.00 mL) was added lithium hydroxide (61.8 mg, 1.473 mmol). The reaction mixture was stirred at room temperature for 8 hours. The mixture was concentrated to remove organics, then was diluted with 8 mL of pH 4 phosphate solution, resulting in a pH 6 (as determined by pH paper) solution. The solution was extracted with EtOAc, then washed with brine, dried (MgSO₄), filtered and concentrated to give Preparation 55B (307 mg, 91%): HPLC: RT=2.875 min (H₂O/MeOH with TFA, CHROMOLITH® ODS, 4.6×50 mm, gradient=4 min, wavelength=220 nm); MS(ES): m/z=343 [M+H⁺]; $^1$H NMR (400 MHz, DMSO-d₆) δ 12.97 (br. s, 1H), 7.95 (d, J=8.1 Hz, 2H), 7.61-7.29 (m, 2H), 5.00 (d, J=7.9 Hz, 2H), 1.41 (s, 18H).

Preparation 55C ((S)-3-((R)-2-((S)-1-Amino-3-cyclopropyl-1-oxopropan-2-yl)-5,5,5-trifluoropentanamido)-9-fluoro-2-oxo-5-phenyl-2,3-dihydro-1H-benzo[e][1,4]diazepin-1-yl)methyl 4-(((di-tert-butoxyphosphoryl)oxy)methyl)benzoate (55C)

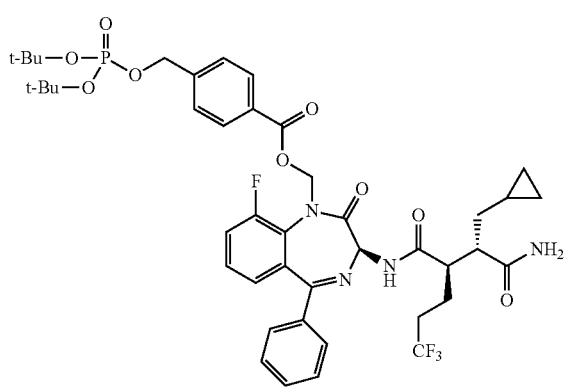

Preparation 55B was prepared from Preparation 44A (77 mg, 0.136 mmol) and Preparation 55B (94 mg, 0.272 mmol) according to the general procedure shown for Preparation 44D. The resulting mixture of two diastereoisomers were separated by preparative SFC chromatography (Berger SFC MGII, Chiral IC 25×3 cm ID, 5 μm, 80/20 CO₂/MeOH, 85 mL/min). Fractions containing product were concentrated, dried overnight under vacuum to afford Preparation 55C (31 mg, 26.3%) as a white solid. HPLC: RT=3.823 min (H₂O/MeOH with H₃PO₄, YMC S5 ODS, 4.6×50 mm, gradient=4 min, wavelength=220 nm); MS(ES): m/z=875[M+H⁺]. $^1$H NMR (400 MHz, methanol-d4) δ 7.69 (d, J=8.4 Hz, 2H), 7.63-7.53 (m, 1H), 7.52-7.38 (m, 4H), 7.34-7.21 (m, 4H), 7.15 (d, J=7.7 Hz, 1H), 6.36 (d, J=10.3 Hz, 1H), 5.97 (d, J=10.3 Hz, 1H), 4.98 (d, J=7.9 Hz, 2H), 2.73 (td, J=10.3, 4.2 Hz, 1H), 2.62 (td, J=10.7, 3.4 Hz, 1H), 2.57-2.41 (m, 1H), 2.24 (td, J=10.5, 5.1 Hz, 1H), 1.87-1.72 (m, 2H), 1.72-1.56 (m, 1H), 1.53-1.41 (m, 19H), 1.22 (ddd, J=13.5, 7.6, 3.5 Hz, 1H), 0.74-0.60 (m, 1H), 0.47-0.35 (m, 2H), 0.13-0.06 (m, 1H), 0.05--0.11 (m, 1H).

Example 55

Example 55 (15 mg, 83%) was prepared from Preparation 55C (20 mg, 0.023 mmol) according to the general procedure shown for Example 44: HPLC: RT=3.045 min (H₂O/MeOH with TFA, CHROMOLITH® ODS, 4.6×50 mm, gradient=4 min, wavelength=220 nm); MS(ES): m/z=763.5 [M+H⁺]; ¹H NMR (400 MHz, methanol-d₄) δ 7.68 (d, J=8.4 Hz, 2H), 7.62-7.52 (m, 1H), 7.51-7.38 (m, 4H), 7.33-7.20 (m, 4H), 7.15 (d, J=7.7 Hz, 1H), 6.36 (d, J=10.3 Hz, 1H), 5.98 (d, J=10.3 Hz, 1H), 5.57-5.46 (m, 1H), 4.99 (d, J=7.3 Hz, 2H), 2.72 (td, J=10.3, 4.1 Hz, 1H), 2.62 (td, J=10.7, 3.5 Hz, 1H), 2.56-2.40 (m, 1H), 2.31-2.12 (m, 1H), 1.88-1.73 (m, 2H), 1.67 (ddd, J=13.6, 10.8, 6.4 Hz, 1H), 1.22 (ddd, J=13.8, 7.7, 3.2 Hz, 1H), 0.69 (d, J=6.2 Hz, 1H), 0.50-0.32 (m, 2H), 0.16-0.06 (m, 1H), 0.00 (dd, J=8.5, 4.3 Hz, 1H).

Comparative Compounds 56 to 60

Comparative Compounds 56 to 60 can be prepared according to the procedures described in U.S. Pat. No. 7,053,084 for Examples 8, 12a, 38, 45a, and 28a, respectively.

TABLE 12

| Comparative Compound | U.S. Pat. No. 7,053,084 | Structure |
|---|---|---|
| 56 | Ex. 8 | 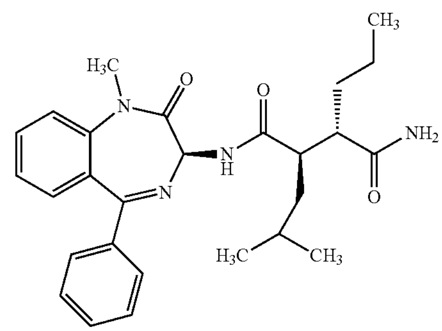 |
| 57 | Ex. 12a | 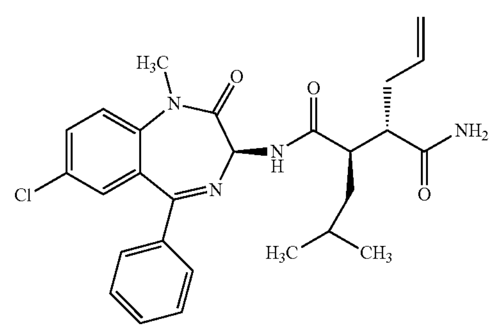 |
| 58 | Ex. 38 | 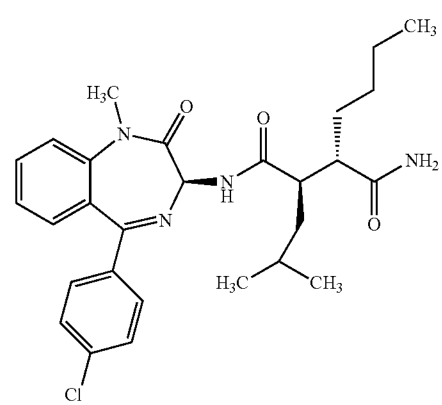 |

TABLE 12-continued

| Comparative Compound | U.S. Pat. No. 7,053,084 | Structure |
|---|---|---|
| 59 | Ex. 45a | 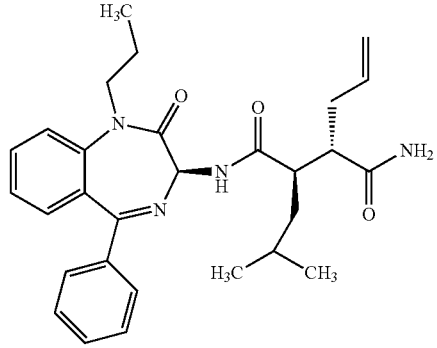 |
| 60 | Ex 28a | 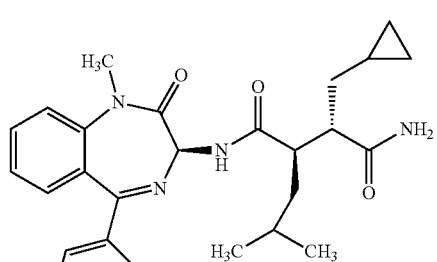 |

BIOLOGICAL ASSAYS

The pharmacological properties of the compounds of this invention may be confirmed by a number of biological assays. The exemplified biological assays, which follow, have been carried out with compounds of the invention.

Notch-CBF1 Transactivation Assay

The Notch-CBF1 (C-promoter binding factor I) cell based transactivation assay is based on the ability of the released Notch intracellular domain fragments (NICDs) to function as transcription factors in conjunction with CBF1 and other nuclear factors. Luciferase assays were used to measure the antagonism of Notch-CBF1 transcriptional activity. HeLa cervical cancer cells are transiently co-transfected with pCDNA3.1/Hygro plasmids containing truncated Notch 1, Notch 2, Notch 3, or Notch 4 receptors and a PGL3 luciferase reporter vector containing 4 copies of CBF1 binding site. The cells were then tested for Notch-CBF1 activity in the absence or presence of test compounds. HeLa cells, maintained in DMEM (high glucose with HEPES), 1× glutamine/penicillin/streptomycin and 10% Fetal Bovine serum, were transiently transfected in a T175 Flask (4.5×10$^6$ cells/flask) using the Monster Transfection Kit (Minis #MIR2906) according to manufacturers specifications. Table 13 denotes respective DNA quantity for the transfections.

TABLE 13

|  | DNA (µg) | CBF1 (µg) | Vector (µg) | Total DNA (µg) |
|---|---|---|---|---|
| human Notch 1 | 6 | 14.4 | 15.6 | 36.0 |
| human Notch 2 | 2 | 14.4 | 19.6 | 36.0 |
| human Notch 3 | 0.3 | 14.4 | 21.3 | 36.0 |
| human Notch 4 | 4 | 14.4 | 17.6 | 36.0 |

Six hours post-transfection, cells were trypsinized and plated into a 384-well black Poly-D-lysine coated tissue culture plate at a density of 5×10$^3$ cells/well in 95 µL assay media (DMEM (high glucose with HEPES), 1× glutamine/penicillin/streptomycin, 0.0125% BSA, 1× non-essential amino acids). Assay media (5 µL) containing test compounds in final concentrations ranging from 5 µM to 8.4×10$^{-5}$ µM (3 fold serial dilutions) were added to the cells and the cell plates were then incubated for 18 hours at 37° C. and 5% $CO_2$. Control wells contained DMSO vehicle (total counts) or 0.5 µM of an in-house small molecule inhibitor (background counts). Duplicates were used for each sample. Luciferase activity was measured after a 20-minute incubation with 50 µl STEADY-GLO® luciferase reagents according to manufacturer's specifications (Promega, Cat. #E2550) and analyzed by Envision plate reader (PerkinElmer, Boston, Mass.).

The antagonist effect of compounds was expressed as 100× [1−(average sample−average background)/(average total−average background)] where sample is the luciferase activity in the presence of test compound, background is equal to the luciferase activity in the presence of the small molecule inhibitor control and the total is signal induced in DMSO wells. Data was plotted using a four parameter logistic fit equation and the $IC_{50}$ value was defined as the concentration of compound that inhibited 50% of the luciferase activity.

Table 14 below lists the Notch 1 and Notch 3 $IC_{50}$ values for Examples 1-43 of this invention and Comparative Compounds 56-59 measured in the Notch-CBF1 Transactivation Assay hereinabove. In some instances, the value is an average of multiple experiments where N is the number of experiments conducted. The compounds of the present invention, as exemplified by the Examples 1-43 showed Notch 1 values of 16.1 nM or less and Notch 3 $IC_{50}$ values of 28.3 nM or less.

TABLE 14

| Example | Notch 1 IC$_{50}$ (nM) | N | Notch 3 IC$_{50}$ (nM) | N |
|---|---|---|---|---|
| 1 | 4.2 | 19 | 6.2 | 20 |
| 2 | 1.7 | 2 | 1.5 | 2 |
| 3 | 5.1 | 2 | 7.5 | 2 |
| 4 | 4.2 | 3 | 8.1 | 3 |
| 5 | 5.1 | 3 | 8.9 | 4 |
| 6 | 7.2 | 5 | 8.6 | 5 |
| 7 | 2.0 | 2 | 3.3 | 2 |
| 8 | 5.6 | 6 | 15.7 | 4 |
| 9 | 1.8 | 3 | 4.9 | 3 |
| 10 | 4.0 | 5 | 9.7 | 5 |
| 11 | 4.0 | 3 | 8.7 | 3 |
| 12 | 6.9 | 2 | 28.3 | 2 |
| 13 | 2.9 | 2 | 5.1 | 2 |
| 14 | 4.3 | 4 | 5.1 | 4 |
| 15 | 12.7 | 2 | 9.3 | 2 |
| 16 | 3.8 | 3 | 16.0 | 3 |
| 17 | 9.7 | 2 | 26.4 | 2 |
| 18 | 6.5 | 2 | 6.9 | 2 |
| 19 | 2.7 | 2 | 7.2 | 2 |
| 20 | 3.4 | 2 | 9.1 | 2 |
| 21 | 2.4 | 2 | 2.4 | 2 |
| 22 | 12.9 | 2 | 12.5 | 1 |
| 23 | 4.8 | 1 | 8.0 | 2 |
| 24 | 3.7 | 3 | 2.7 | 3 |
| 25 | 6.8 | 2 | 5.6 | 2 |
| 26 | 1.9 | 1 | 2.1 | 1 |
| 27 | 4.6 | 2 | 1.6 | 1 |
| 28 | 1.7 | 1 | 1.7 | 1 |
| 29 | 3.1 | 2 | 7.1 | 2 |
| 30 | 2.5 | 3 | 5.2 | 3 |
| 31 | 5.6 | 4 | 7.9 | 4 |
| 32 | 8.3 | 2 | 19.7 | 2 |
| 33 | 3.8 | 2 | 5.9 | 2 |
| 34 | 4.7 | 4 | 7.4 | 4 |
| 35 | 16.1 | 6 | 12.9 | 7 |
| 36 | 7.9 | 4 | 8.3 | 4 |
| 37 | 4.4 | 3 | 11.3 | 2 |
| 38 | 2.3 | 5 | 3.3 | 5 |
| 39 | 13.4 | 2 | 12.0 | 1 |
| 40 | 6.8 | 9 | 6.9 | 9 |
| 41 | 9.1 | 3 | 12.4 | 3 |
| 42 | 1.9 | 3 | 3.5 | 3 |
| 43 | 3.3 | 6 | 4.8 | 6 |
| Comparative Compound 56 | 64.1 | 1 | 48.3 | 1 |
| Comparative Compound 57 | 42.4 | 2 | 74.5 | 2 |
| Comparative Compound 58 | 5.1 | 3 | 13.5 | 4 |
| Comparative Compound 59 | 12.3 | 1 | 12.5 | 1 |

High Throughput (HT) Metabolic Stability Panel

Compounds administered parenterally enter the blood stream and undergo one or more passes through the liver. Compounds that are not readily metabolized by the liver can be administered at therapeutically effective plasma levels for therapeutically effective periods of time.

Orally administered compounds typically are absorbed through the intestinal walls into the blood stream and undergo a first pass through the liver. Compounds that are not readily metabolized in this first pass through the liver can be distributed to other areas of the body in therapeutically effective amounts.

The metabolic stability assay evaluated CYP-mediated metabolic stability in vitro using human, rat, mouse, dog, and/or monkey microsomes after a ten-minute incubation. Each compound was tested in duplicate.

The results of these assays were expressed as the fraction of parent compound remaining in the reaction mixture after a ten-minute incubation (Percent Remaining) In general, these results were used to evaluate only the extent of CYP-mediated, or NADPH-dependent, metabolism of the test compound. When the compound was significantly metabolized (<40-50% remaining), this indicated high clearance of the compound in vivo due to CYP-mediated metabolism. However, if the compound demonstrated moderate (50-80%) or low (>85%) metabolism in these in vitro assays, high clearance was still possible in vivo via other metabolism and elimination pathways.

The percent remaining results of these assays was predictive of compound clearance in vivo, assuming that CYP-mediated metabolism was a predominant elimination pathway. In different microsomal species, the ranges of results were approximately as shown in Table 15.

TABLE 15

Metabolic Stability - Result Interpretation Guidelines

| CYP-Mediated Clearance | Percent Remaining after 10 minutes | | | | |
|---|---|---|---|---|---|
| | Human | Rat | Mouse | Dog | Monkey |
| Low | >90 | >85 | >85 | >90 | >85 |
| Medium | 60-90 | 40-85 | 50-85 | 55-90 | 40-85 |
| High | <60 | <40 | <50 | <55 | <40 |

Methods and Materials

Incubation with Liver Microsomes

Test compound was received as a 3.5 mM stock solution in 100 percent DMSO. The test compound was diluted to create a 50 µM acetonitrile (ACN) solution containing 1.4% DMSO, which was then used as a 100× stock for incubation with microsomes. Each compound was tested in duplicate separately in each of three species in the Metabolic Stability-Human, Rat, and Mouse assay suite or as individual species in the Metabolic Stability-Dog or Metabolic Stability-Monkey suites. Compound, NADPH, and liver microsome solutions were combined for incubation in three steps:

1. 152 µl of liver microsome suspension, protein concentration of 1.1 mg/ml in 100 mM NaP$_i$, pH 7.4, 5 mM MgCl$_2$ buffer, was pre-warmed at 37° C.

2. 1.7 µl of 50 µM compound (98.6% ACN, 1.4% DMSO) was added to the same tube and pre-incubated at 37° C. for 5 minutes.

3. The reaction was initiated by the addition of 17 µl of pre-warmed 10 mM NADPH solution in 100 mM NaP$_i$, pH 7.4.

The reaction components were mixed well, and 75 µl of the reaction mixture was immediately transferred into 150 µl quench/stop solution (zero-time point, T$_0$). Reactions were incubated at 37° C. for 10 minutes and then an additional 75 µl aliquot was transferred into 150 µl quench solution. Acetonitrile containing 100 µM DMN (a UV standard for injection quality control), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, was then transferred to a separate 96-well plate for UV-LC/MS-MS analysis to determine the percent of parent compound that remained in the mixture.

TABLE 16

Metabolic Stability Assay - Reaction Components

| Reaction Components | Final Concentration in the Metabolic Stability Assay |
|---|---|
| Compound (Substrate) | 0.5 µM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| MgCl$_2$ | 5.0 mM |
| 37° C. Incubation time | 0 minutes and 10 minutes |
| Quench/Stop Solution (ACN + 100 µM DMN) | 150 µl |
| Sample of Reaction | 75 µl |
| Sedimentation of Denatured Microsomes | 15 minutes |
| UV-LC/MS analysis of supernatant | 0.17 µM |

Sample Analysis—Instrumentation

HPLC: Pump—Thermo Surveyor; Autosampler—CTC/LEAP HTS; UV detector—Thermo Surveyor PDA plus; Column—VARIAN® C18, 3 µm, 2×20 mm with a 0.5 µm in-line filter; Mobile Phase for structural integrity pre-analysis: (A) 98% water, 2% acetonitrile with 10 mM ammonium acetate; (B) 10% water, 90% acetonitrile with 10 mM ammonium acetate; Mobile Phase for reaction sample analysis: (A) 98% water, 2% acetonitrile with 0.1% formic acid; (B) 2% water, 98% acetonitrile with 0.1% formic acid; (C) 0.1% ammonium hydroxide in water; (D) 0.1% ammonium hydroxide in acetonitrile.

Mass Spectrometer: Thermo TSQ QUANTUM® Ultra triple-quadrupole mass spectrometer.

Sample Analysis—Structural Integrity Pre-Analysis

The Metabolic Stability structural integrity pre-analysis was used to assess the purity of compounds being assayed. Compounds were received in 96-well plates as 57 µl of a 3.5 mM DMSO solution. The 3.5 mM compound DMSO stock solutions were diluted 18-fold with a solution containing equal volumes of acetonitrile, isopropanol, and MilliQ-H$_2$O. The resulting solutions (200 µM) were analyzed for structural integrity by LC-UV/MS on a Thermo LCQ Deca XP Plus ion trap mass spectrometer, using a Waters XBridge C18, 5 µm, 2×50 mm column with a Waters Sentry 2.1 mm guard column, and the LC conditions described in the table below, with a 5 µl injection and a flow rate of 1 ml/min. The acquired data reflected purity by UV absorbance at 220 nm. Only results for those compounds with purity greater than 50% were reported.

TABLE 17

Metabolic Stability - Structural Integrity Gradient

| Gradient Time (min) | A % | B % |
|---|---|---|
| 0.00 | 100 | 0 |
| 4.00 | 0 | 100 |
| 5.00 | 0 | 100 |
| 5.10 | 100 | 0 |
| 6.00 | 100 | 0 |

Sample Analysis—Incubated Samples

MS/MS condition optimization was conducted on a Thermo TSQ QUANTUM® triple-quadrupole mass spectrometer equipped with a heated-electrospray (H-ESI) source by automated infusion to obtain the SRM transitions and their corresponding collision energy values. Compound solutions at a concentration of 20 µM in 1:1 methanol:water were infused at a flow rate of 90 µL/min, then combined with the mobile phase at a flow rate of 50 µL/min before being introduced into the source. All compounds were optimized first using mobile phase A and B (50% A and 50% B), and if necessary, using mobile phase C and D (also with a 50:50 composition). The optimized parameters, including polarity, SRM transition and collision energy, were stored in a MICROSOFT ACCESS® database.

The mass spectrometric conditions obtained from automated infusion were used to analyze incubation samples from the Metabolic Stability assay. The injection volume was 5 µl and the flow rate was 0.8 ml/min. The gradient used was shown in the table below. All samples were injected with the gradient using mobile phase A and B first. If necessary (for instance, for chromatographic reasons), samples were re-injected with the same gradient, but using mobile phase C and D. All LC-MS/MS analysis parameters were captured electronically in the raw data files.

TABLE 18

Metabolic Stability - Sample Analysis Gradient

| Gradient Time (min) | A % (or C %) | B % (or D %) |
|---|---|---|
| 0.00 | 95 | 5 |
| 0.20 | 95 | 5 |
| 0.30 | 0 | 100 |
| 1.05 | 0 | 100 |
| 1.10 | 95 | 5 |
| 1.50 | 95 | 5 |

Data Analysis

Peak integration was performed with the XCALIBUR® software. The percent remaining calculation was performed by comparing the LC-MS/MS peak areas from the $T_{10minute}$ samples to those from the $T_{0miniute}$ samples for each compound.

Quality Control

A set of three compounds was tested along with the test compound in each assay plate. Data was accepted and uploaded only if the results for these control compounds fall into the expected ranges shown below.

TABLE 19

Metabolic Stability Assay - Control Compound Values by Microsome Species

| Compound | Average Percent Remaining ± SD | | | | |
|---|---|---|---|---|---|
| | Human | Rat | Mouse | Dog | Monkey |
| Nefazodone | 0.4 ± 0.4 | 0.7 ± 0.6 | 0.4 ± 0.3 | 0.4 ± 0.4 | 0.6 ± 0.5 |
| Verapamil | 13.3 ± 3.5 | 4.4 ± 2.1 | 13.0 ± 4.2 | 5.6 ± 1.8 | 0.5 ± 0.5 |
| Carbamezepine | 96 ± 6 | 84 ± 9 | 90 ± 10 | 81 ± 7 | 89 ± 13 |

SD = Standard Deviation

Metabolic Stability Half-Life Panel

The rate of metabolism and half-life determined in vitro in human or animal liver microsomes was used to determine intrinsic clearance ($CL_{int}$) and hepatic clearance (CLh,b) of a compound. These parameters were useful for predicting in vivo human clearance, which defines the level of drug exposure in vivo (Obach et al., 1997, 1999).

The metabolic stability half-life assay panel evaluates the time-course and the rate of CYP-mediated (NADPH-dependent) metabolism in vitro in human, rat, mouse, dog and monkey microsomes. The time course spans a 45-minute incubation, and includes 0, 5, 10, 15, 30, and 45 minute time-points, at each of which the amount of test compound remaining in the mixture was measured.

Result Interpretation Guideline

The results of the metabolic stability half-life assay are expressed as a half-life ($T_{1/2}$, min). In general, these results should be used to evaluate only the extent of CYP-mediated, or NADPH-dependent, metabolism of the test compound. When the compound was significantly metabolized ($T_{1/2}$<14 minutes), this indicated high clearance in vivo due to CYP-mediated metabolism. However, if the compound demonstrated moderate (14-70 minutes) or low (>70 minutes) metabolism in these in vitro assays, high clearance was still possible in vivo via other metabolism and elimination pathways.

The results of these assays were predictive of compound clearance in vivo, assuming that CYP-mediated metabolism was a predominant elimination pathway. In human microsomes, the ranges of results were approximately as shown in the following table:

TABLE 20

Metabolic Stability Half-Life-Result Interpretation Guidelines

| CYP-Mediated Clearance | $T_{1/2}$, minutes Human |
|---|---|
| Low | >70 |
| Medium | 14-70 |
| High | <14 |

Methods and Materials

Liver microsomes were purchased from BD-Biosciences (Woburn, Mass.) and NADPH from AppliChem Inc; all other reagents were obtained from Sigma.

Incubation with Liver Microsomes

Test compound was received as a 3.5 mM stock solution in 100 percent DMSO. The test compound was diluted to create a 50 µM acetonitrile (ACN) solution containing 1.4% DMSO, which was then used as a 100-fold stock for incubation with microsomes. Each compound was tested in human, rat, mouse, dog and monkey liver microsomes. Compound, NADPH and liver microsome solutions were combined for incubation in three steps:

1. 450 µl of liver microsome suspension, protein concentration of 1.1 mg/ml in 100 mM $NaP_i$, pH 7.4, 5 mM $MgCl_2$ buffer, was pre-warmed at 37° C.

2. 5 µl of 50 µM compound (98.6% ACN, 1.4% DMSO) was added to the same tube and pre-incubated at 37° C. for 5 minutes.

3. The reaction was initiated by the addition of 50 µl of pre-warmed 10 mM NADPH solution in 100 mM $NaP_i$, pH 7.4.

Reaction components were mixed well, and 65 µl were immediately transferred into 130 µl quench/stop solution (zero-time point, $T_0$). Reactions were incubated at 37° C. for 5, 10, 15, 30 and 45 minutes and at each time-point a 65 µl aliquot was transferred into 130 µl of quench solution. Acetonitrile containing Internal Standard (100 ng/ml), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, was then transferred to a separate 96-well plate for LC/MS-MS analysis to determine the percent of parent compound that was remaining in the mixture.

TABLE 21

Metabolic Stability Half-Life Assays - Reaction Components

| Reaction Components | Final Concentration in the Metabolic Stability Assay |
|---|---|
| Compound (Substrate) | 0.5 µM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| $MgCl_2$ | 5.0 mM |
| 37° C. Incubation time | 0, 5, 10, 15, 30, and 45 minutes |
| Quench/Stop Solution (ACN + 100 µM DMN) | 130 µl |
| Sample of Reaction | 65 µl |
| Sedimentation of Denatured Microsomes | 15 minutes |

Sample Analysis—Instrumentation

HPLC: Pump—Shimadzu LC-20 AD series binary pumps; Autosampler—CTC/LEAP HTS.

Table 22 below lists the CYP-mediated metabolic half life value for Examples 1-43 of this invention and Comparative Compounds 56-60 measured in the human metabolic stability half-life assay. In some instances, the value is an average of multiple experiments where N is the number of experiments conducted. The compounds of the present invention, as exemplified by Examples 1-43 had metabolic stability half life values of 30 minutes or longer. In contrast, Comparative Compounds 56-60 had metabolic stability half life values of 9 minutes or less.

TABLE 22

| Example | HLM ($t_{1/2}$, min) | N |
|---|---|---|
| 1 | 85 | 61 |
| 2 | 46 | 1 |
| 3 | 77 | 1 |
| 4 | 83 | 3 |
| 5 | 74 | 3 |
| 6 | 83 | 3 |
| 7 | 97 | 1 |
| 8 | 37 | 1 |
| 9 | 90 | 1 |
| 10 | 72 | 4 |
| 11 | 76 | 5 |
| 12 | 104 | 1 |
| 13 | >120 | 1 |
| 14 | 41 | 1 |
| 15 | 40 | 2 |
| 16 | 75 | 2 |
| 17 | 60 | 2 |
| 18 | >120 | 2 |
| 19 | 56 | 2 |
| 20 | 106 | 4 |
| 21 | 62 | 2 |
| 22 | 32 | 3 |
| 23 | 69 | 3 |
| 24 | 76 | 2 |
| 25 | 31 | 2 |
| 26 | 96 | 1 |
| 27 | 81 | 1 |
| 28 | 39 | 2 |
| 29 | 99 | 3 |
| 30 | 74 | 1 |
| 31 | 52 | 3 |
| 32 | 55 | 1 |
| 33 | 47 | 2 |
| 34 | >120 | 1 |
| 35 | 36 | 4 |
| 36 | >120 | 1 |
| 37 | 43 | 4 |
| 38 | 70 | 6 |
| 39 | 38 | 1 |
| 40 | 34 | 4 |
| 41 | 45 | 2 |
| 42 | 87 | 4 |
| 43 | 30 | 52 |
| Comparative Ex. 56 | 8 | 1 |
| Comparative Ex. 57 | 6 | 1 |
| Comparative Ex. 58 | 6 | 1 |
| Comparative Ex. 59 | 3 | 1 |
| Comparative Ex. 60 | 9 | 1 |

The exemplified compounds of the invention showed the surprising advantage of low clearance due to CYP-mediated metabolism in the human metabolic stability half life assay. The compounds of the present invention, as exemplified by Examples 1-43, had metabolic half lives in the range of 30 minutes to greater than 120 minutes in the human metabolic stability half life assay. In contrast, Comparative Compounds 56-60 had metabolic half lives of 9 minutes or less in the human metabolic stability half life assay. Comparative Compounds 56-60 showed high clearance in the human metabolic stability assay, indicating that the compounds were removed by liver microsomes.

The compounds of the present invention (Examples 1-43) have been compared to the Comparative Compounds 56-60 disclosed in U.S. Pat. No. 7,456,172, and have been found to be especially advantageous. The compounds of the present invention had the surprising advantage of the combination of activity as inhibitors of Notch 1 and Notch 3 and superior metabolic stability to liver microsomes. As shown in Tables 13 and 21, in the reported tests, Examples 1-43 of this invention had Notch 1 $IC_{50}$ values of 16.1 nM or less and Notch 3 $IC_{50}$ values of 28.3 nM or less; and human metabolic stability half lives of 30 minutes or longer in the human metabolic stability half life assay. In contrast, in similar tests, Comparative Compounds 56-59 had Notch 1 $IC_{50}$ values of in the range of from 5.1 nM to 64.1 nM and Notch 3 $IC_{50}$ values in the range of 12.5 nM to 74.5 nM; and Comparative Compounds 56-60 had human metabolic stability half lives of 9 minutes or less.

Human Tumor Xenograft Models in Mice

All rodents were obtained from Harlan Sprague Dawley Co. (Indianapolis, Ind.), and maintained in an ammonia-free environment in a defined and pathogen—free colony. All mice were quarantined approximately 1 week prior to their use for tumor propagation and drug efficacy testing. Mice were fed food and water ad libitum. The animal care program of Bristol-Myers Squibb Pharmaceutical Research Institute is fully accredited by the American Association for Accreditation of Laboratory Animal Care (AAALAC). All experiments were performed in accordance with Bristol-Myers Squibb (BMS) animal test methods and guidelines.

Tumor xenografts were grown and maintained subcutaneously (SC) in immunocompromized balb/c nu/nu nude or NOD-SCID mice (Harlan Sprague Dawley). Tumors were propagated as subcutaneous transplants in the appropriate mouse strain (Table 23) using tumor fragments obtained from donor mice.

TABLE 23

Histological Types and Host Mouse Strain/Gender Requirement for the Propagation of Various Human Tumor Xenografts in Mice

| Tumor Type | Histology | Mouse Strain | Sex |
|---|---|---|---|
| TALL-1 | ALL | NOD-SCID | female |
| MDA-MB-157 | breast | NOD-SCID | female |
| MDA-MB-468 | breast | NOD-SCID | female |

Preclinical Chemotherapy Trials

The required numbers of animals needed to detect a meaningful response were pooled at the start of the experiment and each was given a subcutaneous implant of a tumor fragment (~20 mg) with a 13-gauge trocar. Tumors were allowed to grow to the pre-determined size window (tumors outside the range were excluded) and animals were evenly distributed to various treatment and control groups. There were typically 8 mice per treatment and control groups, with the exception of experiments conducted in the SAL-IGF (this is not included in Table 23) tumor model, in which there were typically 5 mice per treatment and control group. Treatment of each animal was based on individual body weight. Treated animals were checked daily for treatment related toxicity/mortality. Each group of animals was weighed before the initiation of treatment ($Wt_1$) and then again following the last treatment dose ($Wt_2$). The difference in body weight ($Wt_2-Wt_1$) provides a measure of treatment-related toxicity.

Tumor response was determined by measurement of tumors with a caliper twice a week, until the tumors reached a predetermined "target" size of 0.5 gm or 1 gm depending on the tumor type. Tumor weights (mg) were estimated from the formula:

$$\text{Tumor weight} = (\text{length} \times \text{width}) \div 2$$

Tumor response criteria are expressed in terms of tumor growth inhibition (% TGI). Tumor growth delay is defined as the difference in time (days) required for the treated tumors (T) to reach a predetermined target size compared to those of the control group (C). For this purpose, the tumor weight of a group is expressed as medium tumor weight (MTW).

Tumor growth inhibition is calculated as follows:

$$\% \text{ Tumor Growth Inhibition} = \frac{\left(1 - \frac{T_t}{T_0} * \frac{C_0}{C_t}\right)}{\left(1 - \frac{C_0}{C_t}\right)}$$

where, $C_t$=Median control tumor size at end of treatment
$C_0$=Median control tumor size at treatment initiation
$T_t$=Median tumor size of treated group at end of treatment
$T_0$=Median tumor size of treated group at treatment initiation Activity is defined as the achievement of durable tumor growth inhibition of 50% or greater (i.e., TGI≥50%) or log cell kill of 0.5 or greater (LCK≥0.5) for a period equivalent to at least 1 tumor volume doubling time and drug treatment must be for a period equivalent to at least 2 tumor volume doubling time.

Tumor response was also expressed in terms of tumor growth delay (TGD value), defined as the difference in time (days) required for the treated tumors (T) to reach a predetermined target size compared to those of the control group (C).

Whenever possible, antitumor activity was determined at a range of dose levels up to the maximum tolerated dose (MTD) which is defined as the dose level immediately below which excessive toxicity (i.e., more than one death) occurred. When death occurred, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Potential drug toxicity interaction affecting treatment tolerability is an important consideration in combination chemotherapy trials. Interpretation of combination therapeutic results must be based on comparison of antitumor activity of the best possible response for the single agents versus the combination at comparably tolerated doses. Therefore, therapeutic synergism was defined as a therapeutic effect achieved with a tolerated regimen of the combined agents that exceeded the optimal effect achieved at any tolerated dose of monotherapy. Statistical evaluations of data were performed using Gehan's generalized Wilcoxon test. Statistical significance was declared at P<0.05.

Drug Administration

In in vitro studies, all agents were dissolved in 100% DMSO and serially diluted in media/10% fetal bovine serum. The following excipients were used for administration of the Notch inhibitors to rodents: ETOH/TPGS/PEG300 (10:10:80). Notch inhibitors were typically administered orally on a schedule of QD×15, 10 day-on-2 day-off-5 day-on, although other schedules had also been evaluated and shown to be efficacious. For example, dosing regimen consisting of QD×12, 4 day-on-3 day-off was shown to be equally efficacious as QD×15, 10 day-on-2 day-off-5 day-on. In the BID studies, the second dose was given 6 to 12 hours after the first dose.

In Vivo Antitumor Activity

The antitumor activity of Example 1 administered orally (PO) was evaluated in human tumor xenografts implanted in mice. As shown in FIGS. 12-16, Example 1 exhibited antitumor activity.

Table 24 below lists the antitumor activity of examples of this invention measured in the Human Tumor Xenograft Models in mice. The compounds of the present invention, as exemplified by Examples 1, 10, 35, 37, 40, and 52, showed antitumor activity with oral administration (PO) either BID and/or QD.

TABLE 24

Schedule: QDx10, Oral Administration

| | | Antitumor Activity in TALL-1 (LCK) | |
|---|---|---|---|
| Ex | Dose | BID dosing | QD dosing |
| 1 | 20 | ND | 4.5 |
| 10 | 12 | ND | >2.8 |
| 35 | 20 | 3.1 | ND |
| 37 | 20 | 2.0 | ND |
| 40 | 40 | ND | 1.4 |
| 52 | 20 | ND | 5.7 |

QD—once daily
LCK—Log Cell Kill

Prodrug Evaluation

Male SPRAGUE DAWLEY® rats (250-300 g) were used for the pharmacokinetic studies. Rats were fasted overnight prior to dosing and fed 4 hrs post dose. In each study, groups of animals (N=2-3) received the test compound by oral gavage. Blood samples (~0.3 mL) were collected from the jugular vein into $K_2$EDTA-containing tubes at 0.5, 1, 3, 5, 7, and 24 h post dose. Plasma samples, obtained by centrifugation at 4° C. (1500-2000×g), were stored at −20° C. until analysis by LC/MS/MS.

The pharmacokinetic parameters were obtained by non-compartmental analysis of plasma concentration (determined by LC/MS/MS) vs. time data (ThermoKinetica Software version 5.0). The peak concentration ($C_{max}$) and time for $C_{max}$, $T_{max}$, were recorded directly from experimental observations. The area under the curve from time zero to the last sampling time ($AUC_{0-t}$) was calculated using a combination of linear and log trapezoidal summations. The total plasma clearance (CLTp), steady-state volume of distribution (Vss), apparent elimination half-life ($t_{1/2}$) and mean residence time (MRT) were estimated after IV administration. Estimation of $t_{1/2}$ was made using a minimum of 3 time points with quantifiable concentrations. The absolute oral bioavailability F was estimated as the ratio of dose-normalized AUC values following oral and IV doses. The plasma exposures of Example 1 ($AUC_{0-24h}$ or $AUC_{0-7}$ h) after administration of the prodrugs were compared with the exposure after administration of Example 1. The relative bioavailabilities of the prodrugs to Example 1 were estimated (Table 25).

TABLE 25

| Example | Dose (mg/kg) | $AUC_{0-24\ h}$ of Example 1 after Administration of Prodrug (nM · hr) | % Relative Bioavailability to Example 1 |
|---|---|---|---|
| 49 | 1.23 | 207 | 23 |
| 52 | 1.32 | 429* | 43 |
| 53 | 1.43 | 610 | 64 |
| 55 | 1.47 | 251 | 30 |

*$AUC_{0-7h}$

What is claimed is:

1. A compound of Formula (I):

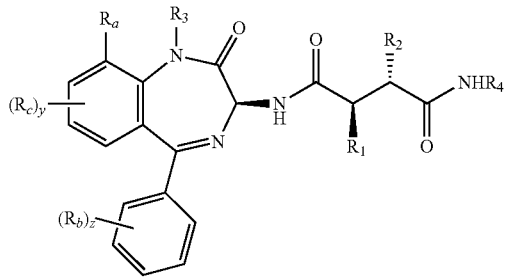

or a salt thereof, wherein:
R₁ is —CH₂CH₂CF₃;
R₂ is —CH₂(cyclopropyl), —CH(CH₃)(cyclopropyl), or —CH₂CH₂CH₃;
R₃ is H, —CH₃, or $R_x$;
R₄ is H or $R_y$;
$R_x$ is: —CH₂OP(O)(OH)₂, —CH₂OC(O)CH(CH(CH₃)₂)NH₂,

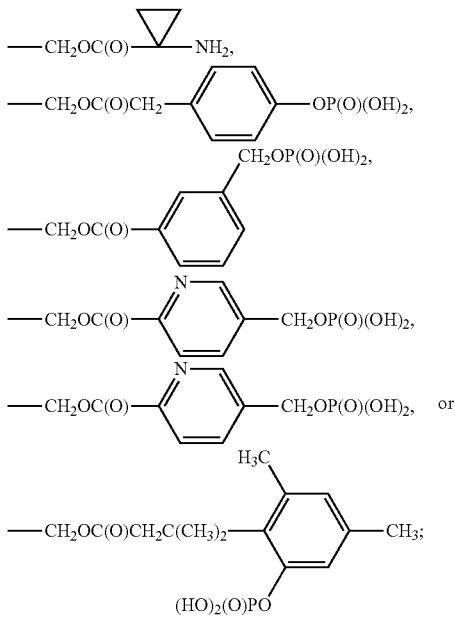

$R_y$ is —SCH₂CH₂NH₂, —SCH₂CH(NH₂)C(O)OH, —SCH₂CH(NH₂)C(O)OCH₃, or

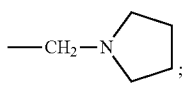

;

$R_a$ is F, Cl, Br, —CN, —OH, —CH₃, —CH₂OH, cyclopropyl, —CF₃, —OCH₃, or —O(cyclopropyl);
each $R_b$ is independently F, Cl, —CH₃, —OCH₃, and/or —CF₃;
$R_c$ is Cl, Br, —CH₃, —OCH₃, or —O(cyclopropyl);

y is zero or 1; and
z is zero, 1, or 2;
provided that if R₃ is $R_x$, then R₄ is H; and
if R₄ is $R_y$, then R₃ is H or —CH₃.

2. The compound according to claim 1 or a salt thereof, wherein:
R₂ is —CH₂(cyclopropyl) or —CH(CH₃)(cyclopropyl).

3. The compound according to claim 1 or a salt thereof, wherein:
R₂ is —CH₂CH₂CH₃.

4. The compound according to claim 1 or a salt thereof, wherein:
R₃ is H or —CH₃; and
R₄ is H.

5. The compound according to claim 1 or a salt thereof, wherein y is zero.

6. The compound according to claim 1 or a salt thereof, wherein:
R₁ is —CH₂CH₂CF₃;
R₂ is —CH₂(cyclopropyl);
R₃ is H or $R_x$;
$R_a$ is F, —CH₃, or —CH₂OH;
$R_b$ is F;
y is zero; and
z is zero or 1.

7. The compound according to claim 1 selected from: (2R, 3S)-3-(Cyclopropylmethyl)-N-((3 S)-9-fluoro-2-oxo-5-phenyl-2,3-dihydro-1H-1,4-benzodiazepin-3-yl)-2-(3,3,3-trifluoropropyl) succinamide (1); (2R,3S)-3-(cyclopropylmethyl)-N-((3S)-9-methoxy-2-oxo-5-(3-(trifluoromethyl)phenyl)-2,3-dihydro-1H-1,4-benzodiazepin-3-yl)-2-(3,3,3-trifluoropropyl)succinamide (2); (2R,3S)—N-((3S)-9-chloro-5-(3-fluoro-5-methylphenyl)-2-oxo-2,3-dihydro-1H-benzo[e][1,4]diazepin-3-yl)-3-(cyclopropylmethyl)-2-(3,3,3-trifluoropropyl)succinamide (3); (2R,3S)-3-(cyclopropylmethyl)-N-((3 S)-5-(3-fluorophenyl)-9-methoxy-2-oxo-2,3-dihydro-1H-1,4-benzodiazepin-3-yl)-2-(3,3,3-trifluoropropyl)succinamide (4); (2R, 3S)-3-(cyclopropylmethyl)-N-((3S)-9-(cyclopropyloxy)-5-(3-fluorophenyl)-2-oxo-2,3-dihydro-1H-1,4-benzodiazepin-3-yl)-2-(3,3,3-trifluoropropyl)succinamide (5); (2R,3S)-3-(cyclopropylmethyl)-N-((3S)-9-(cyclopropyloxy)-2-oxo-5-phenyl-2,3-dihydro-1H-1,4-benzodiazepin-3-yl)-2-(3,3,3-trifluoropropyl)succinamide (6); (2R,3S)—N-((3S)-5-(4-chlorophenyl)-9-cyclopropyl-2-oxo-2,3-dihydro-1H-1,4-benzodiazepin-3-yl)-3-(cyclopropylmethyl)-2-(3,3,3-trifluoropropyl)succinamide (7); (2R,3S)-3-(cyclopropylmethyl)-N-((3S)-9-hydroxy-5-(3-methylphenyl)-2-oxo-2,3-dihydro-1H-1,4-benzodiazepin-3-yl)-2-(3,3,3-trifluoropropyl)succinamide (8); (2R,3S)-3-(cyclopropylmethyl)-N-((3S)-9-methyl-2-oxo-5-(3-(trifluoromethyl)phenyl)-2,3-dihydro-1H-1,4-benzodiazepin-3-yl)-2-(3,3,3-trifluoropropyl)succinamide (9); (2R,3S)-3-(cyclopropylmethyl)-N-((3S)-5-(3-fluorophenyl)-9-methyl-2-oxo-2,3-dihydro-1H-1,4-benzodiazepin-3-yl)-2-(3,3,3-trifluoropropyl)succinamide (10); (2R, 3S)-3-(cyclopropylmethyl)-N-((3 S)-9-methyl-2-oxo-5-phenyl-2,3-dihydro-1H-1,4-benzodiazepin-3-yl)-2-(3,3,3-trifluoropropyl) succinamide (11); (2R,3S)-3-(cyclopropylmethyl)-N-((3S)-5-(4-fluorophenyl)-9-methyl-2-oxo-2,3-dihydro-1H-1,4-benzodiazepin-3-yl)-2-(3,3,3-trifluoropropyl)succinamide (12); (2R,3S)—N-((3S)-9-chloro-5-(2-methylphenyl)-2-oxo-2,3-dihydro-1H-1,4-benzodiazepin-3-yl)-3-(cyclopropylmethyl)-2-(3,3,3-trifluoropropyl)succinamide (13); (2R,3S)-3-(cyclopropylmethyl)-N-(9-cyclopropyl-2-oxo-5-phenyl-2,3-dihydro-1H-1,4-benzodiazepin-3-yl)-2-(3,3,3-trifluoropropyl)succinamide (14); (2R,3S)—N-((3S)-9- methyl-2-oxo-5-phenyl-2,3-dihydro-1H-1,4-benzodiazepin-3-yl)-3-propyl-2-(3,3,3-trifluoropropyl)succinamide (15); (2R,3S)-3-(cyclopropylmethyl)-N-((3S)-9-fluoro-5-(4-methylphenyl)-2-oxo-2,3-dihydro-1H-1,4-benzodiazepin-3-yl)-2-(3,3,3-trifluoropropyl)succinamide (16); (2R,3S)-3-(cyclopropylmethyl)-N-((3S)-9-fluoro-7-methyl-2-oxo-5-phenyl-2,3-dihydro-1H-1,4-benzodiazepin-3-yl)-2-(3,3,3-trifluoropropyl)succinamide (17); (2R,3S)-3-(cyclopropylmethyl)-N-((3 S)-9-fluoro-8-methyl-2-oxo-5-phenyl-2,3-dihydro-1H-1,4-benzodiazepin-3-yl)-2-(3,3,3-trifluoropropyl)succinamide (18); (2R,3S)-3-(cyclopropylmethyl)-N-((3S)-9-fluoro-5-(3-methylphenyl)-2-oxo-2,3-dihydro-1H-1,4-benzodiazepin-3-yl)-2-(3,3,3-trifluoropropyl)succinamide (19); (2R,3S)-3-(cyclopropylmethyl)-N-((3S)-9-fluoro-1-methyl-2-oxo-5-phenyl-2,3-dihydro-1H-1,4-benzodiazepin-3-yl)-2-(3,3,3-trifluoropropyl)succinamide (20); (2R,3S)—N-((3S)-5-(4-Chlorophenyl)-9-methoxy-2-oxo-2,3-dihydro-1H-1,4-benzodiazepin-3-yl)-3-(cyclopropylmethyl)-2-(3,3,3-trifluoropropyl)succinamide (21); (2R,3S)-3-(cyclopropylmethyl)-N-((3S)-9-fluoro-5-(3-methoxyphenyl)-2-oxo-2,3-dihydro-1H-1,4-benzodiazepin-3-yl)-2-(3,3,3-trifluoropropyl) succinamide (22); (2R,3S)-3-(cyclopropylmethyl)-N-((3S)-9-fluoro-5-(3-fluorophenyl)-2-oxo-2,3-dihydro-1H-1,4-benzodiazepin-3-yl)-2-(3,3,3-trifluoropropyl)succinamide (23); (2R,3S)—N-((3S)-5-(3-chlorophenyl)-9-fluoro-2-oxo-2,3-dihydro-1H-1,4-benzodiazepin-3-yl)-3-(cyclopropylmethyl)-2-(3,3,3-trifluoropropyl)succinamide (24); (2R,3S)—N-((3S)-5-(4-chlorophenyl)-9-methoxy-2-oxo-2,3-dihydro-1H-1,4-benzodiazepin-3-yl)-3-propyl-2-(3,3,3-trifluoropropyl)succinamide (25); (2R,3S)—N-((3S)-9-chloro-5-(3-chlorophenyl)-2-oxo-2,3-dihydro-1H-benzo[e][1,4]diazepin-3-yl)-3-(cyclopropylmethyl)-2-(3,3,3-trifluoropropyl)succinamide (26); (2R,3S)—N-((3S)-9-chloro-5-(4-chlorophenyl)-2-oxo-2,3-dihydro-1H-1,4-benzodiazepin-3-yl)-3-(cyclopropylmethyl)-2-(3,3,3-trifluoropropyl)succinamide (27); (2R,3S)—N-((3S)-9-chloro-5-(4-chlorophenyl)-2-oxo-2,3-dihydro-1H-1,4-benzodiazepin-3-yl)-3-propyl-2-(3,3,3-trifluoropropyl)succinamide (28); (2R,3S)-3-(cyclopropylmethyl)-N-((3S)-9-fluoro-8-methoxy-2-oxo-5-phenyl-2,3-dihydro-1H-1,4-benzodiazepin-3-yl)-2-(3,3,3-trifluoropropyl)succinamide (29); (2R,3S)—N-((3S)-9-chloro-5-(3-methylphenyl)-2-oxo-2,3-dihydro-1H-1,4-benzodiazepin-3-yl)-3-(cyclopropylmethyl)-2-(3,3,3-trifluoropropyl)succinamide (30); (2R,3S)-3-(cyclopropylmethyl)-N-((3S)-9-methoxy-5-(3-methylphenyl)-2-oxo-2,3-dihydro-1H-1,4-benzodiazepin-3-yl)-2-(3,3,3-trifluoropropyl)succinamide (31); (2R,3S)—N-((3 S)-9-cyano-2-oxo-5-phenyl-2,3-dihydro-1H-1,4-benzodiazepin-3-yl)-3-propyl-2-(3,3,3-trifluoropropyl)succinamide (32); (2R,3S)—N-((3S)-9-methoxy-2-oxo-5-phenyl-2,3-dihydro-1H-1,4-benzodiazepin-3-yl)-3-((1-methylcyclopropyl)methyl)-2-(3,3,3-trifluoropropyl)succinamide (33); (2R,3S)-3-(cyclopropylmethyl)-N-((3S)-8,9-dichloro-2-oxo-5-phenyl-2,3-dihydro-1H-1,4-benzodiazepin-3-yl)-2-(3,3,3-trifluoropropyl)succinamide (34); (2R,3S)—N-((3S)-2-oxo-5-phenyl-9-(trifluoromethyl)-2,3-dihydro-1H-1,4-benzodiazepin-3-yl)-3-propyl-2-(3,3,3-trifluoropropyl) succinamide (35); (2R,3S)-3-(cyclopropylmethyl)-N-((3S)-2-oxo-5-phenyl-9-(trifluoromethyl)-2,3-dihydro-1H-1,4-benzodiazepin-3-yl)-2-(3,3,3-trifluoropropyl)succinamide (36); (2R,3S)—N-((3S)-9-fluoro-2-oxo-5-phenyl-2,3-dihydro-1H-1,4-benzodiazepin-3-yl)-3-propyl-2-(3,3,3-trifluoropropyl) succinamide (37); (2R,3S)-3-(cyclopropylmethyl)-N-((3S)-9-methoxy-2-oxo-5-phenyl-2,3-dihydro-1H-1,4-benzodiazepin-3-yl)-2-(3,3,3-trifluoropropyl)succinamide (38); (2R,3S)—N-((3S)-8-bromo-9-methoxy-2-oxo-5-phenyl-2,3-dihydro-1H-1,4-benzodiazepin-3-yl)-3-propyl-2-(3,3,3-trifluoropropyl)succinamide (39); (2R,3S)—N-((3S)-9-methoxy-2-oxo-5-phenyl-2,3-dihydro-1H-1,4-benzodiazepin-3-yl)-3-propyl-2-(3,3,3-trifluoropropyl)succinamide (40); (2R,3S)—N-((3S)-9-hydroxy-2-oxo-5-phenyl-2,3-dihydro-1H-1,4-benzodiazepin-3-yl)-3-propyl-2-(3,3,3-trifluoropropyl) succinamide (41); (2R,3S)—N-((3S)-9-chloro-2-oxo-5-phenyl-2,3-dihydro-1H-1,4-benzodiazepin-3-yl)-3-(cyclopropylmethyl)-2-(3,3,3-trifluoropropyl)succinamide (42); (2R,3S)—N-((3 S)-9-chloro-2-oxo-5-phenyl-2,3-dihydro-1H-1,4-benzodiazepin-3-yl)-3-propyl-2-(3,3,3-trifluoropropyl)succinamide (43); ((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl (4-(phosphonooxy)phenyl)acetate (44); ((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl dihydrogen phosphate (45); ((3S)-3-(((2R)-2-((1S)-1-Amino-3-cyclopropyl-1-oxopropan-2-yl)-5,5,5-trifluoropentanoyl)amino)-9-fluoro-2-oxo-5-phenyl-2,3-dihydro-1H-1,4-benzodiazepin-1-yl)methyl 3-((phosphonooxy)methyl)benzoate (46); ((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl 5-((phosphonooxy)methyl)-2-pyridinecarboxylate (47); ((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl 3-(2,4-dimethyl-6-(phosphonooxy)phenyl)-3-methylbutanoate (48); S-(((2S,3R)-2-(Cyclopropylmethyl)-6,6,6-trifluoro-3-(((3S)-9-fluoro-2-oxo-5-phenyl-2,3-dihydro-1H-1,4-benzodiazepin-3-yl)carbamoyl) hexanoyl)amino)-L-cysteine.TFA (49); (2S,3R)—N1-((2-Aminoethyl)sulfanyl)-2-(cyclopropylmethyl)-N4-((3S)-9-fluoro-2-oxo-5-phenyl-2,3-dihydro-1H-1,4-benzodiazepin-3-yl)-3-(3,3,3-trifluoropropyl)succinamide.TFA (50); Methyl S-(((2S,3R)-2-(cyclopropylmethyl)-6,6,6-trifluoro-3-(((3S)-9-fluoro-2-oxo-5-phenyl-2,3-dihydro-1H-1,4-benzodiazepin-3-yl) carbamoyl) hexanoyl)amino)-L-cysteinate.TFA (51); ((3S)-3-(((2R)-2-((1S)-2-Amino-1-(cyclopropylmethyl)-2-oxoethyl)-5,5,5-trifluoropentanoyl)amino)-9-fluoro-2-oxo-5-phenyl-2,3-dihydro-1H-1,4-benzodiazepin-1-yl)methyl L-valinate (52); ((3S)-3-(((2R)-2-((1S)-2-Amino-1-(cyclopropylmethyl)-2-oxoethyl)-5,5,5-trifluoropentanoyl) amino)-9-fluoro-2-oxo-5-phenyl-2,3-dihydro-1H-1,4-benzodiazepin-1-yl)methyl 1-aminocyclopropanecarboxylate (53); (2S,3R)-2-(Cyclopropylmethyl)-N$^4$-((3S)-9-fluoro-2-oxo-5-phenyl-2,3-dihydro-1H-1,4-benzodiazepin-3-yl)-N$^1$-(1-pyrrolidinylmethyl)-3-(3,3,3-trifluoropropyl)succinamide (54); ((3S)-3-(((2R)-2-((1S)-2-amino-1-(cyclopropylmethyl)-2-oxoethyl)-5,5,5-trifluoropentanoyl) amino)-9-fluoro-2-oxo-5-phenyl-2,3-dihydro-1H-1,4-benzodiazepin-1-yl)methyl 4-((phosphonooxy)methyl) benzoate (55); and salts thereof.

8. A pharmaceutical composition comprising at least one compound according to claim 1 or a pharmaceutically acceptable salt thereof; and a pharmaceutically acceptable carrier.

* * * * *